(12) United States Patent
Esfandyarpour et al.

(10) Patent No.: US 10,570,449 B2
(45) Date of Patent: *Feb. 25, 2020

(54) SYSTEMS AND METHODS FOR BIOLOGICAL ANALYSIS

(71) Applicant: GenapSys, Inc., Redwood City, CA (US)

(72) Inventors: Hesaam Esfandyarpour, Redwood City, CA (US); Hamid Rategh, Cupertino, CA (US); Meysam R. Barmi, Menlo Park, CA (US); Kosar B. Parizi, Redwood City, CA (US); Kambiz Kaviani, Palo Alto, CA (US)

(73) Assignee: GENAPSYS, INC., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/726,217

(22) Filed: Oct. 5, 2017

(65) Prior Publication Data

US 2018/0155780 A1 Jun. 7, 2018

Related U.S. Application Data

(63) Continuation of application No. 14/653,230, filed as application No. PCT/US2014/027544 on Mar. 14, 2014, now Pat. No. 9,809,852.

(60) Provisional application No. 61/800,443, filed on Mar. 15, 2013, provisional application No. 61/799,483, filed on Mar. 15, 2013, provisional application No. 61/801,929, filed on Mar. 15, 2013, provisional application No. 61/799,396, filed on Mar. 15, 2013, provisional application No. 61/800,410, filed on Mar. 15, 2013, provisional application No. 61/799,944, filed on Mar. 15, 2013, provisional application No. 61/801,560, filed on Mar. 15, 2013.

(51) Int. Cl.
*C12Q 1/68* (2018.01)
*C12Q 1/6874* (2018.01)
*G01N 27/74* (2006.01)

(52) U.S. Cl.
CPC .......... *C12Q 1/6874* (2013.01); *G01N 27/745* (2013.01)

(58) Field of Classification Search
CPC ........... C12Q 2563/116; C12Q 1/6874; C12Q 2565/607; C12Q 1/6825; C12Q 1/6869; C12Q 2523/307; C12Q 2563/143; C12Q 2565/629; C12Q 2527/119; C12Q 2535/122; C12Q 2565/543; C12Q 1/6844
See application file for complete search history.

(56) References Cited

U.S. PATENT DOCUMENTS

| | | | |
|---|---|---|---|
| 2,014,761 | A | 9/1935 | Faust |
| 4,072,576 | A | 2/1978 | Arwin et al. |
| 5,344,545 | A | 9/1994 | Tsukada et al. |
| 5,407,799 | A | 4/1995 | Studier et al. |
| 5,466,348 | A | 11/1995 | Holm-Kennedy |
| 5,602,042 | A | 2/1997 | Farber |
| 5,612,181 | A | 3/1997 | Fourmentin-Guilbert |
| 5,795,782 | A | 8/1998 | Church et al. |
| 5,834,197 | A | 11/1998 | Parton |
| 6,046,097 | A | 4/2000 | Hsieh et al. |
| 6,087,095 | A | 7/2000 | Rosenthal et al. |
| 6,210,891 | B1 | 4/2001 | Nyren et al. |
| 6,327,410 | B1 | 12/2001 | Walt et al. |
| 6,632,655 | B1 | 10/2003 | Mehta et al. |
| 6,833,246 | B2 | 12/2004 | Balasubramanian |
| 6,870,235 | B2 | 3/2005 | Abstreiter et al. |
| 6,953,958 | B2 | 10/2005 | Baxter et al. |
| 7,081,192 | B1 | 7/2006 | Wang et al. |
| 7,095,010 | B2 | 8/2006 | Scherer et al. |
| 7,223,540 | B2 | 5/2007 | Pourmand et al. |
| 7,238,536 | B1 | 7/2007 | Schlenoff |
| 7,242,241 | B2 | 7/2007 | Toumazou et al. |
| 7,270,981 | B2 | 9/2007 | Armes et al. |
| 7,282,370 | B2 | 10/2007 | Bridgham et al. |
| 7,291,496 | B2 | 11/2007 | Holm-Kennedy |
| 7,312,085 | B2 | 12/2007 | Chou et al. |
| 7,317,216 | B2 | 1/2008 | Holm-Kennedy |
| 7,323,305 | B2 | 1/2008 | Leamon et al. |
| 7,361,466 | B2 | 4/2008 | Korlach et al. |
| 7,399,590 | B2 | 7/2008 | Piepenburg et al. |
| 7,435,561 | B2 | 10/2008 | Piepenburg et al. |
| 7,485,428 | B2 | 2/2009 | Armes et al. |
| 7,615,382 | B2 | 11/2009 | Wang et al. |
| 7,645,596 | B2 | 1/2010 | Williams et al. |
| 7,649,358 | B2 | 1/2010 | Toumazou et al. |
| 7,666,598 | B2 | 2/2010 | Piepenburg et al. |
| 7,682,837 | B2 | 3/2010 | Jain et al. |

(Continued)

FOREIGN PATENT DOCUMENTS

| | | |
|---|---|---|
| CN | 1337580 A | 2/2002 |
| CN | 101120098 A | 2/2008 |

(Continued)

OTHER PUBLICATIONS

Andreotti, et al. Immunoassay of infectious agents. Biotechniques. Oct. 2003;35(4):850-9.
Bell, et al. Detection of Bacillus anthracis DNA by LightCycler PCR. J Clin Microbiol. Aug. 2002;40(8):2897-902.
Boo, et al. Electrochemical nanoneedle biosensor based on multiwall carbon nanotube. Anal Chem. Jan. 15, 2006;78(2):617-20.
Brouns, et al. Small CRISPR RNAs guide antiviral defense in prokaryotes. Science. Aug. 15, 2008;321(5891):960-4.

(Continued)

*Primary Examiner* — Cynthia B Wilder
(74) *Attorney, Agent, or Firm* — Wilson Sonsini Goodrich & Rosati

(57) ABSTRACT

Provided herein are devices and methods suitable for sequencing, amplifying, analyzing, and performing sample preparation procedures for nucleic acids and other biomolecules.

25 Claims, 85 Drawing Sheets

(56) References Cited

U.S. PATENT DOCUMENTS

| | | |
|---|---|---|
| 7,686,929 B2 | 3/2010 | Toumazou et al. |
| 7,692,219 B1 | 4/2010 | Holm-Kennedy |
| 7,695,907 B2 | 4/2010 | Miyahara et al. |
| 7,763,427 B2 | 7/2010 | Piepenburg et al. |
| 7,824,890 B2 | 11/2010 | Hoser et al. |
| 7,835,871 B2 | 11/2010 | Kain et al. |
| 7,875,440 B2 | 1/2011 | Williams et al. |
| 7,888,013 B2 | 2/2011 | Miyahara et al. |
| 7,932,034 B2 | 4/2011 | Esfandyarpour et al. |
| 7,948,015 B2 | 5/2011 | Rothberg et al. |
| 8,023,113 B2 | 9/2011 | El et al. |
| 8,030,000 B2 | 10/2011 | Piepenburg et al. |
| 8,039,817 B2 | 10/2011 | Feng et al. |
| 8,062,848 B2 | 11/2011 | Goldstein et al. |
| 8,062,850 B2 | 11/2011 | Piepenburg et al. |
| 8,071,308 B2 | 12/2011 | Piepenburg et al. |
| 8,114,591 B2 | 2/2012 | Toumazou et al. |
| 8,128,796 B2 | 3/2012 | Ishige et al. |
| 8,129,118 B2 | 3/2012 | Weindel et al. |
| 8,137,569 B2 | 3/2012 | Harnack et al. |
| 8,152,991 B2 | 4/2012 | Briman et al. |
| 8,154,093 B2 | 4/2012 | Bradley et al. |
| 8,173,080 B2 | 5/2012 | Lebl et al. |
| 8,173,401 B2 | 5/2012 | Chang et al. |
| 8,179,296 B2 | 5/2012 | Kelly et al. |
| 8,257,925 B2 | 9/2012 | Brown et al. |
| 8,274,040 B2 | 9/2012 | Zhong et al. |
| 8,301,394 B2 | 10/2012 | Chen et al. |
| 8,315,817 B2 | 11/2012 | Kain et al. |
| 8,392,126 B2 | 3/2013 | Mann |
| 8,426,134 B2 | 4/2013 | Piepenburg et al. |
| 8,460,875 B2 | 6/2013 | Armes et al. |
| 8,486,625 B2 | 7/2013 | Gunderson et al. |
| 8,518,670 B2 | 8/2013 | Goldstein et al. |
| 8,574,846 B2 | 11/2013 | Piepenburg et al. |
| 8,580,507 B2 | 11/2013 | Piepenburg et al. |
| 8,585,973 B2 | 11/2013 | Esfandyarpour |
| 8,637,253 B2 | 1/2014 | Piepenburg et al. |
| 8,649,011 B2 | 2/2014 | McCaffrey et al. |
| 8,673,560 B2 | 3/2014 | Leamon et al. |
| 8,778,848 B2 | 7/2014 | Lin et al. |
| 8,778,849 B2 | 7/2014 | Bowen et al. |
| 8,865,077 B2 | 10/2014 | Chiou et al. |
| 8,865,078 B2 | 10/2014 | Chiou et al. |
| 8,914,241 B2 | 12/2014 | Kain et al. |
| 8,969,002 B2 | 3/2015 | Esfandyarpour et al. |
| 9,045,796 B2 | 6/2015 | Gunderson et al. |
| 9,063,117 B2 | 6/2015 | Gourley |
| 9,150,915 B2 | 10/2015 | Esfandyarpour et al. |
| 9,184,099 B2 | 11/2015 | Baghbani-Parizi et al. |
| 9,187,783 B2 | 11/2015 | Esfandyarpour et al. |
| 9,188,594 B2 | 11/2015 | Fahmy et al. |
| 9,274,077 B2 | 3/2016 | Esfandyarpour et al. |
| 9,399,217 B2 | 7/2016 | Oldham et al. |
| 9,434,983 B2 | 9/2016 | Esfandyarpour |
| 9,533,305 B2 | 1/2017 | Esfandyarpour et al. |
| 9,689,835 B2 | 6/2017 | Liu et al. |
| 9,809,852 B2 * | 11/2017 | Esfandyarpour .... C12Q 1/6874 |
| 9,822,401 B2 | 11/2017 | Oberstrass et al. |
| 9,926,596 B2 | 3/2018 | Esfandyarpour et al. |
| 9,945,807 B2 | 4/2018 | Baghbani-Parizi et al. |
| 9,990,381 B2 | 6/2018 | Eltoukhy et al. |
| 10,059,982 B2 | 8/2018 | Esfandyarpour et al. |
| 10,093,975 B2 | 10/2018 | Esfandyarpour et al. |
| 10,100,356 B2 | 10/2018 | Esfandyarpour et al. |
| 10,125,393 B2 | 11/2018 | Esfandyarpour et al. |
| 10,260,095 B2 | 4/2019 | Esfandyarpour et al. |
| 10,266,892 B2 | 4/2019 | Esfandyarpour et al. |
| 10,472,674 B2 | 11/2019 | Esfandyarpour et al. |
| 10,494,672 B2 | 12/2019 | Esfandyarpour et al. |
| 2002/0132245 A1 | 9/2002 | Boles et al. |
| 2002/0148739 A2 | 10/2002 | Liamos et al. |
| 2003/0078314 A1 | 4/2003 | Johnson et al. |
| 2003/0209432 A1 | 11/2003 | Choong et al. |
| 2004/0014201 A1 | 1/2004 | Kim et al. |
| 2004/0023253 A1 | 2/2004 | Kunwar et al. |
| 2004/0033492 A1 | 2/2004 | Chen |
| 2004/0136866 A1 | 7/2004 | Pontis et al. |
| 2004/0197793 A1 | 10/2004 | Hassibi et al. |
| 2005/0009022 A1 | 1/2005 | Weiner et al. |
| 2005/0019784 A1 | 1/2005 | Su et al. |
| 2005/0032076 A1 | 2/2005 | Williams et al. |
| 2005/0084980 A1 | 4/2005 | Koo et al. |
| 2005/0098434 A1 | 5/2005 | Gundel et al. |
| 2005/0123937 A1 | 6/2005 | Thorp et al. |
| 2005/0129526 A1 | 6/2005 | Dukhin et al. |
| 2005/0200648 A1 | 9/2005 | Doak et al. |
| 2005/0218464 A1 | 10/2005 | Holm-Kennedy |
| 2006/0008824 A1 | 1/2006 | Ronaghi et al. |
| 2006/0105373 A1 | 5/2006 | Pourmand et al. |
| 2006/0147955 A1 | 7/2006 | Allawi et al. |
| 2006/0170931 A1 | 8/2006 | Guo et al. |
| 2006/0199193 A1 | 9/2006 | Koo et al. |
| 2006/0222569 A1 | 10/2006 | Barten et al. |
| 2007/0132043 A1 | 6/2007 | Bradley et al. |
| 2007/0184463 A1 | 8/2007 | Molho et al. |
| 2007/0275375 A1 | 11/2007 | Van et al. |
| 2008/0009420 A1 | 1/2008 | Schroth et al. |
| 2008/0032294 A1 | 2/2008 | Kawarada et al. |
| 2008/0032295 A1 | 2/2008 | Toumazou et al. |
| 2008/0161200 A1 | 7/2008 | Yu et al. |
| 2008/0166727 A1 | 7/2008 | Esfandyarpour et al. |
| 2008/0171325 A1 | 7/2008 | Brown et al. |
| 2008/0176817 A1 | 7/2008 | Zhou et al. |
| 2008/0187915 A1 | 8/2008 | Polonsky et al. |
| 2008/0241841 A1 | 10/2008 | Murakawa et al. |
| 2008/0286762 A1 | 11/2008 | Miyahara et al. |
| 2008/0302732 A1 | 12/2008 | Soh et al. |
| 2008/0318243 A1 | 12/2008 | Haga et al. |
| 2009/0000957 A1 | 1/2009 | Dubin et al. |
| 2009/0005259 A1 | 1/2009 | Drmanac |
| 2009/0026082 A1 | 1/2009 | Rothberg et al. |
| 2009/0029385 A1 | 1/2009 | Christians et al. |
| 2009/0032401 A1 | 2/2009 | Ronaghi et al. |
| 2009/0048124 A1 | 2/2009 | Leamon et al. |
| 2009/0127589 A1 | 5/2009 | Rothberg et al. |
| 2009/0166221 A1 | 7/2009 | Ishige et al. |
| 2009/0170716 A1 * | 7/2009 | Su ........................ C12Q 1/6869 506/9 |
| 2009/0170724 A1 | 7/2009 | Balasubramanian et al. |
| 2009/0181385 A1 | 7/2009 | McKernan et al. |
| 2009/0191594 A1 | 7/2009 | Ohashi |
| 2010/0000881 A1 | 1/2010 | Franzen et al. |
| 2010/0035252 A1 | 2/2010 | Rothberg et al. |
| 2010/0072080 A1 | 3/2010 | Karhanek et al. |
| 2010/0078325 A1 | 4/2010 | Oliver |
| 2010/0105035 A1 | 4/2010 | Hashsham et al. |
| 2010/0112588 A1 | 5/2010 | Farinas et al. |
| 2010/0137143 A1 | 6/2010 | Rothberg et al. |
| 2010/0137413 A1 | 6/2010 | Cummins et al. |
| 2010/0151479 A1 | 6/2010 | Toumazou et al. |
| 2010/0159461 A1 | 6/2010 | Toumazou et al. |
| 2010/0163414 A1 | 7/2010 | Gillies et al. |
| 2010/0167938 A1 | 7/2010 | Su et al. |
| 2010/0188073 A1 | 7/2010 | Rothberg et al. |
| 2010/0197507 A1 | 8/2010 | Rothberg et al. |
| 2010/0209922 A1 | 8/2010 | Williams et al. |
| 2010/0255595 A1 | 10/2010 | Toumazou et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2010/0317531 A1 | 12/2010 | Balasubramanian et al. |
| 2010/0330570 A1 | 12/2010 | Vander et al. |
| 2011/0008775 A1 | 1/2011 | Gao et al. |
| 2011/0039266 A1 | 2/2011 | Williams et al. |
| 2011/0117026 A1 | 5/2011 | Tseng et al. |
| 2011/0118139 A1 | 5/2011 | Mehta et al. |
| 2011/0123991 A1 | 5/2011 | Hoser |
| 2011/0159481 A1 | 6/2011 | Liu et al. |
| 2011/0171655 A1 | 7/2011 | Esfandyarpour et al. |
| 2011/0177498 A1 | 7/2011 | Clarke et al. |
| 2011/0183321 A1 | 7/2011 | Williams et al. |

(56) References Cited

U.S. PATENT DOCUMENTS

| | | |
|---|---|---|
| 2011/0195253 A1 | 8/2011 | Hinz et al. |
| 2011/0195459 A1 | 8/2011 | Hinz et al. |
| 2011/0201057 A1 | 8/2011 | Carr et al. |
| 2011/0201506 A1 | 8/2011 | Hinz et al. |
| 2011/0217697 A1 | 9/2011 | Rothberg et al. |
| 2011/0230375 A1 | 9/2011 | Rothberg et al. |
| 2011/0241081 A1 | 10/2011 | Rothberg et al. |
| 2011/0247933 A1 | 10/2011 | Rothberg et al. |
| 2011/0248319 A1 | 10/2011 | Rothberg et al. |
| 2011/0248320 A1 | 10/2011 | Rothberg et al. |
| 2011/0259745 A1 | 10/2011 | Dehlinger et al. |
| 2011/0263463 A1 | 10/2011 | Rothberg et al. |
| 2011/0287432 A1 | 11/2011 | Wong et al. |
| 2011/0287945 A1 | 11/2011 | Rothberg et al. |
| 2011/0294115 A1 | 12/2011 | Williams et al. |
| 2011/0311979 A1 | 12/2011 | Brown et al. |
| 2012/0013392 A1 | 1/2012 | Rothberg et al. |
| 2012/0014837 A1 | 1/2012 | Fehr et al. |
| 2012/0021918 A1 * | 1/2012 | Bashir .......... B82Y 15/00 506/2 |
| 2012/0034607 A1 | 2/2012 | Rothberg et al. |
| 2012/0037961 A1 | 2/2012 | Rothberg et al. |
| 2012/0040844 A1 | 2/2012 | Rothberg et al. |
| 2012/0045844 A1 | 2/2012 | Rothberg et al. |
| 2012/0052489 A1 | 3/2012 | Gordon et al. |
| 2012/0055811 A1 | 3/2012 | Rothberg et al. |
| 2012/0055813 A1 | 3/2012 | Rothberg et al. |
| 2012/0061239 A1 | 3/2012 | Elibol et al. |
| 2012/0061255 A1 | 3/2012 | Rothberg et al. |
| 2012/0061256 A1 | 3/2012 | Rothberg et al. |
| 2012/0061733 A1 | 3/2012 | Rothberg et al. |
| 2012/0065093 A1 | 3/2012 | Rothberg et al. |
| 2012/0071363 A1 | 3/2012 | Rothberg et al. |
| 2012/0085660 A1 | 4/2012 | Rothberg et al. |
| 2012/0088682 A1 | 4/2012 | Rothberg et al. |
| 2012/0094871 A1 | 4/2012 | Hinz et al. |
| 2012/0129173 A1 | 5/2012 | Piepenburg et al. |
| 2012/0129703 A1 | 5/2012 | Rothberg et al. |
| 2012/0129728 A1 | 5/2012 | Rothberg et al. |
| 2012/0129732 A1 | 5/2012 | Rothberg et al. |
| 2012/0135870 A1 | 5/2012 | Rothberg et al. |
| 2012/0135893 A1 | 5/2012 | Drmanac et al. |
| 2012/0138460 A1 | 6/2012 | Baghbani-Parizi et al. |
| 2012/0156728 A1 | 6/2012 | Li et al. |
| 2012/0157322 A1 | 6/2012 | Myllykangas et al. |
| 2012/0173159 A1 | 7/2012 | Davey et al. |
| 2012/0175252 A1 | 7/2012 | Toumazou et al. |
| 2012/0222496 A1 | 9/2012 | Mamigonians |
| 2012/0247977 A1 | 10/2012 | Rothberg et al. |
| 2012/0258456 A1 | 10/2012 | Armes et al. |
| 2012/0258499 A1 | 10/2012 | Piepenburg et al. |
| 2012/0264617 A1 | 10/2012 | Pettit |
| 2012/0295819 A1 | 11/2012 | Leamon et al. |
| 2012/0302454 A1 | 11/2012 | Esfandyarpour |
| 2012/0322054 A1 | 12/2012 | Rothberg et al. |
| 2012/0322113 A1 | 12/2012 | Erlander et al. |
| 2013/0005613 A1 | 1/2013 | Leamon et al. |
| 2013/0023011 A1 | 1/2013 | Leamon et al. |
| 2013/0059290 A1 | 3/2013 | Armes |
| 2013/0059762 A1 | 3/2013 | Leamon et al. |
| 2013/0090860 A1 | 4/2013 | Sikora et al. |
| 2013/0109577 A1 | 5/2013 | Korlach et al. |
| 2013/0183211 A1 | 7/2013 | Senftleber |
| 2013/0203634 A1 | 8/2013 | Jovanovich et al. |
| 2013/0225421 A1 | 8/2013 | Li et al. |
| 2013/0231254 A1 | 9/2013 | Kawashima et al. |
| 2013/0281307 A1 | 10/2013 | Li et al. |
| 2014/0034497 A1 | 2/2014 | Davis et al. |
| 2014/0099674 A1 | 4/2014 | Piepenburg et al. |
| 2014/0106338 A1 | 4/2014 | Fischer et al. |
| 2014/0235457 A1 | 8/2014 | Esfandyarpour et al. |
| 2014/0272952 A1 | 9/2014 | May et al. |
| 2014/0329699 A1 | 11/2014 | Esfandyarpour |
| 2015/0316502 A1 | 11/2015 | Mohanty et al. |
| 2015/0344943 A1 | 12/2015 | Oberstrass |
| 2015/0368707 A1 | 12/2015 | Esfandyarpour et al. |
| 2015/0376681 A1 | 12/2015 | Gupta et al. |
| 2015/0376692 A1 | 12/2015 | Esfandyarpour et al. |
| 2016/0076097 A1 | 3/2016 | Esfandyarpour et al. |
| 2016/0077049 A1 | 3/2016 | Baghbani-Parizi et al. |
| 2016/0273032 A1 | 9/2016 | Esfandyarpour et al. |
| 2016/0340721 A1 | 11/2016 | Esfandyarpour |
| 2017/0065977 A1 | 3/2017 | Esfandyarpour et al. |
| 2017/0073750 A1 | 3/2017 | Esfandyarpour et al. |
| 2017/0088575 A1 | 3/2017 | Ju et al. |
| 2017/0211141 A1 | 7/2017 | Gordon et al. |
| 2019/0017103 A1 | 1/2019 | Esfandyarpour |
| 2019/0177790 A1 | 6/2019 | Esfandyarpour et al. |
| 2019/0177791 A1 | 6/2019 | Esfandyarpour et al. |
| 2019/0226019 A1 | 7/2019 | Esfandyarpour |
| 2019/0226021 A1 | 7/2019 | Esfandyarpour et al. |

FOREIGN PATENT DOCUMENTS

| | | |
|---|---|---|
| CN | 101405083 A | 4/2009 |
| CN | 101848757 A | 9/2010 |
| CN | 101918590 A | 12/2010 |
| CN | 102980922 A | 3/2013 |
| EP | 0676623 * | 5/1990 |
| EP | 0676623 A2 | 10/1995 |
| EP | 1333089 A1 | 8/2003 |
| EP | 1499738 B1 | 7/2008 |
| EP | 1992706 A2 | 11/2008 |
| EP | 2290096 A2 | 3/2011 |
| EP | 2336361 A2 | 6/2011 |
| EP | 2428588 A2 | 3/2012 |
| EP | 2287341 B1 | 2/2013 |
| EP | 1759012 B1 | 5/2013 |
| EP | 2660336 A1 | 11/2013 |
| JP | 2006512583 A | 4/2006 |
| JP | 2008525822 A | 7/2008 |
| JP | 2010513869 A | 4/2010 |
| JP | 2010517040 A | 5/2010 |
| JP | 2010517041 A | 5/2010 |
| JP | 2010518401 A | 5/2010 |
| WO | WO-0118246 A1 | 3/2001 |
| WO | WO-0137958 A2 | 5/2001 |
| WO | WO-0142508 A2 | 6/2001 |
| WO | WO-0227909 A2 | 4/2002 |
| WO | WO-02061146 A1 | 8/2002 |
| WO | WO-2004027024 A2 | 4/2004 |
| WO | WO-2004076683 A2 | 9/2004 |
| WO | WO-2005008450 A2 | 1/2005 |
| WO | WO-2005108612 A2 | 11/2005 |
| WO | WO-2005121363 A2 | 12/2005 |
| WO | WO-2006050346 A2 | 5/2006 |
| WO | WO-2007030505 A1 | 3/2007 |
| WO | WO-2007041619 A2 | 4/2007 |
| WO | WO-2007098049 A2 | 8/2007 |
| WO | WO-2008076406 A2 | 6/2008 |
| WO | WO-2008132643 A1 | 11/2008 |
| WO | WO-2009012112 A1 | 1/2009 |
| WO | WO-2009052348 A2 | 4/2009 |
| WO | WO-2009074926 A1 | 6/2009 |
| WO | WO-2009122159 A2 | 10/2009 |
| WO | WO-2009150467 A1 | 12/2009 |
| WO | WO-2010008480 A2 | 1/2010 |
| WO | WO-2010026488 A2 | 3/2010 |
| WO | WO-2010037085 A1 | 4/2010 |
| WO | WO-2010041231 A2 | 4/2010 |
| WO | WO-2010047804 A1 | 4/2010 |
| WO | WO-2010075188 A2 | 7/2010 |
| WO | WO-2010138187 A1 | 12/2010 |
| WO | WO-2010141940 A1 | 12/2010 |
| WO | WO-2011106556 A2 | 9/2011 |
| WO | WO-2012047889 A2 | 4/2012 |
| WO | WO-2012166742 A2 | 12/2012 |
| WO | WO-2013082619 A1 | 6/2013 |
| WO | WO-2013119765 A1 | 8/2013 |
| WO | WO-2013188582 A1 | 12/2013 |
| WO | WO-2014012107 A2 | 1/2014 |
| WO | WO-2014043143 A1 | 3/2014 |
| WO | WO-2014152625 A1 | 9/2014 |
| WO | WO-2015089238 A1 | 6/2015 |

(56) References Cited

FOREIGN PATENT DOCUMENTS

| WO | WO-2015138696 A1 | 9/2015 |
|---|---|---|
| WO | WO-2015161054 A2 | 10/2015 |
| WO | WO-2018017884 | 1/2018 |
| WO | WO-2019060628 A1 | 3/2019 |

OTHER PUBLICATIONS

Cagnin, et al. Overview of electrochemical DNA biosensors: new approaches to detect the expression of life. Sensors (Basel). 2009;9(4):3122-48. doi: 10.3390/s90403122. Epub Apr. 24, 2009.
Carte, et al., Cas6 is an endoribonuclease that generates guide RNAs for invader defense in prokaryotes. Genes Dev. Dec. 15, 2008;22(24):3489-96.
Cho, et al. Bis-aptazyme sensors for hepatitis C virus replicase and helicase without blank signal. Nucleic Acids Res. Nov. 27, 2005;33(20):e177.
Co-pending U.S. Appl. No. 15/655,616, filed Jul. 20, 2017.
Daniels, et al. Label-Free Impedance Biosensors: Opportunities and Challenges. Electroanalysis. Jun. 2007;19(12):1239-1257.
Daniels, et al. Simultaneous Measurement of Nonlinearity and Electrochemical Impedance for Protein Sensing Using Two-Tone Excitation. 30th Annual International IEEE EMBS Conference. Vancouver, British Columbia, Canada, Aug. 20-24, 2008. 5753-5756.
Didion, et al., Invaders: Recognition of Double-Stranded DNA by Using Duplexes Modified with Interstrand Zippers of 2'-O-(Pyren-1-yl)methyl-ribonucleotides. Chembiochem. Sep. 2, 2013;14(13):1534-1538. doi: 10.1002/cbic.201300414. Epub 2013 Aug. 23, 2013.
Dimov, et al. Stand-alone self-powered integrated microfluidic blood analysis system (SIMBAS). Lab Chip. Mar. 7, 2011;11(5):845-50.
Edman, et al. Electric field directed nucleic acid hybridization on microchips. Nucleic Acids Res. Dec. 15, 1997; 25(24): 4907-14.
Ellington, et al. In vitro selection of RNA molecules that bind specific ligands. Nature. Aug. 30, 1990;346(6287):818-22.
Esfandyarpour, et al. 3D modeling of impedance spectroscopy for protein detection in nanoneedle biosensors. Proceedings of the COMSOL Conference 2007, Boston.
Esfandyarpour, et al. 3D Modeling of Impedance Spectroscopy for Protein Detection in Nanoneedle Biosensors. Proceedings of the International Comsol Conference 2007, Boston, MA, USA, pp. 169-173 (Oct. 4-6, 2007).
Esfandyarpour, et al. A Novel Nanoneedle Biosensor for DNA Sequencing (abstract). Dec. 31, 2008. Available at http://www.nsti.org/Nanotech2008/showabstract.html?absno=1522.
Esfandyarpour, et al. Geometrical Optimization of Pyrophosphate Concentration in Thermosequencing Platform for DNA Sequencing. Proceedings of the COMSOL Conf. 2007, Boston.
European search report and search opinion dated Jan. 5, 2015 for EP Application No. 12792216.9.
European search report and search opinion dated Mar. 12, 2014 for EP Application No. 11831452.5.
European search report and search opinion dated Jul. 13, 2015 for EP Application No. 12852490.7.
Finn, et al. Efficient incorporation of positively charged 2', 3'-dideoxynucleoside-5'-triphosphates by DNA polymerases and their application in 'direct-load' DNA sequencing. Nucleic Acids Res. Aug. 15, 2003;31(16):4769-78.
Gao, et al. Silicon nanowire arrays for label-free detection of DNA. Anal Chem. May 1, 2007;79(9):3291-7. Epub Apr. 4, 2007.
Gardeniers, et al. Silicon micromachined hollow microneedles for transdermal liquid transport. Journal of Microelectromechanical Systems. 2003;12(6):855-862.
Guiducci, et al. A Biosensor for Direct Detection of DNA Sequences Based on Capacitance Measurements. ESSDERC 2002, pp. 479-482.
Haurwitz, et al. Sequence- and structure-specific RNA processing by a CRISPR endonuclease. Science. Sep. 10, 2010;329(5997):1355-8.
Hollis, et al. Structure of the gene 2.5 protein, a single-stranded DNA binding protein encoded by bacteriophage T7. Proc Natl Acad Sci U S A. Aug. 14, 2001;98(17):9557-62. Epub Jul. 31, 2001.
International search report and written opinion dated Feb. 26, 2013 for PCT/US2012/039880.
International search report and written opinion dated Mar. 19, 2013 for PCT/US2012/067645.
International search report and written opinion dated Apr. 13, 2012 for PCT/US2011/054769.
International search report and written opinion dated Aug. 21, 2014 for PCT Application No. PCT/US2014/027544.
International search report and written opinion dated Oct. 26, 2015 for PCT/US2015/026135.
Javanmard, et al. A microfluidic platform for electrical detection of DNA hybridization. Sens Actuators B Chem. May 20, 2011;154(1):22-27. Epub Mar. 30, 2010.
Javanmard, et al. Electrical Detection of Proteins and DNA Using Bioactivated Microfluidic Channels: Theoretical and Experimental Considerations. J Vac Sci Technol B Microelectron Nanometer Struct Process Meas Phenom. Nov. 2009;27(6):3099-3103.
Kaushik, et al. Lack of pain associated with microfabricated microneedles. Anesth Analg. Feb. 2001;92(2):502-4.
Kim, et al. Replication of DNA microarrays prepared by in situ oligonucleotide polymerization and mechanical transfer. Anal Chem. Oct. 1, 2007;79(19):7267-74.
Kitano, et al. Molecular structure of RNA polymerase and its complex with DNA. J Biochem. Jan. 1969;65(1):1-16.
Kunin, et al. Evolutionary conservation of sequence and secondary structures in CRISPR repeats. Genome Biol. 2007;8(4):R61.
Kurosaki, et al. Rapid and simple detection of Ebola virus by reverse transcription-loop-mediated isothermal amplification. J Virol Methods. Apr. 2007;141(1):78-83.
Lee, et al. Ion-sensitive field-effect transistor for biological sensing. Sensors (Basel). 2009;9(9):7111-31. doi: 10.3390/s90907111. Epub Sep. 7, 2009.
Lin, et al. Replication of DNA microarrays from zip code masters. J Am Chem Soc. Mar. 15, 2006;128(10):3268-72.
Liu, et al. Immobilization of DNA onto poly(dimethylsiloxane) surfaces and application to a microelectrochemical enzyme-amplified DNA hybridization assay. Langmuir. Jul. 6, 2004;20(14):5905-10.
Makarova, et al. A putative RNA-interference-based immune system in prokaryotes: computational analysis of the predicted enzymatic machinery, functional analogies with eukaryotic RNAi, and hypothetical mechanisms of action. Biol Direct. Mar. 16, 2006;1:7.
Manickam, et al. A CMOS Electrochemical Impedance Spectroscopy (EIS) Biosensor Array. IEEE Trans Biomed Circuits Syst. Dec. 2010;4(6):379-90. doi: 10.1109/TBCAS.2010.2081669.
Margulies, et al. Genome sequencing in microfabricated high-density picolitre reactors. Nature. Sep. 15, 2005;437(7057):376-80. Epub Jul. 31, 2005.
Notice of allowance dated Mar. 28, 2016 for U.S. Appl. No. 13/481,858.
Notice of Allowance dated May 12, 2017 for U.S. Appl. No. 14/653,230.
Notice of allowance dated May 19, 2016 for U.S. Appl. No. 13/481,858.
Notice of allowance dated Jun. 3, 2015 for U.S. Appl. No. 14/596,111.
Notice of allowance dated Jul. 1, 2015 for U.S. Appl. No. 13/824,129.
Notice of Allowance dated Jul. 6, 2017 for U.S. Appl. No. 14/653,230.
Notice of Allowance dated Jul. 10, 2017 for U.S. Appl. No. 14/688,764.
Notice of allowance dated Jul. 13, 2015 for U.S. Appl. No. 14/596,111.
Notice of Allowance dated Jul. 20, 2017 for U.S. Appl. No. 14/688,764.
Notice of Allowance dated Jul. 31, 2017 for U.S. Appl. No. 14/119,859.
Notice of allowance dated Aug. 25, 2015 for U.S. Appl. No. 14/596,111.
Notice of allowance dated Sep. 1, 2015 for U.S. Appl. No. 14/596,111.

(56) References Cited

OTHER PUBLICATIONS

Notice of Allowance dated Sep. 8, 2017 for U.S. Appl. No. 14/653,230.
Notice of allowance dated Nov. 21, 2014 for U.S. Appl. No. 13/632,513.
Notice of allowance dated Dec. 3, 2015 for U.S. Appl. No. 13/838,816.
Notice of allowance dated Dec. 15, 2015 for U.S. Appl. No. 13/838,816.
Notomi, et al. Loop-mediated isothermal amplification of DNA. Nucl Acids Res. Jun. 15, 2000; 28(12):E63.
Office action dated Jan. 28, 2014 for U.S. Appl. No. 13/838,816.
Office action dated Jan. 29, 2014 for U.S. Appl. No. 13/481,858.
Office action dated Jan. 30, 2015 for U.S. Appl. No. 13/481,858.
Office Action dated Feb. 14, 2017 for U.S. Appl. No. 14/653,230.
Office Action dated Apr. 5, 2017 for U.S. Appl. No. 14/859,725.
Office action dated Apr. 6, 2016 for U.S. Appl. No. 14/835,070.
Office action dated Apr. 9, 2015 for U.S. Appl. No. 14/596,111.
Office Action dated Apr. 24, 2017 for U.S. Appl. No. 14/119,859.
Office action dated May 1, 2015 for U.S. Appl. No. 13/824,129.
Office action dated Jul. 18, 2013 for U.S. Appl. No. 13/481,858.
Office action dated Jul. 23, 2014 for U.S. Appl. No. 13/824,129.
Office action dated Jul. 25, 2014 for U.S. Appl. No. 13/481,858.
Office Action dated Sep. 1, 2017 for U.S. Appl. No. 14/361,902.
Office action dated Sep. 2, 2014 for U.S. Appl. No. 13/632,513.
Office action dated Oct. 7, 2015 for U.S. Appl. No. 13/838,816.
Office action dated Nov. 5, 2013 for U.S. Appl. No. 13/632,513.
Office action dated Dec. 17, 2015 for U.S. Appl. No. 13/481,858.
Office action dated Dec. 17, 2015 for U.S. Appl. No. 14/835,070.
Office action dated Dec. 19, 2014 for U.S. Appl. No. 13/838,816.
Patolsky, et al. Electrical detection of single viruses. Proc Natl Acad Sci U S A. Sep. 28, 2004;101(39):14017-22. Epub Sep. 13, 2004.
Patolsky, et al. Fabrication of silicon nanowire devices for ultrasensitive, label-free, real-time detection of biological and chemical species. Nat Protoc. 2006;1(4):1711-24.
Piepenburg, et al. DNA detection using recombination proteins. PLoS Biol. Jul. 2006;4(7):e204.
Ren, et al. Rapid and sensitive detection of hepatitis B virus 1762T/1764A double mutation from hepatocellular carcinomas using LNA-mediated PCR clamping and hybridization probes. Journal of Virological Methods. 2009; 158(1-2):24-29.
Roosen-Runge, et al. Protein diffusion in crowded electrolyte solutions. Biochim Biophys Acta. Jan. 2010;1804(1):68-75. doi: 10.1016/j.bbapap.2009.07.003. Epub Jul. 17, 2009.
Rothberg, et al. An integrated semiconductor device enabling non-optical genome sequencing. Nature. Jul. 20, 2011; 475(7356); pp. 348-352. With Supplementary Information, 25 pages.
Sabounchi, et al. Sample concentration and impedance detection on a microfluidic polymer chip. Biomed Microdevices. Oct. 2008;10(5):661-70. doi: 10.1007/s10544-008-9177-4.
Safir, et al. Fabrication of an insulated probe on a self-assembled metallic nanowire for electrochemical probing in cells. IEEE 2006, pp. 898-900.
Senapati, et al. A nonamembrane-based nucleic acid sensing platform for portable diagnostics. Topics in Current Chemistry. Apr. 27, 2011; 304:153-169.
Sivamani, et al. Microneedles and transdermal applications. Expert Opin Drug Deliv. Jan. 2007;4(1):19-25.
Sosnowski, et al. Rapid determination of single base mismatch mutations in DNA hybrids by direct electric field control. Proc Natl Acad Sci U S A. Feb. 18, 1997; 94(4): 1119-1123.
Terns, et al. CRISPR-based adaptive immune systems. Curr Opin Microbiol. Jun. 2011;14(3):321-7.
U.S. Appl. No. 13/397,581, filed Feb. 15, 2012.
Van Der Oost, et al. CRISPR-based adaptive and heritable immunity in prokaryotes. Trends Biochem Sci. Aug. 2009;34(8):401-7.
Voelkerding, et al. Next generation sequencing: from basic research to diagnostics. Clin. Chem. 2009; 55(4):641-658.
Wang, et al. Interaction of the Cas6 riboendonuclease with CRISPR RNAs: recognition and cleavage. Structure. Feb. 9, 2011;19(2):257-64.

Yazdanpanah, et al. Selective self-assembly at room temperature of individual freestanding Ag2Ga alloy nanoneedles. J. Appl. Phys. 98, pp. 073510-7 (2005).
Zhang, et al. Dielectrophoresis for manipulation of micro/nano particles in microfluidic systems. Anal Bioanal Chem. Jan. 2010;396(1): 401-20.
Zheng, et al. Multiplexed electrical detection of cancer markers with nanowire sensor arrays. Nat Biotechnol. Oct. 2005;23(10):1294-301. Epub Sep. 18, 2005.
Bobrow et al. Fundamentals of Electrical Engineering, 1995, Holt, Rinehart and Winston, Inc.
Brown et al. Ac electroosmotic flow in a DNA concentrator. Microfluid Nanofluid 2:513-523 (2006).
Cheng et al. Single-stranded DNA concentration by electrokinetic forces. J. Micro/Nanolith. MEMS MOEMS 8(2):021107 (Jun. 9, 2009). Abstract only.
Co-pending U.S. Appl. No. 15/950,005, filed Apr. 10, 2018.
Co-pending U.S. Appl. No. 15/896,572, filed Feb. 14, 2018.
Co-pending U.S. Appl. No. 16/007,829, filed Jun. 13, 2018.
Co-pending U.S. Appl. No. 16/007,969, filed Jun. 13, 2018.
Co-pending U.S. Appl. No. 16/039,016, filed Jul. 18, 2018.
Cui et al., "Nanowire Nanosensors for Highly Sensitive and Selective Detection of Biological and Chemical Species", Science, vol. 293, pp. 1289-1292 (2001).
EP14767683.7 Extended European Search Report dated Oct. 25, 2016.
Esfandyarpour. Nano-Biotechnology toward Diagnostic Industry: Obstacles and Opportunities. NSTI-Nanotech, vol. 4, p. 421 (2007). Abstract Only.
Examination Report dated Jun. 7, 2016 for Singapore Patent Application No. SG11201402760V.
Fritz et al. Electronic detection of DNA by its intrinsic molecular charge. PNAS 99(22):14142-14146 (2002).
Hsu et al. Wafer-scale silicon nanopillars and nanocones by Langmuir-Blodgett assembly and etching. Applied Physic Lett. 93:133109-1-133109-3 (2008).
Kuhr. Capillary Electrophoresis. Anal. Chem. 62:403R-414R (1990).
Lei et al. Electrokinetic DNA concentration in Microsystems. Sensors and Actuators. A 156(2) (2009). Abstract only.
Moser et al. Biosensor arrays for simultaneous measurement of glucose, lactate, glutamate, and glutamine. Biosens. & Bioelect. 17:297-302 (2002).
Parizi et al. A Semiconductor Nanobridge Biosensor for Electrical Detection of DNA Hybridization. IEEE Int'l SOI Conference, 2 pgs. (Oct. 6-9, 2008).
Parizi et al. An Internally Amplified Signal SOI Nano-bridge Biosensors for Electrical Detection of DNA Hybridization. IEEE Int'l SOI Conference, 2 pgs. (Oct. 5-8, 2009).
Parizi et al. BioFET for Detection of Biological Species. Stanford University, CIS (Computer-Information-System) Catalog, 1 sheet (2008).
Parizi et al. BioFET Sensor. CIS 2007—Stanford University, 33 pgs. (2007).
Parizi et al. Poster—An Internally Amplified Signal SOI Nanobridge Biosensor for Electrical Detection of DNA Hybridization or Sequence. Poster—1 sheet (Summer 2009).
Parizi et al. Poster BioFET Sensor. CIS 2007—Stanford University, 18 pgs. (2007).
Parizi et al. BioFET Sensor. CIS ADCOM Fall 2009 Stanford University, 28 pgs (Nov. 2009).
Pascault. A Finite Element Study of the DNA Hybridization Kinetics on the Surface of Microfluidic Devices. Thesis, M.S. Chem. Engineer., Worcester Polytechnic Institute, p. 1-148 (Apr. 2007).
PCT/US2014/069624 International Search Report dated May 22, 2015.
Poghossian et al. Possibilities and limitations of label-free detection of DNA hybridization with field-effect-based devices. Sensors and Actuators B 111-112:470-480 (2005).
Ramos et al. AC electric-field-induced fluid flow in microelectrodes. J Colloid Interface Sci 217:420-422 (1999).
U.S. Appl. No. 14/859,725 Notice of Allowance dated Jul. 27, 2018.
U.S. Appl. No. 15/028,899 Notice of Allowance dated Jul. 25, 2018.
U.S. Appl. No. 16/007,969 Office Action dated Aug. 15, 2018.

(56) References Cited

OTHER PUBLICATIONS

U.S. Appl. No. 14/081,358 Notice of Allowance dated May 16, 2016.
U.S. Appl. No. 14/936,245 Notice of Allowance dated Sep. 22, 2017.
U.S. Appl. No. 14/936,245 Notice of Allowance dated Dec. 6, 2017.
Stein, D.; Deurvorst, Z.; van der Heyden, F. H. J.; Koopmans, W. J. A.; Gabel, A.; Dekker, C. Electrokinetic Concentration of DNA Polymers in Nanofluidic Channels. Nano Lett. 2010, 10, 765-772.
U.S. Appl. No. 15/028,899 Notice of Allowance dated Jun. 27, 2018.
U.S. Appl. No. 14/361,902 Notice of Allowance dated May 21, 2018.
U.S. Appl. No. 14/859,725 Notice of Allowance dated May 30, 2018.
U.S. Appl. No. 15/183,406 Office Action dated Jun. 21, 2018.
U.S. Appl. No. 15/230,048 Notice of Allowance dated Apr. 5, 2018.
Wilke et al. A micromachined capillary electrophoresis chip with fully integrated electrodes for separation and electochemical detection. Biosens. and Bioelect. 19:149-153 (2003).
Williams, et al. Etch rates for micromachining processing. Journal of Microelectromechanical Systems 5(4):761-778 (1996).
European Search Report dated Nov. 14, 2017 for European Patent Application No. EP15779780.4.
International Search Report and Written Opinion dated Nov. 16, 2017 for International PCT Patent Application No. PCT/US2017/43159.
Notice of Allowance dated Dec. 8, 2017 for U.S. Appl. No. 14/119,859.
Office Action dated Dec. 18, 2017 for U.S. Appl. No. 15/028,899.
Smolina et al. End invasion of peptide nucleic acids (PNAs) with mixed-base composition into linear DNA duplexes. Nucleic Acids Research. vol. 33. No. 11. pp. e146-e146. Sep. 25, 2005.
Zanoli et al. Isothermal Amplification Methods for the Detection of Nucleic Acids in Microfluidic Devices. Biosensors. vol. 3. No. 1. pp. 18-43. Dec. 27, 2012.
Co-pending U.S. Appl. No. 15/726,193, filed Oct. 5, 2017.
European Search Report dated Oct. 11, 2017 for European Patent Application No. EP14869402.9.
Office Action dated Mar. 4, 2016 for U.S. Appl. No. 14/081,358.
Office Action dated Oct. 5, 2015 for U.S. Appl. No. 14/081,358.
Office Action dated Oct. 23, 2017 for U.S. Appl. No. 14/859,725.
Peng et al. Interdigitated Array Electrodes with Magnetic Function as a Particle-Based Biosensor. Sensors, 2007 IEEE. pp. 1097-1100.
Saias et al. Design, modeling and characterization of microfluidic architectures for high flow rate, small footprint microfluidic systems. Lab Chip. Mar. 7, 2011;11(5):822-32.
Tamayol et al. Laminar Flow in Microchannels With Noncircular Cross Section. J. Fluids Eng 132(11), 111201 (Nov. 3, 2010) (9 pages).
Betz et al. KlenTaq polymerase replicates unnatural base pairs by inducing a Watson-Crick geometry. Nat Chem Biol 8:612-614 (2012).
Co-Pending U.S. Appl. No. 16/137,408, filed Sep. 20, 2018.
Co-pending U.S. Appl. No. 16/141,215, filed Sep. 25, 2018.
PCT/US2018/052072 International Search Report and Written Opinion dated Jan. 18, 2019.
U.S. Appl. No. 16/007,969 Notice of Allowance dated Nov. 26, 2018.
U.S. Appl. No. 14/361,902 Office Action dated Oct. 7, 2016.
U.S. Appl. No. 14/859,725 Notice of Allowance dated Sep. 11, 2018.
U.S. Appl. No. 15/183,406 Office Action dated Mar. 8, 2019.
U.S. Appl. No. 15/360,369 Office Action dated Nov. 29, 2018.
U.S. Appl. No. 15/655,616 Office Action dated Feb. 26, 2019.
U.S. Appl. No. 15/726,193 Office Action dated Apr. 16, 2019.
U.S. Appl. No. 16/007,829 Notice of Allowance dated Nov. 26, 2018.
U.S. Appl. No. 16/007,829 Office Action dated Sep. 17, 2018.
U.S. Appl. No. 16/283,531 Office Action dated Jul. 18, 2019.
U.S. Appl. No. 16/283,544 Notice of Allowance dated Jul. 11, 2019.
U.S. Appl. No. 14/859,725 Notice of Allowance dated Jun. 19, 2018.
U.S. Appl. No. 15/360,369 Notice of Allowance dated Jul. 5, 2019.
U.S. Appl. No. 15/950,005 Office Action dated Jan. 28, 2019.
Sakata et al. DNA Sequencing Based on Intrinsic Molecular Charges. Angew Chem Int Ed 45:2225-2228 (2006).
EP19162225.7 Extended European Search Report dated Sep. 18, 2019.
U.S. Appl. No. 15/360,369 Notice of Allowance dated Oct. 10, 2019.
U.S. Appl. No. 15/360,369 Notice of Allowance dated Sep. 4, 2019.
U.S. Appl. No. 15/655,616 Notice of Allowance dated Sep. 13, 2019.
U.S. Appl. No. 15/726,193 Notice of Allowance dated Aug. 29, 2019.
U.S. Appl. No. 15/950,005 Notice of Allowance dated Sep. 13, 2019.
U.S. Appl. No. 16/137,408 Office Action dated Aug. 9, 2019.
Co-pending U.S. Appl. No. 16/592,545, filed on Oct. 3, 2019.
Co-pending U.S. Appl. No. 16/598,591, filed on Oct. 10, 2019.
U.S. Appl. No. 15/655,616 Notice of Allowance dated Oct. 10, 2019.
U.S. Appl. No. 16/137,408 Office Action dated Nov. 19, 2019.
U.S. Appl. No. 16/283,531 Notice of Allowance dated Nov. 22, 2019.
Co-pending U.S. Appl. No. 16/694,367, filed on Nov. 25, 2019.

* cited by examiner

SDP: Strand Displacement Polymerase

FIG. 36
| Magnet shape | Magnet size (um) | Magnet shape |
|---|---|---|
| Square dot | Width: 0.1 ~ 3 um |  |
| Plus dot | Length: 0.1 ~ 3 um<br>Width: 0.1 ~ 3 um |  |
| Cross dot | Width: 0.1 ~ 3 um<br>With ears at the edges |  |
| Vertical rectangle dot | Length: 0.1 ~ 3 um<br>Width: 0.1 ~ 3 um |  |
| Horizontal rectangle dot | Length: 0.1 ~ 3 um<br>Width: 0.1 ~ 3 um | 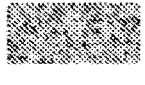 |
| Bar | Length: 1 ~ 5 um<br>Width: 0.1 ~ 3 um<br>Gap: 0.1 ~ 2 um |  |

FIG. 38

| Force | Symbol | Description |
|---|---|---|
| Magnetic | $F_M$ | From fringe magnetic field between two magnetic bars |
| Gravity | $F_g$ | Gravitational force based on mass of the bead |
| Friction | $F_f$ | Friction between bead and surface |
| Normal | $F_N$ | Surface normal force |
| Lift | $F_L$ | The vertical force from the fluid mainly from pressure |
| Drag | $F_D$ | The horizontal force from the fluid mainly from shear stress on the surface |

FIG. 39

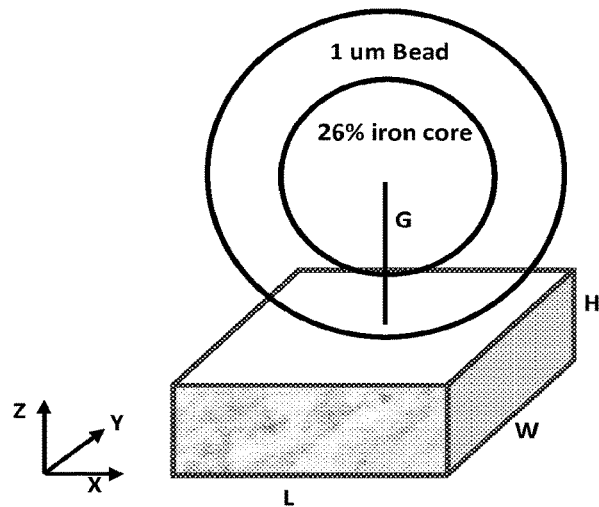

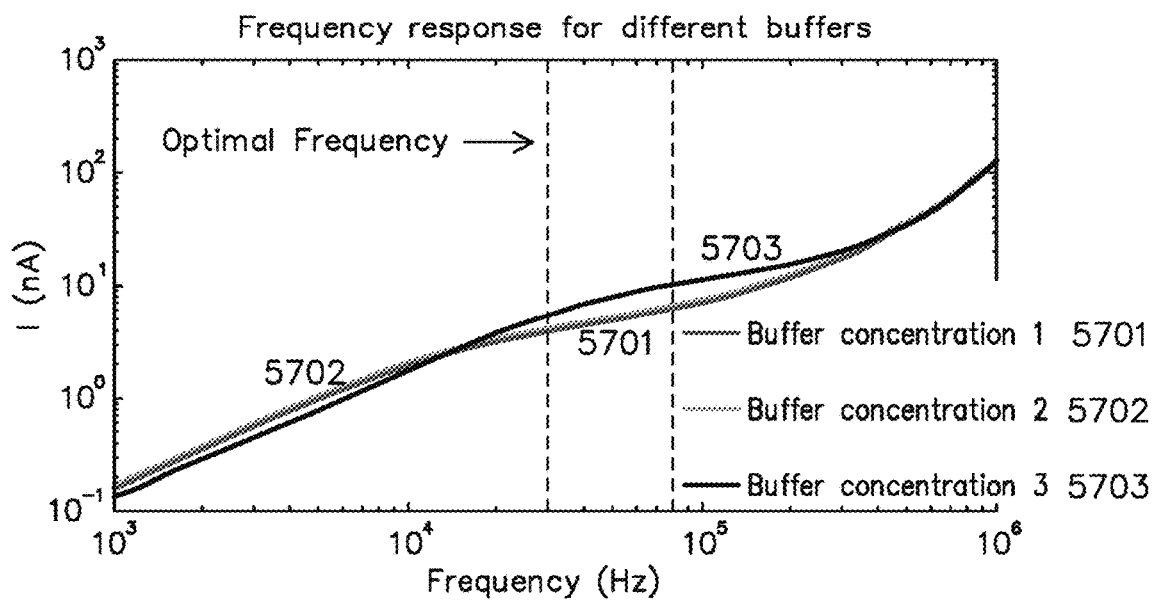
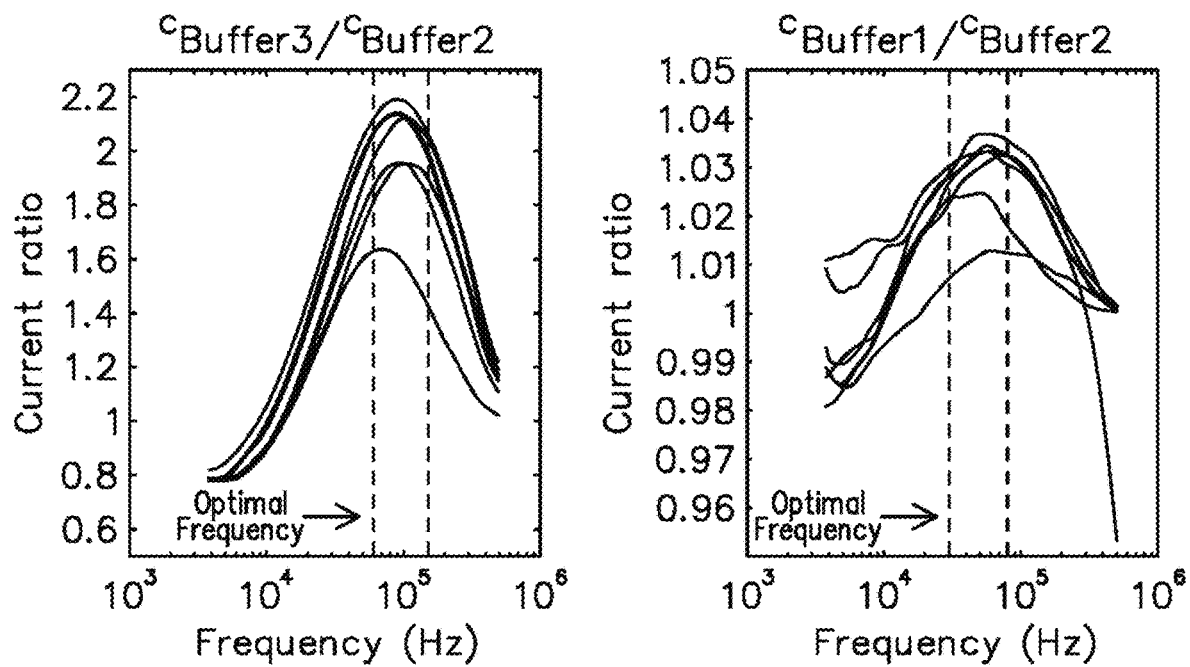

Frequency response during DNA sequencing run

Current change after bead loading for bead detection

Current change after DNA incorporation

SYSTEMS AND METHODS FOR BIOLOGICAL ANALYSIS

CROSS-REFERENCE

This application is a continuation of U.S. application Ser. No. 14/653,230, filed Jun. 17, 2015, which claims the benefit of PCT Application No. PCT/US2014/027544, filed Mar. 14, 2014, which claims the benefit of U.S. Provisional Patent Application No. 61/799,396, filed Mar. 15, 2013, U.S. Provisional Patent Application No. 61/799,483, filed Mar. 15, 2013, U.S. Provisional Patent Application No. 61/799,944, filed Mar. 15, 2013, U.S. Provisional Patent Application No. 61/800,410, filed Mar. 15, 2013, U.S. Provisional Patent Application No. 61/800,443, filed Mar. 15, 2013, U.S. Provisional Patent Application No. 61/801,560, filed Mar. 15, 2013, and U.S. Provisional Patent Application No. 61/801,929, filed Mar. 15, 2013, each of which applications is incorporated herein by reference in its entirety and for all purposes.

BACKGROUND

The goal to elucidate the entire human genome has created interest in technologies for rapid nucleic acid (e.g., DNA) sequencing, both for small and large scale applications. Important parameters are sequencing speed, length of sequence that can be read during a single sequencing run, and amount of nucleic acid template required to generate sequencing information. Large scale genome projects are currently too expensive to realistically be carried out for a large number of subjects (e.g., patients). Furthermore, as knowledge of the genetic basis for human diseases increases, there will be an ever-increasing need for accurate, high-throughput DNA sequencing that is affordable for clinical applications. Practical methods for determining the base pair sequences of single molecules of nucleic acids, preferably with high speed and long read lengths, may provide measurement capability.

Nucleic acid sequencing is a process that can be used to provide sequence information for a nucleic acid sample. Such sequence information may be helpful in diagnosing and/or treating a subject with a condition. For example, the nucleic acid sequence of a subject may be used to identify, diagnose and potentially develop treatments for genetic diseases. As another example, research into pathogens may lead to treatment for contagious diseases. Unfortunately, though, existing sequencing technology of the status quo is expensive and may not provide sequence information within a time period and/or at an accuracy that may be sufficient to diagnose and/or treat a subject with a condition.

SUMMARY

Recognized herein is the need for improved devices and methods for sequencing, amplifying, analyzing, and/or performing sample preparation procedures for nucleic acids and other biomolecules.

An aspect of the disclosure provides a method for nucleic acid sequencing, comprising: (a) directing a plurality of particles onto an array of sensors, wherein an individual particle among the plurality of particles comprises a template nucleic acid molecule coupled thereto, wherein the array comprises a plurality of sensors, wherein an individual sensor among the plurality of sensors comprises a transmitter electrode and a receiver electrode, which transmitter electrode or receiver electrode is shared with at least another individual sensor among the plurality of sensors; (b) positioning the individual particle adjacent to the individual sensor; (c) performing a primer extension reaction on the template nucleic acid molecule at the individual sensor; and (d) during or subsequent to performing the primer extension reaction, measuring a signal that is indicative of a change in impedance between the transmitter electrode and receiver electrode.

In some embodiments, the primer extension reaction comprises growing a nucleic acid strand that is complementary to the template nucleic acid molecule. In some embodiments, the performing a primer extension reaction on the template nucleic acid molecule at the individual sensor may comprise directing nucleotides or nucleotide analogs onto the array of sensors. In some embodiments, the nucleotides or nucleotide analogs can be directed onto the array of sensors sequentially. Moreover, the method can further comprise (i) directing a primer onto the array, (ii) bringing the primer in contact with the nucleic acid molecule, and (iii) hybridizing the primer with the template nucleic acid molecule. In some embodiments, the at least another individual sensor can be directly adjacent the individual sensor. In some embodiments, the at least another individual sensor can be separated from the individual sensor by one or more intermediate sensors of the array of sensors. In some embodiments, the at least another individual sensor may comprise at least 1, 2, 3, 4, 5, 6, 7, 8, 9, or 10 other individual sensors of the array of sensors.

Moreover, the individual particle may be positioned at the individual sensor such that the transmitter electrode and receiver electrode are electrically coupled to a Debye layer of the individual particle. In some embodiments, the individual particle can be positioned at the individual sensor such that at least one of the transmitter electrode and receiver electrode is coupled with the individual particle. In some embodiments, the transmitter electrode and receiver electrode can be electrically isolated. For example, the transmitter electrode and receiver electrode can be electrically isolated by one or more electrically insulating layers. In some embodiments, the transmitter electrode and receiver electrode are electrically isolated in the absence of the individual particle positioned adjacent thereto.

Furthermore, the individual particle can be positioned adjacent to the transmitter electrode and receiver electrode, thereby bringing the transmitter electrode in electrical communication with the receiver electrode. In some embodiments, the transmitter electrode or receiver electrode, but not both, may be shared with the at least another individual sensor. In some embodiments, the transmitter electrode can be shared with the at least another individual sensor.

Also, the method can further comprise amplifying the template nucleic acid molecule, including amplifying the template nucleic acid molecule prior to performing a primer extension reaction on the template nucleic acid molecule at the individual sensor. In some embodiments, the template nucleic acid molecule can be amplified while subjecting the individual particle to an electric field. In some embodiments, the template nucleic acid molecule can be amplified while the individual particle is held at the individual sensor.

Additionally, the individual particle can be positioned adjacent to the individual sensor using an electric field and/or magnetic field provided by aid individual sensor. In some embodiments, the individual particle may be positioned adjacent to the individual sensor using an electric field and a magnetic field. In some embodiments, the magnetic field can be constant, and the electric field can be independently controllable to provide (i) a net attractive force to direct the individual particle to the individual sensor or (ii) a net repulsive force to direct the individual particle away from the individual sensor. In some embodiments, the electric field can be constant, and the magnetic field can be independently controllable to provide (i) a net attractive force to direct the individual particle to the individual sensor or (ii) a net repulsive force to direct the individual particle away from the individual sensor. In some embodiments, the individual sensor is independently addressable from other sensors in the array of sensors.

Moreover, the method can comprise measuring a signal that is indicative of a change in impedance across (i) the individual particle or (ii) a fluid environment comprising the individual particle. In some embodiments, the array of sensors may be planar. In addition, the directing a plurality of particles onto an array of sensors, wherein an individual particle among the plurality of particles comprises a template nucleic acid molecule coupled thereto, wherein the array comprises a plurality of sensors, wherein an individual sensor among the plurality of sensors comprises a transmitter electrode and a receiver electrode, which transmitter electrode or receiver electrode is shared with at least another individual sensor among the plurality of sensors may further comprise (i) flowing a fluid comprising the plurality of particles along a channel to the array, (ii) with the plurality of particles in the array, stopping or altering the flow of the fluid, and (iii) removing excess beads from the array.

In some embodiments, the method can further comprise using Joule-heating-induced flow of a fluid comprising the individual particle, the template nucleic acid molecule, reagents for nucleic acid amplification, reagents for the primer extension reaction, and/or products of the primer extension reaction, to isolate and/or concentrate the fluid at the individual sensor. In some embodiments, the particles are nucleic acid nanoballs.

An additional aspect of the disclosure provides a system for nucleic acid sequencing, comprising: (a) an array of sensors comprising a plurality of sensors, wherein an individual sensor among the plurality of sensors comprises a transmitter electrode and a receiver electrode, which transmitter electrode or receiver electrode is shared with at least another individual sensor among the plurality of sensors; and (b) a computer processor that is electrically coupled to the array of sensors and programmed to measure a signal that is indicative of a change in impedance between the transmitter electrode and receiver electrode during or subsequent to a primer extension reaction on a template nucleic acid molecule at the individual sensor.

In some embodiments, the at least another individual sensor may be directly adjacent the individual sensor. In some embodiments, the at least another individual sensor can be separated from the individual sensor by one or more intermediate sensors of the array of sensors. In some embodiments, the at least another individual sensor may comprise at least 1, 2, 3, 4, 5, 6, 7, 8, 9, or 10 other individual sensors of the array of sensors.

Moreover, the system may further comprise a particle that is positioned at the individual sensor such that the transmitter electrode and receiver electrode are electrically coupled to a Debye layer of the individual particle. In some embodiments, the particle can be positioned at the individual sensor such that at least one of the transmitter electrode and receiver electrode is coupled with the particle. In some embodiments, the transmitter electrode and receiver electrode can be electrically isolated. For example, the transmitter electrode and receiver electrode can be electrically isolated by one or more electrically insulating layers. In some embodiments, the transmitter electrode and receiver electrode are electrically isolated in the absence of a particle positioned adjacent thereto.

Furthermore, the transmitter electrode or receiver electrode, but not both, may be shared with the at least another individual sensor. In some embodiments, the individual sensor can further comprise an electric field element and a magnetic field element. In some embodiments, the magnetic field element can provide a constant magnetic field and the electric field element can provide an electric field that is independently controllable to provide (i) a net attractive force to direct the individual particle to the individual sensor or (ii) a net repulsive force to direct the individual particle away from the individual sensor. In some embodiments, the electric field element can provide a constant magnetic field and the magnetic field element can provide a magnetic field that is independently controllable to provide (i) a net attractive force to direct the individual particle to the individual sensor or (ii) a net repulsive force to direct the individual particle away from the individual sensor. In some embodiments, the electric field element can be integrated with the magnetic field element. In some embodiments, the individual sensor is independently addressable from other sensors in the array of sensors.

Additionally, the computer processor can be programmed to measure a signal that is indicative of a change in impedance across (i) the individual particle, (ii) a Debye layer of the individual particle, and/or (iii) a fluid environment comprising the individual particle. In some embodiments, the array of sensors is planar. In some embodiments, the system further comprises a fluid flow apparatus that is in fluid communication with the array. In some embodiments, the array is part of a chip that is removable from the fluid flow apparatus. In some embodiments, the system further comprises a nucleic acid amplification module and sample preparation module in fluid communication with the fluid flow apparatus, wherein the modules are removable from the fluid flow apparatus. In some embodiments, the fluid flow apparatus may be a microfluidic device.

Another aspect of the disclosure provides an integrated point of care system for sensing and/or analyzing a biological sample from a subject, comprising: (a) a chip comprising a plurality of sensors as part of an array of sensors, wherein an individual sensor among the plurality of sensors comprises a transmitter electrode and a receiver electrode, which transmitter electrode or receiver electrode is shared with at least another individual sensor among the plurality of sensors; (b) a sample preparation module that is adapted to receive the biological sample from the subject and generate a processed sample; (c) a fluid flow system in fluid communication with the sample preparation module and the array, wherein the fluid flow system is adapted to direct at least a portion of the processed sample from the sample preparation module to the array; and (d) a computer processor that is electrically coupled to the chip and programmed to measure a signal that is indicative of a change in impedance between the transmitter electrode and receiver electrode when the processed sample is adjacent to the individual sensor.

In some embodiments, the at least another individual sensor can be directly adjacent the individual sensor. In some embodiments, the at least another individual sensor can be separated from the individual sensor by one or more intermediate sensors of the array of sensors. In some embodiments, the at least another individual sensor may comprise at least 1, 2, 3, 4, 5, 6, 7, 8, 9, or 10 other individual sensors of the array of sensors.

Moreover, the processed sample can comprise a plurality of particles each having an analyte coupled thereto, which analyte is generated from the biological sample by the sample preparation module. In some embodiments, the point of care system can further comprise a particle among the plurality of particles that is positioned at the individual sensor such that the transmitter electrode and receiver electrode are electrically coupled to a Debye layer of the individual particle. In some embodiments, the particle can be positioned at the individual sensor such that at least one of the transmitter electrode and receiver electrode is coupled with the particle.

Additionally, the transmitter electrode and receiver electrode may be electrically isolated. For example, the transmitter electrode and receiver electrode can be electrically isolated by one or more electrically insulating layers. In some embodiments, the transmitter electrode and receiver electrode may be electrically isolated in the absence of a particle positioned adjacent thereto. In some embodiments, the transmitter electrode or receiver electrode, but not both, may be shared with the at least another individual sensor.

Furthermore, the individual sensor may comprise an electric field element and a magnetic field element. In some embodiments, the magnetic field element can provide a constant magnetic field and the electric field element can provide an electric field that is independently controllable to provide (i) a net attractive force to direct the individual particle to the individual sensor or (ii) a net repulsive force to direct the individual particle away from the individual sensor. In some embodiments, the electric field element can provide a constant magnetic field and the magnetic field element can provide a magnetic field that is independently controllable to provide (i) a net attractive force to direct the individual particle to the individual sensor or (ii) a net repulsive force to direct the individual particle away from the individual sensor. In some embodiments, the electric field element may be integrated with the magnetic field element. In some embodiments, the individual sensor may be independently addressable from other sensors in the array of sensors.

Moreover, the computer processor may be programmed to measure a signal that is indicative of a change in impedance across (i) the processed sample, (ii) a Debye layer of the processed sample, and/or (iii) a fluid environment comprising the processed sample, when the processed sample is disposed adjacent to the individual sensor. In some embodiments, the array of sensors can be planar. In some embodiments, the fluid flow system may be part of a microfluidic device. In some embodiments, the chip can be removable from the microfluidic device. In some embodiments, the sample preparation module may comprise a nucleic acid amplification module and a sample preparation module.

In addition, the biological sample may be whole blood. In some embodiments, the processed sample may comprise one or more of a nucleic acid(s), protein(s), antibody(ies), antigen(s) and cell(s). In some embodiments, the computer processor can be in a housing that is separate from the chip. In some embodiments, a cartridge may comprise the chip and the cartridge can be inserted into or removed from the housing. In some embodiments, the computer processor and the chip may be in the same housing. In some embodiments, the point of care system may be capable of detecting more than one of a nucleic acid, a protein, an antibody, an antigen, and a cell.

Another aspect of the present disclosure provides a computer readable medium comprising machine executable code that, upon execution by one or more computer processors, implements any of the methods above or elsewhere herein.

Another aspect of the present disclosure provides a system comprising one or more computer processors and a computer readable medium coupled to the one or more computer processors. The computer readable medium comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 36 is a table that includes example magnet configurations.

FIG. 38 is a legend for the schematic of FIG. 37.

FIG. 39 is a schematic of an example carrier coupled to a magnetic element.

FIG. 57 is a graphic depiction of example electrode operation.

FIG. 58 is a set of graphic depictions of example electrode operation.

DETAILED DESCRIPTION

Figure 1A:
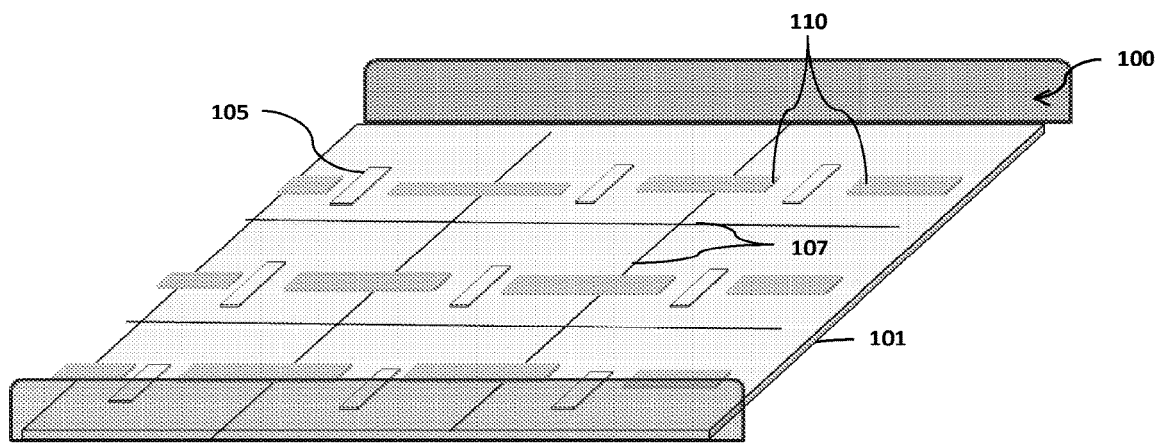
FIG. 1A shows a schematic of an example sensor array.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "analyte," as used herein, generally refers to any type of biological molecule including, for example, simple intermediary metabolites, sugars, lipids, and hormones as well as macromolecules such as complex carbohydrates, phospholipids, nucleic acids (e.g., DNA, RNA, mRNA, miRNA, rRNA, tRNA), polypeptides and peptides. Further non-limiting examples of analytes include drugs, drug candidates, prodrugs, pharmaceutical agents, drug metabolites, biomarkers such as expressed proteins and cell markers, antibodies, serum proteins, cholesterol and other metabolites, electrolytes, metal ions, polysaccharides, genes, proteins, glycoproteins, glycolipids, lectins, growth factors, cytokines, vitamins, enzymes, enzyme substrates, enzyme inhibitors, steroids, oxygen and other gases found in physiologic fluids (e.g., CO2), cells, cellular constituents, cell adhesion molecules, plant and animal products, cell surface markers (e.g., cell surface receptors and other molecules identified herein as receptor proteins), and cell signaling molecules. Non-limiting examples of protein analytes include membrane associated proteins (e.g., extracellular membrane proteins, intracellular membrane proteins, integral membrane proteins, or transiently membrane-associated proteins), cytosolic proteins, chaperone proteins, proteins associated with one or more organelles (e.g., nuclear proteins, nuclear envelope proteins, mitochondrial proteins, golgi and other transport proteins, endosomal proteins, lysosomal proteins, etc.), secreted proteins, serum proteins, and toxins. Non-limiting examples of analytes for detection include Adiponectin, Alanine Aminotransferase (ALT/GPT), Alpha-fetoprotein (AFP), Albumin, Alkaline Phosphatase (ALP), Alpha Fetoprotein, Apolipoprotein A-I (Apo A-I), Apolipoprotein B (Apo B), Apolipoprotein B/Apoplipoprotien A-1 Ratio (Apo B/A1 ratio), Aspartate Aminotransferase (AST/GOT), AspirinWorks® (1'-Dehydro-Thromboxane B2), Bicarbonate (CO2), Bilirubin, Direct (DBIL), Bilirubin, Total (TBIL), Blood Urea Nitrogen (BUN), Carboxy terminal collagen crosslinks (Beta-CrossLaps), Calcium, Cancer Antigen 125 (CA 125), Cancer Antigen 15-3 (CA 15-3), Cancer Antigen 19-9 (CA 19-9), Carcinoembryonic Antigen (CEA), Chloride (Cl), Complete Blood Count w/differential (CBC), C-peptide, C-reactive protein (CRP-hs), Creatine Kinase (CK), Creatinine (serum), Creatinine (urine), Cytochrome P450, Cystatin-C, D-Dimer, Dehydroepiandrosterone Sulfate (DHEA-S), Estradiol, F2 Isoprostanes, Factor V Leiden, Ferritin, Fibrinogen (mass), Folate, Follicle-stimulating Hormone (FSH), Free Fatty Acids/Non-Esterified Fatty Acids (FFA/NEFA), Fructosamine, Gamma-glutamyl Transferase (GGT), Glucose, HbA1c & estimated Average Glucose (eAG), HDL2 subclass, High-density Lipoprotein Cholesterol (HDL-C), High-density Lipoprotein Particle Number (HDL-P), High-sensitivity C-reactive Protein (hs-CRP), Homocysteine, Insulin, Iron and TIBC, Lactate dehydrogenase (LDH), Leptin, Lipoprotein (a) Cholesterol (Lp(a) chol), Lipoprotein (a) Mass (Lp(a) mass), Lipoprotein-associated Phospholipase A2 (Lp-PLA2), Low-density Lipoprotein Cholesterol, Direct (LDL-C), Low-density Lipoprotein Particle Number (LDL-P), Luteinizing Hormone (LH), Magnesium, Methylenetetrahydrofolate reductase (MTHFR), Micro-albumin, Myeloperoxidase (MPO), N-terminal Pro b-type Natriuretic Peptide (NT-proBNP), Non-High-density Lipoprotein Cholesterol, Omega-3 Fatty Acid Profile, Osteocalcin, Parathyroid Hormone (PTH), Phosphorus, Potassium (K+), Prostate Specific Antigen, total (PSA, total), Prothrombin, Resistin, Sex Hormone Binding Globulin (SHBG), Small Dense Low-density Lipoprotein (sdLDL), Small dense low-density Lipoprotein/Low-density Lipoprotein Cholesterol Ratio (sd LDL/LDL-C ratio), Sodium (NA+), T Uptake, Testosterone, Thyroid-stimulating hormone (TSH), Thyroxine (T4), Total Cholesterol (TCHOL), Total Protein, Triglycerides (TRIG), Triiodothyronine (T3), T4 (free), Uric Acid, Vitamin B12, 25-hydroxy-vitamin D, clotting factors (e.g., factor I (fibrinogen), factor II (prothrombin), factor III (tissue thromboplastin), factor IV (calcium), factor V (proaccelerin), factor VI (no longer considered active in hemostasis), factor VII (proconvertin), factor VIII (antihemophilic factor), factor IX (plasma thromboplastin component; Christmas factor), factor X (stuart factor), factor XI (plasma thromboplastin antecedent), factor XII (hageman factor), factor XIII (fibrin stabilizing factor)).

The term "aptamer," as used herein, generally refers to a peptide, nucleic acid, or a combination thereof that is selected for the ability to specifically bind one or more target analytes. Peptide aptamers are affinity agents that generally comprise one or more variable loop domains displayed on the surface of a scaffold protein. A nucleic acid aptamer is a specific binding oligonucleotide, which is an oligonucleotide that is capable of selectively forming a complex with an intended target analyte. The complexation is target-specific in the sense that other materials, such as other analytes that may accompany the target analyte, do not complex to the aptamer with as great an affinity. It is recognized that complexation and affinity are a matter of degree; however, in this context, "target-specific" means that the aptamer binds to target with a much higher degree of affinity than it binds to contaminating materials. The meaning of specificity in this context is thus similar to the meaning of specificity as applied to antibodies, for example. The aptamer may be prepared by any known method, including synthetic, recombinant, and purification methods. Further, the term "aptamer" also includes "secondary aptamers" containing a consensus sequence derived from comparing two or more known aptamers to a given target.

The term "antibody," as used herein, generally refers to immunoglobulins such as IgA, IgG, IgM, IgD, and IgE, whether monoclonal or polyclonal in origin. The methods for binding and elution for the binding pairs for affinity chromatography depend on the binding pair used, and are generally well known in the art. As one example, solutes with polyhistidine labels may be purified using resins including but not limited to commercially available resins such as Superflow Ni-NTA (Qiagen) or Talon Cellthru Cobalt (Clontech). Polyhistidine-labeled solutes may, for example, be eluted from such resins with buffers containing imidzole or glycine. Buffers for ion exchange chromatography may be selected such that the binding pair used is soluble in the buffer. Buffers are typically single phase, aqueous solutions, and may be polar or hydrophobic.

The term "adjacent to," as used herein, generally means next to, in proximity to, or in sensing or electronic vicinity (or proximity) of. For example, a first object adjacent to a second object can be in contact with the second object, or may not be in contact with the second object but may be in proximity to the second object. In some examples, a first object adjacent to a second object is within about 0 micrometers ("microns"), 0.001 microns, 0.01 microns, 0.1 microns, 0.2 microns, 0.3 microns, 0.4 microns, 0.5 microns, 1 micron, 2 microns, 3 microns, 4 microns, 5 microns, 10 microns, or 100 microns of the second object.

Integrated Sequencing Platforms

Figure 63:
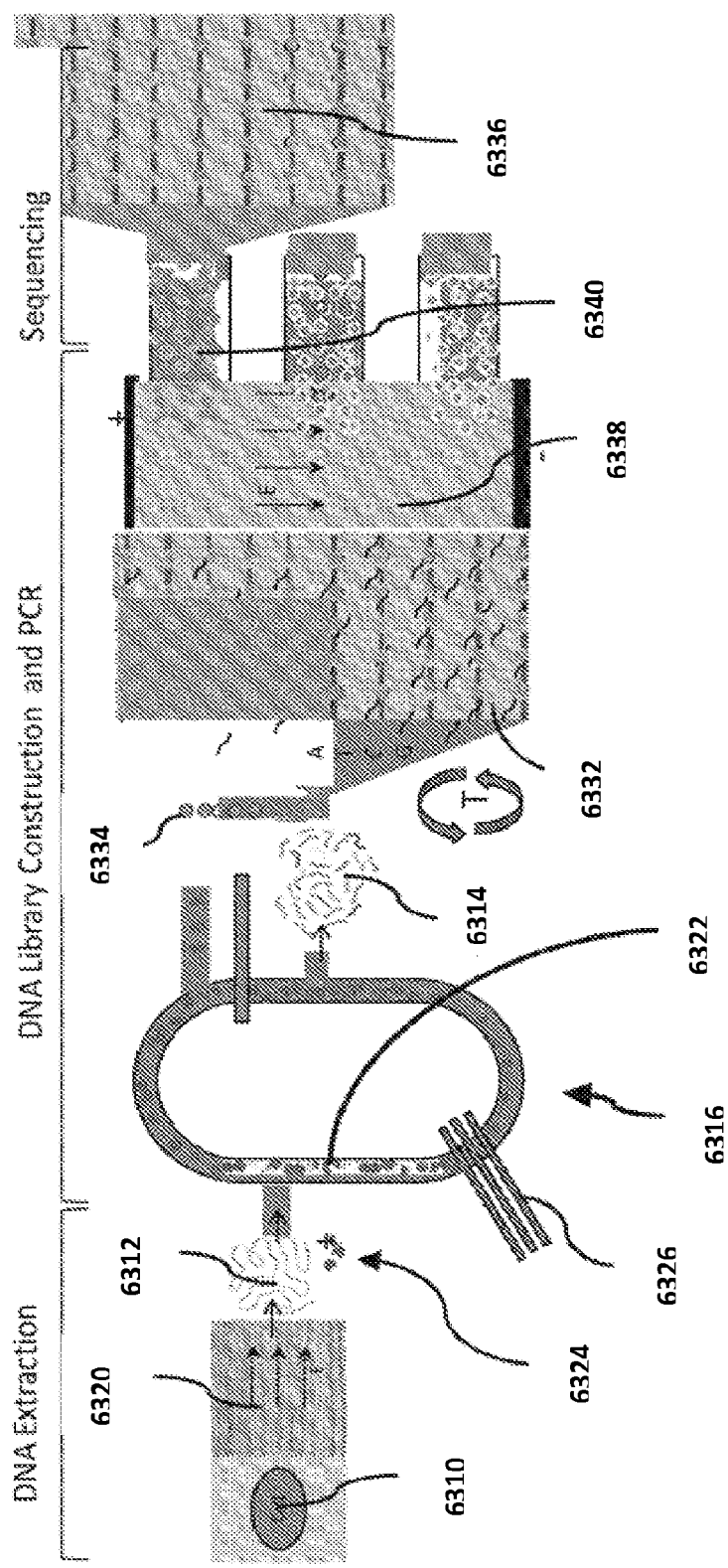
FIG. 63 is a schematic of an example system for sequencing a nucleic acid.

An integrated sequencing platform may include a nucleic acid (e.g., DNA) extraction system, a library construction system, an amplification system, an enrichment system, and a sequencing system. In some embodiments the systems may be separate and/or in modular format. In some embodiments, the integrated sequencing platform can include one, two, three, four, or all five of these systems. In some cases, the systems can be integrated within a single microfluidic device and/or a single array (e.g., a re-usable array). An example of such an integrated platform is depicted in FIG. 63. Additional examples of such integrated sequencing platforms can be found in PCT Patent Application No. PCT/US2011/054769, PCT Patent Application No. PCT/US2012/039880, PCT Patent Application No. PCT/US2012/067645, and U.S. patent application Ser. No. 13/481,858, each of which is incorporated herein by reference in its entirety.

In some embodiments, nucleic acid (e.g., deoxyribonucleic acid (DNA)) amplification and sequencing may be performed sequentially within the same system. In such cases, sample nucleic acid may be associated with a plurality of carriers, such as, for example, beads or other types of particles. In some cases, the carriers may be magnetic carriers, such as, for example, magnetic beads or paramagnetic beads. In some cases, the magnetic carriers can be entered into an array (e.g., a substantially planar array comprising a substantially planar substrate) of magnetic features such that the magnetic carriers are held in place by a localized magnetic field at each position (e.g., pixel) of the array. In some embodiments, carriers (including magnetic carriers) can be held in place at each position of an array (e.g., a substantially planar array) by electrostatic force via one or more electrodes due to the charge of the carrier or the associated nucleic acid. In other embodiments, the carriers can be held in place at each position of the array by physical trenches or wells. In some embodiments, the carriers can be held in place at each position of the array by interaction of a species bound to the carrier with a species bound to the array (e.g., hybridization of oligonucleotides or via ligand-capture moiety pairs). Upon immobilization of the carriers to an array, amplification of the associated nucleic acid and sequencing of the amplified nucleic acid can be completed sequentially.

In some embodiments, carriers may be first entered into an array (e.g., via flow through microfluidic channels associated with the array) and captured by the array. After carrier capture, sample nucleic acid may be contacted with the array (e.g., via flow through microfluidic channels associated with the array) and subsequently captured by the carriers. Capture may occur, for example, via nucleic acids associated with the carriers and capable of hybridizing with the sample nucleic acid. Such nucleic acids may also be used as primers for amplification reactions described elsewhere herein.

Alternatively, a surface of the array (e.g., sensor surface, array substrate surface, etc.) may comprise means suitable for capturing sample nucleic acid, including nucleic acids capable of hybridizing with the sample nucleic acid. Such nucleic acids may also be capable of serving as primers for amplification reactions described elsewhere herein. Such a configuration may be suitable for amplifying and sequencing a nucleic acid in the absence of a carrier.

In some embodiments, the sample nucleic acid may be provided to an array at extremely dilute concentrations in order to obtain a desired ratio of molecules of sample nucleic acid to carrier. For example, ratios of one molecule of nucleic acid for one carrier (e.g., bead), one molecule of nucleic acid for two carriers, one molecule of nucleic acid for three carriers, one molecule of nucleic acid for five beads, or less, etc may be desired.

During amplification reactions, one or more electrodes at a sensor position of the array may be used for concentration of reagents useful for nucleic acid amplification, forming a "virtual well" associated with a carrier, sensor, or substrate at the array position via an electric field. Virtual wells can permit amplification of nucleic acids at a sensor position without cross-contamination of reactants with those of other sensors of the array. In certain embodiments, amplification within a virtual well can generate a clonal population of nucleic acid associated with a carrier, sensor surface, or substrate associated with the virtual well.

Nucleic acid amplification may be performed in multiple cycles if desired. Once a first round of amplification is completed after contacting an array with sample nucleic acid, an array may be washed in order to remove any unbound amplicons and other reagents in solution. Following washing, a second round of a second round of amplification may be completed, by contacting the array with sample nucleic acid and subjecting captured sample nucleic acid to appropriate conditions. Where clonal populations are generated, the sample may bind only to sites (e.g., carriers, sensor surfaces, etc.) not already comprising amplicons, as sites with amplicons from first round of amplification may be fully loaded amplicons. The process may be repeated for any number of amplification cycles until capture sites are exhausted. Utilizing multiple rounds of amplification may help eliminate double Poisson distribution problems and help ensure that each sensor site is associated with only nucleic acid sequence, such as a clonal population of amplicons attached to a carrier. Moreover, multiple rounds of amplification may also help maximize the use of an array, as each round of amplification can better ensure that all of the pixels of the array of occupied with amplicons for sequencing.

Moreover, during sequencing reactions, one or more of the same electrodes and/or different electrodes may be used to detect a reaction of interest, such as nucleotide incorporation. In some cases, sensing may be completed using a NanoNeedle and/or NanoBridge sensor, or other electrical or optical sensors suitable for detection. A NanoBridge sensor may function as a pH or charge sensor, as described in U.S. Published Patent Application No. US 2012/0138460, titled "BIOSENSOR DEVICES, SYSTEMS AND METHODS THEREFOR", which is incorporated herein by reference in its entirety. A sensor (e.g., nanoneedle sensor) may function as a charge, conductivity and/or impedance sensor, as described in PCT Patent Application No. PCT/US2011/054769, PCT Patent Application No. PCT/US2012/039880, PCT Patent Application No. PCT/US2012/067645, and U.S. patent application Ser. No. 13/481,858, each of which is incorporated herein by reference in its entirety. For example, the reaction of interest may be DNA sequencing.

The detection may be based on at least one of local pH change, local impedance change, local heat detection, local capacitance change, local charge concentration (or change thereof), and local conductivity change, such as local conductivity change of a carrier, a nucleic acid (or other analyte) associated with the carrier and/or a sensor. Such measurements may be made by directly detecting (or detecting signals that are indicative of) a local pH change, local impedance change, local heat detection, local capacitance change, local charge concentration (or change thereof), and local conductivity change, such as local conductivity change of a carrier, a nucleic acid (or other analyte) associated with the carrier and/or a sensor. In some cases, detection occurs within the Debye length of (i) a carrier, (ii) a nucleic acid associated with a carrier or sensor, and/or (iii) a sensor. Such a sensor configuration is described, for example, in PCT Patent Application No. PCT/US2011/054769, PCT Patent Application No. PCT/US2012/039880, PCT Patent Application No. PCT/US2012/067645, and U.S. patent application Ser. No. 13/481,858, each of which is incorporated herein by reference in its entirety.

Following the completion of sequencing, carriers/nucleic acids may be dissociated from the array, the carriers and array optionally separated from bound species and washed, and either or both of the carriers and array subsequently re-used for another round of amplification and/or sequencing. Dissociation of a carrier from the array may be completed, for example, by removal/reversal of a magnetic and/or electric field used to hold the carrier in place. In addition or as an alternative, fluid flow and/or other type of field (e.g., external magnetic field, external electric field) capable of exerting forces sufficient for overcoming magnetic and/or electrostatic forces used to hold a carrier in place may also be used to dissociate the carrier from an array. Where nucleic acids are directly associated with the array, in the absence of a carrier, the array may be treated with appropriate means (e.g., enzymatic means, chemical means, thermal means, etc.) to remove bound nucleic acids from the array. In some cases, though, it may be desirable to remove a carrier or nucleic acid from an array prior to amplification and/or sequencing. Such removal can be achieved in analogous fashion as described above.

In some embodiments, a combined amplification and sequencing system may comprise a magnetic array that can trap a magnetic bead or particle by magnetic force at a plurality of the array positions. In some cases, a magnetic bead may be a paramagnetic bead. Each of the array positions may also comprise electrodes capable of producing electric fields and/or functioning as sensors. Each magnetic bead or particle can comprise a DNA segment that may be clonally amplified, for example, with the aid of electric fields generated by one or more of the electrodes at each array position.

In some embodiments, a combined amplification and sequencing system may comprise an array of electrodes that can trap a magnetic bead or particle by electrostatic force at a plurality of the array positions. In some cases, a magnetic bead may be a paramagnetic bead. One or more of the same electrodes or different electrodes at each of the array positions may also be capable of producing electric fields and/or functioning as sensors. Each magnetic bead or particle can comprise a DNA segment that may be clonally amplified, for example, with the aid of electric fields generated by one or more of the electrodes at each array position.

An example of a combined amplification and sequencing system and use of the example system is depicted in FIG. 1. As shown in FIG. 1A, the system 100 may include an array on a substrate 101 that can comprise sensors (e.g., nanosensors) 105 sometimes in communication with microfluidic channels defined within the platform. Sensors 105 may be associated with substrate 101, and substrate 101 may also be associated with magnetic 110 and electrode 105 and 107 elements. Magnetic beads may be positioned over the sensors 105 by magnetic 110 or electrode 105 and 107 elements. The magnetic elements may form localized magnetic fields and the electrode elements may form localized electric fields in order to position a carrier at each sensor 105 of the array. Moreover, the magnetic and/or electric fields may create an area of confinement for carriers at each position of the array.

Figure 1B:
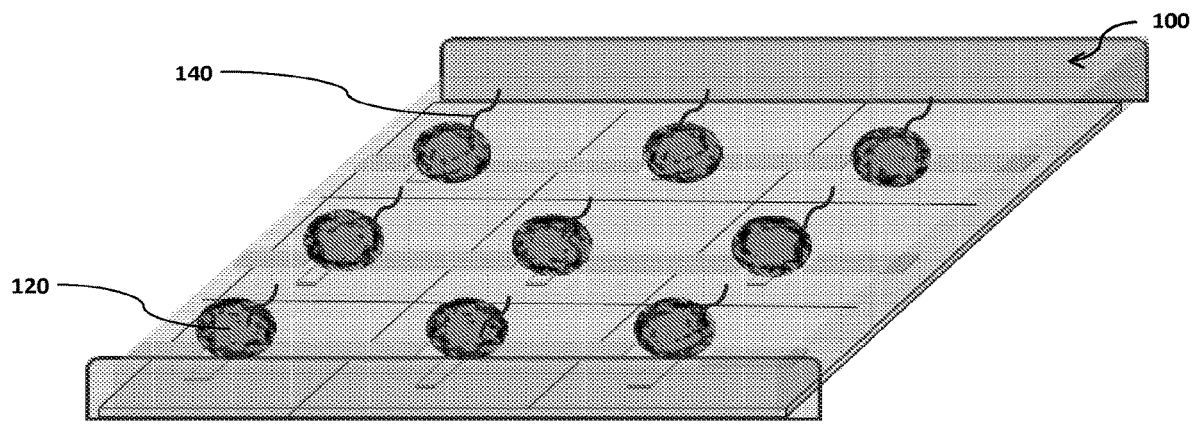
FIG. 1B shows a schematic of an example sensor array with carriers immobilized to the array.

As shown in FIG. 1B, a sample comprising DNA 140 (e.g., DNA fragments) may be conveyed into the system 100. In some cases, introduction of the DNA 140 may be via microfluidic channels associated with the array. As shown, the array may be configured with pre-localized magnetic beads 120 and the magnetic beads may be associated with primers capable of hybridizing with DNA 140, such that DNA 140 is captured by and becomes associated with the beads 120. The magnetic beads 120 may be positioned on the array via the magnetic elements 110 and/or electrode 105 and 107 elements. Alternatively or in addition, primers may be attached, bound, or associated with a sensor at a position of the array and used to trap DNA 140 at the sensor.

Figure 1C:
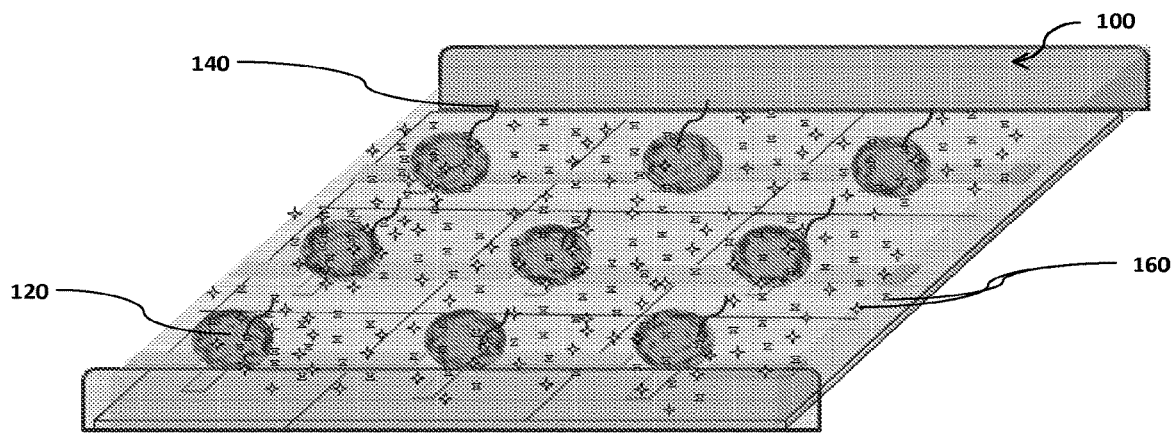
FIG. 1C shows a schematic of an example sensor array with carriers immobilized to the array and in contact with reagents suitable for nucleic acid amplification.

As shown in FIG. 1C, reagents 160 (e.g., polymerase, deoxyribonucleotides (dNTPs), and additional primers) may be simultaneously, previously, or subsequently introduced to the array. In some cases, introduction of the reagents 160 may be via flow through microfluidic channels associated with the array, such that the reagents 160 are contacted with the magnetic beads 120 via flow. Via magnetic and/or electrostatic forces from the appropriate array elements, the magnetic beads 120 can be maintained in the desired position as reagents 160 make contact with the magnetic beads 120 via flow.

Figure 1D:
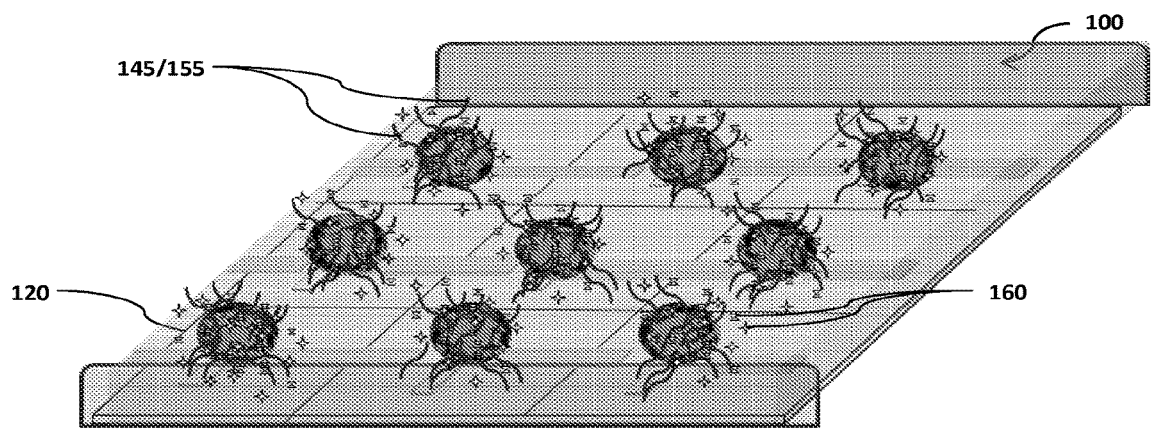
FIG. 1D shows a schematic of an example sensor array where nucleic acid amplification occurs at each array pixel.

As shown in FIG. 1D, the DNA 140 associated with magnetic beads 120 can be clonally amplified to produce amplified DNA 145 and 155 on the surface of the magnetic beads 120. Clonal amplification may be completed using any suitable means including a polymerase chain reaction (PCR), a primer extension reaction, isothermal amplification, or other techniques.

Figure 1E:
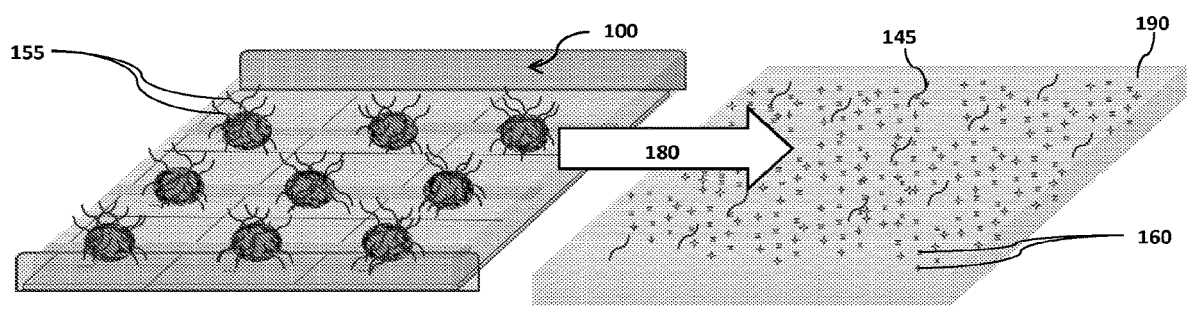
FIG. 1E shows a schematic example of removing reagents from an example sensor array.

As shown in FIG. 1E, the magnetic beads 120 in the array may be washed 180, removing unbound amplicons 145 and reagents 160 in solution following amplification of DNA 140. The result is magnetic beads 120 comprising clonal sets of amplified DNA 155 associated with array positions. Washing 180 may be completed by any suitable means, such as, for example, washing with a buffer solution at a flow rate sufficient to remove the unbound amplicons 145 and reagents 160 in solution, but insufficient to detach the magnetic beads 120 from their respective positions on the array.

Figure 1F:
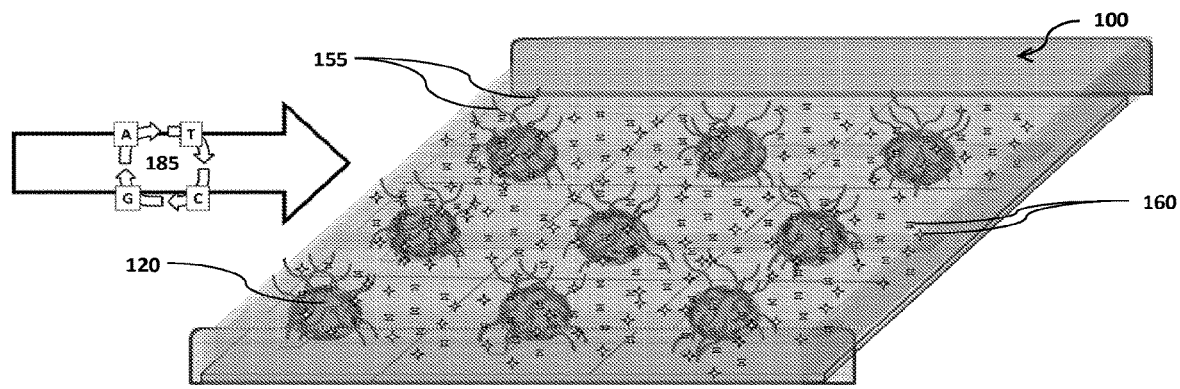
FIG. 1F shows a schematic of an example sensor array where nucleic acids are sequenced at each pixel of the array.

As shown in FIG. 1F, another aliquot of reagents 160 (e.g., polymerase, primers, etc.) and sequential cycles of individual dNTPs 185 may then be contacted (e.g., via flow) with the sensor array, permitting incorporation of the dNTPs into the amplified DNA 155 of magnetic beads 120. dNTPs may be introduced in individual cycles, e.g., cycle 1=A, cycle 2=T, etc. where there may be a wash step with buffer in between each cycle to help reduce the chance of contamination from unincorporated nucleotides. Polymerase used for the sequencing reaction, may be the same type of polymerase that is used for the amplification reaction, or may be a different type of polymerase, and can be introduced prior to or with introduction of the dNTPs. Detection of the incorporated dNTPs during each cycle can be used to sequence the amplified DNA 155, and, thus, the original sample DNA 140. Detection may occur, for example, via one or both of electrodes 105 and 107. In some cases, electrodes 105 and 107 can detect nucleotide incorporation events by measuring local impedance changes of the magnetic beads 120 and/or the amplified DNA (or other nucleic acid) 155 associated with the magnetic beads 120. Such measurement can be made by directly measuring local impedance change or measuring a signal that is indicative of local impedance change. In some cases, detection of impedance occurs within the Debye length of the magnetic beads 120 and/or the amplified DNA 155 associated with the magnetic beads 120.

Additional examples of combined amplification and sequencing systems, for example, may be found in PCT Patent Application No. PCT/US2011/054769, PCT Patent Application No. PCT/US2012/039880, PCT Patent Application No. PCT/US2012/067645, and U.S. patent application Ser. No. 13/481,858, which are incorporated herein by reference in their entireties.

In some embodiments, after amplification of sample nucleic acid onto carriers, but before sequencing, the carriers subjected to amplification conditions may be sorted in an enrichment system, such as, for example, an electrophoretic sorter, where sorting is achieved via electrophoretic force applied to carriers. The electrophoretic sorter may be part of a system used to conduct amplification and sequencing, or it may be part of a different system. In the electrophoretic sorter, null carriers (e.g., carriers without amplicons), as well as carriers subject to incomplete amplification or those comprising overly short amplicons, can be sorted from carriers comprising the desired amplicons. Additional examples of enrichment systems and electrophoretic sorters are described in PCT Patent Application No. PCT/US2011/054769, PCT Patent Application No. PCT/US2012/039880, PCT Patent Application No. PCT/US2012/067645, and U.S. patent application Ser. No. 13/481,858, which are incorporated herein by reference in their entireties.

An electrophoretic sorter may comprise channels capable of accepting sorted carriers. Carriers (e.g., beads) with appropriate amounts of amplified product and with amplicons of adequate length may have sufficient charge to be pulled off to an outlet channel. Where the electrophoretic sorter is a separate system, such carriers can be collected from the outlet channel and provided back into the amplification/sequencing system for sequencing, wherein the steps of introducing reagents and detecting nucleotide incorporation events may occur as described above.

Carriers (e.g., beads) without appropriate amounts of amplified product and/or without amplicons of adequate length may flow through the electrophoretic sorter and, instead, be directed into a waste channel. The carriers may be collected from the waste channel and may be reused for another cycle of amplification or other purpose upon appropriate cleaning to remove any undesirable species. For example, carriers may be washed with a bleaching agent, such as hydrogen peroxide, to help ensure that no contaminants remain on the carriers so that they may be reused.

The arrays and methods described herein can be used for a variety of applications and detection of different biological or biochemical moieties in addition to nucleic acids, such as antibody-antigen detection, protein detection, cell analysis, drug-discovery or screening, ligand, small molecules or other types of analysis. Moreover, the devices and methods described herein are not limited to DNA applications, and may be used for reactions and analysis of interest for RNA, protein detection, small molecules, etc. or other biomolecules.

In addition to sequencing reactions and/or nucleotide incorporation events, arrays and associated sensors may also be useful in sensing other biomolecules (e.g., oligonucleotides, proteins, small molecules, peptides, etc.) and/or reactions of interest using any of the methods and devices described herein, including directly measuring local impedance change or measuring a signal that is indicative of local impedance change.

In some embodiments, a sensor may detect a nucleic acid hybridization reaction. For example, a carrier (e.g., a bead) may be linked to a nucleic acid and hybridization of the nucleic acid with another nucleic acid (e.g., a primer or oligonucleotide probe) may be detected. In some embodiments, a sensor may detect a protein-protein interaction. For example, a carrier (e.g., a bead) may be coupled to a protein species (e.g., antibody, antibody fragment, peptide, etc.) capable of binding with an additional protein (e.g., a ligand). Binding of the additional protein to the protein species coupled to the carrier may be detected. Binding of small molecules to species linked to carriers may also be detected. In some cases, a plurality of detection methods may be employed to detect a biomolecule or a biological reaction of interest. Non-limiting examples of additional detection methods include an enzyme-linked immunosorbent assay (ELISA), detection of a tag (e.g., optical dyes, fluorescent dyes), detection of a released or generated species during a biological reaction of interest, etc.

A sensor (e.g., an individual sensor) described herein may be independently addressable. An independently addressable sensor as used herein, can refer to an individual sensor in an array whose response can be independently detected from the responses of other sensors in the array. An independently addressable sensor can also refer to an individual sensor in an array that can be controlled independently from other sensors in the array.

Carriers

Carriers (charged or neutral carriers, magnetic or non-magnetic carriers) may be of any suitable shape, including non-spherical shapes. In some embodiments, as described above, carriers may be beads. In other embodiments, the carrier may be a dendritic structure including a dendritic structure formed by a self-assembled three-dimensional DNA network. A dendritic carrier may have an enlarged surface area compared to other carriers such as beads. Increased surface area may be useful in improving the number of primers (and, thus, amplicons) that can be associated with nucleic acid amplicons. Moreover, a dendritic carrier may be spherical, substantially planar, oval, or any other shape. In some embodiments, primers may be attached to a dendritic carrier and used, for example, to capture nucleic acids from samples and, in some cases, amplify the captured nucleic acids.

Figure 2A:
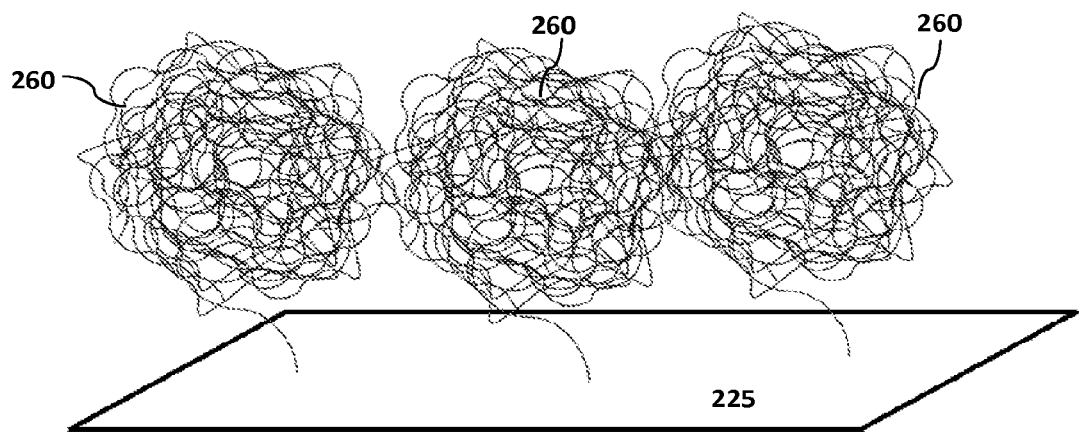
FIGS. 2A-2C show schematics of example carriers comprising nucleic acid nanoballs.
Figure 2B:
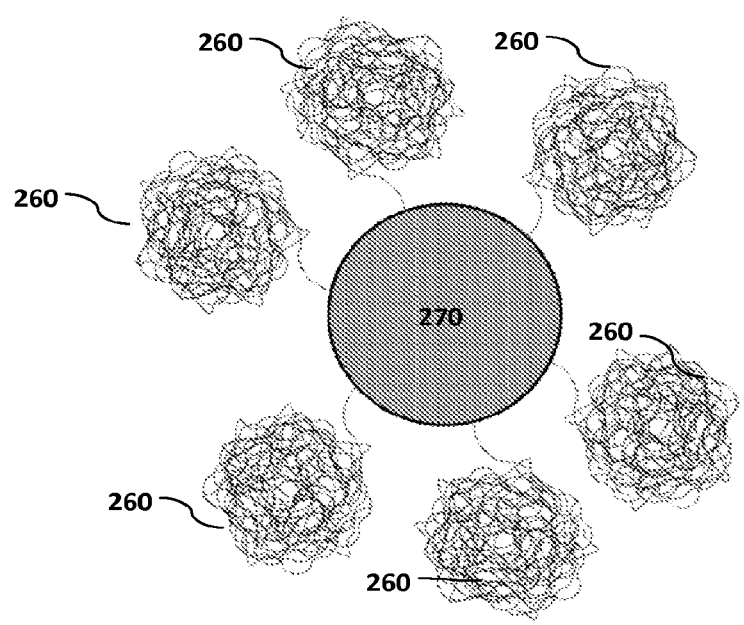

In some embodiments, a nucleic acid nanoball (e.g., DNA or RNA nanoball) may be used associated with a carrier or may be used as a carrier. A nucleic acid nanoball generally refers to a nucleic acid particle with at least one dimension on the nanometer scale. The particle can be a three-dimensional particle. A nucleic acid nanoball may be created by any suitable method, such as, for example, rolling circle replication techniques. In some cases, a nucleic acid nanoball may be free (e.g., not associated with a surface) or they may be bound to a surface (e.g., surface of an array, surface of a sensor, etc.), as shown in an example depicted in FIG. 2A. As shown in FIG. 2A, nucleic acid nanoballs 260 are bound to surface 225. As illustrated in FIG. 2B, nanoballs 260 may be bound to a carrier such as a magnetic bead 270, which can allow for specific placement in a desired location on an array.

Figure 2C:
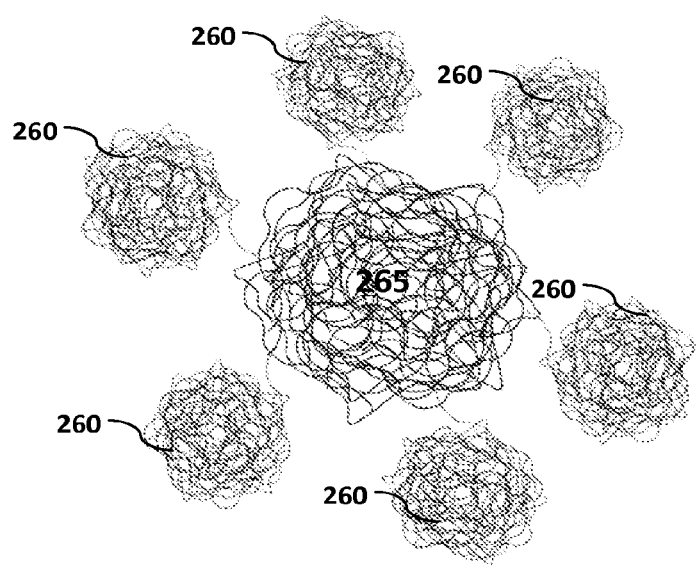

In some embodiments, a nanoball may be attached to a dendritic carrier or other types of particles, such as beads. A carrier may be porous or partially porous. If a carrier is porous or partially porous, the pore size may be of sufficient size as to permit free movement of nucleic acid (e.g., DNA), polymerase, dNTPs and other moieties useful for primer extension sequencing or other applications as appropriate. In some cases, a nanoball may be associated with another nanoball that serves as a carrier, an example of which is shown in FIG. 2C. As shown in FIG. 2C, the nanoballs 260 may be bound to a carrier nanoball 265.

In some embodiments, the nanoballs may be immobilized on surfaces such as the surface of a sensor, surface of an electrode, surface of a carrier (e.g., bead), etc. Such a surface can have any shape such as spherical, flat, rectangular, crystalline, irregular, wells, etc. In some embodiments, the substrate material may include, for example, silicon, silicon-based material, glass, modified or functionalized glass, magnetic material, plastic, metal, ceramic, gels, acrylic resins, biological material, etc. Nanoballs may be attached to a surface by any suitable method, with non-limiting examples that include nucleic acid hybridization, biotin streptavidin binding, thiol binding, photo-activated binding, covalent binding, antibody-antigen, physical confinement via hydrogels or other porous polymers, etc., or a combination thereof. In some cases, nanoballs may be digested with a nuclease (e.g., DNA nuclease) in order to generate smaller nanoballs or fragments from the nanoballs.

Figure 3:
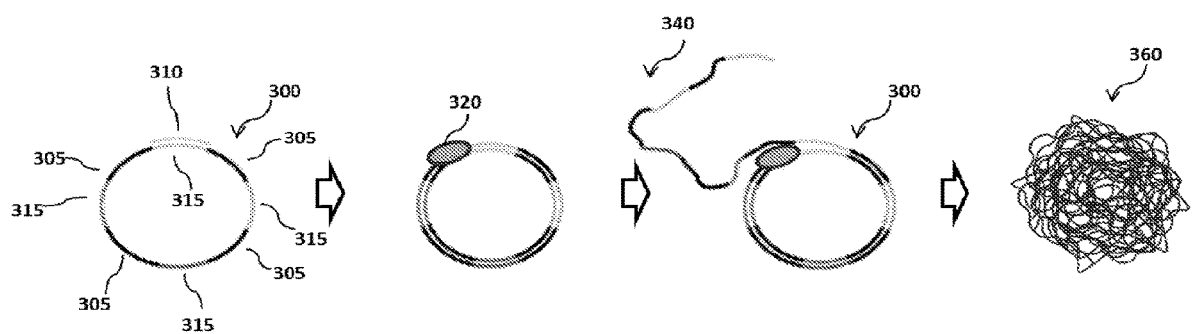
FIG. 3 shows a schematic example of an amplification method suitable for generating a nucleic acid nanoball.

In some embodiments, nanoballs may be used in nucleic acid amplification. As shown in FIG. 3, rolling circle replication may be used to amplify, to form nanoballs. A primer 310 may be bound to a single-stranded circularized template nucleic acid 300. The circularized template nucleic acid may include identical template nucleic acid regions 305 that are separate by adaptor regions 315. A strand displacing polymerase 320 may be used to amplify the circularized nucleic acid template. Thus the nucleic acid template 300 may be repeatedly sequenced by allowing the primer extension reaction to continue for many cycles completely around the circular nucleic acid sample 300, with the strand displacing polymerase (SDP) 320 displacing the newly synthesized nucleic acid strand 340. The rolling circle replication may take place using a nucleic acid primer attached to a carrier, such as a bead, or a solid surface. In some embodiments, the newly synthesized nucleic acid strand may be formed into a nanoball 360 due to complementarity that may exist between the adaptor regions 315 of the amplified nucleic acid 340. The nanoball 360 may also be used as a carrier for DNA amplification.

Nanoballs may be fabricated of species other than DNA or RNA, such as from a monomer or polymer, such as polystyrene. A Nanoball, such as a polystyrene nanoball, may be dissolved subsequent to sequencing, using an organic solvent such as acetone. Dissolution of a nanoball can free any attached species such as nucleic acids such that they can be washed away from the nanoball (e.g., via fluid flow). Nanoballs may be porous or made of multiple types of monomers or polymers.

In some embodiments, a nucleic acid (e.g., DNA) network may be used as a carrier or in addition to a carrier, such, as for example a bead or nanoball. A network generally refers to the folding of long single stranded nucleic acid into a desired 2-D or 3-D structure. For example, the structure may be a rectangle, a tube, a sphere, a crystalline structure, etc. or any other shape. Networks take advantage of the specificity of Watson-Crick base pairing in utilizing synthetic nucleic acid "staple strands" to bind the nucleic acid in various locations in order to form a nucleic acid network, such as, for example a DNA nanostructure. Nucleic acid networks may be generated, for example, by combining pre-synthesized nucleic acid or oligonucleotide strands that are designed for binding. In some embodiments, suitable amplification methods may be used to amplify a nucleic acid to form networks, with non-limiting examples that include bridge amplification or rolling circle amplification to create specific topographies.

Figure 2D:
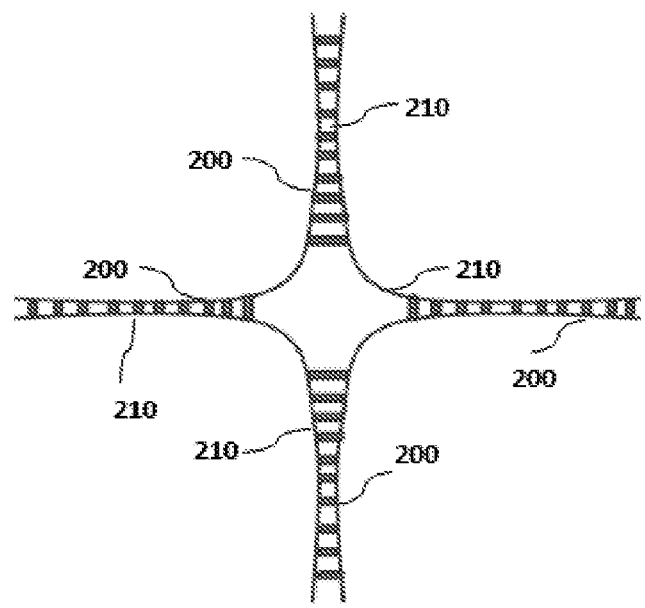
FIGS. 2D-2G show schematic examples of nucleic acid networks.
Figure 2E:
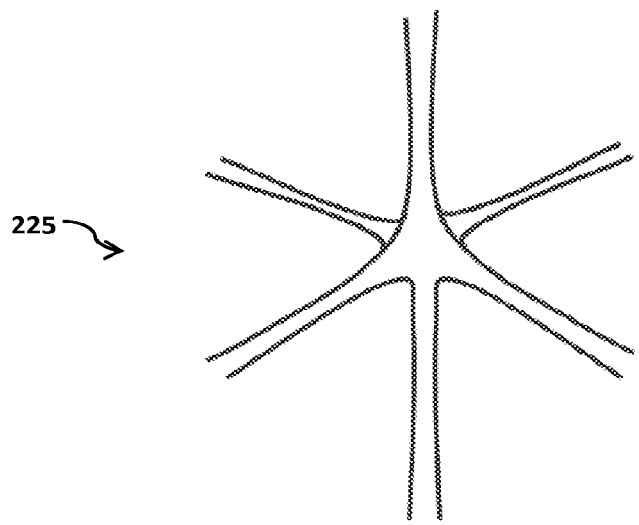
Figure 2F:
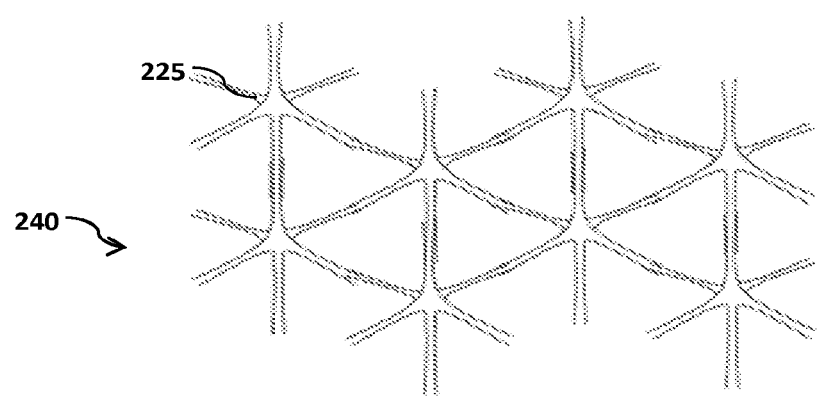
Figure 2G:
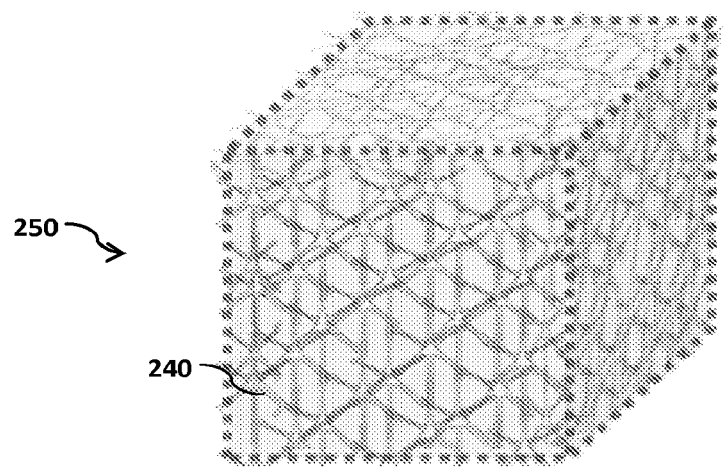

An example of generating a DNA network is shown in FIGS. 2D-F. As shown in FIG. 2D, in some embodiments, DNA strands 200 and complementary DNA strands 210 may be paired to form a four-prong structure 220. As shown in FIG. 2E, this four prong structure may be expanded by base pairing a plurality of DNA strands in order to form, for example, a six-prong DNA structure 225. As illustrated in FIG. 2F, this structure 225 may be base-paired with other DNA structures 225 in order to form a DNA network 240. DNA strands may be paired such that there are binding sites for sample nucleic acid. Binding sites can be, for example, single stranded DNA sequences overhanging from the DNA network and exposable to a bulk solution. Such single stranded overhanging DNA portions may serve as binding sites for target molecules, such as sample nucleic acid and/or amplicons that are ready for sequencing. A DNA network may be used to form a variety of larger structures of varied shapes, such as, for example, boxes or spheres. Such larger structures may be used as carriers. An example shape is shown in FIG. 2G, where a three-dimensional (3-D) "box" 250 is formed from a DNA network 240. The box 250 may be used as a carrier.

In some embodiments, peptide nucleic acid (PNA) can be used to create a nucleic acid network (e.g., such as a box or sphere) which can reduce the charge associated with the network and provide for easier attachment of sample nucleic acid molecules. Moreover, the reduction in charge may reduce noise that can be detected by a sensor during a sequencing reaction.

In some embodiments, nucleic acid network structures can be used in nucleic acid amplification. For example, the network structures may be used as carriers for binding sample nucleic acids, such that it can be subsequently amplified. Following amplification, amplicons generated during amplification may be also bound to the network.

Nucleic acid nanoballs and networks can include various types of nucleic acids, such as DNA, RNA, or variants thereof (e.g., circularized RNA or DNA). The nucleic acids can be single stranded or double stranded.

An advantage of using nucleic nanoballs and/or network structures as carriers can be that they can be porous. Porosity can allow for a large surface area that may be used to bind a greater number of molecules of sample nucleic acid. In addition, a high level of porosity may also allow for good access to bulk solution, both for the purpose of attaching sample nucleic acid and also for washing.

Array Configuration

Arrays may have varied configurations depending upon the particular device and/or desired performance/functionality of a device. In some cases, the pixels in an array may be regularly configured, pseudo-regularly configured, or may be configured in an irregular fashion. The shape of an array may vary. In some cases, an array may be in the shape of a rectangle, a square, a circle, a triangle, a hexagon, a staggered, wrench shaped, X-shaped, or any other shape, etc. or other shape with the pixels forming a grid comprising columns and rows. Moreover, the pixel density of an array may vary and the particular density may affect the array's high throughput capabilities. Pixel density may be increased by optimizing the configuration of electrodes in order to use available space in a more efficient manner. In some embodiments, an array may be 512×512 pixels, 1024×1024 pixels, 1024×2000 pixels, 10000×10000 pixels, or of another density. Pixel pitch size may also vary. For example, the pixel pitch of an array may be about 1 µm, 1.5 µm, 2.5 µm, 3 µm, 4 µm, 5 µm, 10 µm, 20 µm, 100 µm, etc.

Magnetic Elements, Magnetic Fields, and Magnetic Force

Figure 4:
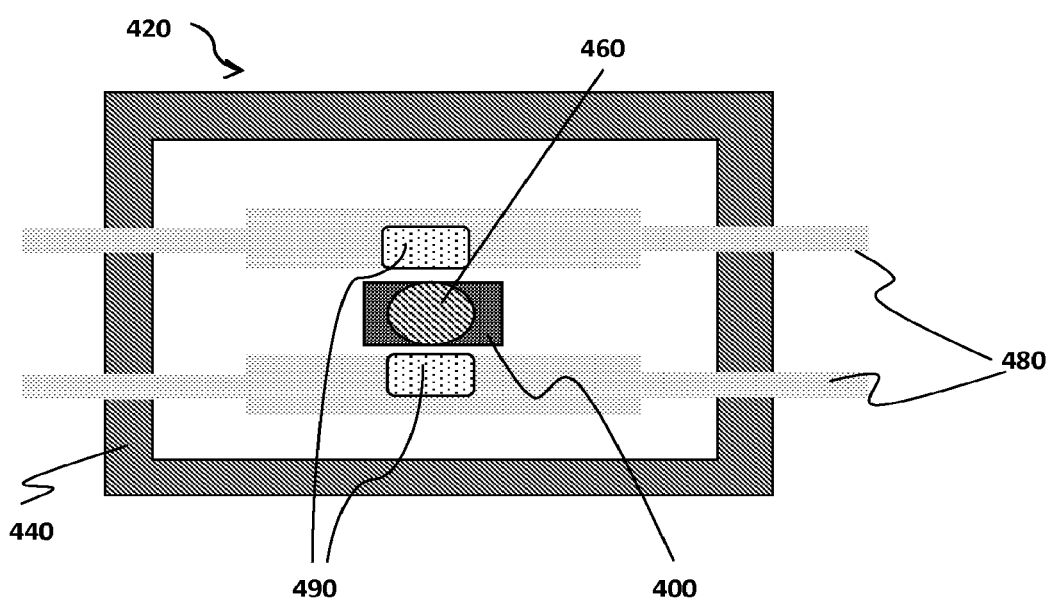
FIG. 4 shows an example pixel comprising a sensor of a sensor array.

As described elsewhere herein, magnetic elements can be incorporated into a device. For example, as depicted in FIG. 4, a magnetic region 400 can be associated with a particle or pixel 420 in order to retain a bead 460. The magnetic region can be formed by a single magnet (where the bead can rest on it), or it can be formed by two magnets, such as, for example, magnetic bars. These two magnets may run through the middle of the pixel 420, with the end of the magnets facing each other at or near the middle of the sensor. This configuration may create a gap (not shown) between the two magnets, near the middle of the sensor. A magnetic force may result from this configuration, and a carrier, such as a bead, may be retained by this force, resting on or within the gap. This gap size can be, for example, 50 nm, 100 nm, 0.25 µm, 1 µm, 1.5 µm, 2 µm, 2.5 µm, etc. wide. The gap size may be optimized to allow for a desired magnetic force upon the bead. Varying parameters such as, for example, gap size can lead to optimization of such factors as bead capture efficiency.

Reagents such as, for example sample nucleic acid (e.g., sample nucleic acid comprising DNA template strands), DNA polymerase, primers, etc. can be then passed over the sensor (e.g., via fluid through an associated microfluidic channel) and contained by an outer electrode 440 of virtual pixel 420. This outer electrode 440 may have a negative charge or electric potential (voltage) in order to keep the negatively charged sample nucleic acid molecules within the area of pixel 420. The bead 460 may be located between two inner electrodes 480, a portion of which remain uncovered 490 by a dielectric layer. During amplification of the sample nucleic acid, the sample nucleic acid and reagents may be concentrated in that region. In some cases, the voltage of the two inner electrodes 480 can be alternated to aid in retaining species at pixel 420 and/or potentially prevent bubble generation, prevent interference of pH modulation near the electrodes on the reaction of interest.

In some embodiments, the magnetic elements may be composed of, for example, Ni, Fe, Co, CoPt, CrCoPt, NiCoPt, a combination thereof, or another combination of materials. Moreover, various aspects of magnets may be altered in order to achieve a desired magnetic force and field. Such aspects may include, for example, the magnet material, number of layers, thickness, length, sharpness of edges, shape, configuration etc.

A magnetic element may be composed of a paramagnetic material, for example aluminum, platinum, etc., or any other paramagnetic material or a ferromagnetic material, for example, iron, nickel, etc., or any other ferromagnetic or paramagnetic material, or a combination of materials. In some cases, magnets may be electromagnets, permanent magnets, or electrodes, or other different subsystems to generate electromagnetic fields. In some embodiments, a magnetic region or magnetic field may be generated via an electromagnetic structure or techniques, such as, for example, a coil with passing current, other types of electromagnetic field generation, or via MEMS-based techniques (e.g., a MEMS-based electromagnetic array). FIG. 36 shows a table outlining additional example magnet shapes and sizes, such as for example, dot magnets and bar magnets. In some cases, dot magnets may be 0.1, 0.2, 0.3, 0.4, 0.5, 0.6, 0.7, 0.8, 0.9, 1, 5, 10, 20, 50, 100, 500, etc. am in width and/or length.

Figure 5A:
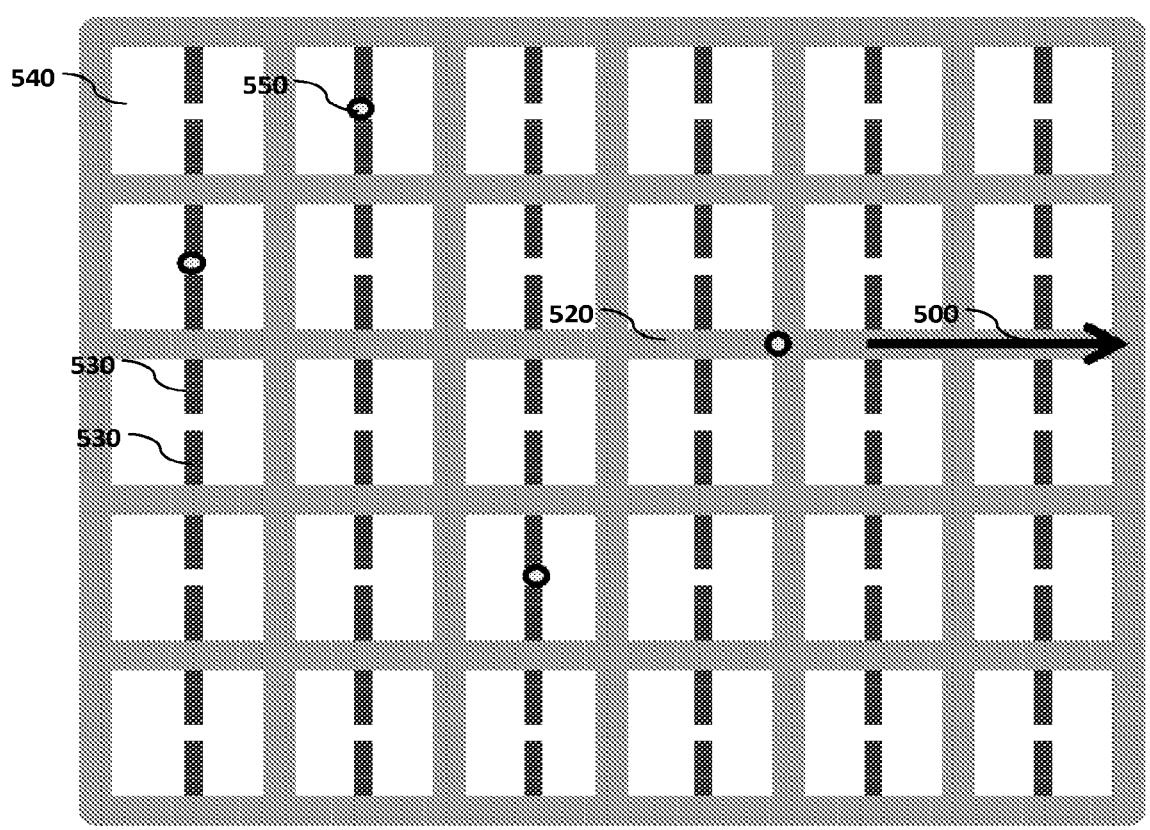
FIGS. 5A-5E show schematics of various example sensor arrays.

The efficiency of capturing carriers or other species via a magnetic array may be tuned by positioning the magnetic array with respect to flows used to supply carriers and/or reagents to the array. In some cases, magnetic elements of an array may be oriented perpendicular to flow and such a configuration may not be optimum for maximizing capture of carriers. For example, some carriers may be captured by the magnetic elements of the virtual wells during flow, and other carriers may pass through spaces between pixels of the array. Such spaces between pixels may not have magnetic elements and/or the magnetic field from a nearby pixel may not be sufficiently strong to capture the carriers. As shown in FIG. 5A, a flow 500 configuration that is perpendicular to the magnetic elements 530 allows for a relatively straight path between the pixels 540 and increases the likelihood that a bead 550 will continue on a straight path through the rows of space 520 between pixels 540 instead of over a pixel 540 where a bead 550 may be confined by a magnetic element 530.

Figure 5B:
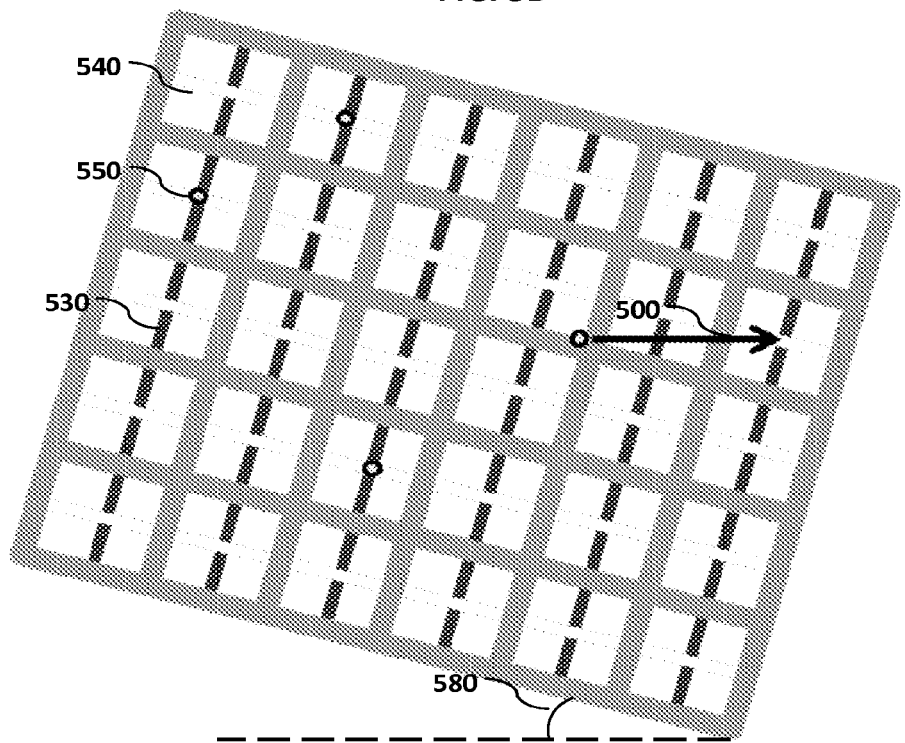
Figure 5C:
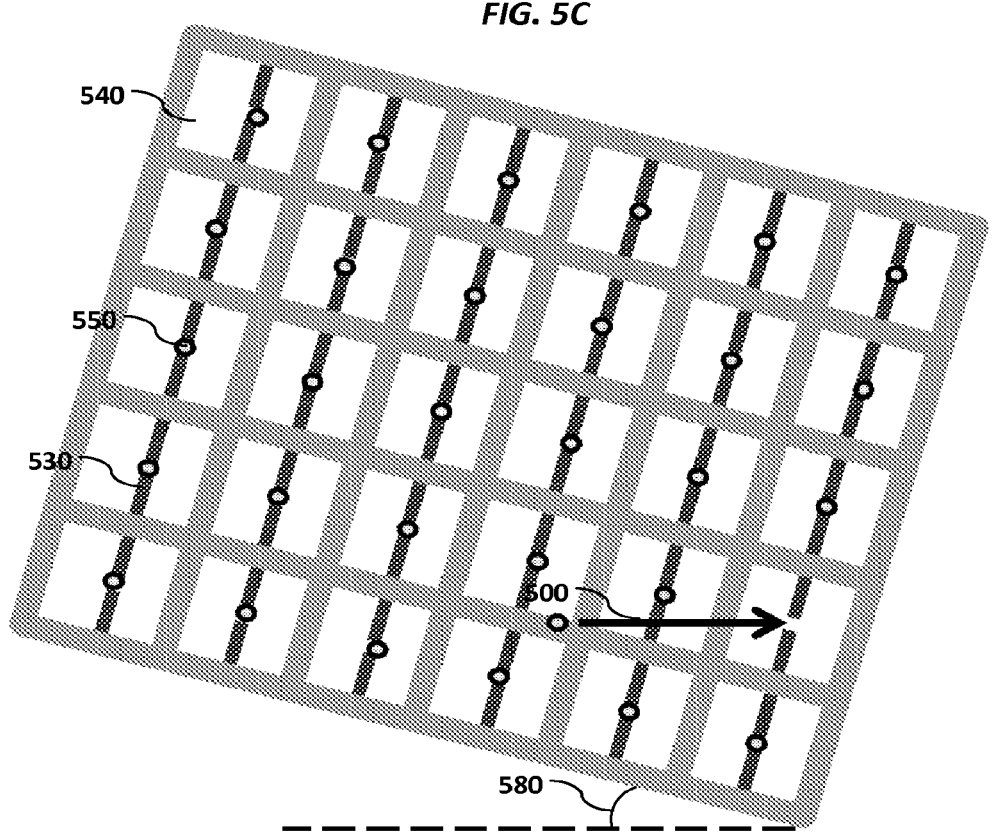

In some embodiments, magnetic elements within the array may be positioned at a non-perpendicular angle with respect to the input flow, such that the spaces between pixels of the array are at non-parallel angle with respect to the input flow. An array may be positioned with respect to flow, such that its magnetic elements are at an angle. The angle at which an array is positioned with respect to flow, for example, may be about or at least about 1°, 2°, 3°, 4, 5°, 6°, 70, 8°, 9°, 10°, 11°, 12°, 13°, 14°, 15°, 16°, 17°, 18°, 19°, 20°, 21°, 22°, 23°, 24°, 25°, 26°, 27°, 28°, 29°, 30°, 35°, 40°, 45°, 50°, or more. Optimization of the positioning of an array with respect to flow can give rise to of higher efficiency capture of magnetic carriers and more uniform reagent distribution, with an example shown in FIGS. 5B and 5C. As shown in FIG. 5B, when a bead 550 flows 500 through the array the chances that it will pass over a pixel 540 are greater with an angled configuration 580. As shown in FIG. 5C, using angled configuration 580 can permit a higher loading of carriers into the array.

Figure 5D:
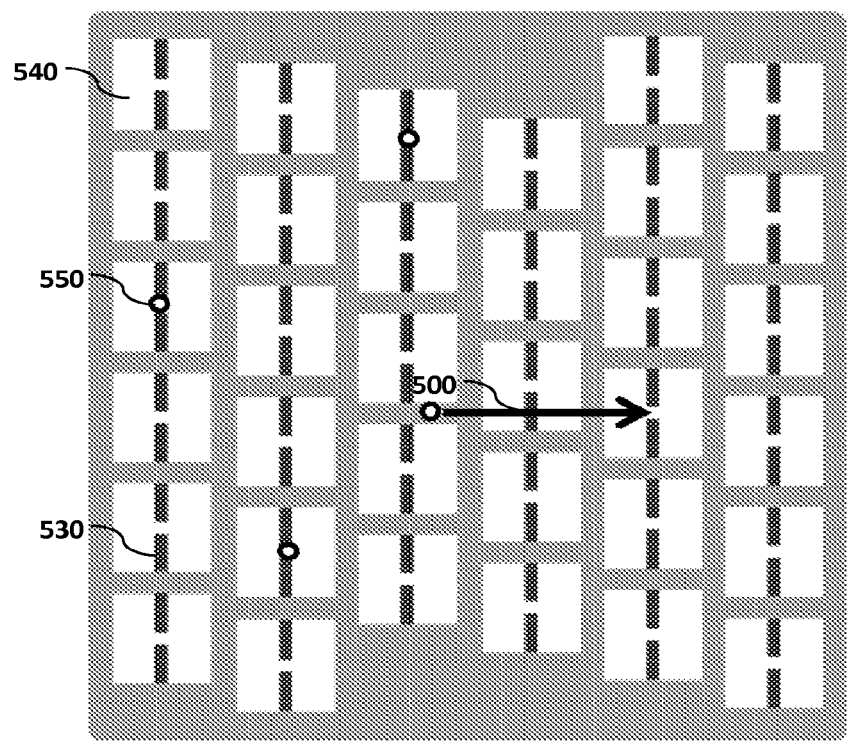
Figure 5E:
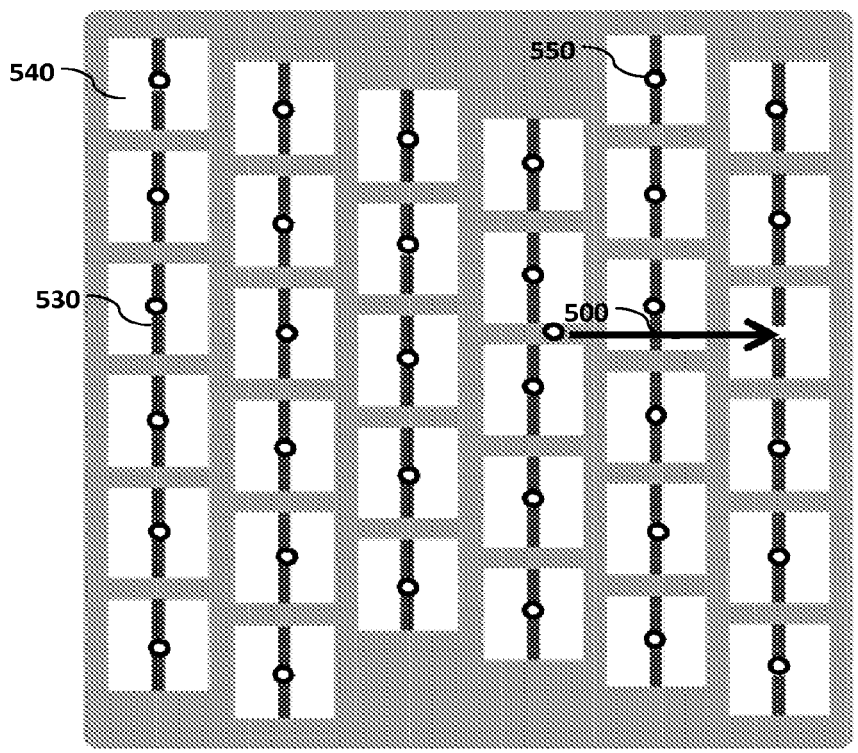

The positioning of magnetic elements within an array may also be optimized to improve the association of carriers with array pixels. For example, a staggered arrangement of magnetic elements, as opposed to a regular grid-like pattern, may be useful in improving the association of carriers with array pixels. For example, as shown in FIG. 5D, each column of pixels 540 in the magnetic array may be offset with respect to alignment with the previous column. This arrangement may help to increase bead 550 loading efficiency because of the minimization of rows of empty space. FIG. 5E, shows how using a staggered configuration can permit a higher loading of carriers into the array. In some cases, a combination of staggered positioning of magnetic elements and angled configurations of arrays with respect to flow may be used to improve the capture of carriers into the array.

In some embodiments, a carrier (e.g., bead) may sit proximate to a dot magnet. In some cases, a carrier may be partially or entirely immobilized on a surface of a dot magnet. The strength of the dot magnet may depend on a variety of factors including: magnetic material, the number of layers, magnet size (e.g., thickness, width, height), direction of post magnetization (e.g., horizontal, vertical), etc. or another factor.

Figure 37:
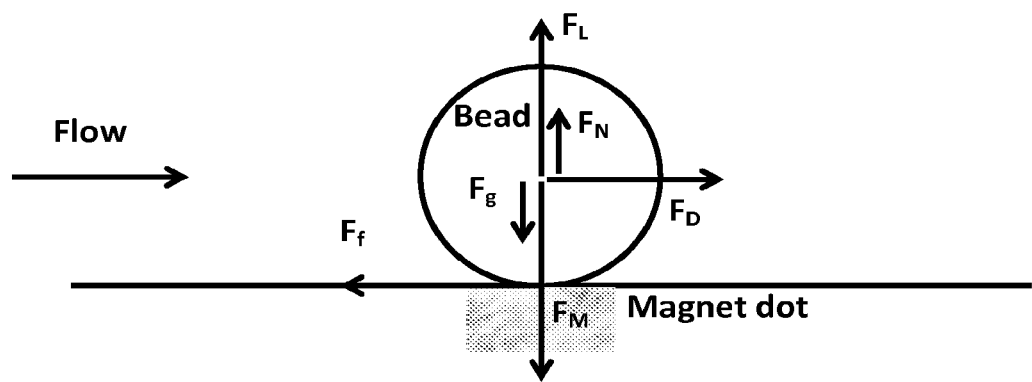
FIG. 37 is a schematic of example forces that can be exerted on a carrier.

In some embodiments, there may be a number of forces acting on a carrier (e.g., bead). FIGS. 37 and 38 provide examples of such forces. Two forces which may act on a carrier, for example, may be a magnetic force and a viscous force. The magnetic force may hold the carrier in place at its appropriate pixel on a magnetic array, and the viscous force from a fluid flow can push the carrier away from its appropriate pixel on a magnetic array. In order to keep the carrier in its desired pixel, the magnetic force is generally greater than the viscous force.

In some cases, the following expression, $F=\nabla \times H_{ext}=0$, may be used estimated the force (F) on a magnetizable object, so long as the fields are static, and the body is non-conducting.

The magnetic flux density, B, can be calculated from the solution to the Maxwell equations for static magnets using Remanence field, $B_r$, for the block magnet. Here, it may be assumed that $B_r=1$ T and the equation may be solved for the magnetic field. Then, the magnetic force on the iron core of 1 µm beads may be calculated.

Figure 40:
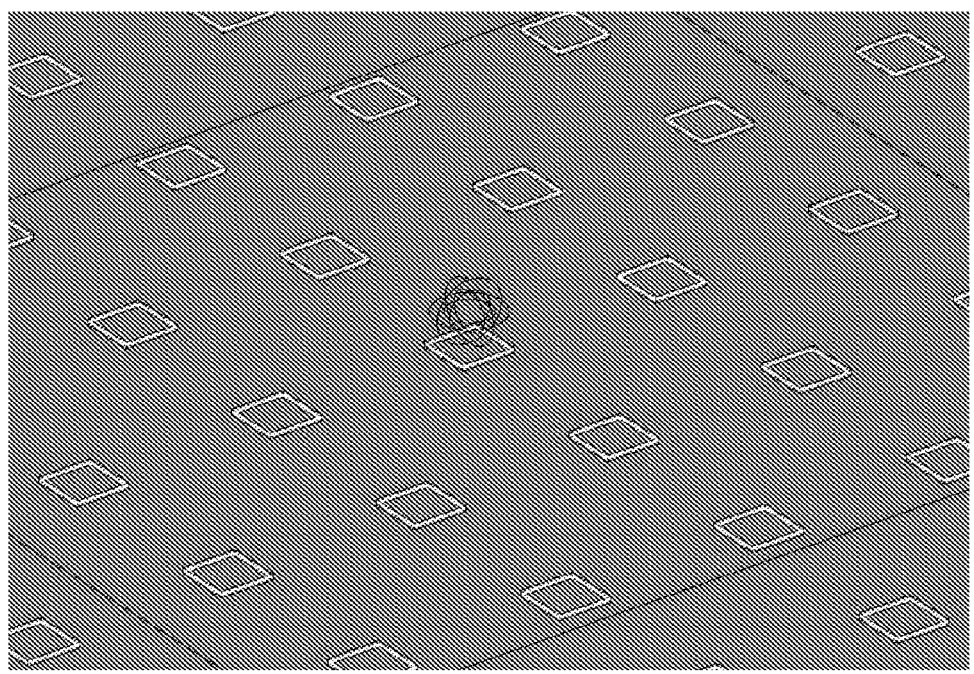
FIG. 40 is a schematic of example magnetic field lines generated by a magnetic element of an array.

FIG. 39 shows an example schematic of an example bead captured by a dot magnet. As shown in FIG. 39, a three-dimensional (3-D) depiction of a 1 µm bead with a 26% iron core captured by a dot magnet that has a length (L), a width (W), and a height (H). The figure also shows that the three dimensions are on an X, Y, and a Z axis. There is a gap length (G) measured from the center of the iron core to the surface of the magnet. FIG. 40 shows a schematic of magnetic field lines generated by an example dot magnet.

In some embodiments, magnetic force exerted by a magnetic element on a carrier may depend on the distance between the carrier and the magnetic element and/or the particular geometry of the magnetic element. In some cases, the magnetic force in a horizontal direction may be substantially higher than the magnetic force achieved in a vertical direction. In some cases, with respect to rectangular dot magnets, the magnetic force exerted by the dot magnet may be higher when the direction of magnetization is parallel to the longer side of the rectangular dot magnet. In some embodiments, if the thickness of the magnetic element is increased, the magnetic force may increase slightly with respect to a horizontal direction. In some cases, such an increase, however, may be substantially higher with respect to a vertical direction. In some embodiments, with respect to horizontal magnetization for square dot magnets, magnetic force exerted by the magnet may increase when the size of the magnetic dots is increased. With respect to vertical magnetization for square dot magnets, the size of the magnet may be optimized such that the magnetic force is maximized.

Electrodes and Electrode Sensors

Sensors of the present disclosure, such as nanobridge and nanoneedle sensors, can include at least 1, 2, 3, 4, 5, 6, 7, 8, 9, or 10 electrodes for sensing signals associated with species in solution, such as signals associated with a nucleic acid sequencing reaction or the detection of an analyte in solution (e.g., protein or antibody). Such electrodes can be electrically isolated and can be configured to be electrically coupled to a species being detected. The species can be in solution, coupled to a surface of an electrode, or coupled to a particle (e.g., bead in solution). In some examples, an electrode is coupled to a Debye layer of the particle. In an example, at least two electrodes are coupled to a Debye layer (e.g., are within the Debye layer) of the particle. In an example, at least one electrode is touching a bead and another electrode is touching or at least within the Debye layer of the bead. The Debye layer can have a Debye length.

The arrangement of electrodes within an array may vary, depending upon the particular configuration desired. In some embodiments, there may be one or more transmitter and one or more receiver electrodes per pixel of an array. A transmitter electrode generally refers to an electrode that provides a current and a receiver electrode generally refers to an electrode that receives a current. In some cases, in the absence of a species to couple to the transmitter and receiver electrodes, electrical current does not flow from the transmitter to the receiver. For example, in the absence of a particle (e.g., bead) coupled to the transmitter and receiver electrodes, a circuit having the transmitter and receiver electrodes is open and an electrical current will not flow from the transmitter electrode to the receiver electrode. However, when the transmitter and receiver electrodes are electrically coupled to the Debye layer of the particle (or other species in solution), the circuit is closed and current flows from the transmitter electrode to the receiver electrode. In some cases, at least one of the transmitter or receiver electrodes is "shared" between neighboring pixels. Sharing of one of the electrodes may allow for a more efficient use of space and a reduction in the number of electronic components. In some embodiments, a transmitter electrode may be shared by the beads of neighboring pixels. In some embodiments, a receiver electrode may be shared by the beads of neighboring pixels. In some embodiments, both transmitter and receiver electrodes can be shared by the beads of neighboring pixels. In some embodiments, the transmitter and/or receiver electrodes may be considered to be shared by the pixels themselves if the system does not utilize carriers, such as beads. In some embodiments, a transmitter electrode may function as a receiver electrode depending upon, for example, the configuration of the circuit. In some embodiments, a receiver electrode may function as a transmitter electrode depending upon, for example, the configuration of the circuit.

In some embodiments, where an array includes electrodes that are shared between neighboring pixels, the number of electrodes (E) in the array may be expressed as a function of the number (N) of pixels. For example, the number of electrodes (E) in the array may be equal to N, N+1, N+2, N+3, N+4, N+5, N+6, N+7, N+8, N+9, N+10, N+11, N+12, N+13, N+14, N+15, N+16, N+17, N+18, N+19, N+20, N+21, N+22, N+23, N+24, N+25, N+26, N+27, N+28, N+29, N+30, N−1, N−2, N−3, N−4, N−5, N−6, N−7, N−8, N−9, N−10, N−11, N−12, N−13, N−14, N−15, N−16, N−17, N−18, N−19, N−20, N−21, N−22, N−23, N−24, N−25, N−26, N−27, N−28, N−29, N−30, 2N−1, 2N−2, 2N−3, 2N−4, 2N−5, 2N−6, 2N−7, 2N−8, 2N−9, 2N−10, 2N−11, 2N−12, 2N−13, 2N−14, 2N−15, 2N−16, 2N−17, 2N−18, 2N−19, 2N−20, 2N−21, 2N−22, 2N−23, 2N−24, 2N−25, 2N−26, 2N−27, 2N−28, 2N−29, or 2N−30. The expression that describes a particular array can depend, for example, upon the particular arrangement of shared electrodes within the particular array.

In some cases, at least a subset of sensors in an array can share the same transmitter electrode but have separate receiver electrodes. As an alternative, at least the subset of sensors can share the same receiver electrode but have separate transmitter electrodes. Such configuration can be implemented, for example, by having the sensors in a square or rectangular grid pattern, or a hexagonal pattern.

In some situations, a given sensor of an array has at least two sensing electrodes. One of the sensing electrodes can be a transmitter electrode and another of the sensing electrodes can be a receiver electrode. The electrode scan be situated in a planar configuration. One electrode can be situated directly below a particle and another electrode can be situated at a periphery of the particle. Both electrodes can be coupled to a Debye layer (e.g., within a Debye layer) of the particle during sensing.

Figure 24A:
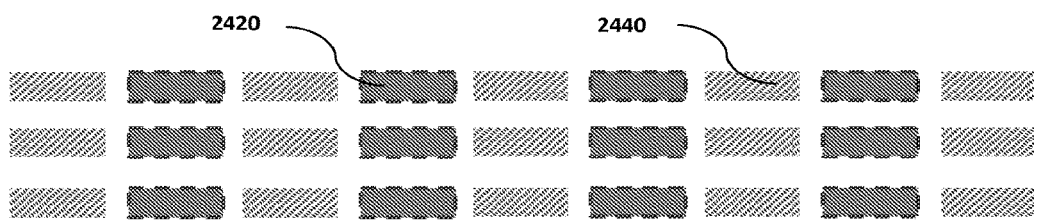
FIGS. 24A-C show schematics electrodes in an array.
Figure 24B:
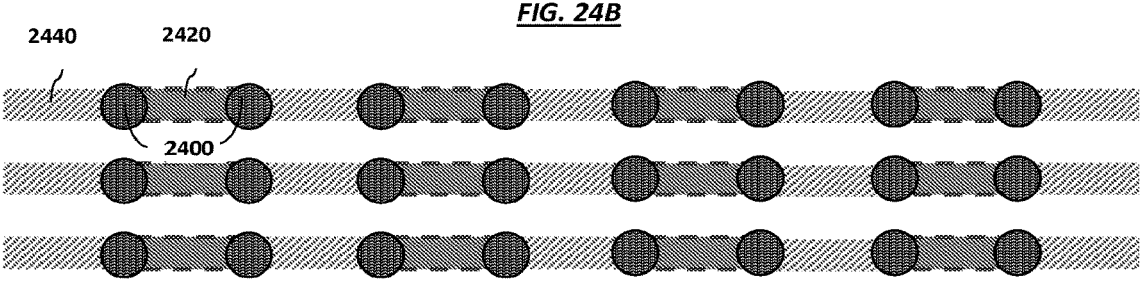

An example of shared electrodes between array pixels is shown in FIG. 24A. As shown in FIG. 24A, receiver electrode 2420 is shared by two pixels of an array, wherein each pixel includes a transmitter electrode 2440. As shown in FIG. 24B carriers 2400 (e.g., beads) can be immobilized at each pixel between a shared receiver electrode 2420 and a transmitter electrode 2440 associated with a pixel, such that detection will happen around the carrier. FIG. 24B shows a receiver electrode 2420 shared between two neighboring beads 2400 such that the receiver electrode is used by each bead in the detection of the reaction of interest.

Figure 24C:
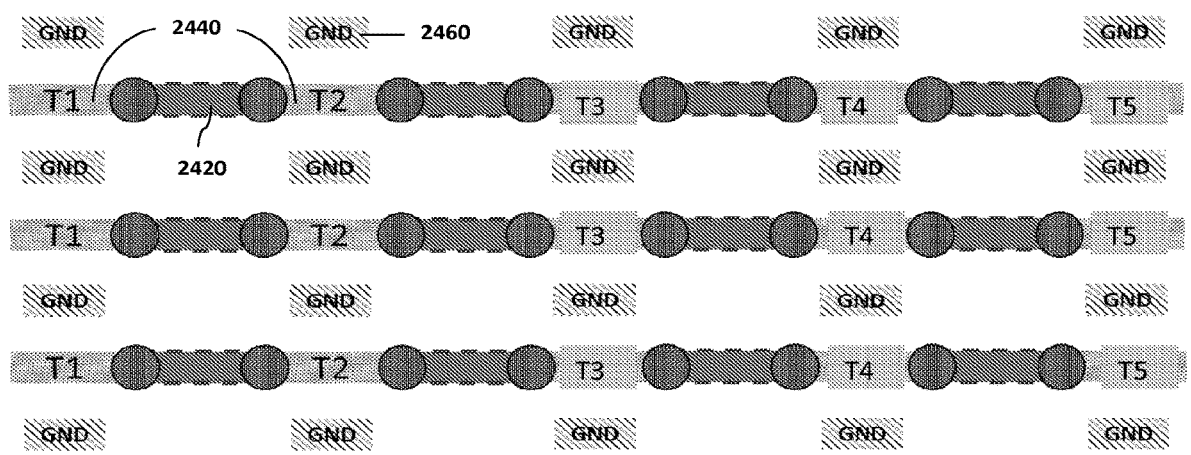

Electrode-sharing by neighboring pixels may aid in enhancing the high throughput capabilities of an array, but may be susceptible to a reduction in signal to noise ratio due to cross-talk between pixels. The time frame in which certain electrodes are activated may be adjusted in order to help reduce potential cross-talk and reduce the readout rate of the associated array circuitry. In one embodiment, as shown in an example of FIG. 24C, an array of electrodes may comprise receiver electrodes 2420 and transmitter electrodes 2440, wherein one receiver electrode 2420 is shared between two beads 2400. In some cases, there may be ground electrodes 2460 that can be used to shield the electrodes from potential cross talk between neighboring electrodes. The ground electrode may make a short path to absorb unwanted current through the buffer. Thus, the receiver electrode may only receive the current flow from the bead not the current from bulk solution. In other embodiments, the system may not use beads and the current flow may come from other types of carriers. In another embodiment, if the system does not use carriers, the current flow may come from the sensing element of the system. The transmitter electrodes 2440 in FIG. 24C are labeled T1 T2, T3, T4, and T5 in order to help illustrate that they may be activated in five time phases in order to help reduce crosstalk. For example, all of the T1 transmitter electrodes in the array can transmit signal during time phase 1 to their corresponding receiver electrodes 2420. The T2, T3, T4, and T5 transmitter electrodes do not transmit during phase 1 and may act as ground electrodes. After the signal from the T1 transmitter electrodes collected on the receiver electrodes 2420 and the output signal is generated, the roles of the T1 and T2 transmitter electrodes may switch and time phase 2 may commence.

During time phase 2, the T2 transmitter electrodes may transmit signal to their corresponding receiver electrodes 2420 and the T1, T3, T4, and T5 transmitter electrodes can act as ground electrodes. In this manner, neighboring transmitter electrodes are not activated during the same time period, thus allowing for a signal to the receiver electrode 2420 that is less likely to be distorted by noise.

During time phase 3, the T3 transmitter electrodes may transmit signal to their corresponding receiver electrodes 2420 and the T1, T2, T4, and T5 transmitter electrodes can act as ground electrodes. In this manner, neighboring transmitter electrodes are not activated during the same time period, thus allowing for a signal to the receiver electrode 2420 that is less likely to be distorted by noise.

During time phase 4, the T4 transmitter electrodes may transmit signal to their corresponding receiver electrodes 2420 and the T1, T2, T3, and T5 transmitter electrodes can act as ground electrodes. In this manner, neighboring transmitter electrodes are not activated during the same time period, thus allowing for a signal to the receiver electrode 2420 that is less likely to be distorted by noise.

During time phase 5, the T5 transmitter electrodes may transmit signal to their corresponding receiver electrodes 2420 and the T1, T2, T3, and T4 transmitter electrodes can act as ground electrodes. In this manner, neighboring transmitter electrodes are not activated during the same time period, thus allowing for a signal to the receiver electrode 2420 that is less likely to be distorted by noise.

In some embodiments, every second, third, fourth, fifth, sixth, seventh, eighth, ninth, tenth, etc. transmitter electrode 2440 may be activated and any other non-activated transmitter electrodes may serve as ground electrodes in any combination. For example electrode 1 can be turned off, and electrodes 2 and 3 turned on, electrode 4 turned off, etc. In another embodiment, electrode 1 can be turned on, electrodes 2-5 turned off, electrode 6 turned on, etc. where the "off" electrodes are set to ground.

In addition to the configuration of electrodes within an array, adjusting electrode shape and size may allow for optimization with respect to, for example, increasing baseline current and sensitivity. As described above, a pixel may comprise one or more transmitter and one or more receiver electrodes. The shapes and sizes of the transmitter and receiver electrodes may be optimized depending upon the particular functionality and performance of the electrodes desired.

Figure 25A:
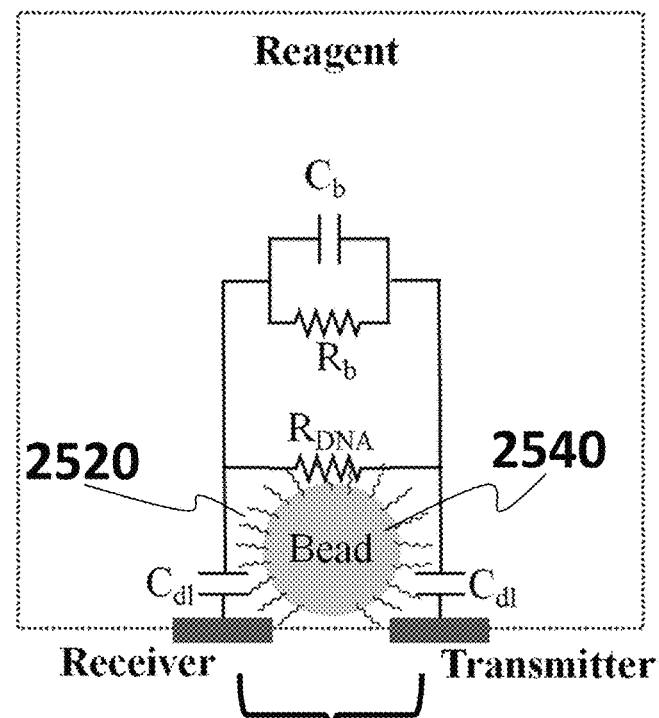
FIG. 25A is a schematic of an example sensor.
Figure 25B:
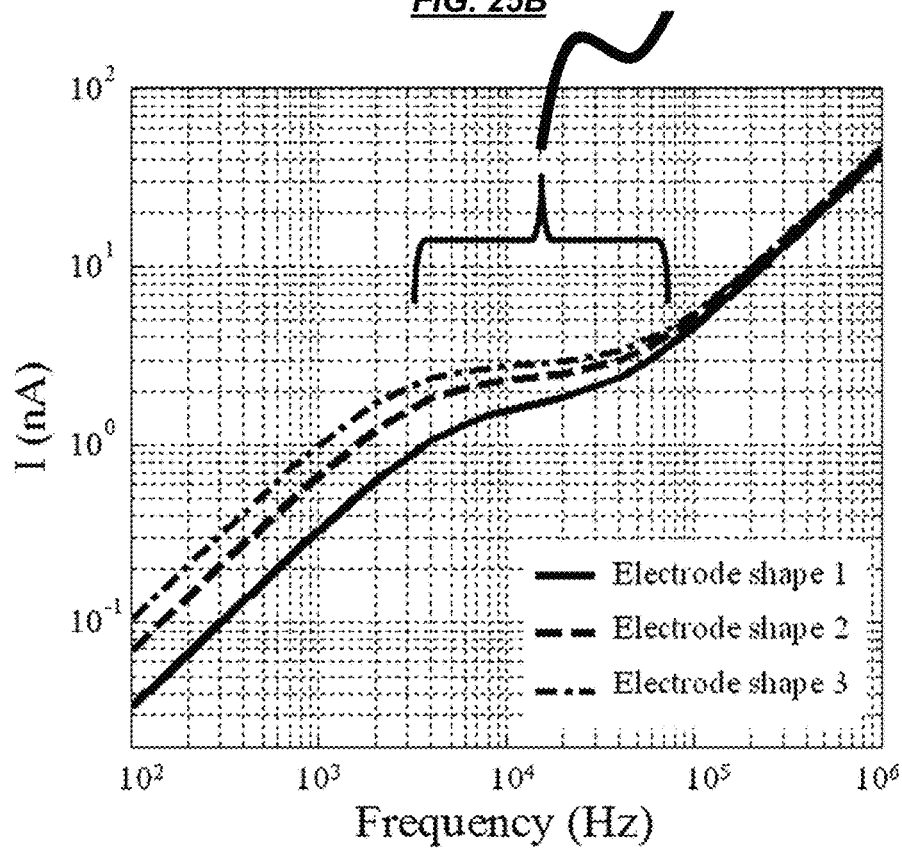
FIGS. 25B-25C are graphic representations of operating example electrodes.
Figure 25C:
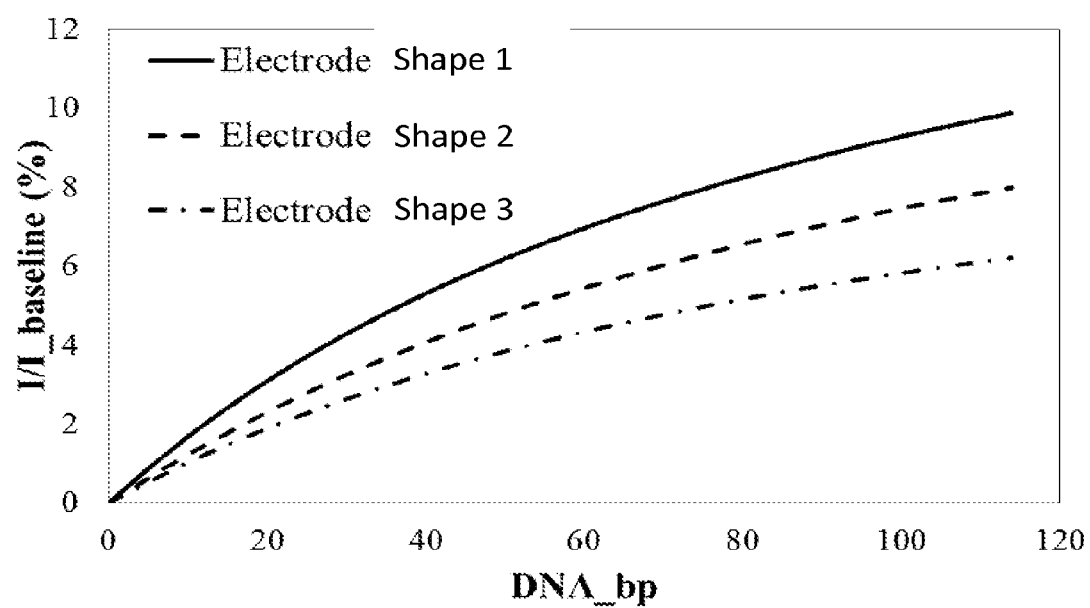
Figure 25D:
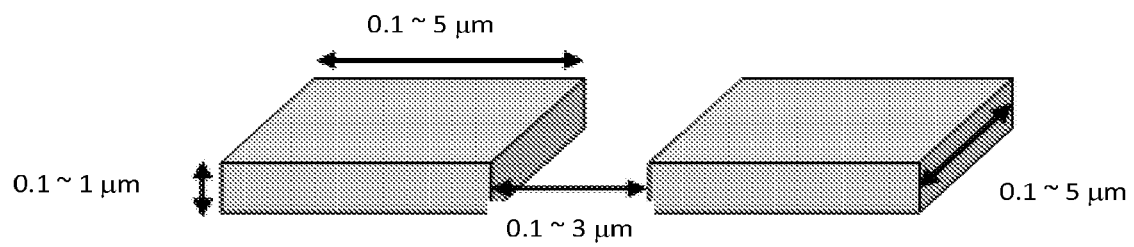
FIG. 25D is a schematic of example electrodes.

FIG. 25D provides an illustration of example electrode embodiments and example ranges in electrode length (0.1-5 µm), width (0.1-5 µm), height (0.1-5 µm), and separation distance (0.1-3 µm) between electrodes. The electrode sizes can be between 7 nm to 70 nm or between 70 nm to 700 nm or between 700 nm to 7 µm, in length, weight and depth. In the example shown in FIG. 25D, the electrodes are rectangular with height of 2 µm, width of 1, 2, or 3 µm, and depth of 2 µm. The electrodes are spaced 1 µm apart. Moreover, in some cases, an electrode (e.g., a transmitter electrode, receiver electrode, ground electrode, etc.) may be about 0.5 µm, 1.0 µm, 1.5 µm, 2.0 µm, 2.5 µm, 3 µm, 3.5 µm, 4 µm, 4.5 µm, 5 µm, 5.5 µm, 6.0 µm, 7.0 µm, 8.0 µm, 9.0 µm, 10 µm, 20 µm, or more in length and 0.5 µm, 1.0 µm, 1.5 µm, 2.0 µm, 2.5 µm, 3 µm, 3.5 µm, 4 µm, 4.5 µm, 5 µm, 5.5 µm, 6.0 µm, 7.0 µm, 8.0 µm, 9.0 µm, 10 µm, 20 µm, or more in width, depending on pixel pitch.

Figure 26:
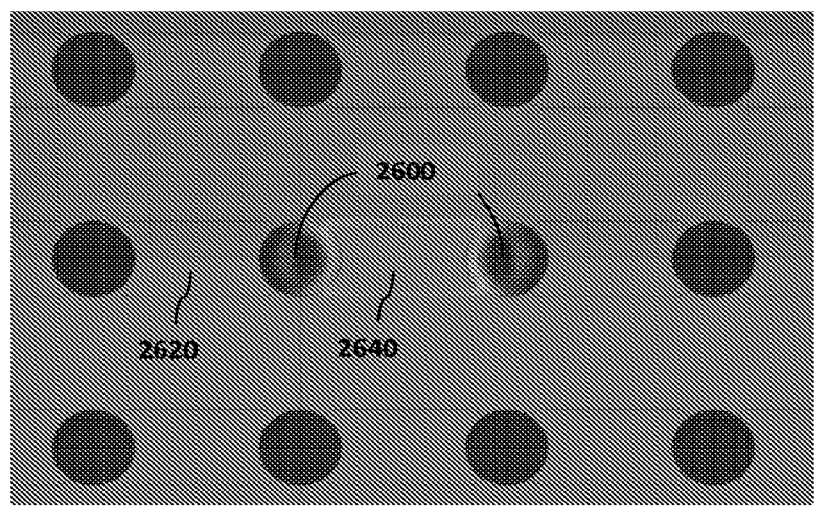
FIG. 26 is a schematic of example electrodes in an array.

An example configuration of transmitter and receiver electrodes is shown in FIG. 26. As demonstrated in FIG. 26, a transmitter/receiver electrode 2640 of a pixel may have a rectangular shape, optionally with rounded corners. The receiver/transmitter electrode 2620 may also have a rectangular shape, optionally with rounded corners, and a carrier (e.g., bead) 2600 can rest on or proximate to one end of the receiver/transmitter electrode 2640. As shown in FIG. 26, the receiver/transmitter electrode 2620 may be shared between two carriers 2600 of neighboring pixels. The transmitter and receiver electrodes may have the same, or different, dimensions.

Figure 27A:
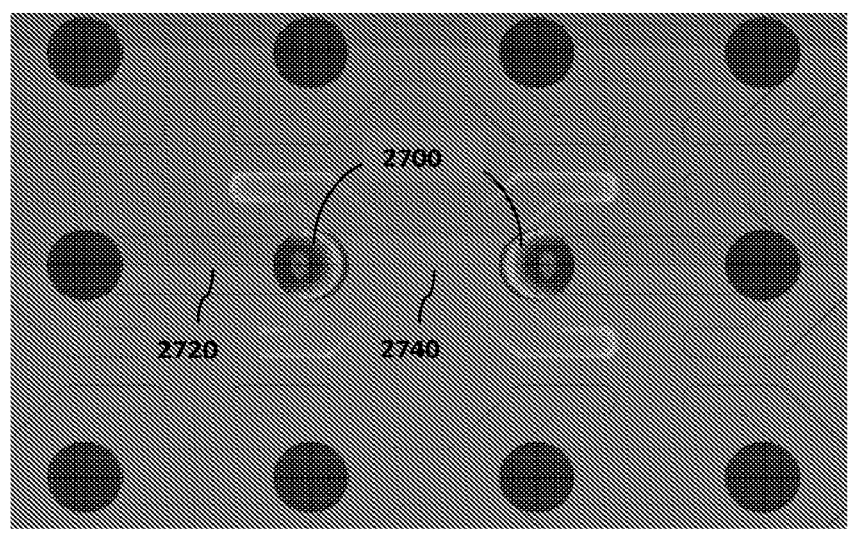
FIGS. 27A-D are schematics of example electrodes in an array.
Figure 27B:
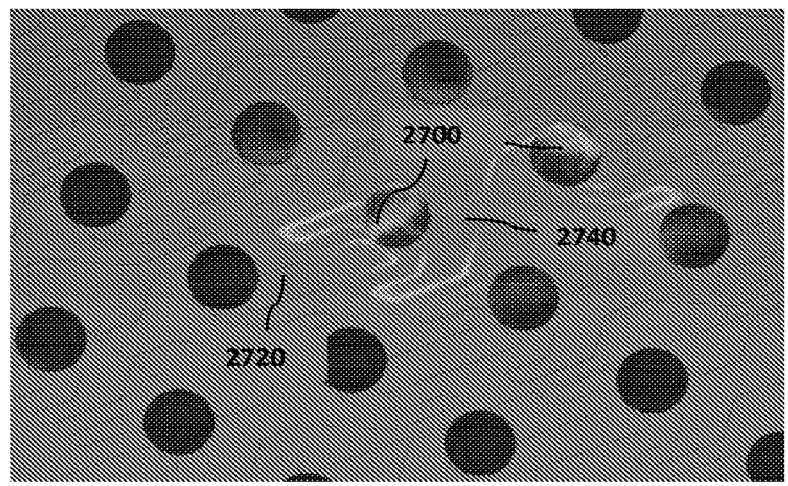
Figure 27C:
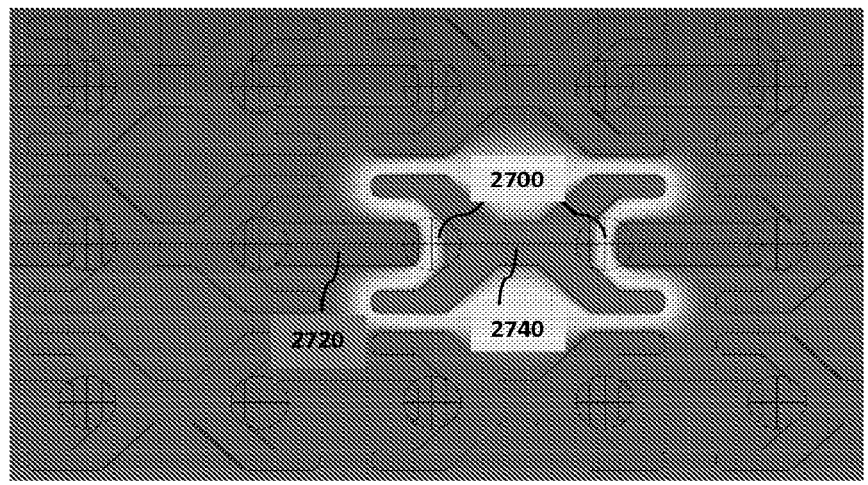

Another example configuration of transmitter and receiver electrodes is shown in FIG. 27A. As demonstrated in FIG. 27A, the transmitter/receiver electrode 2740 of the pixel may have a modified-wrench shape. The receiver/transmitter electrode 2720 may have a rectangular shape, optionally with rounded corners, wherein a carrier (e.g., a bead) 2700 can rest on or proximate to one end of the receiver/transmitter electrode 2720, and the receiver/transmitter electrode 2720 may be shared between two beads of neighboring pixels. FIG. 27B shows a top-angled view and FIG. 27C shows a top view schematic of the configuration in FIG. 27A. Such a configuration as shown in FIGS. 27A-C may improve isolation of a carrier from other carriers in an array, which may result in an increase in the current from all areas of the carrier. This configuration may also increase the sensitivity to conductivity change.

Figure 27D:
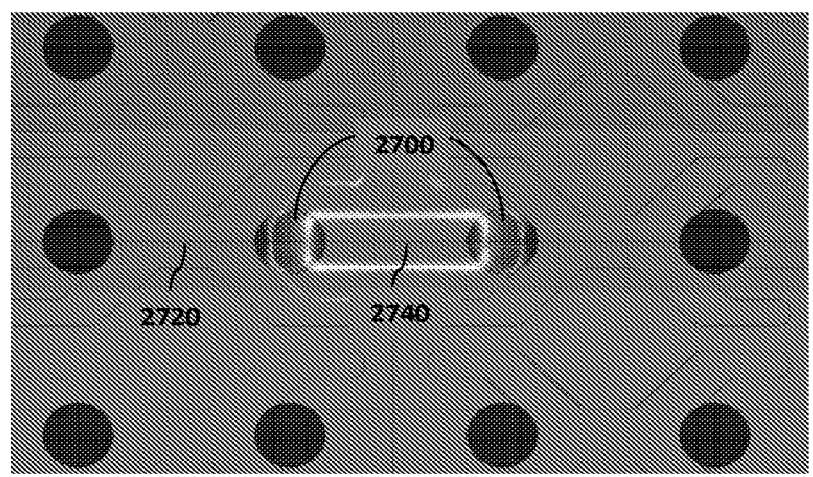

Another example configuration of transmitter and receiver electrodes is shown in FIG. 27D. As demonstrated in FIG. 27D, the receiver/transmitter electrode 2720 of the pixel may have a modified-wrench shape, wherein a carrier (e.g., bead) 2700 can rest on or proximate to an inner curved portion of the receiver/transmitter electrode 2720. The receiver/transmitter electrode may be shared between two carriers 2700 of neighboring pixels. The transmitter/receiver electrode 2740 of the pixel may have a rectangular shape, optionally with rounded corners.

Figure 28:
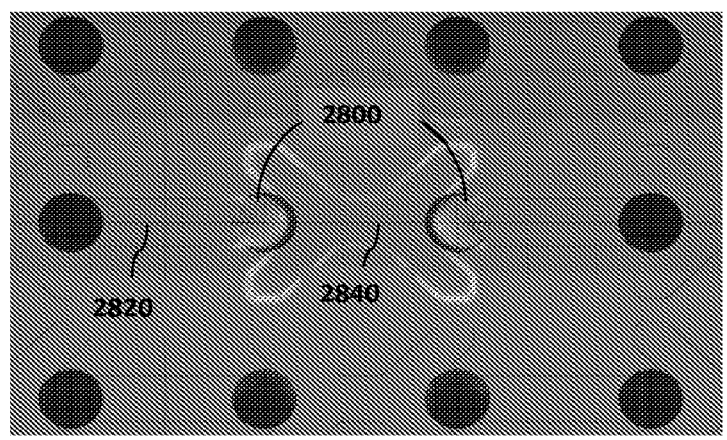
FIG. 28 is a schematic of example electrodes in an array.

Another example configuration of transmitter and receiver electrodes is shown in FIG. 28. As demonstrated in FIG. 28, the transmitter/receiver electrode 2840 of the pixel may have an "X" shape. The receiver/transmitter electrode 2820 may have a rectangular shape, optionally with rounded corners, wherein a carrier (e.g., bead) 2800 rests on or proximate to an inner corner portion of the receiver/transmitter electrode 2820, and may be shared between two carriers 2800 of neighboring pixels.

In some embodiments, a carrier may rest on or proximate a transmitter electrode. The transmitter electrode may be shared between two carriers of neighboring pixels. The transmitter and receiver electrodes of a sensor may comprise any combination of the above mentioned electrode shapes, or any other shape, such as square, circular, rectangular, irregular, etc. In some embodiments, the shape of the electrodes may be optimized to prevent bubble generation.

Figure 29A:
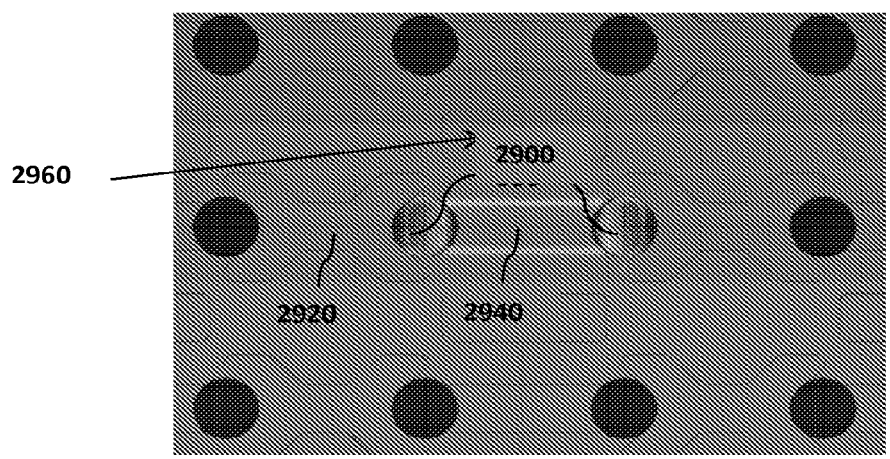
FIGS. 29A-B are schematics of example electrodes in an array.
Figure 29B:
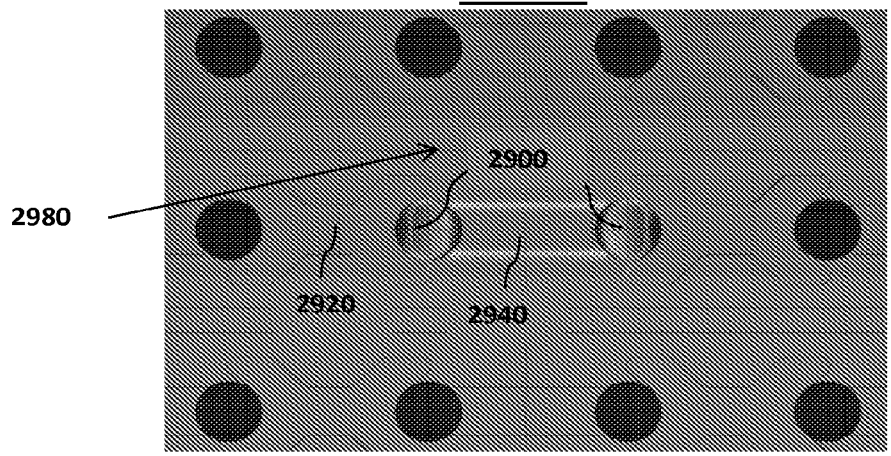

In a further embodiment, the pixel may contain a ground electrode, as shown in FIG. 29A. The ground electrode 2960 may act as a barrier, helping to shield receiver/transmitter electrodes 2920 in neighboring pixels from cross-talk from transmitter/receiver electrodes 2940. The addition of the ground electrode 2960 may reduce output signal that is generated as a result of measurement of the bulk solution instead of the area on or near the beads 2900 where a reaction of interest, such as a nucleotide incorporation reaction, may be detected. In another embodiment, as shown in FIG. 29B, there may be a ground line 2980, in addition to or instead of a ground electrode.

FIG. 25A provides an example schematic demonstrating various example signal paths that may be detected by receiving and transmitting electrodes 2500. $C_b$ and $R_b$ represent the equivalent electrical capacitance and resistance due to a bulk (chemical buffer) solution in communication with the electrodes, respectively. $R_{DNA}$ is the equivalent electrical resistance due to the region in close proximity of DNA strands 2520 fixed on a bead 2540. $C_{DNA}$, not shown, represents the capacitance associated with the bead and DNA strands fixed on the bead, which is effectively in parallel to $R_{DNA}$ as a lump element. $R_{DNA}$ is different than $R_b$ due to a modified concentration of mobile ions in close proximity and associated to the fixed DNA strands (in the Debye layer of the beads and/or DNA strands). Modulation of $R_{DNA}$ due to nucleotide incorporation on the template DNA strand 2520 fixed on the bead 2540 can be used by a sensor (e.g., a NanoNeedle, a set of two or more electrodes, a differential amplifier, a CMOS sensor, or other types of sensors) to detect the nucleotide incorporation event, and, thus sequence of DNA strand 2520. $C_{dl}$ is the double layer (or Debye layer, which has a Debye length) capacitance associated with the receiving and/or transmitting electrodes 2500. In some embodiments, by cyclic injection of nucleotides, a change in impedance of a carrier, nucleic acid, and/or sensor may be measured by the sensor and can be used to identify the sequence of the DNA strand 2520. In some cases, measurement of impedance occurs within the Debye layer of the carrier, nucleic acid, and/or sensor. In other cases, all four nucleotides can be introduced simultaneously and the signal from each incorporation event can be decoupled if where sensors provide sufficient detection sensitivity and time resolution.

In some embodiments, labels may be used to amplify the amount of signal from a nucleotide incorporation event and a change in the impedance. Such a label can comprise a charged moiety, a physical barrier (e.g., metallic nanoballs—platinum, gold silver, etc.), a chemical or biochemical moiety, or a polymer-based molecule, or compound that can increase the measured signal by the sensor. The effect on current will depend on the particular label used and its corresponding conductivity. For example, a metal label would increase current, whereas a polymer label would decrease current.

FIG. 25B shows the current measured by example sensors of different shape, such as a NanoNeedle, comprising two electrodes versus the frequency of the applied signal during a sequencing reaction. Since voltage is fixed and impedance is equal to voltage over current, the plots represent the inverse of impedance measured by the sensor and, thus, changes due to nucleotide incorporation. Referring now to FIG. 25B, to measure the change in resistance due to nucleotide incorporation, the sensor may operate around mid-range frequency 2510 in order to help eliminate the effect of any capacitances between electrodes. To measure the capacitive change due to nucleotide incorporation, the sensor may operate in low range frequency.

For the example shown in FIG. 25B, a frequency lower than 30 kHz was used. In some embodiments, low frequency operating conditions may depend on the size and/or geometry of one or more electrodes of a sensor, as well as the spacing of the transmitter and receiver electrodes. As an example, FIG. 25C shows an example where changing the shape of the electrodes may lead to an increase in sensitivity, as can be seen by a larger change in the percentage of current over baseline current as the incorporation of nucleotide base pairs for DNA sequencing proceeds.

At low frequencies, the double layer capacitance may dominate the impedance and the sensitivity of the sensor to changes in resistance can become small. At high frequencies, the parasitic capacitance between the two electrodes may dominate. As current goes between electrodes, the sensitivity to changes in resistance can decrease. Therefore, based on the electrode size and geometry, the optimum operating condition can be achieved for the highest sensitivity of the sensor.

Figure 25E:
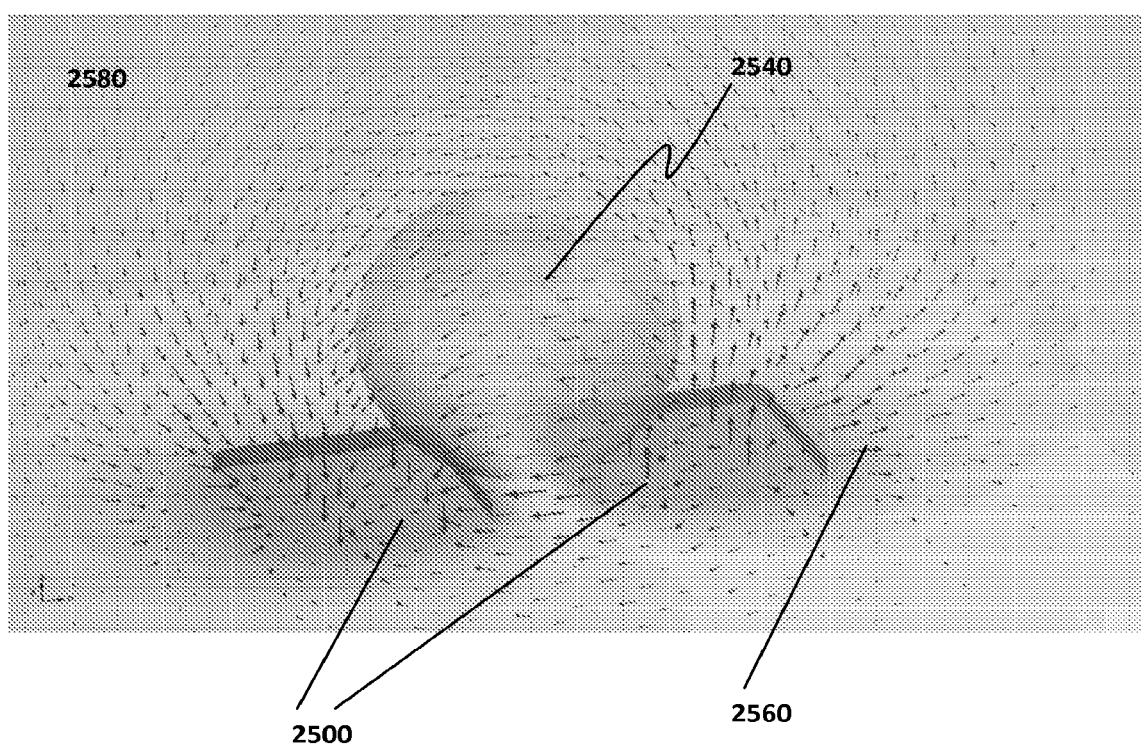
FIG. 25E is a schematic of example electric field lines generated from example electrodes.

FIG. 25E provides an example schematic of electric field lines generated from electrodes 2500. The electric field lines 2560 of FIG. 25E show how the portions of the electrodes 2500 that are the farthest from the bead mainly sense changes in the resistance or capacitance of the bulk solution 2580. The electric field lines at the portions of the electrodes that are farthest from the bead have a direction that points away from the bead, indicating that the current path is through the reagent, not around the bead. In some embodiments where the electrodes are smaller and closer to the bead, a larger portion of current goes around the bead, which can increase the sensitivity of the sensor. There may be an optimum electrode configuration that increases the baseline current as well as sensitivity in order to better detect nucleotide incorporation events.

Figure 59:
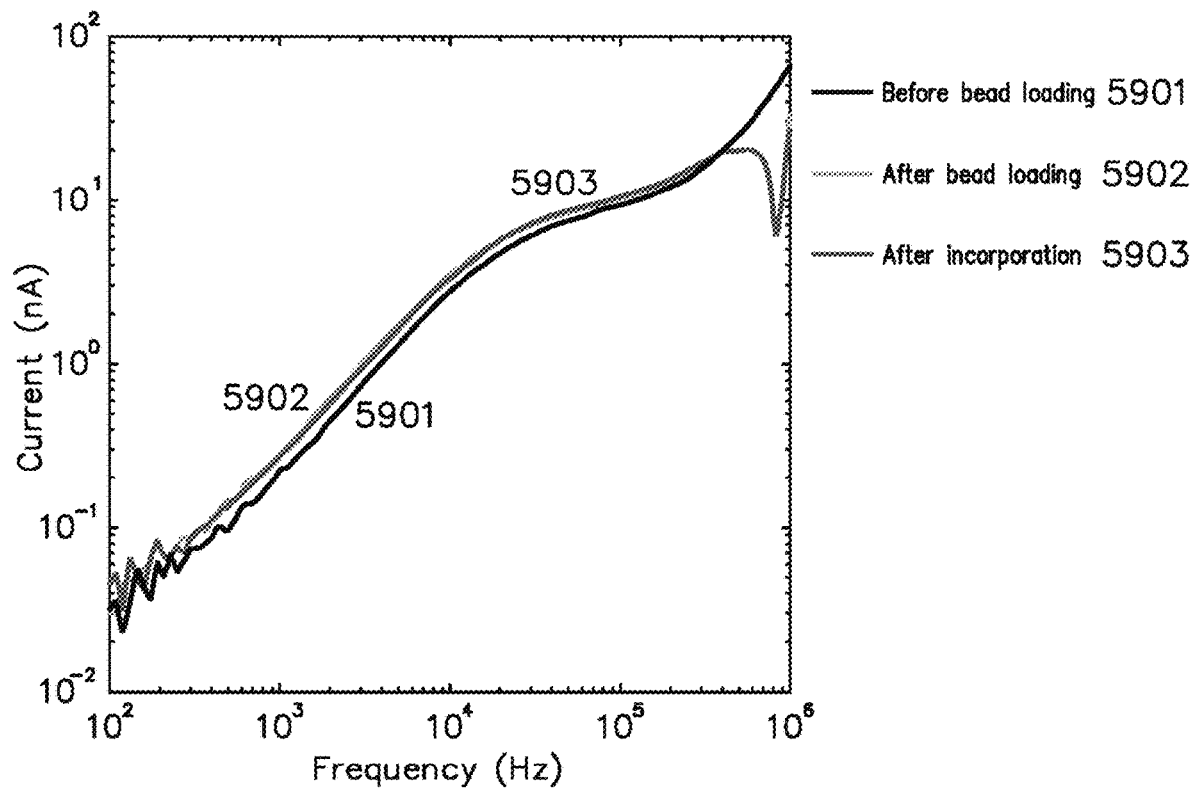
FIG. 59 is a graphic depiction of example electrode operation.
Figure 60:
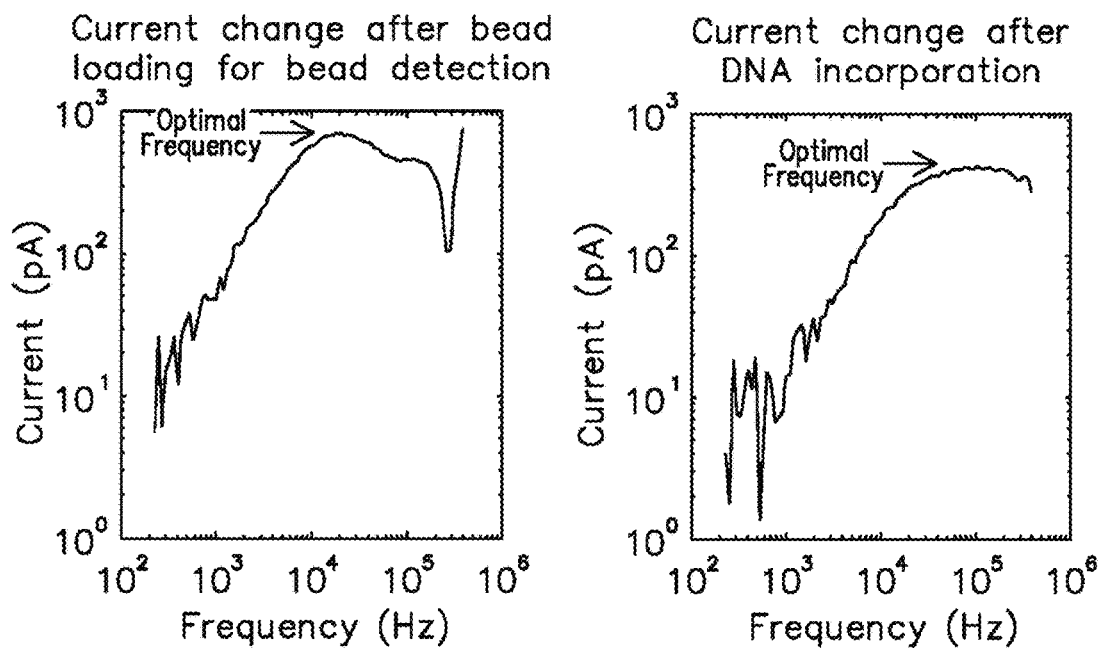
FIG. 60 is a set of graphic depictions of example electrode operation.

In some embodiments, the frequency response of the sensors (e.g., sensors comprising one or more electrodes) may be measured using frequency sweeps of the applied voltage. As shown in an example of FIG. 57, the flat region of the curve (between the vertical dashed lines) represents an example frequency region that a sensor may operate in a more resistive/conductive modality when measuring sample in varied buffer concentrations. FIG. 58 shows an example of the ratio of currents measured in a sensor when samples are measured in buffers of different concentrations. Example optimal operating frequencies (e.g., 10 kHz~40 kHz, 30 kHz~80 kHz, 60 kHz~150 kHz, 300 kHz~650 kHz, 800 kHz~1.2 MHz, 1.1 MHz~2.5 MHz, etc.) are shown between the dashed vertical lines. Each trace in FIG. 58 represents an individual sensor from which measurements were obtained. FIG. 59 displays example currents measured at various frequencies for sensors before bead loading 5901, after bead loading 5902, and after nucleic acid incorporation events (e.g., a 61-base pair incorporation in FIG. 59) 5903. Frequency response for each of the events 5901, 5902, and 5903 can be estimated from the plots. FIG. 60 shows graphic depictions of an example of change in frequency response due to a reaction (right panel) (e.g., dNTP incorporation or DNA extension) or change in the fluidic environment adjacent to a sensor (e.g., bead loading) (left panel). In some embodiments, a change in frequency response can be used for detection. In some embodiments, selective frequency points can be used as a representation of a whole frequency response for the purpose of detection (e.g., dual or multi-frequency schemes). In some cases, there can be an optimal frequency of operation for a given detection parameter.

In some examples, a sensor may be constructed of graphene or another semiconductor that has low density of states. Such materials may be used instead of silicon where desired and can also be used to construct a resistor. In some cases, the sensitivity of a sensor constructed of such materials may be generally increased, as a small modulation of the sensor's charge may result in larger changes in its conductivity or capacitance. In some cases, less density of states of materials used to construct a sensor can result in higher signal to noise ratios and signal level. In some embodiments, a sensor may be a nanosensor, such as, for example, a NanoBridge sensor.

Electrode-Magnet Configuration

Electrode and magnets may be arranged in a variety of configurations depending upon the particular device and or uses of a device desired. For example, an array may include magnetic features in order to facilitate more efficient capture of carriers, such as for example beads. In some embodiments, there may be one bead associated with each pixel, and each pixel may have one electrode and one magnetic element. The electrode and magnet may be configured such that the electrode is located on top of the magnetic element or below the magnetic element. In some embodiments, an array pixel may comprise an electrode with a magnetic element located underneath the electrode. A carrier (e.g., bead) may rest on top of the electrode-magnet structure.

In some cases, the magnetic element may be covered by a thin layer of material, such as, for example, a thin layer of dielectric material, gold, and/or platinum. Such a layer of material may help to reduce corrosion of the magnet that can occur due to exposure to the surrounding environment, such as for example buffer conditions in the solution.

In some cases, an adhesion layer may be deposited below or on a magnetic element prior to its deposition on an array. The adhesion layer may have, for example, a "bar" shape. The adhesion layer may consist of, for example, Chromium, Titanium, or another adhesive material. This adhesive layer may be about 1, 2, 3, 4, 5, 6, 7, 8, 9, 10, 11, 12, 13, 14, 15, 20 nm, or more in thickness or may be another thickness. The bar may be magnetized through sputtering of a magnetic layer. The magnetic layer may consist of, for example, iron, nickel or cobalt, or combinations thereof, or any other magnetic material. The sputtered magnetic layer may be more or less than, for example, 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 150 nm, 200 nm, 250 nm, 300 nm, 350 nm, 400 nm, 410 nm, etc. in thickness.

Figure 30:
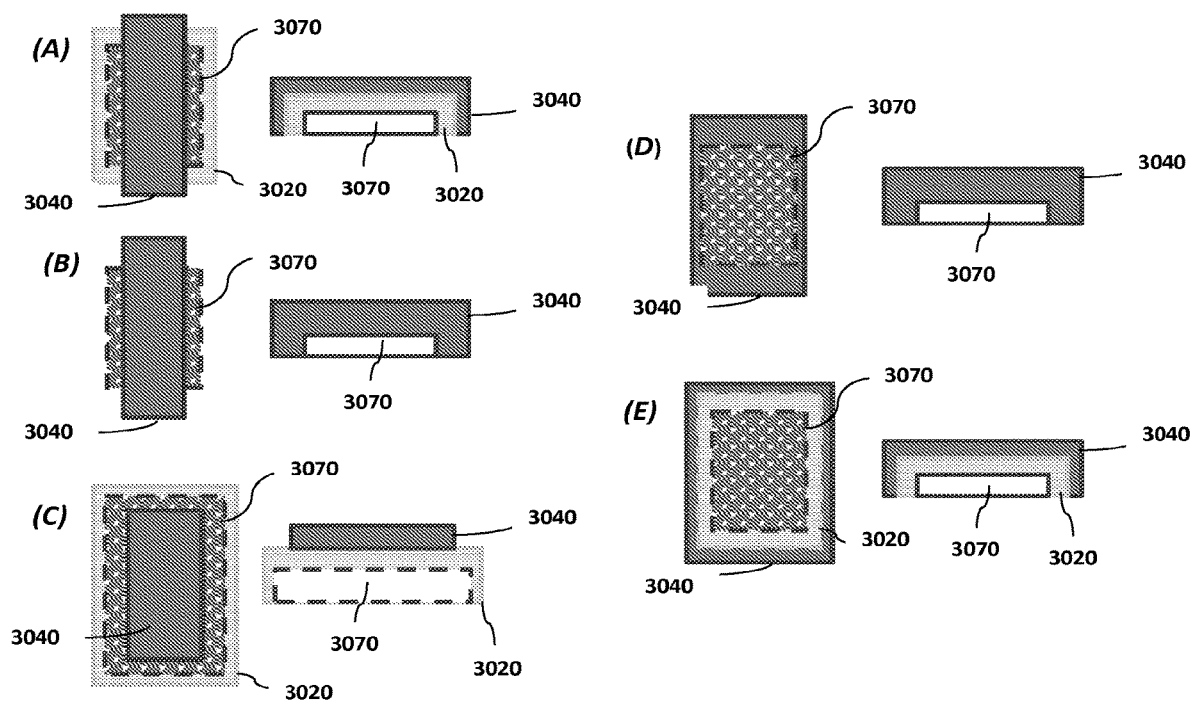
FIG. 30, panels "(A)"-"(E)", are schematics of magnetic element-electrode configurations.

FIG. 30, panels "(A)"-"(E)", show various examples of magnetic element-electrode configurations. As shown in FIG. 30, panels "(A)"-"(E)", exemplary embodiments include, but are not limited to: FIG. 30, panel "(A)", A magnet 3070 covered by a thin dielectric layer 3020 with an electrode layer 3040 on top of dielectric layer 3020. In some embodiments, electrode 3040 may have a greater length than the dielectric layer 3020 and/or the electrode 3040; FIG. 30, panel "(B)", Some portion of magnet 3070 may be covered directly by electrode 3040 with no dielectric layer 3020; FIG. 30, panel "(C)", Magnet 3070 may be covered by dielectric layer 3020, and electrode 3040 can be smaller than the magnet 3070 that rests on top of dielectric layer 3020 FIG. 30, panel "(D)", Electrode 3040 may cover all of magnet 3070, with no dielectric layer 3020 associated with the structure; FIG. 30, panel "(E)", Magnet 3070 may have electrode 3040 directly on top where electrode 3040 may cover all of magnet 3070 and the thin dielectric layer 3020 can be sandwiched between electrode 3040 and magnet 3070.

Figure 31:
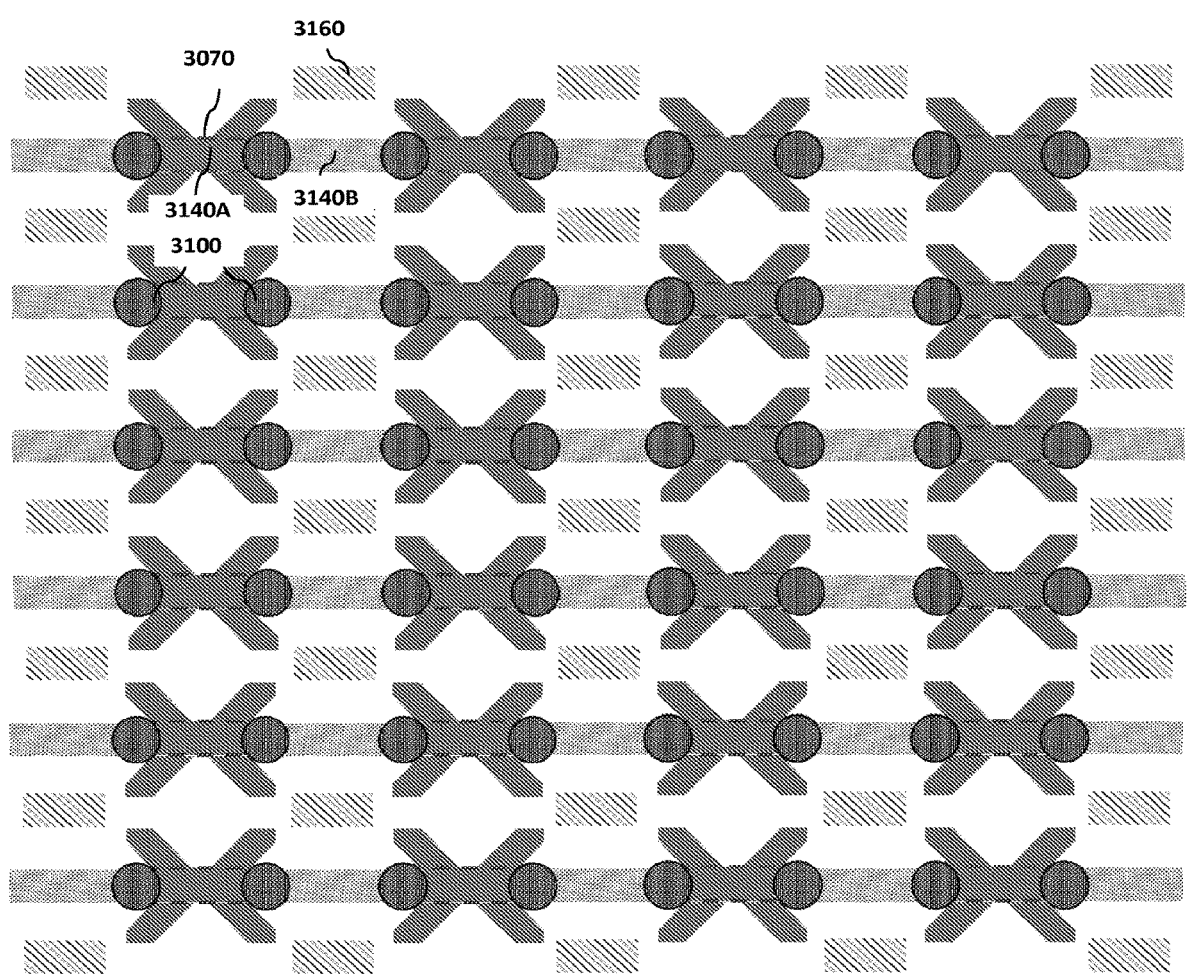
FIG. 31 is a schematic of example electrodes in an array.

In a further embodiment, there may be other electrodes associated with the pixel in addition to an electrode-magnet layered structure, an example of which is shown in FIG. 31. FIG. 31 shows an example array of pixels, wherein each pixel comprises a modified-X shaped electrode 3140A and a magnetic element 3070 (represented by the dashed lines) located underneath the electrode 3140A. Electrode 3140A is proximate to bead 3100. Rectangular electrodes 3140B and ground electrodes 3160 are also associated with each pixel. The modified X-shape electrodes 3140A may be transmitter electrodes, or they may be receiver electrodes. In a further embodiment, the rectangular electrodes 3140B may be the transmitter electrodes, or they may be the receiver electrodes.

Figure 32:
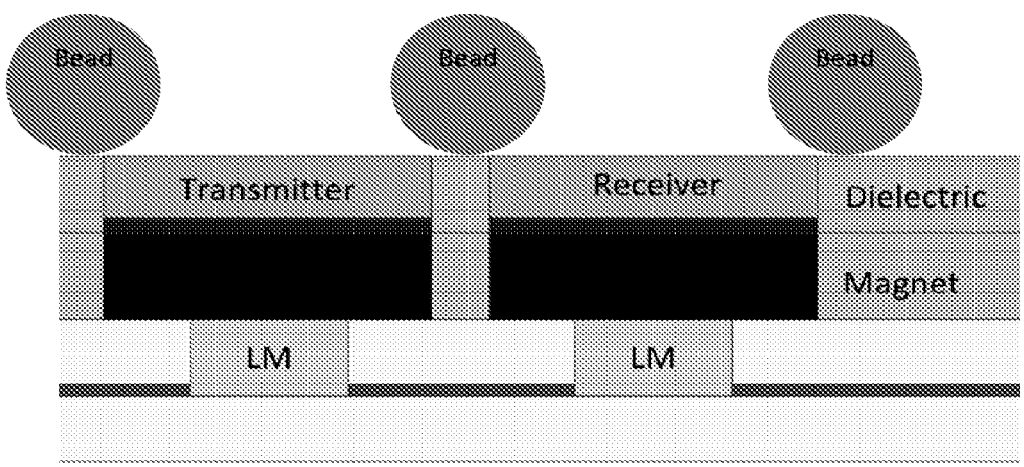
FIG. 32 is a schematic of an example configuration of elements of an array.

In some examples, as shown in an example side view in FIG. 32, the magnetic element may be a bar magnet (represented by a black box in FIG. 32), in some cases with a long rectangular shape or other shape. The magnetic layer may be used as a connection via between CMOS electronics and a post-CMOS electrode. In some cases, the bar magnets of the array may have a small gap in between magnets where carriers (e.g., beads) may be captured by the magnetic element.

Figure 33:
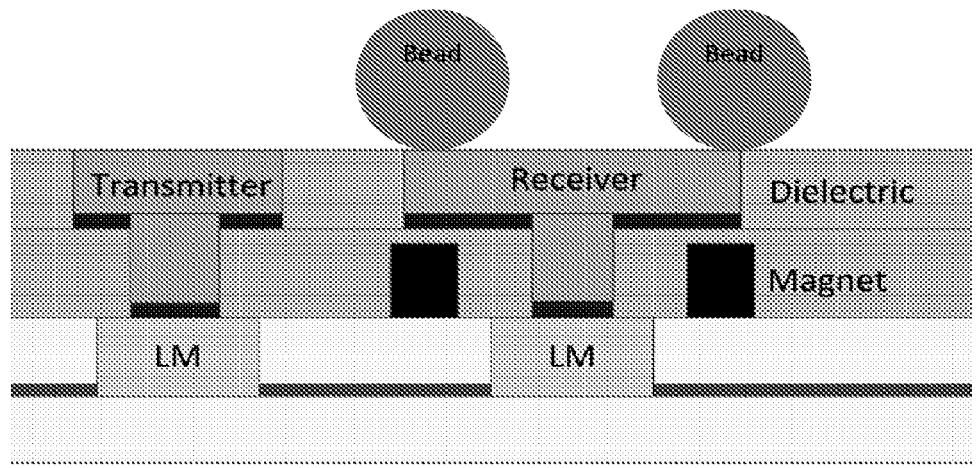
FIG. 33 is a schematic of an example configuration of elements of an array.

In some examples, as shown in a side view in FIG. 33, a magnetic element in an array pixel may be a dot magnet. In such cases, a carrier (e.g., bead) may be captured by the magnetic element such that it is located proximate to a single dot magnet. Moreover, a dot magnet of a pixel may be proximate to one end of a receiver electrode. In some cases, a dot magnet may be located between a transmitter and a receiver electrode. The transmitter and receiver electrodes can be connected to CMOS electronics through vias or another suitable route.

Figure 34:
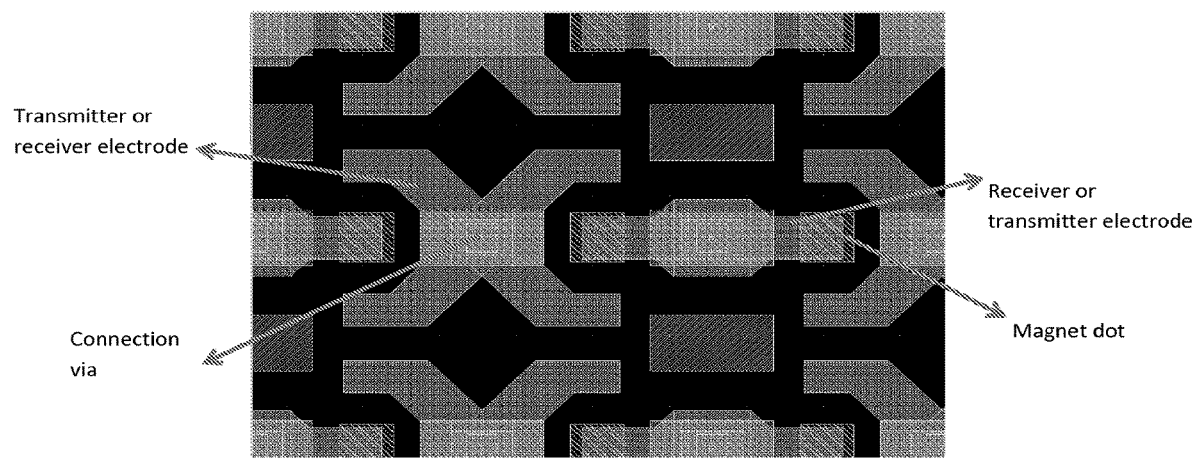
FIG. 34 is a schematic of an example configuration of elements of an array.
Figure 35:
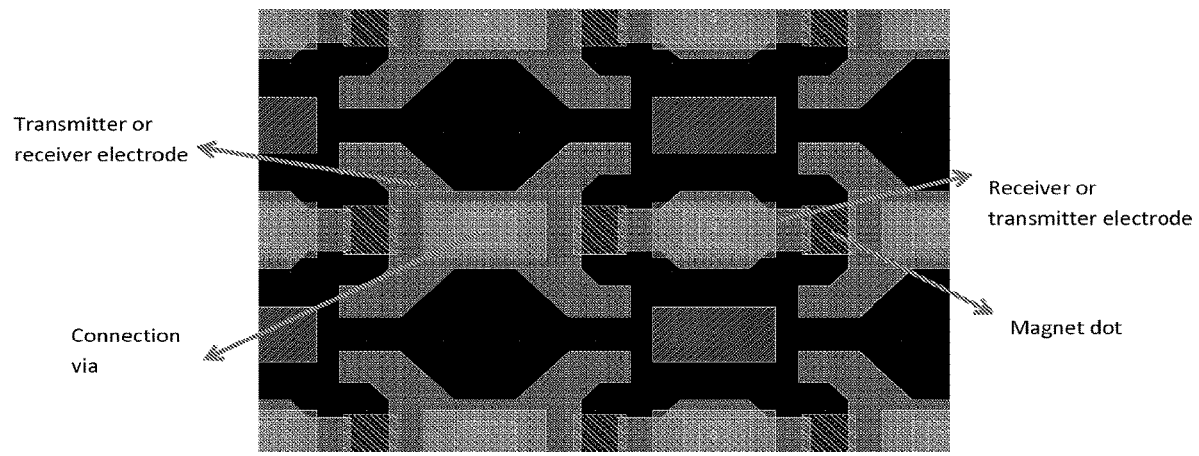
FIG. 35 is a schematic of an example configuration of elements of an array.

FIGS. 34 and 35 show additional configurations of dot magnetic elements an electrodes. FIG. 34 shows a top view of an example dot magnet configuration where the dot magnet is located proximate to one end of the receiver/transmitter electrodes. FIG. 35 shows a top view of a dot magnet configuration where the dot magnet is located between the transmitter/receiver and receiver/transmitter electrodes.

Row/Column Multiplexing

The output signal from an individual receiver electrode may be measured individually, but potential problems can arise, however, with this type of configuration because the high data readout rate that results from this setup may place excessive demands on a readout system. Furthermore, such a setup may lead to an increased number of electronics, such as for example, electrical lines connecting each receiver electrode to the output circuitry. In some embodiments, the receiver electrodes may be multiplexed to allow for a reduced readout rate, increased signal to noise ratio as a result of reduced cross-talk, and fewer electronics.

Figure 41:
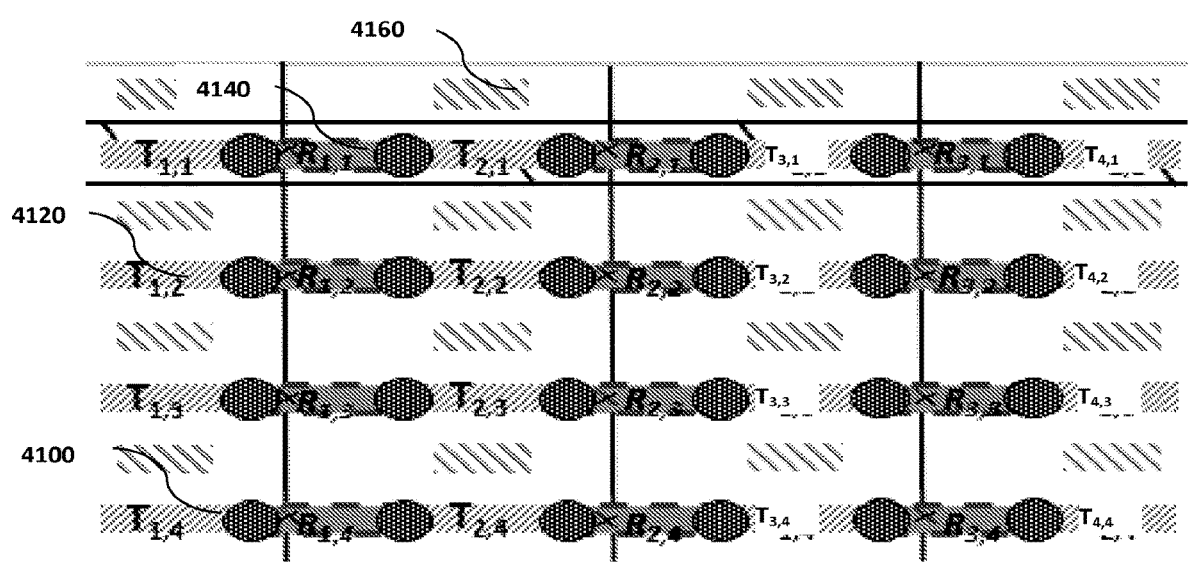
FIG. 41 is a schematic of example electrode configurations in an array.

FIG. 41 shows, in one embodiment, an array where there is multiplexing with respect to both rows and columns in the array. In some embodiments, the receiver electrodes may be multiplexed according to their corresponding column or row. Thus, the output signal can be read on a per column or per row basis, as opposed to the readout associated with individual sensors. In a further embodiment, the receiver electrodes may be configured such that every $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, $20^{th}$, $n^{th}$, etc. receiver electrode or all the receiver electrodes in a column or row are connected.

In some embodiments, all the receiver electrodes in a column or row may share the same electronics. In some cases, by transmitting only on one row or column, then only the receiver electrodes on the active rows or columns will detect signals. Close proximity of receiver electrodes in the same column or row, however, can result in increased cross-talk current between receiver electrodes. In some cases, a transmitter electrode in one row may transmit. In such cases, the receiver electrodes from adjacent rows as well as the active row can contribute to the receiver signal. To mitigate and reduce receiver electrode crosstalk, every other receiver electrode in the same column may be connected to the same receiver line. In some embodiments, every $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, $20^{th}$, $n^{th}$, etc. receiver electrode may share the same receiver line. In some cases, receiver lines from the same column or row can be multiplexed into a single receive circuitry without impacting readout rate. Furthermore, in cases where the same receiver circuitry is used across multiple columns or rows, the result can be a reduced number of receive electronics, sometimes at the expense of reduced readout rate.

An example configuration of electrode multiplexing is shown in FIG. 41. As shown in FIG. 41, beads 4100 share the same receiver electrode 4140 and the receiver electrodes 4140 are configured such that every electrode in a column is connected to the same line. This is illustrated in the figure by an "X" designation each time a receiver electrode 4140 is connected to the line. Optionally, ground electrodes 4160 may be used in order to help reduce crosstalk between pixels.

In a further embodiment, in FIG. 41 the transmitter electrodes 4120 may be multiplexed on a per row basis. The transmitter electrodes may be configured such that every $2^{nd}$ (shown) transmitter in a row is connected to the same line, or in other embodiments every $3^{rd}$, $4^{th}$, $5^{th}$, $10^{th}$, $20^{th}$, $n^{th}$ etc. transmitter electrodes may be connected to further reduce the crosstalk between pixels.

Figure 42:
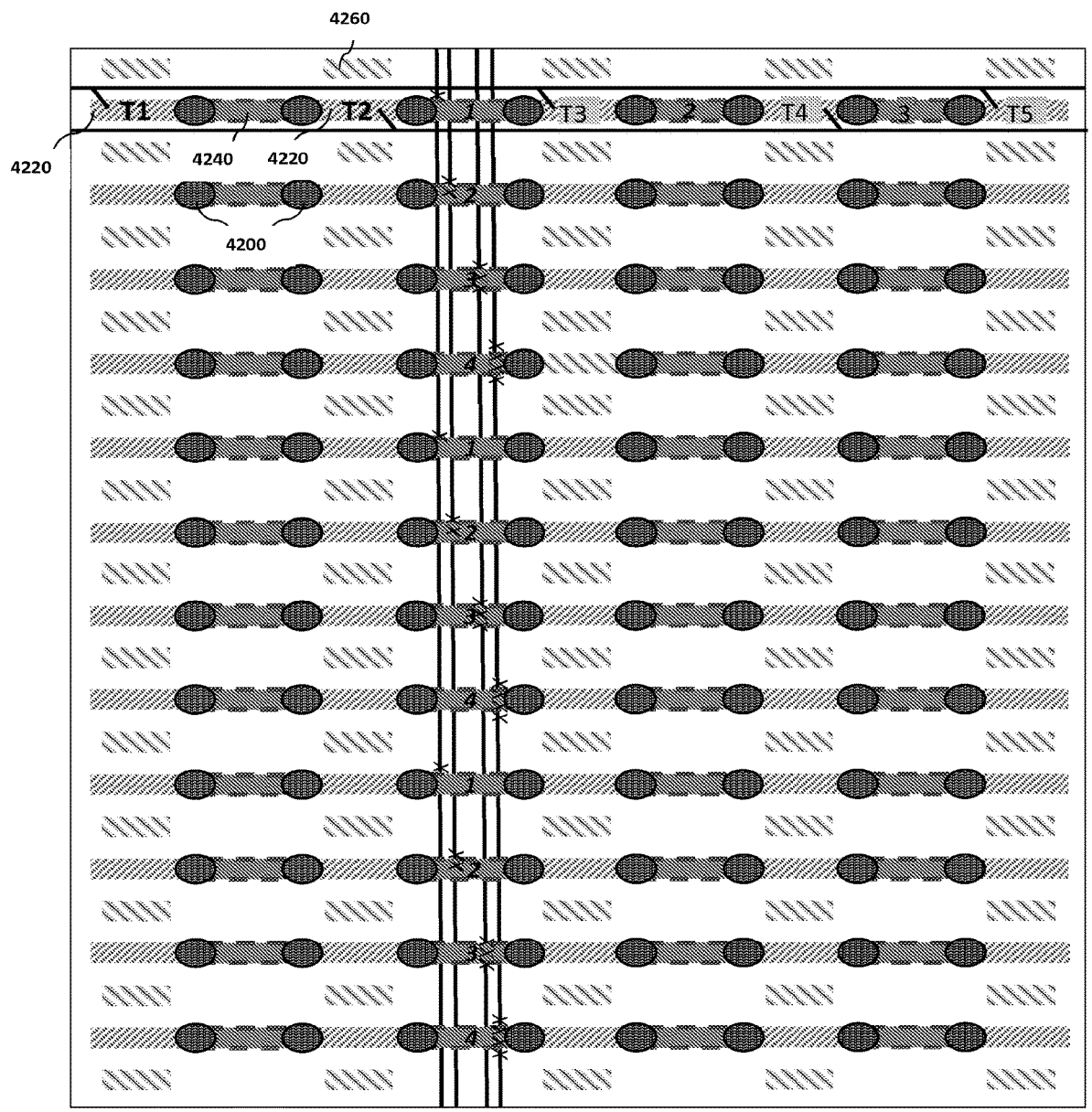
FIG. 42 is a schematic of example electrode configurations in an array.

An example configuration of electrode multiplexing is shown in FIG. 42. As shown in FIG. 42, beads 4200 sharing the same receiver electrode 4240 and the receiver electrodes 4240 are configured such that every $4^{th}$ electrode in a column is connected to the same line. This is illustrated in the figure by an "X" designation each time a receiver electrode 4240 is connected to the line. For example, in FIG. 42 when each electrode "2" is connected to the same line, this is designated by "XX", every third electrode connection is designated by "XXX", etc. In a further embodiment, when each receiver electrode "2" is activated, receiver electrodes "1", "3", and "4" may be used as ground electrodes. Optionally, ground electrodes 4260 may be used in order to help reduce crosstalk between pixels.

In a further embodiment, in FIG. 42 the transmitter electrodes 4220 may be multiplexed on a per row basis. The transmitter electrodes may be configured such that every $2^{nd}$, $3^{rd}$, $4^{th}$, $5^{th}$, $10^{th}$, $20^{th}$, $n^{th}$ etc. transmitter electrodes are connected.

Figure 43:
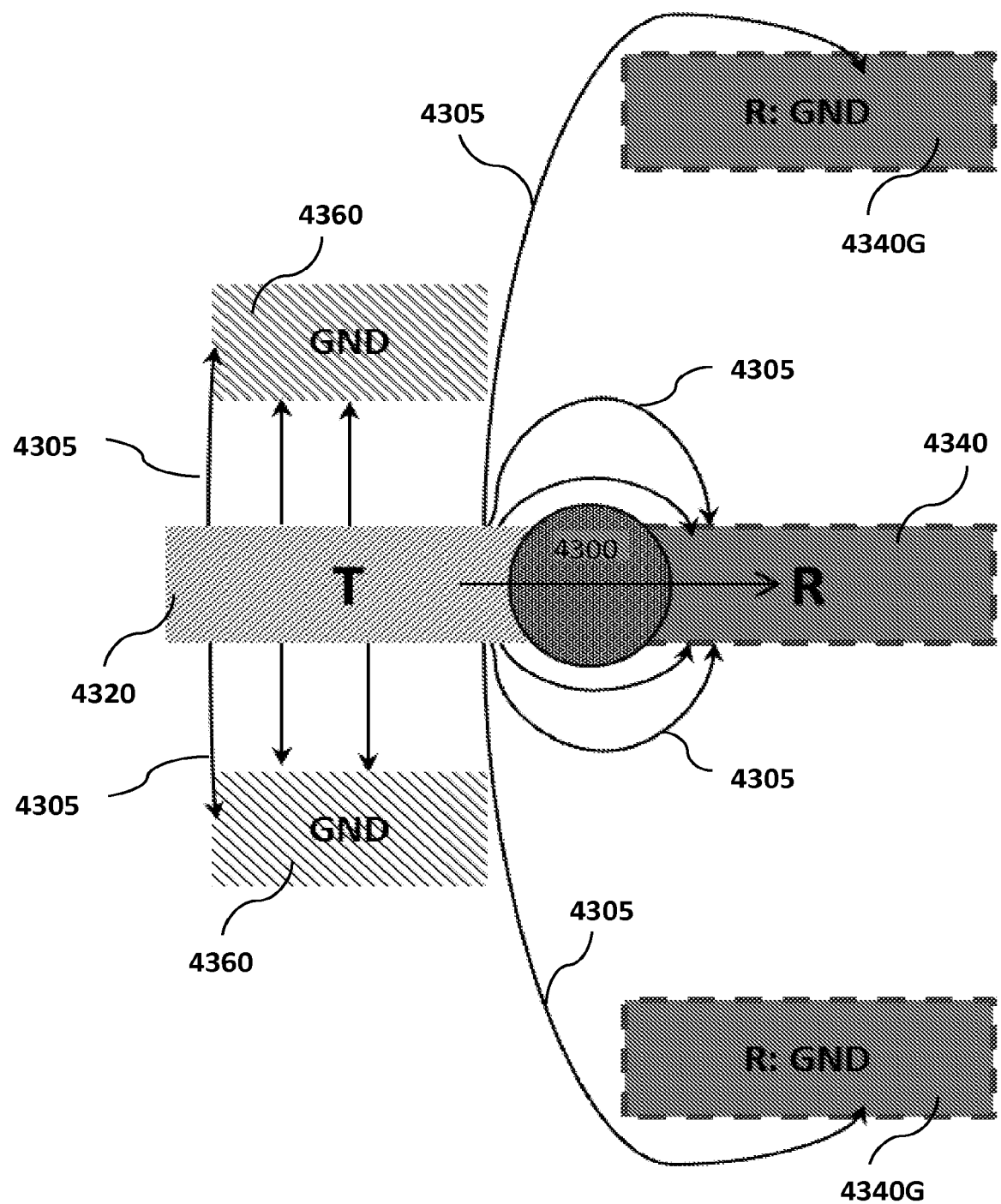
FIG. 43 is a schematic of example electrodes at a pixel of an array.

In some embodiments, as shown in FIG. 42, the transmitter electrodes 4220 may be connected such that every fifth electrode is connected to the same line. Multiplexing and a reduction in cross-talk may be achieved by, for example, activating electrodes (e.g., T1 electrodes in FIG. 42) on the line first during time phase 1 and measuring the signal from nucleotide incorporation events via the receiver electrode 4240. At this time, electrodes on another line (e.g., T2 electrodes shown in FIG. 42) may be grounded. After the signal detection is complete, the T1 electrodes may be grounded and time phase 2 may commence wherein the T2 electrodes may be activated such that the incorporation event on or around the other bead can be detected. The pattern may be continued (e.g., T3 electrodes activated during time phase 3, T4 electrodes activated during time phase 4, T5 electrodes activated during time phase 5) for the T3, T4, and T5 electrodes. An example of current flow in an individual pixel is shown in FIG. 43. As shown in FIG. 43, the path of the current 4305 travels from the activated transmitter electrode 4320 to the activated receiver electrode 4340 as well as to the ground electrodes 4360 and receiver electrodes set to ground 4340G.

Figure 44:
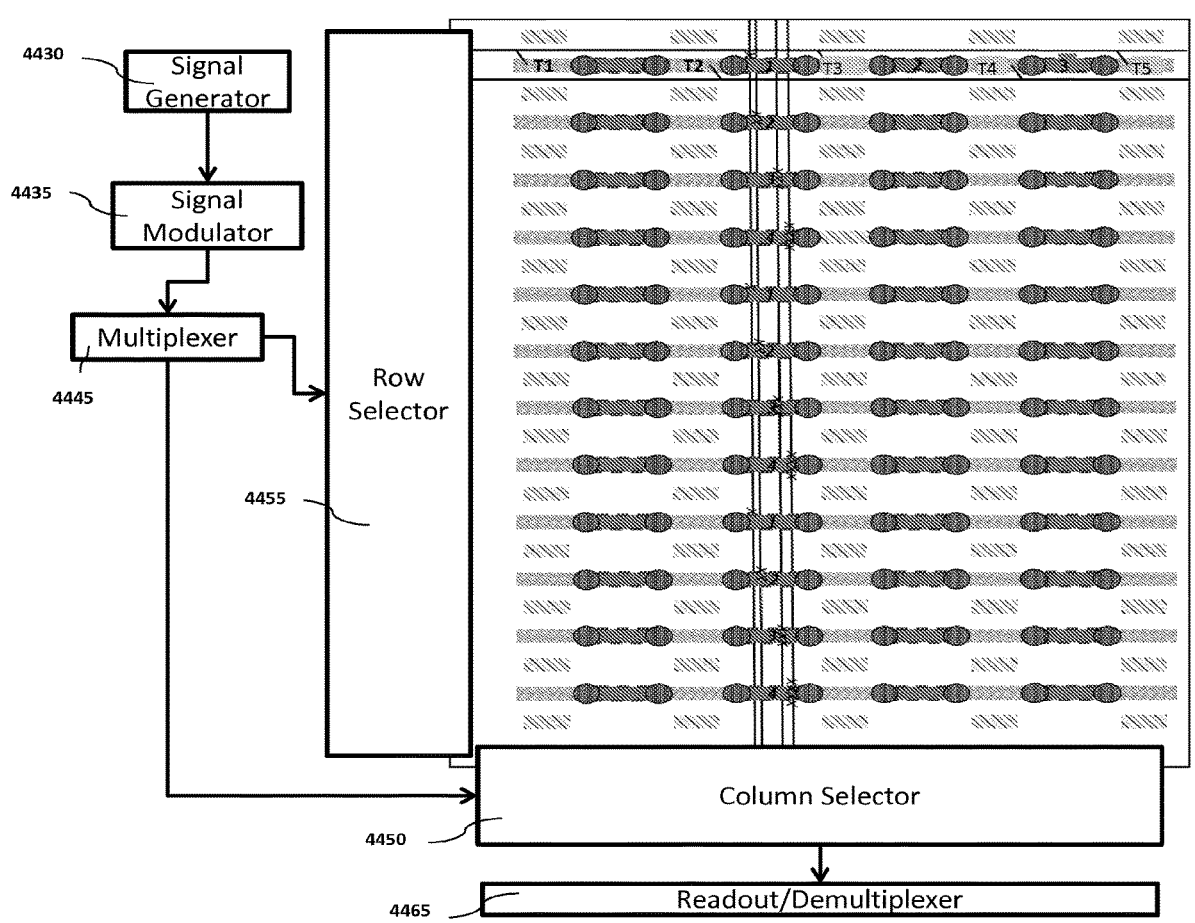
FIG. 44 is a schematic of an example array coupled to example control and readout modules.

In some embodiments, individual rows and/or columns may be activated via circuitry on the periphery of the array. An example of an array in communication with periphery electronics is shown in FIG. 44. As shown in FIG. 44, a signal generator 4430 sends a signal to a signal modulator 4435 and finally to a multiplexer 4445. Column multiplexing may be controlled via a column selector 4450 and the row multiplexing may be controlled via a row selector 4455. The row and/or column selectors may select one or more of the rows and/or columns, respectively, to be activated while the other rows and/or columns are inactivated or set to ground. The data output from the rows and columns may be sent to demultiplexer/readout circuitry 4465.

Figure 45:
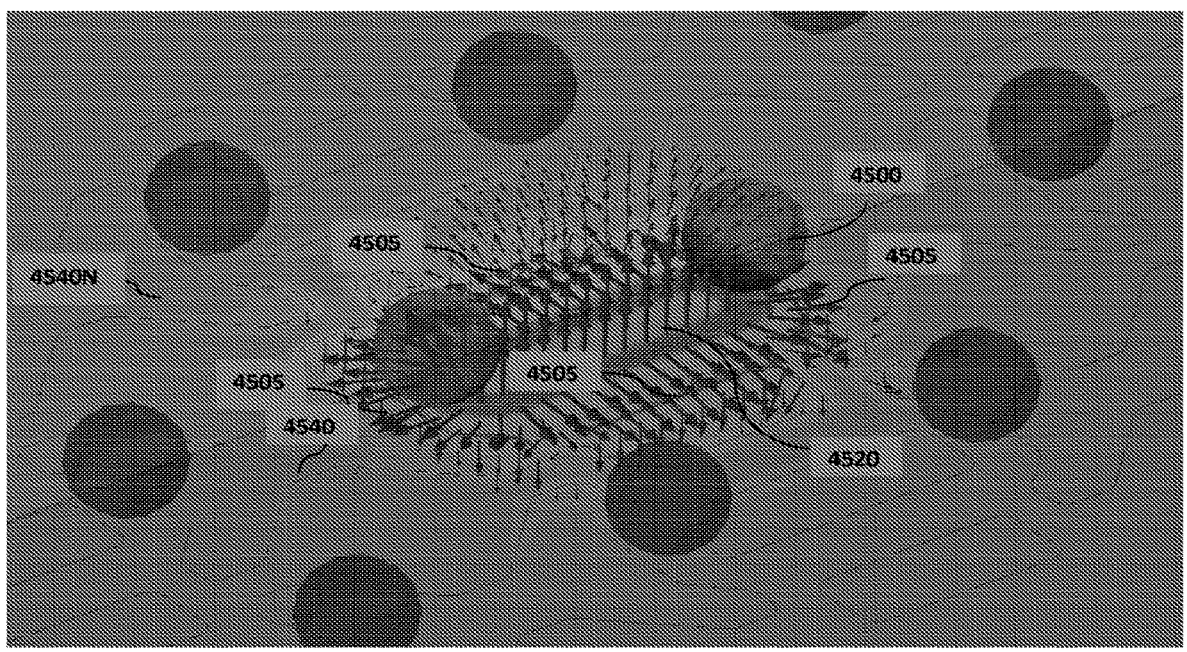
FIG. 45 is a schematic of example electrodes of an array.

In some embodiments, ground electrodes as well as inactivated transmitter and receiver electrodes may be used to reduce cross talk and noise. This reduction in cross talk and noise may be achieved by preventing current from travelling from activated transmitters to receiving electrodes outside of their own pixel. Using this configuration, the activated receiver only receives current from its corresponding transmitter. In addition, undesired current through a bulk solution in contact with a pixel may be minimized by using a ground configuration. In some embodiments, using this configuration, most of the current 4505 through the bulk solution has a shorter path to the ground electrode rather than to the receiver electrode of a neighboring pixel 4540N. Thus, in some cases, most of the current 4505 detected by the receiving electrodes 4540, therefore, can come from a bead 4500 and the incorporation events around the bead 4500, as shown in an example array of FIG. 45. The ratio between the current due to incorporation events to the base sensor current can increase, which can simplify the electronics that may be sufficient for detection of incorporation events.

In another embodiment, multiplexing may be synchronized by the flow of buffer and reagents. This may decrease the reading time required by the system.

Reusability & Monitoring

In some embodiments, amplification and/or sequencing arrays may be reused by the removal of carriers (e.g., beads) from the array. Removal may be done, for example, by the application of an external magnet field, which may result from the movement of a permanent magnet or the activation of a magnet, to pull, move or dislodge carriers from wherein they are held in an array. Alternatively or in addition, carriers may be released through chemical and/or enzymatic means.

After removing the carriers from an array, it may be possible to reuse the array by bringing new carriers (or regenerated carriers previously removed) into the array, often again in a one to one correspondence with sensors in the array. In some embodiments, reusability of an array can be monitored or controlled by counting the number of times the array is used. Counting may be accomplished in various ways. For example, if an array uses electromagnets, the number of times the array is used can be determined from electrical control of the magnet. In another example, a sensor (e.g., an electronic sensor) can be used to count the number of times the array has been used. In another example, monitoring a particular species (e.g., a primer or adaptor) used for system operation, amplification, and/or sequencing can be used to count the number of times the array has been used. In another example, a specific buffer, reagents, etc. with or without a specific "starting primer" or "starting adaptor" can be used.

A reusable amplification and sequencing system may provide a number of advantages. The cost of sequencing has a number of parts. For sequencing using electronic sensors, one of the major costs is the cost of the processed silicon itself, that is, the sensor. This may be particularly true if the sensor is not re-useable. The magnetic and/or electrostatic array design may allow for reuse without the need for wells fairly, as nucleic acids or other species can be configured not to be bound (e.g., attached a carrier such as a magnetic bead) to a sensor, and the carriers can be easily removed, for example, by reducing or removing the magnetic field which holds the carriers in place. In other embodiments, beads may be removed by increasing the flow rate or using other types of fields (e.g., electric).

Selective Bead Retention/Removal

Figure 6:
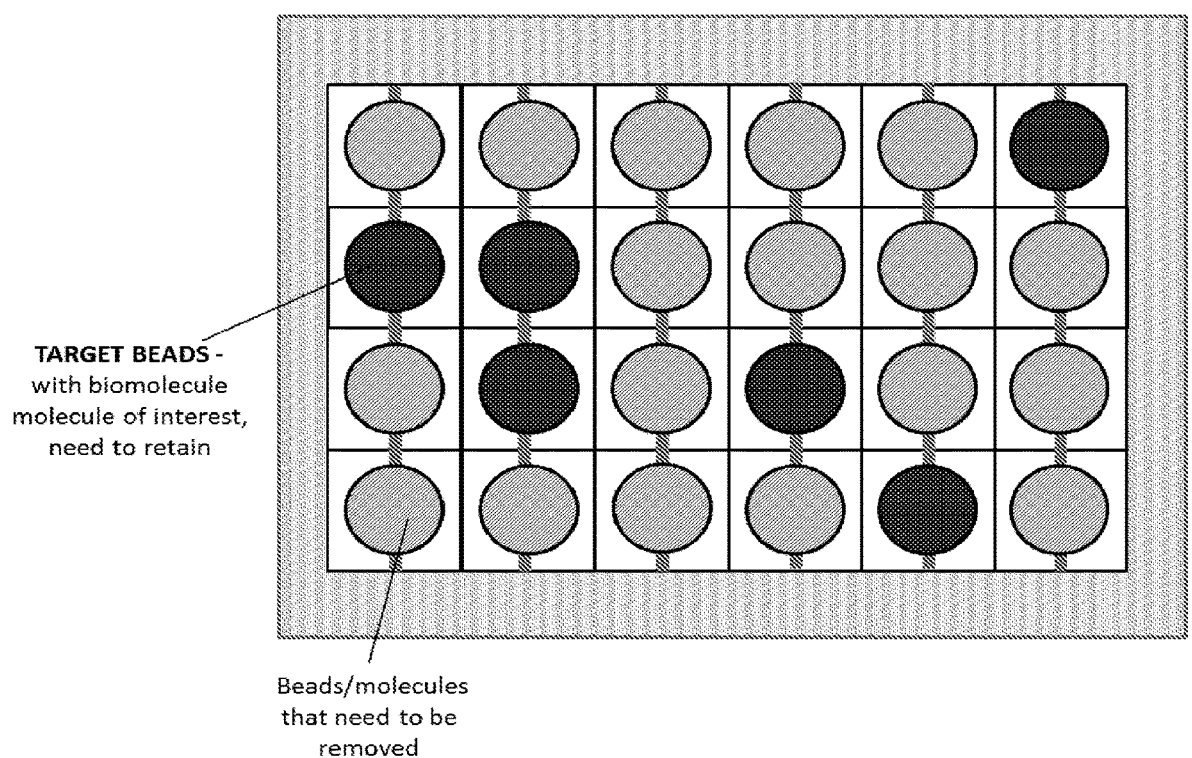
FIG. 6 shows an example sensor array with carriers immobilized to the sensor array.

In certain situations, it may be desirable, to be able to selectively retain or repel one or more carriers, such as beads, as shown in FIG. 6. Such methods, as described below, may allow for selective targeting of carriers to pixels. In some embodiments, carriers that are bound to a certain biomolecule (e.g., nucleic acid) of interest may be selected and either retained or removed at appropriate position(s) of an array as described below.

Figure 7:
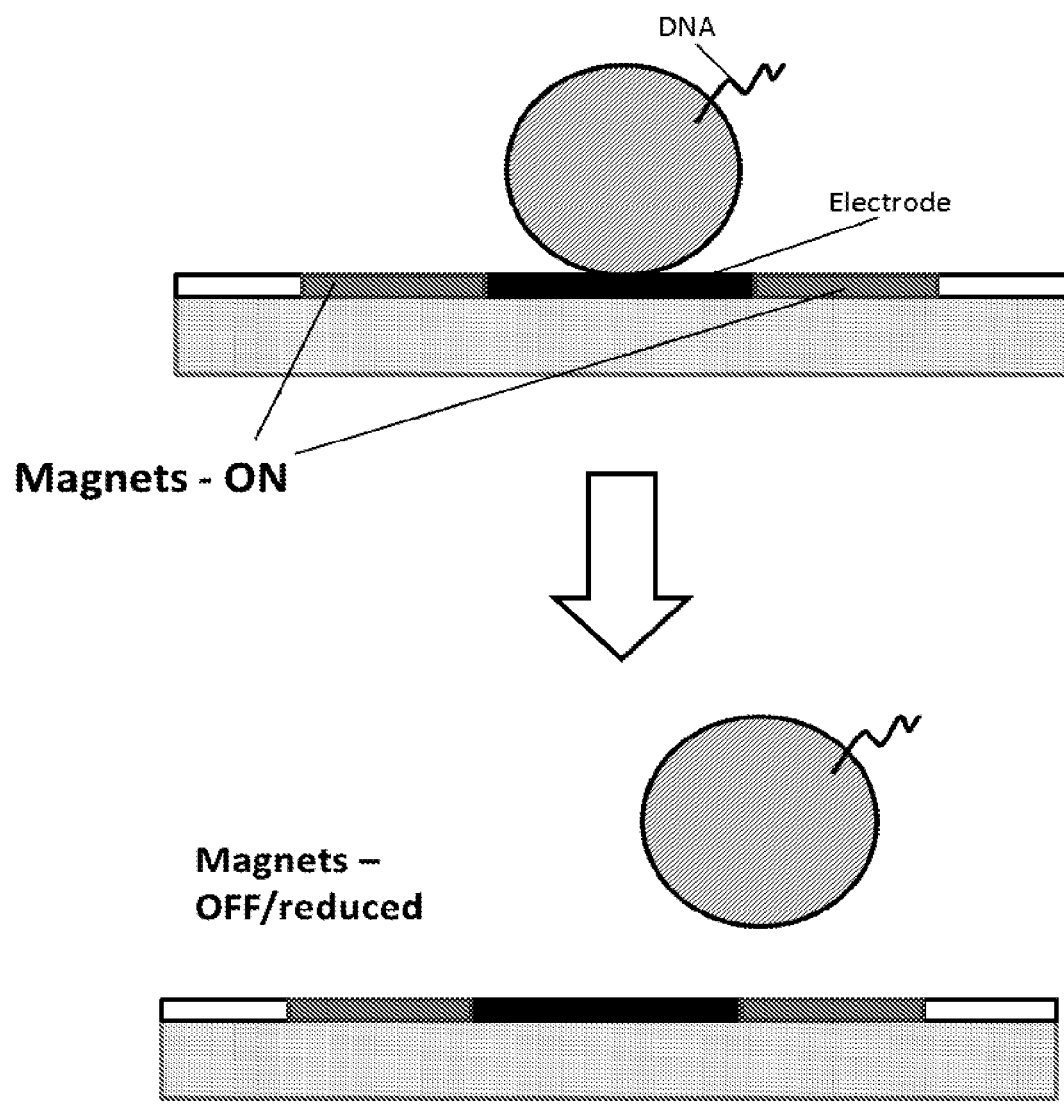
FIG. 7 is a schematic of an example method for removing an immobilized carrier from a sensor array.

In some embodiments, carriers may be selectively removed from an array pixel by modulation of the magnetic field at the desired pixels. For example, as shown in FIG. 7, a magnetic element associated with a pixel may comprise an electromagnet and the electromagnetic field may be reduced or turned off to a release an associated carrier (e.g., a bead as shown in FIG. 7). In some cases, the electromagnet may comprise a magnetic core surrounded by a looped, electrically conductive material. The electrically conductive material may be insulated from the core. In some cases, the magnetic element may be ferromagnetic or paramagnetic. Where a paramagnetic magnetic element is used, a magnetic field may be induced in the magnetic element through the application of an external magnetic field.

Figure 8:
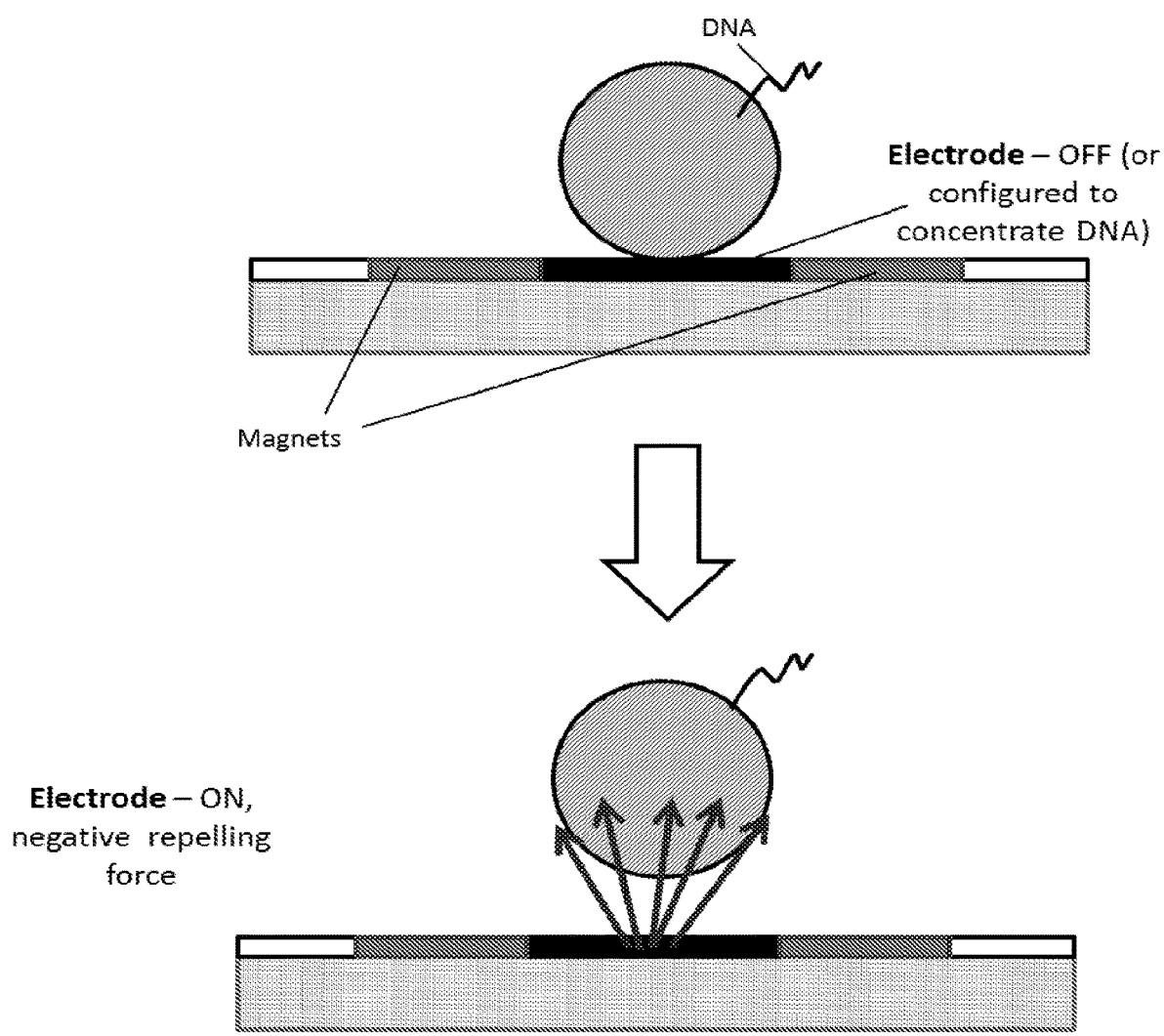
FIG. 8 is a schematic of an example method for removing an immobilized carrier from a sensor array.

In another example shown in FIG. 8, an electrostatic dislodging or repelling force may be used to dislodge a carrier from a desired array pixel. A pixel may be configured such that one or more electrodes are located underneath the carrier (e.g., a bead shown in FIG. 8). Charge exerted by the electrode may be reversed, increased, decreased, or turned on and off selectively depending on the desired effect on the carrier. The electrode may have, for example, a strong negative charge, and such strong negative charge repels the associated carrier away, as shown in FIG. 8. Electrodes used to dislodge a bead from a pixel may be those suitable for use in amplification and sequencing devices/methods described elsewhere herein.

Figure 9:
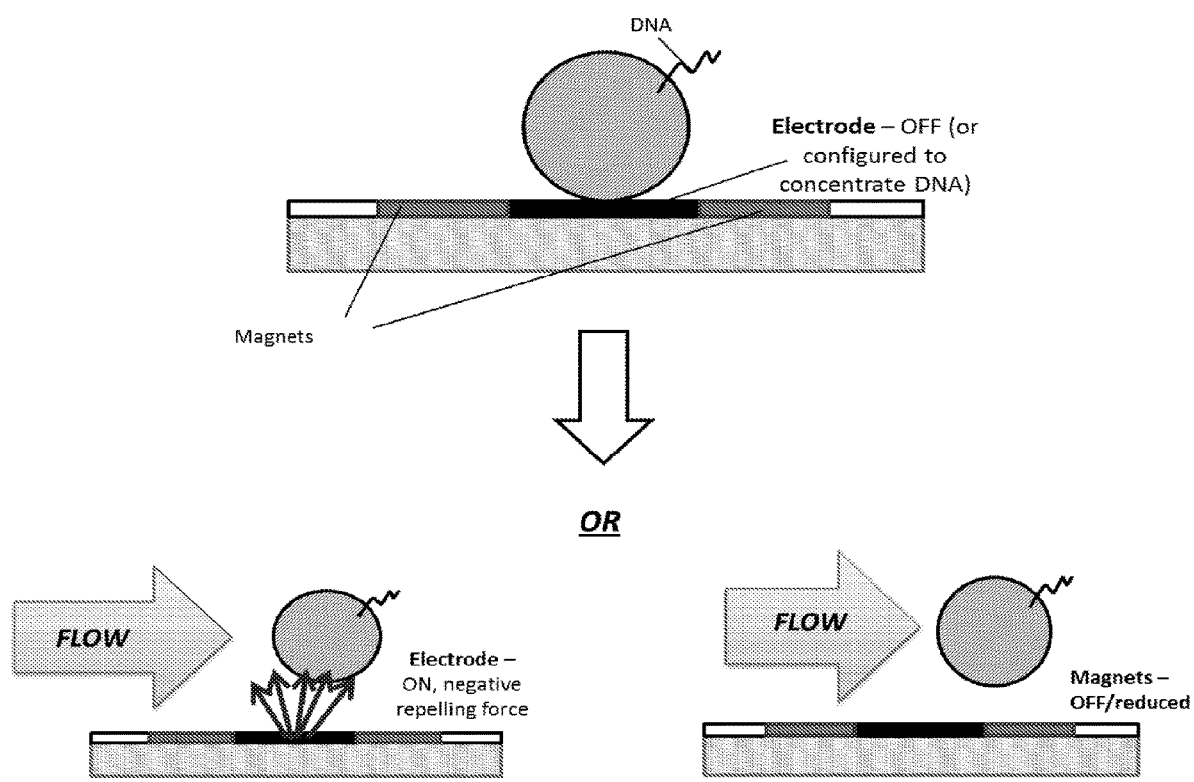
FIG. 9 is a schematic of an example method for removing an immobilized carrier from a sensor array.
Figure 10:
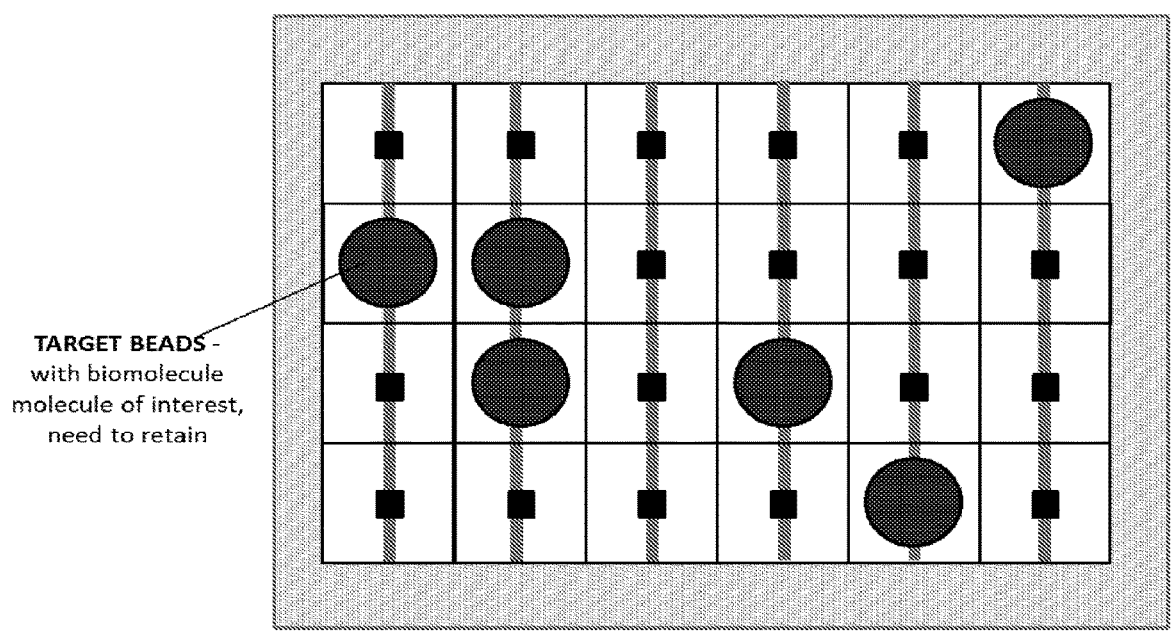
FIG. 10 shows an example sensor array with carriers immobilized to the sensor array.

In some cases, modulation of magnetic elements and/or electrodes at a pixel as described above may be combined with fluid flow through the array to dislodge certain beads. For example, the flow can be used after turning off or reducing the magnetic force on the associated carrier or after applying a dislodging force via an electrode. An example of a result of selective removal of carriers from the array shown in FIG. 9 is shown in FIG. 10. As shown in FIG. 10, desired beads are retained in desired pixels, with the rest of the beads removed from the array.

Methods for selective removal and/or retention of carriers may be used for identifying a molecule with a desired sequence from a pool of molecules in a sample. Such identification may be useful in identifying species that can be used for long DNA synthesis. Synthesizing long pieces of DNA can be important in a number of biotech applications. Constructing longer DNA typically includes the construction of longer pieces via the assembly of shorter pieces or by using shorter pieces to introduce desired changes into pre-existing longer pieces of DNA. Thus, identification of such shorter molecules with desired sequence from a pool of molecules in a sample can be useful in synthesizing long DNA. High-throughput sequencing provides a means for rapidly screening through pools of synthesized DNA molecules. If DNA can be directly recovered from a specific location of an array after sequencing, it may be possible to avoid many challenges (e.g., pipetting robots, bar-coding, cloning, etc.) associated with current approaches that use high-throughput or low-throughput sequencing methods now used to validate pools of synthesized molecules. The ability to choose a specific bead (with a specific DNA sequence) can allow for sequence-based targeted analysis.

In some embodiments, selective removal and/or retention of carriers may be used for more efficient and/or more selective carrier washing. Furthermore, selective removal and/or retention of carriers may enhance the effects of dislodging carriers via fluid flow, since fluid flow may not always be sufficient to remove carriers from the array.

Valve Systems and Minimizing Dead Volume

In some embodiments, it may be desirable to integrate a valve system as part of a flow cell, such as for example a sensor array in communication with flow channels, such as, for example, microfluidic channels. A valve system can enable the flow of samples and other materials to various sections of a flow cell, such that different samples may be used in different sections of a flow cell. In some cases, a valve system may be integrated adjacent to a flow cell, whereby the valve system and flow cell may form a sealing interface with each other. In some embodiments, a valve system and a flow cell can be located proximate to each other on the same mount, such as for example, the same microfluidic chip. A valve system can also include one or more waste valves such that fluids may be removed from the valve system prior to flowing into various sections of a flow cell. For example, if there is a significant amount of dead volume in the valve system, it can be desirable to remove fluid which may have an unacceptable level of cross contamination (e.g., reagents from a previous cycle) from a previous fluid.

In some embodiments, it may be desirable to integrate a valve device with the flow cell such that there may be various input channels, which can include inputs for reagents. For example, the various input channels may include channels for the four dNTPs (e.g., for DNA sequencing reactions), one or more buffer channels, salts channels, enzyme channels, and channels for other moieties that may be used for a desired reaction, such as the incorporation of nucleotides. Input channels may also be employed for various buffers and wash reagents, polymerase containing buffers, which may also contain salts and any other moieties needed for polymerization, reagents needed to strip any coatings from the flow cell, reagents which may be needed to re-coat the flow cell, buffers which also include a phosphatase, or other reagents.

In some embodiments, the valve device may be fabricated from polydimethylsiloxane (PDMS). In another embodiment the valve device can be fabricated from glass with magnetically or pneumatically activated elastomeric valves. In some embodiments, it may be desirable to bond a valve and a fluidics PDMS manifold to a silicon device. It can be desirable to increase the bonding strength between the PDMS and the silicon device, for example, to promote stability in the overall structure. In some embodiments, it may be desirable to use plasma activated PDMS to improve bond strength. As plasma treatments which have too much power or too much pressure may actually decrease the bond strength of PDMS to silicon, lower power levels and pressures can be used to address this potential issue. In one embodiment, it may be suitable to use a pressure between 500 mili Torr and 30 miliTorr and a power level between 10 and 60 watts while using, for example, a 790 series Plasma-Therm.

Figure 46:
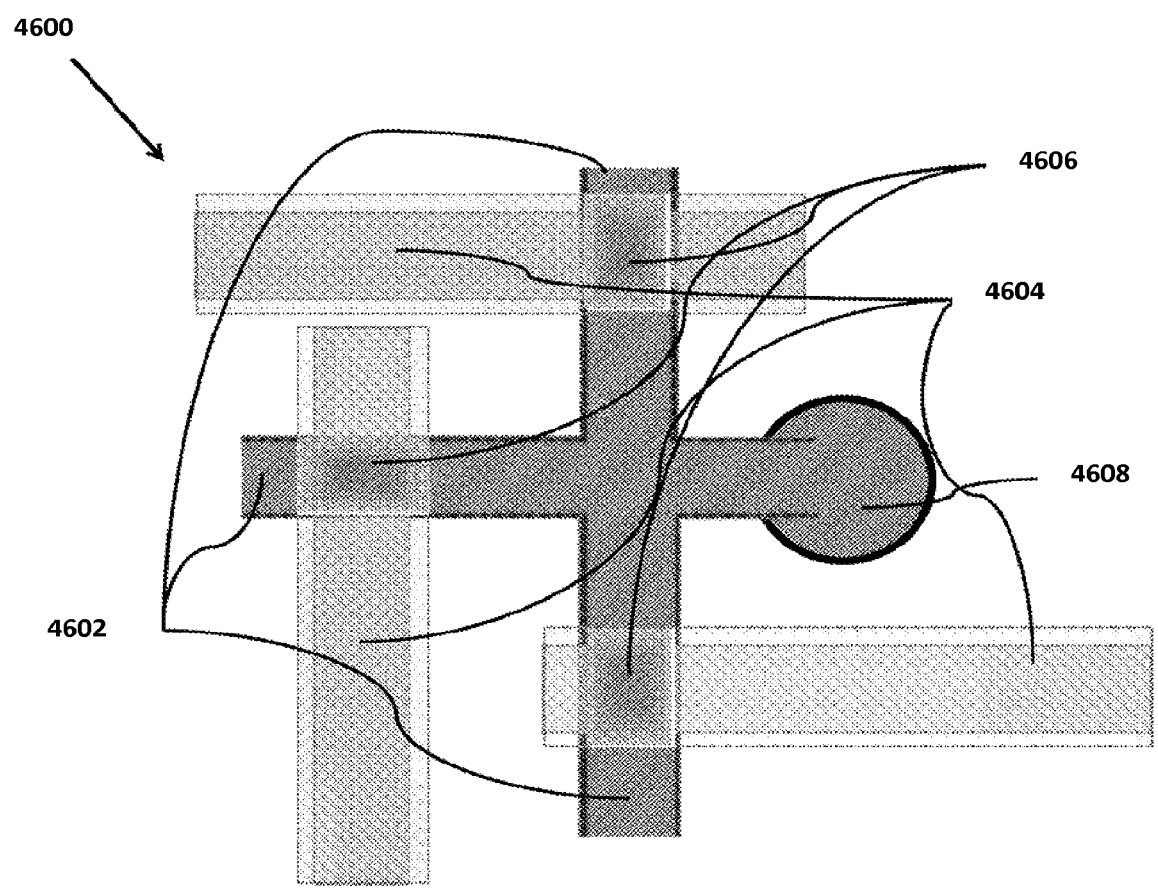
FIG. 46 is a schematic depicting an example valve system.

For a device fabricated of PDMS or other similar materials, it can be possible to use several pressure valves to control the flow of reagents. With such valves it is possible to have several valves in close proximity to each other, and the valves may be very close to a central channel, reducing dead volume, an example of which is shown in FIG. 46. As shown in FIG. 46, which shows a reagent valve system 4600 with three reagent input lines 4602 with valves 4606, each of which can be configured to flow towards the input to a flow cell 4608, under the control of pressure control lines 4604.

Figure 47:
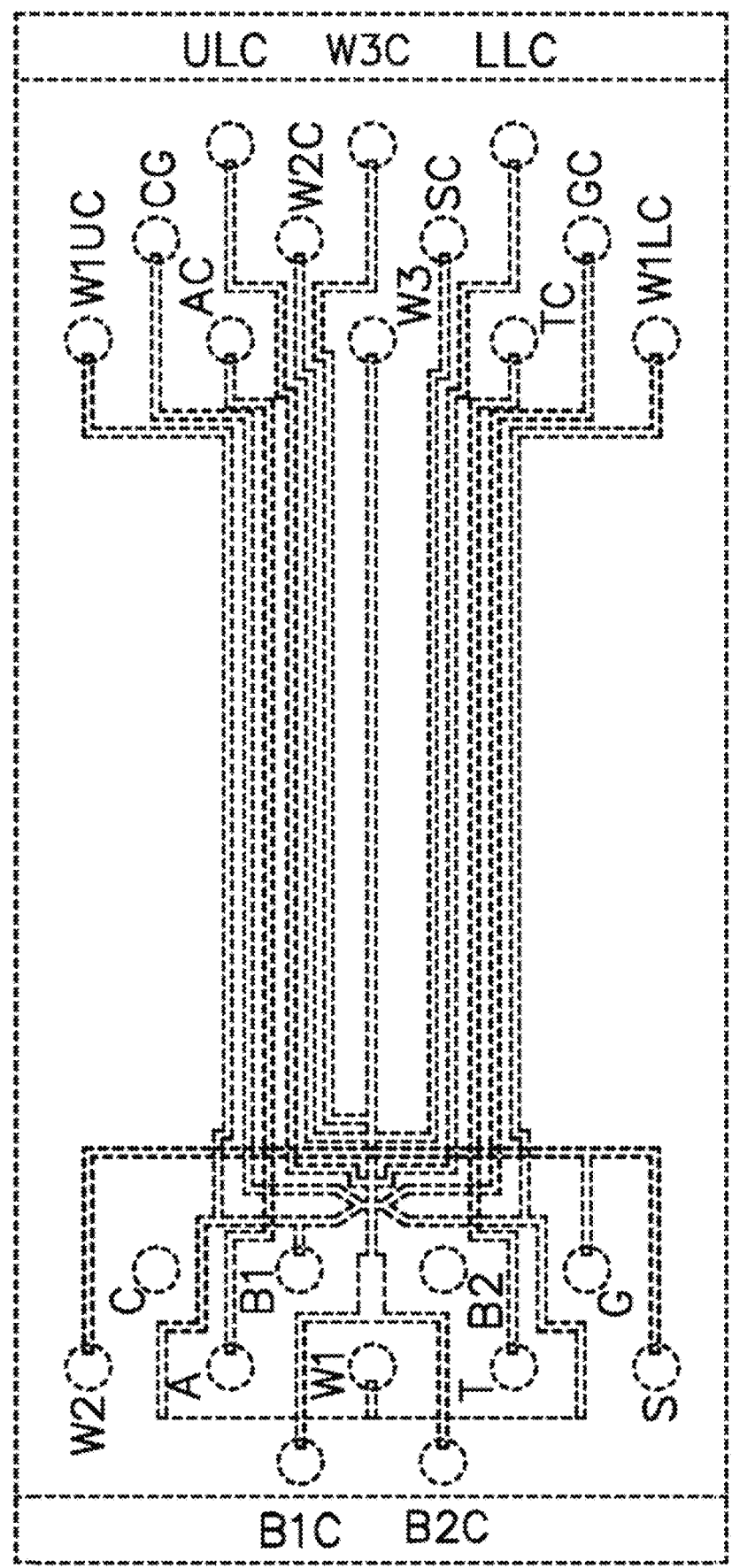
FIG. 47 is a schematic depicting an example valve system.

For a more complex system, where more reagent inputs are desired, the simple valve system 4600 of FIG. 46 may be insufficient, as it has but three reagent inputs lines 4602. In alternative embodiments, as shown in examples of FIGS. 47 and 48, many more inputs can be enabled in a device. Such an approach can also permit clearing of dead volume within a channel. For the example valve system shown in FIG. 47, inputs can include input ports for dATP, dTTP, dCTP, dGTP, a first buffer, a second buffer, and sample. Output port can include a first waste output port, a second waste output port, and a third waste output port. Control lines can be in place for each input and output port, with additional control lines to control the direction of flow between activated ports. A waste port is shown immediately prior to the flow cell, so that any remnant reagent from a previous flow may be removed, allowing a clean transition from one reagent to another, without diffusion from any dead volumes in the valve system.

Figure 48:
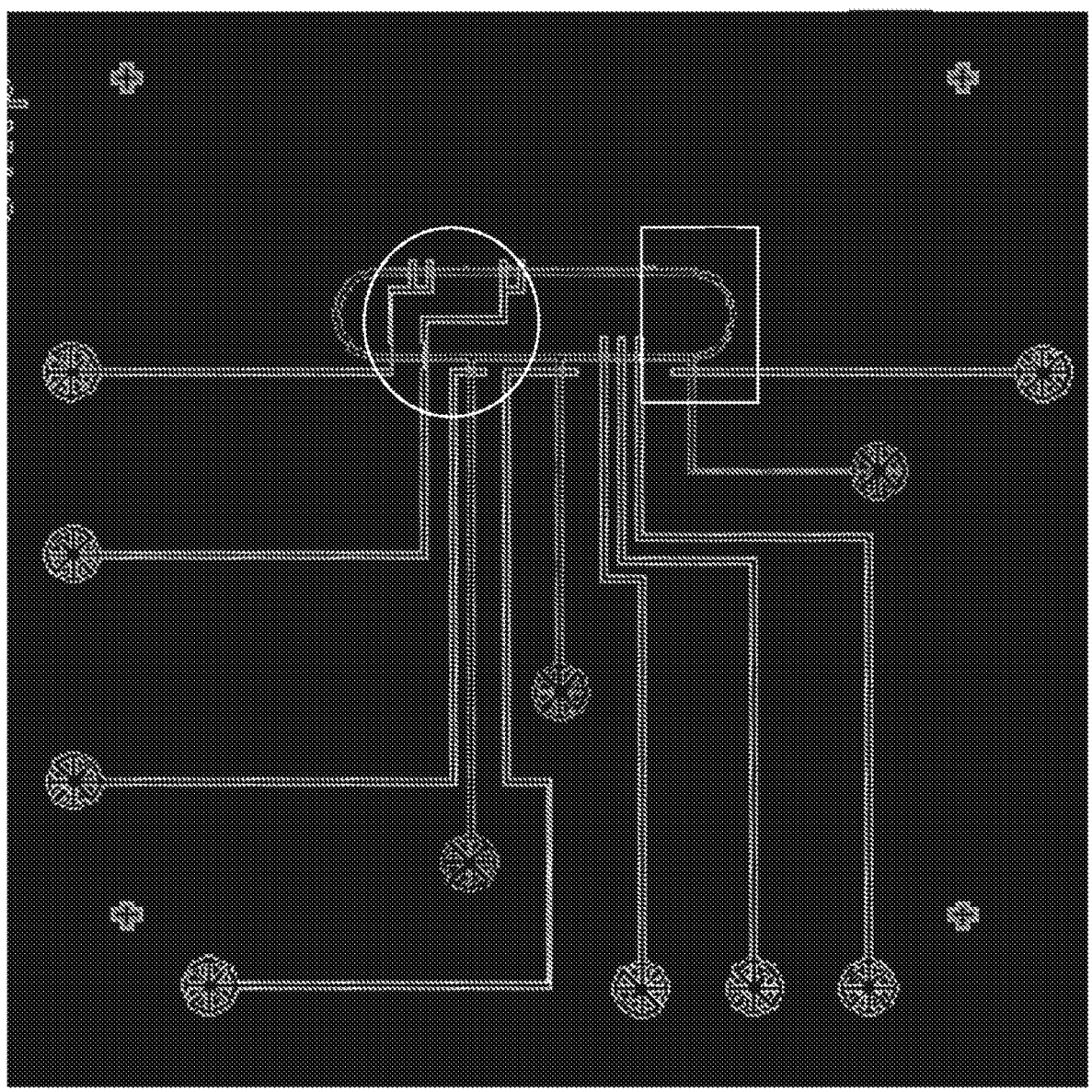
FIG. 48 is a schematic depicting an example valve system.
Figure 49:
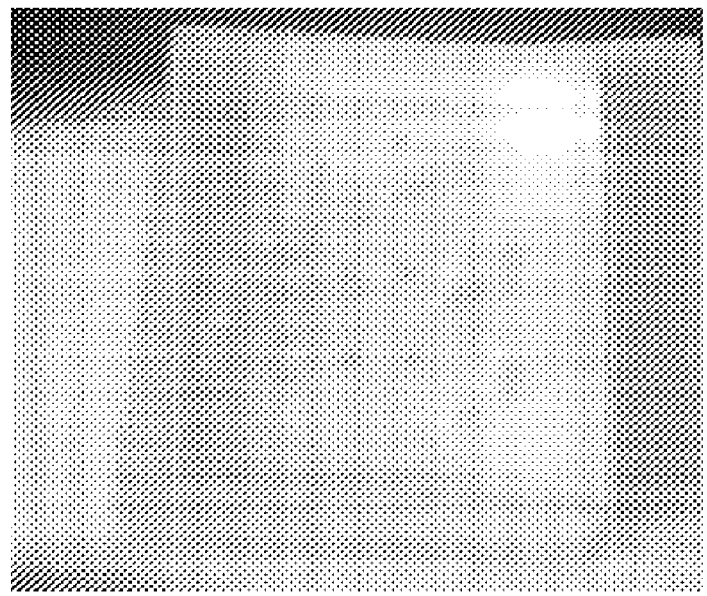
FIG. 49 is a photograph of an example valve system.

FIG. 48 depicts an example valve system with an oval flow path, such that all input valve port positions have a path to an outlet (waste) port in both directions from an input valve port position. Valves as shown in FIG. 46 may be used for each valve systems shown in FIGS. 47 and 48 or in an embodiment of a reagent valve system as shown in FIG. 49, wherein a photograph of an example PDMS valve system is shown.

Figure 50:
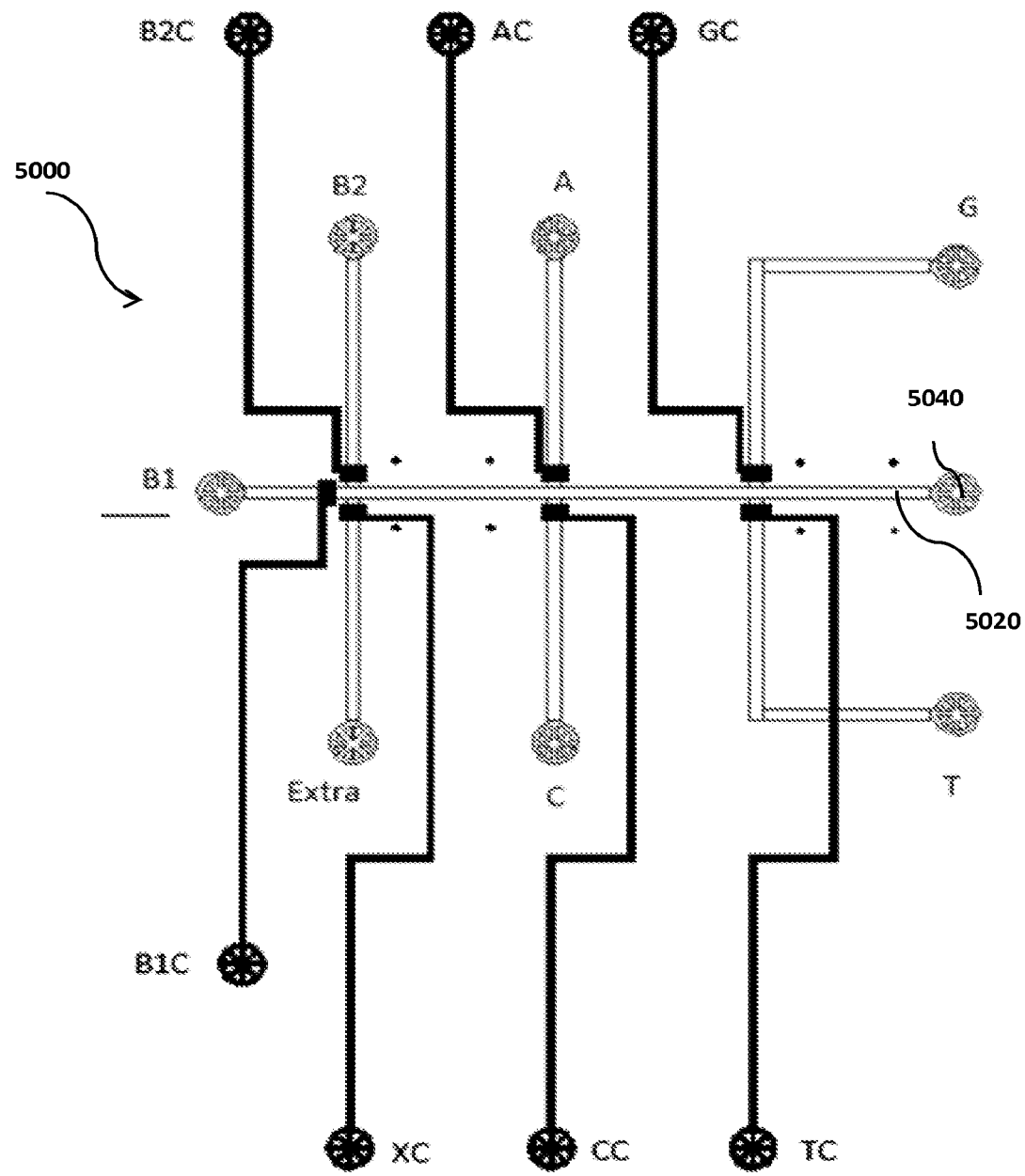
FIG. 50 is a schematic depicting an example valve system.

Dead volume may generally refer to one regions in the channels (e.g., microfluidic channels) and/or chambers of a flow cell that may need to be washed between cycles in order to remove contaminants. In some embodiments, the dead volume may be a region located between a valves and a channel leading to a flow cell, as shown by the schematic depiction of an example valve system in FIG. 50. As shown in FIG. 50, the valve system 5000 may include buffer input channels (B1 and B2) as well as reagent input channels (A, C, T, and G). Also shown is a sensor channel 5040 that can lead to a flow cell (not shown). A valve function can be performed by control lines that open or close their corresponding channel. For example, control line B1C can regulate the flow to/from the B1 input channel, B2C can regulate the flow to/from the B2 input channel, and AC, GC, TC, CC, can each regulate the A, G, T, and C input channels, respectively. A central channel 5020 can connect all of the input channels. The volume that encompasses the central channel 5020 up until the point where the sensor channel 5040 begins may be considered the dead volume (shown by dashed lines) of valve system 5000. In some cases, this volume may be washed between reagent cycles in order to prevent contamination.

In some cases, depending on the location of the valves, the dead volume may be calculated from the reagent input location to the flow cell if the valves are located substantially in the same location as the reagent input.

Figure 51:
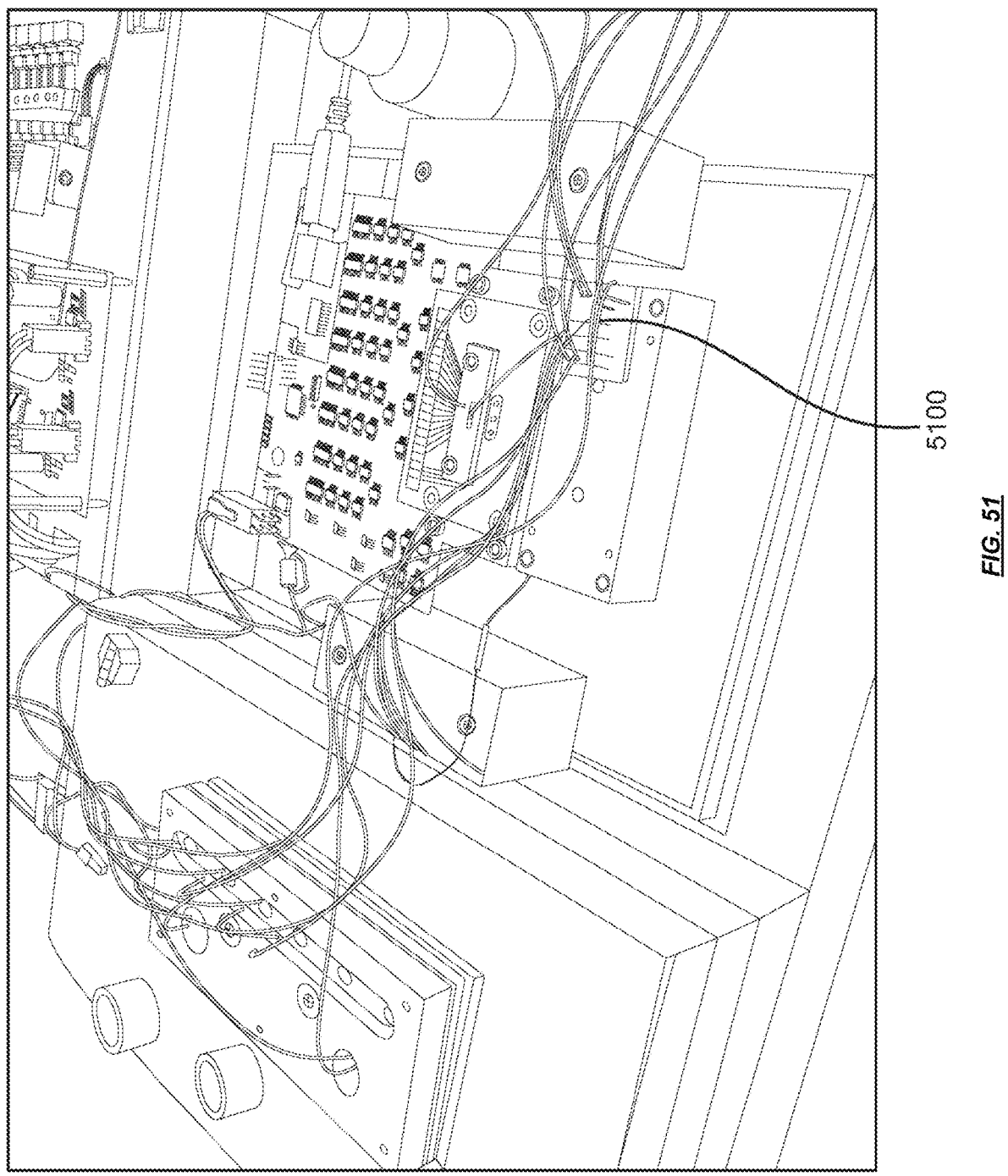
FIG. 51 is a photograph of a chip comprising a valve system.

In some embodiments, in order to reduce dead volume, an input system with multiple inlet valves may be placed directly on a chip comprising a flow cell, as shown in an example system in FIG. 51. As shown in FIG. 51, a valve system is located directly on a chip 5100. On-chip placement may allow for a reduction in dead as it can allow for minimizing the distance between the valves or the distance from the input location to the flow cell. A reduction in dead volume may allow for a more efficient system and may also prevent waste of reagents.

Constant Flow and Stop-Flow Carrier Methods for Carrier Loading

In some cases, it may be desirable to provide small volumes to an array via flow, such as, for example, picoliter volumes. For injecting picoliter amounts of amplification or sequencing reagents into a fluidic system, a magnetic array may utilize microfluidics. For example, the microfluidic platform may contain lines for injecting/delivering reactants to pixels of the array. For sequencing embodiments, the microfluidic system may be used to control sequential injections of dNTPs to appropriate species within the array, such as the array substrates or carriers immobilized to an array via localized magnetic fields.

Figure 55:
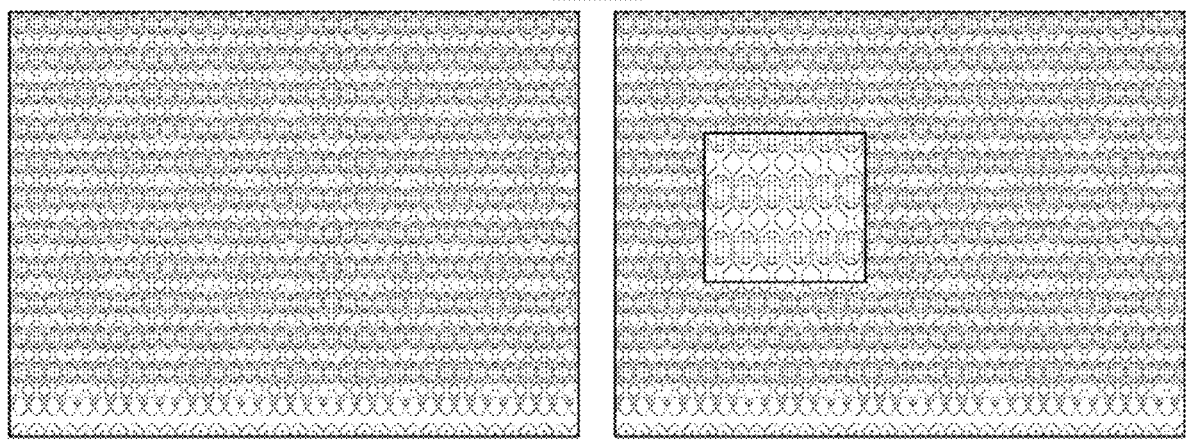
FIG. 55 is a set of photographs depicting loading of arrays with carriers.
Figure 56:
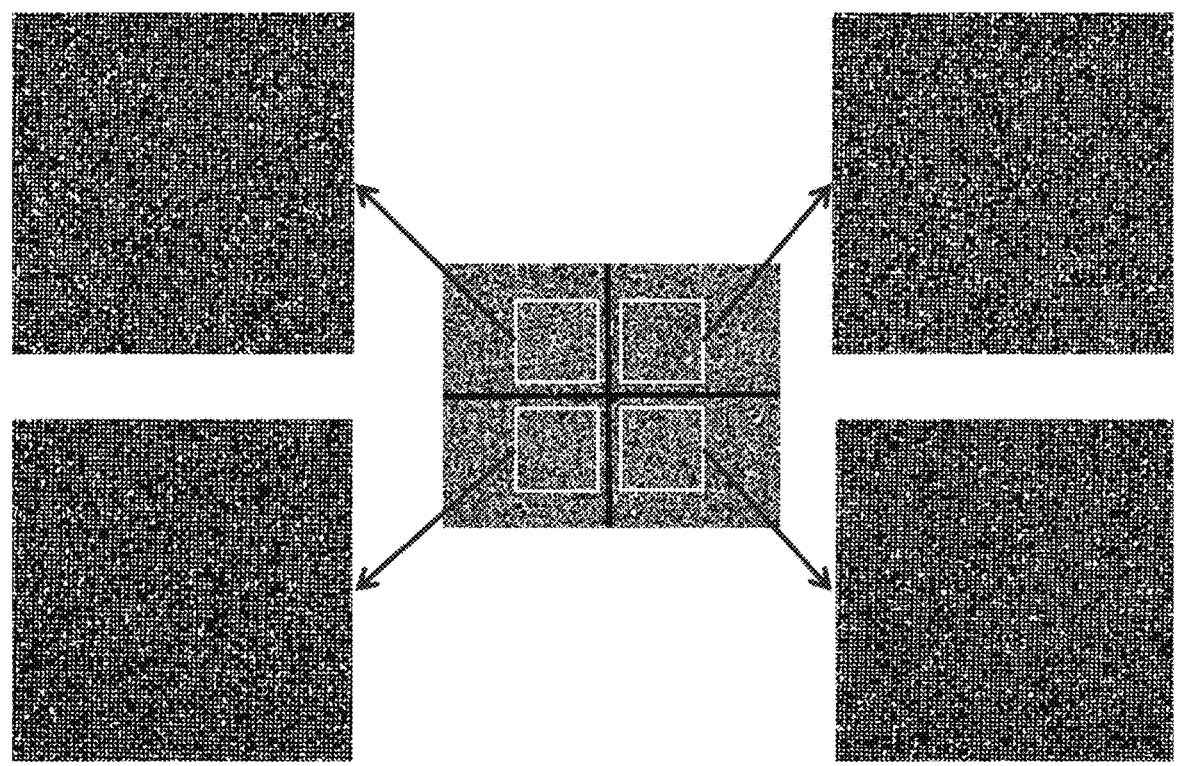
FIG. 56 is a set of photographs depicting loading of arrays with carriers.

In some cases, carriers (e.g., beads) may be supplied to an array via injection of beads into microfluidic channels of a magnetic array at a constant flow rate. In such cases, the flow rate generally needs to be fast enough for the process to be efficient, yet slow enough to allow for the beads to be immobilized at pixels. In some embodiments, it may be desirable to have one carrier immobilized per pixel. In some embodiments, beads may be flowed into a chamber at a substantially constant rate to load the beads onto an array. FIG. 55 shows an example array of sensors before bead loading (left) and the array of sensors after bead loading with single beads. FIG. 56 shows, an example of bead loading onto an array of a microfluidic chip. Each bright white spot represents the presence of a bead. This example shows that the chip may be loaded with more than 90% single beads.

In some cases, constant flow may be insufficient at supplying carriers to an array. One problem that may arise with this technique is that due to constant flow, many carriers may never drift down far enough to either come to rest in a pixel or, in the case of magnetic nanosensor arrays, come close enough to be in the range of the magnetic field of a pixel.

Figure 54A:
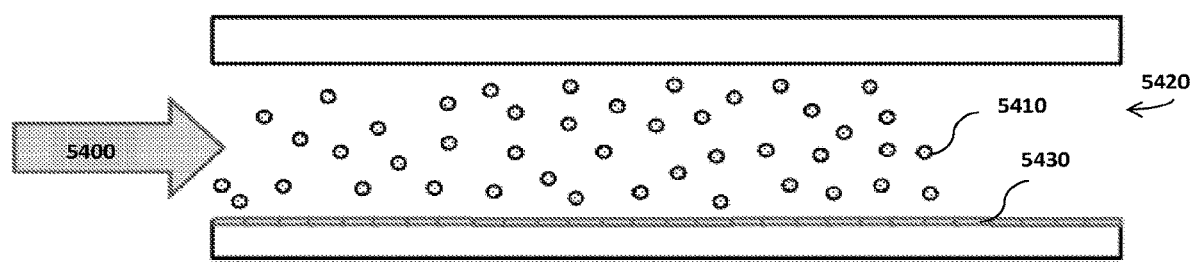
FIGS. 54A-D are schematics of example steps of an example method to load carriers onto an array.

Stop-flow techniques may be used to overcome the challenges of constant flow techniques and can improve loading efficacy and efficiency. FIG. 54A-D illustrate an example stop flow technique. FIG. 54A shows a schematic of an example side view of a microfluidic channel 5420 wherein an array of pixels 5430 is located at the bottom of channel 5420. As shown in FIG. 54A, a stop-flow methods may comprise flowing a solution that contains the carriers (e.g., beads 5410) into the channel 5420 proximate to the pixels 5430 of the array. The flow 5400 of solution may be set to flow at a constant rate.

Figure 54B:
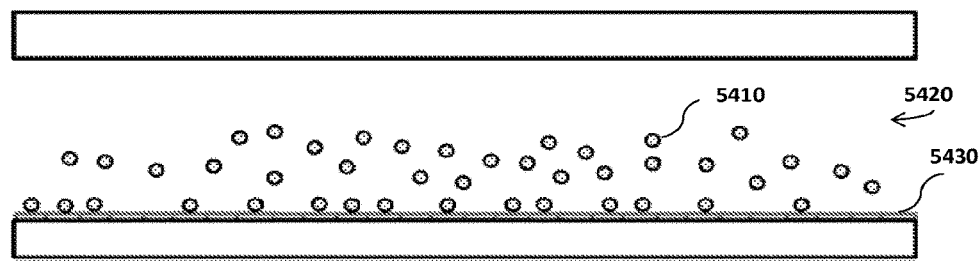
Figure 54C:
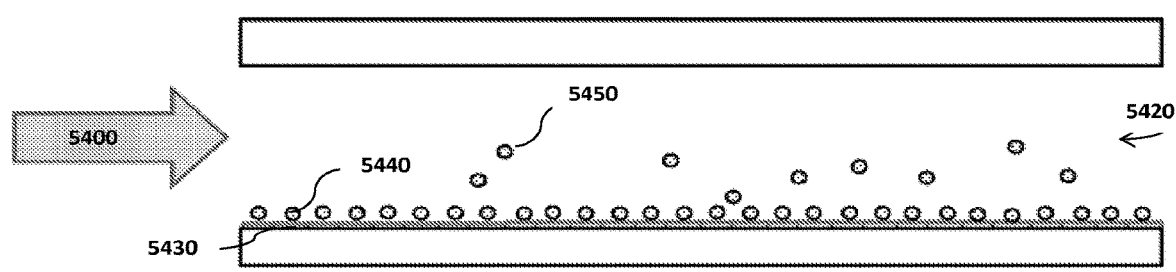
Figure 54D:
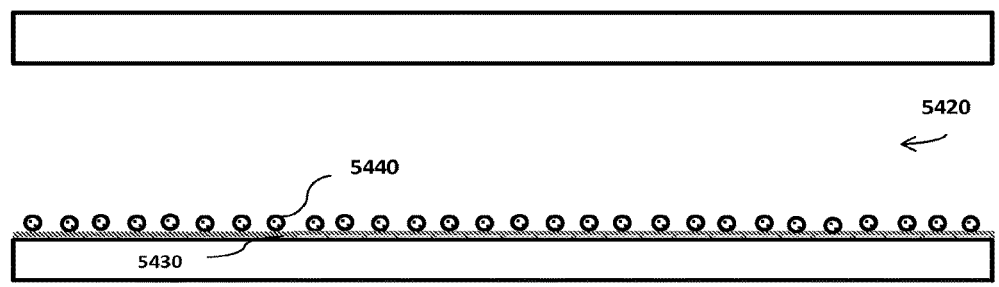

Next, as illustrated in FIG. 54B, once the carriers 5410 have entered channel 5420 and traveled directly above or proximate to the array of pixels 5430, the flow is stopped. The sudden stop in flow may allow more of the carriers to drift down to the pixels than may otherwise be possible using a conventional loading technique. In an example, the flow can be stopped suddenly by terminating power to a fluid flow device (e.g., pump) and/or suddenly inducing the flow of a fluid along a direction that is opposite that of the fluid having the carriers. In some cases, an electric and/or magnetic field can be used to immobilize the carriers when the flow of fluid is stopped. As shown in FIG. 54C, shows a number of carriers 5410 have drifted down to settle in a pixel 5430. Following settling of the carriers 5410, a wash solution may be flowed 5400 into the microfluidic channel 5420 in order to wash off any excess carriers 5450 that have not settled within a pixel 5430. The flow 5400 generally has sufficient velocity in order to wash out the excess carriers 5450, but not such a high velocity that it removes pixel-bound carriers 5440 from their position in a pixel 5430. An electric and/or magnetic field can be used to retain the carriers within the pixel 5430. FIG. 54D shows that the result of this process may be a higher carrier fill efficiency with, in some cases, one pixel-bound carrier 5440 per pixel 5430.

In some embodiments, an initial carrier (e.g., bead) loading step may be performed at a constant flow rate. In other embodiments, an initial carrier loading step may be performed at varied flow rates. In some embodiments, as an alternative to or in addition to stopping flow, the direction and/or flow rate of a fluid comprising carriers may be altered or alternated to allow for improved delivery of carriers to an array. In some embodiments, excess carriers may be washed off of an array by washing with solution, such as, for example a buffer solution. As an alternative or in addition, excess beads may also be removed by magnetic, electrical, physical, chemical, etc. or any other suitable removal methods.

In some embodiments, a nano or micro-scale nebulizer may be used to help spread beads down to the bottom of a microfluidic chamber and towards the pixels of an array in the chamber. The nebulizer may be located at or proximate to the top of the microfluidic chamber.

In some embodiments, one method for washing the carriers (e.g., beads) may be through the use of larger carriers (e.g., beads) flowed through the microfluidic channel in order to loosen/and or knock the carriers off of the array. Some examples of materials that the larger beads may be composed of include glass, metal, plastics or polymers, acrylic, nylon, etc. or any other material. In other embodiments, the carrier beads may be washed using other beads that are the same size or smaller, but have sufficient velocity or mass such that the carrier beads may be loosened or removed from the array.

Hydrophobic Materials in Channels

Various microfluidic systems use valves to control the flow of solution through microfluidic channels. In some instances, there may be a need to reduce the number of valves in the system and/or provide an additional means of stopping of retarding fluidic flow, including at specified time. A hydrophobic layer may be deposited on some portion of the inner surface of a microfluidic channel in order to allow for the regulation of flow through the channel. In some embodiments, a microfluidic channel or some portion of it may be partially or entirely composed of hydrophobic material. In some embodiments, a hydrophobic material may be deposited around the circumference of a microfluidic channel, creating a hydrophobic "band." The diameter of the hydrophobic band may depend on the diameter of the microfluidic channel. In some embodiments, a hydrophobic material may be deposited on more than one wall or portion of a microfluidic channel. The hydrophobic material may be deposited using layer by layer (LBL) deposition or any other suitable method.

Figure 52:
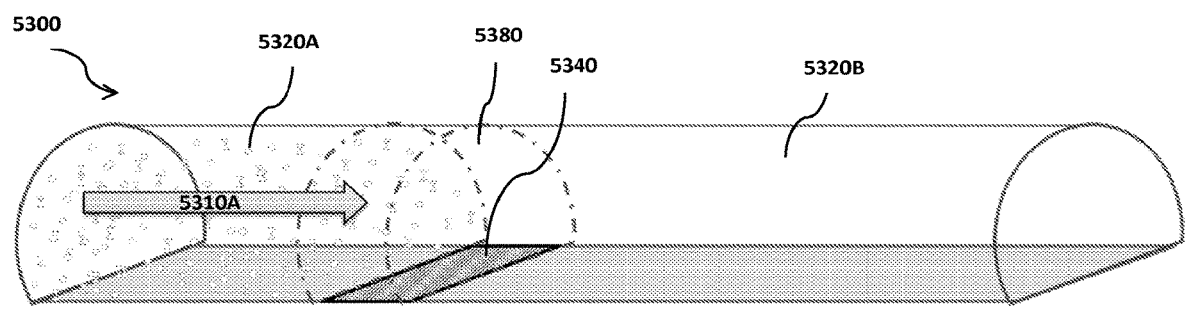
FIG. 52 is a schematic of a step of an example method using fluidic channels coated with hydrophobic materials.
Figure 53A:
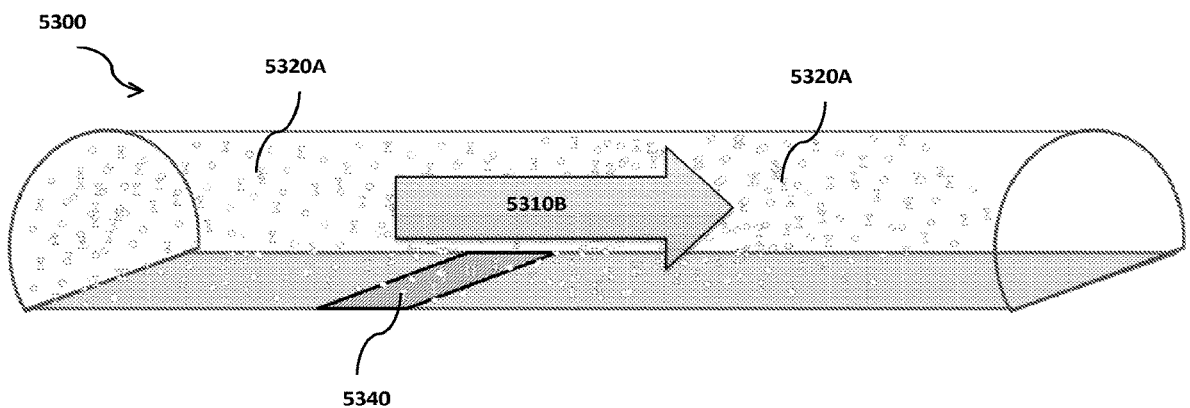
FIGS. 53A-B are schematics of steps of an example method using fluidic channels coated with hydrophobic materials.
Figure 53B:
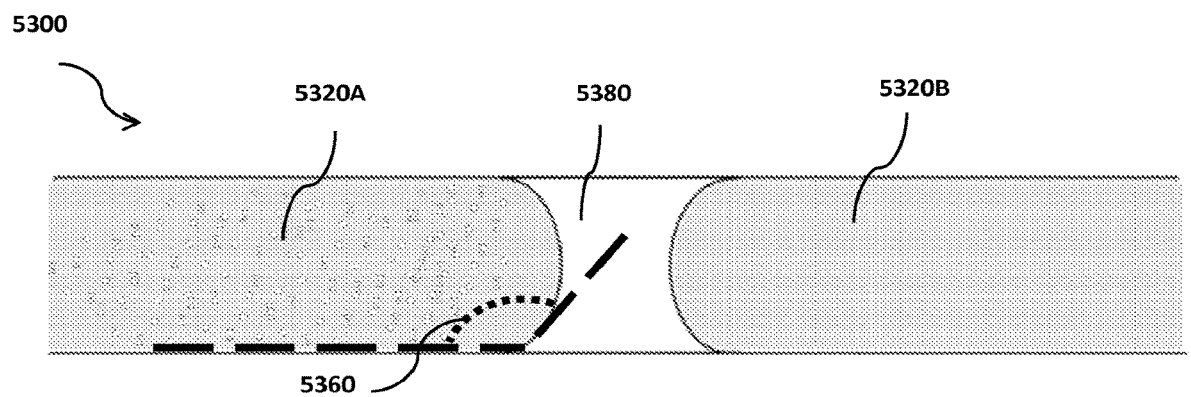

Depending on its velocity, when the fluid reaches a hydrophobic microfluidic channel or the hydrophobic portion of a microfluidic channel, the flow may be stopped due to the interaction at the boundary layer between the fluid and the hydrophobic material. An example of hydrophobic coatings used to alter flow is shown in FIGS. 52 and 53A-B. As illustrated in FIGS. 52, 53A, and 53B, the hydrophobic material 5340 may be deposited on a portion of the bottom of the microfluidic channel 5300. As illustrated in FIG. 52, a portion of the bulk solution 5320A may be separated from another portion of the bulk solution 5320B by the hydrophobic material 5340. The area of separation 5380 is shown using dashed lines. A relatively small rate of flow 5310A may be present, but may not be sufficient to overcome the pressure required to pass hydrophobic portion 5340. In some embodiments, the bulk solution 5320A may contain reagents that differ from those in bulk solution 5320B (or bulk solution 5320B) and in this manner the hydrophobic portion 5340 may act as a passive valve, separating the solution.

Following, reagent retardation via hydrophobic material 5340, higher flows may be used to push the reagents through the channel. As shown in FIG. 53A, a higher rate of flow 5310B may be used to overcome the hydrophobic portion 5340 such that there is no longer a fluidic separation area 5380. In this manner, bulk solution 5320A may pass hydrophobic area 5340.

The fluidic separation area 5380 results due to the interaction between the hydrophobic area 5340 and bulk fluid 5320A/B, an example of which is shown in FIG. 53B. As show in FIG. 53B, a side view of microfluidic channel 5300, the interaction between the fluid 5320A/B and the hydrophobic material 5340 increases the contact angle 5360 of the fluid 5320A as it reaches the hydrophobic interface, resulting in a separation of fluid 5380 in the channel. In this manner, the hydrophobic material may be used as a passive valve for regulating flow. For a channel of the same diameter, the pressure required to pass the hydrophobic area is greater than the pressure required to pass a non-hydrophobic portion. As such, the flow may be resumed upon application of a greater pressure to the fluidic input and this may be sufficient to overcome the hydrophobic portion of the channel, resulting in flow across the hydrophobic material and no separation of the fluid.

Figure 53C:
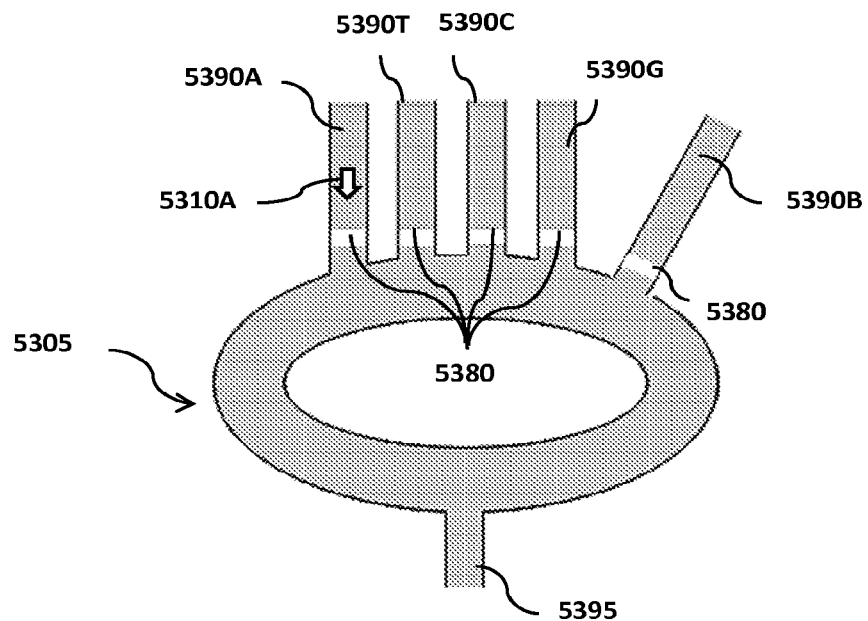
FIGS. 53C-D are schematics of example manifolds.
Figure 53D:
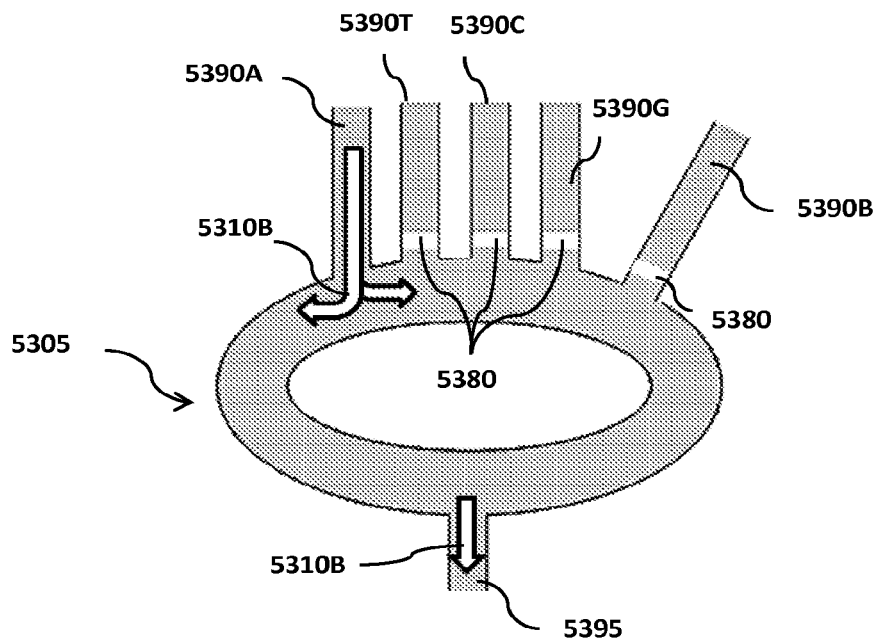

The location of passive valves in the microfluidic system may depend on the overall configuration desired. In some embodiments, there may be a manifold leading to the input of a flow cell, so that any reagents remaining from a previous use of the manifold may be removed, an example of which in FIGS. 53C and 53D. FIG. 53C shows the fluidic separation areas (passive valves) 5380 where the hydrophobic material is located and that a small fluid flow 5310A may be insufficient to "open" the passive valve. A sufficiently large fluid flow 5310B, as shown in FIG. 53D, may be used to open the passive valve, allowing for the reagents from an input channel to reach the flow cell.

For example, a dATP reagent may commence to flow from a dATP input channel 5390A, around both sides of a liquid loop channel 5305, and into the input channel for a flow cell 5395. Then, the pressure applied to the dATP reagent channel 5390A may be reduced or eliminated such that the fluid is separated at the location of the passive valve 5380. A buffer wash cycle may then commence where pressure can be applied to a buffer input channel 5390B such that the fluid is able to cross over the area of the passive valve 5380, into the liquid loop channel 5305, and finally into the flow cell input channel 5395. Then, the pressure applied to the buffer channel 5390B may be reduced or eliminated such that the fluid is separated at the location of the passive valve 5380. This process may be continued with a dTTP input channel 5390T, a dCTP input channel 5390C, and a dGTP input channel 5390G, wherein the input of nucleotides is alternated with the input of buffer in order to wash the liquid loop channel 5305, the flow cell input channel 5395, and the flow cell in between cycles of different reagents.

Wall Support

Amplification and/or sequencing arrays (e.g., chips) may have one or more large chambers where the sequencing/amplification array can be located. In some cases, structural fidelity may become an issue when there is a relatively large reaction chamber. For example, the "ceiling" above an array may begin to sag inward proximate to the midpoint between sidewalls of a chamber. Thus, structural reinforcements may be used in order to promote improved structural integrity, which may result in a more durable and long-lasting device. Structural reinforcements may be, for example, wall supports placed in one or more locations within a reaction chamber such that the weight of the chamber ceiling is more uniformly distributed.

Isothermal and Solid Phase Amplification Methods

Isothermal Amplification Methods

Polynucleotide amplification is often used for generating large amounts of nucleic acid samples for robust sequencing measurement, and in particular, sequencing by synthesis. Present embodiments provide systems and methods applied in polynucleotide amplification. Some examples of polynucleotides that may be amplified according to the systems and methods include DNA, cDNA, modified DNA, synthetic DNA, RNA, mRNA, modified RNA, synthetic RNA, etc. In some embodiments, the polynucleotide may be single stranded or double stranded.

Some nucleic acids may need to undergo prior treatment via a suitable protocol before amplification methods described herein may be completed. In one embodiment, for example, mRNA or total RNA may be need to be reversed transcripted to cDNA with reverse transcriptase, like Superscriptase, and with a primer containing Poly A or random hexamer tagged with nick restriction enzyme sites, a,b,c. The RNA template can be digested by RNAse H, or base and the generated single stranded, complementary (cDNA) can be ready as a template for amplification. In some cases, an appropriate primer for the cDNA template can be a random primer or a degenerate primer.

In some embodiments, an isothermal amplification reaction may be achieved by use of a first nucleotide primer that comprises a specific, or predetermined, sequence. In other embodiments, the first primer may comprise a randomized sequence. In a further embodiment, the first primer may be a degenerated primer. In some embodiments, the first primer may be an oligonucleotide or an oligonucleotide analog. A plurality of first primers having the same sequence may be used. In the alternative, the use of a plurality of first primers having sequences that differ from each other is also contemplated. In another embodiment, the first primers may have the same or similar annealing temperature and may not have any or minimal complementarities between them.

In some embodiments, it may be desirable to have a sufficiently high concentration of first primers such that amplification reaction efficiency may be optimized. In a further embodiment, it can be desirable to select first primers that are less likely to produce primer-dimer amplification reactions. The first primer can be attached to a substrate, such as for example, a surface such as a microsensor or glass slide, or a carrier such as a microparticle or a bead. In some embodiments, the carrier may be a magnetic bead ranging in size, for example, of 20 μm or less, 5 μm or less, 500 nm or less, or 50 nm or less, etc.

In other embodiments, the substrate may have a flat surface, a porous surface, a crystalline surface, etc. In some embodiments the substrate may be a carrier that is a solid carrier, a porous carrier, a quantum dot, etc. In further embodiments, the substrate can have any shape such as spherical, flat, rectangular, crystalline, irregular, wells, etc. In some embodiments, the substrate material may comprise, for example, silicon, silicon-based material, glass, modified or functionalized glass, magnetic material, plastic, metal, ceramic, gels, acrylic resins, biological material, etc.

In some embodiments, the first primer may be attached to the substrate through any suitable attachment method. Some exemplary attachment methods include DNA hybridization, biotin streptavidin binding, thiol binding, photo-activated binding, covalent binding, antibody-antigen, physical confinement via hydrogels or other porous polymers, etc., or a combination of methods. In some embodiments, more than one type of primer may be attached to the same or different types of substrates.

In one embodiment, the first primer may be, for example, 5, 10, 20, 30, 40, 50, 60, 70, etc. base pairs long and hybridize to a desired target sequence. In some embodiments, it may be preferable to select primers that have low self-complementarity and high stability in the desired temperature or pH range of the amplification reaction.

In some embodiments, wherein the substrate comprises, for example, a bead, the bead may be prepared according to the attachment methods described above such that there is more than one copy of the first primer attached to the bead. The concentration of the first primers may depend on the reagents used and the nature of the specific primers selected. In some embodiments, for example, the concentration of first primers on a substrate, such as a magnetic bead, may be 1,000, 10,000, 50,000, 100,000, 200,000, 500,000, 1 million, 5 million, 10 million, 50 million, etc. first primers per bead, or another concentration wherein the primers may have the same or different sequences. Each bead may be attached to first primers having the same or different sequences from the primers attached to other beads. In a further embodiment, bead-primer complexes can be arranged in amplification arrays that contain, for example, 1,000, 10,000, 100,000, 500,000, 1 million, 10 million, 500 million, 1 billion, etc. primer-bound beads.

In an alternative embodiment, a combination of primer-bound substrates, such as for example both beads and planar microsensors, may be used in an amplification array.

In some embodiments, at least some portion of the first primer may be complementary to a DNA template used in an isothermal amplification reaction. Other reagents may be used for DNA amplification that include, for example, buffers, deoxyribonucleotide triphosphates (dNTPs), ions (e.g., $Mg^{2+}$), co-factors, primers, polymerase, betain, DMSO, etc.

In order to allow for target-specific hybridization of the primer and template nucleic acid and to prevent non-specific hybridization with other nucleic acids, reaction conditions may be optimized according to some embodiments. Non-specific hybridization may be reduced by using stringent reaction conditions or by denature at higher temperature and ramp down to the melting temperature (Tm) of the primer. The use of stringent reaction conditions can help avoid the generation of unwanted reactions. In some embodiments, stringency may be increased by the addition of organic co-solvents such as, for example, 1-methyl 2-pyrrolidinone, formamide, DMSO, polyethyleneimine, polyethylene glycol, etc.

In some embodiments, temperature ranges such as, for example, 20-95° C. can be used for the isothermal DNA amplification reaction. The desired temperature may depend on the type of reagents, such as enzymes, that are used.

Figure 11:
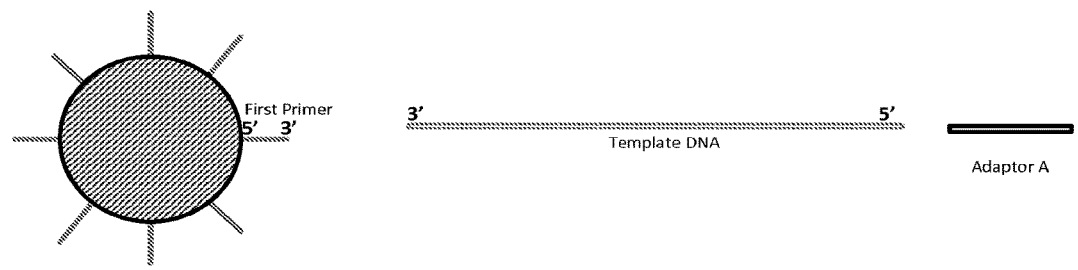
FIG. 11 is a schematic of an example step in an amplification method.

In some embodiments, as shown in FIG. 11, a first primer may be attached to a carrier, such as for example a bead, in a 5' to 3' direction. In an alternative embodiment, the first primer may be attached to the bead such that one or both ends of the first primer are free and exposed to solution. The 5' end of the first primer may be attached to the bead by any suitable method, such as, for example covalent means. A polynucleotide template with a sequence in the 3' end that has at least some portion complementary to the first primer, such as a DNA template, may be added.

The template nucleic acid used for the amplification reaction may be DNA, RNA, PNA, LNA, a DNA-RNA hybrid, etc. The nucleic acid selected for amplification may be selected from a broad range of sizes or lengths, for example, 10, 20, 30, 40, 50, 60, 70, 80, 90, 100, 200, 300, 500, 700, 1000, 2000, 5,000, 10,000, etc. base pairs. The nucleic acid may be single stranded or double stranded. In some embodiments, a single stranded DNA template may be used as the template nucleic acid for DNA amplification. The nucleic acid template can be acquired from any virtually any source that contains nucleic acids, such as for example from bacteria, human or animal tissue, plant tissue, fluids such as blood, food, environmental samples, etc.

Figure 12:
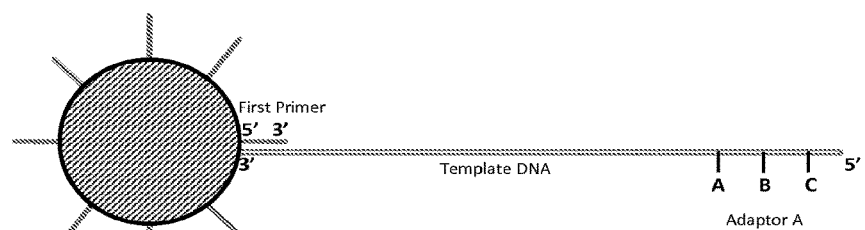
FIG. 12 is a schematic of an example step in an amplification method.

In some embodiments, as shown in FIG. 12, the DNA template may contain a sequence ("Adaptor A") at the 5' end that may contain one or more nick restriction enzyme sites. This adaptor sequence may be, for example, 5, 10, 20, 30, 40, 50, 100, etc. base pairs long. Nick restriction enzymes, also called nicking endonucleases, can be utilized. Nicking endonucleases recognize specific sites on the template DNA and generate a nick on the template DNA strand on or near the recognition site. The nick is generated in the phosphodiester backbone on or near the recognition site. In one embodiment, these enzymes only nick one strand of a double stranded DNA molecule. Examples of nicking endonucleases that may be used include, but are not limited to: N. BstNBI, Nt.CviPII, Nt.AlwI, Nt.BspQI, Nb.BsmI, etc. or a combination of nicking endonucleases. The nicking endonuclease, in some embodiments, may be selected to be thermostable. In other embodiments, DNAzymes or Ribozymes may be used to nick DNA.

In some embodiments, a sequence independent method to introduce nicks or gaps into a DNA strand may involve amplification of template DNA with primers, one of which contains one or more modified nucleotides, such as for example dU. In an alternative embodiment, an adaptor containing one or more dU nucleotides can be ligated to the 5' end of template DNA. Upon full extension of the first primer, until the 5' end of the template DNA strand that contains modified nucleotides, the latter modified nucleotides can be excised by any of commercially available N-glycosylases/AP-lyases. Thus, the resulting single-stranded gaps may serve as binding sites for strand displacing DNA polymerase. One example of a commercially available product that can be used for this purpose is USER Enzyme (mixture of Uracil DNA glycosylase and Endonuclease VIII) and it can be obtained from New England BioLabs (NEB). Uracil DNA glycosylase catalyses the excision of uracil base, forming an abasic (apyrimidinic) site while leaving the phosphodiester backbone intact. The lyase activity of Endonuclease VIII breaks the phosphodiester backbone at the 3' and 5' sides of the abasic site so that base-free deoxyribose is released. Although the remaining 3' phosphate may be a hindrance for extension by DNA polymerase, it can be removed by including *E. coli* Endonuclease IV (NEB) into the mixture.

In some embodiments, The dU gapping site can be introduced into the clonal double-stranded DNA by ligation of either nicking or dU site adaptors.

The DNA template may anneal to the first primer in the orientation that enables first primer extension leading to the synthesis of a DNA strand complementary to the template DNA, as shown in FIG. 12. In some embodiments, the DNA template may anneal to the first primer in a 3' to 5' direction and is amplified by contacting the DNA template-first primer complex with a DNA polymerase and dNTPs. A polymerase is an enzyme that catalyzes the extension and formation of a complementary polynucleotide based on a template nucleotide. For example, DNA polymerase incorporates dNTPs to allow for the synthesis of a DNA strand that is complementary to the DNA template strand, starting from the first primer region. DNA polymerase moves in a 3' to 5' direction along the template strand, and synthesizes the complementary DNA strand in a 5' to 3' direction.

In some embodiments, it may be desirable to select a DNA polymerase that has no, or limited, exonuclease activity, either in the 3' to 5' or the 5' to 3' direction. In other embodiments, it may be desirable to choose a polymerase that has exonuclease activity to allow for "proofreading" of the growing complementary DNA strand. Since exonuclease activity may depend on ionic concentration, pH, temperature, buffer, monovalent ionic composition, divalent ionic composition, trivalent ionic composition, concentration or presence of dNTPs, etc. these factors can be optimized to obtain the desired level of exonuclease activity.

Some examples of DNA polymerase that may be used according to some embodiments include, but are not limited to, Klenow DNA polymerase, Taq DNA polymerase, T4 DNA polymerase, VENT DNA polymerase, T7 DNA polymerase, Bst DNA polymerase, Bsu DNA polymerase, etc. or a combination of different DNA polymerases. In a further embodiment, the DNA polymerase may be selected to be thermostable.

Figure 13:
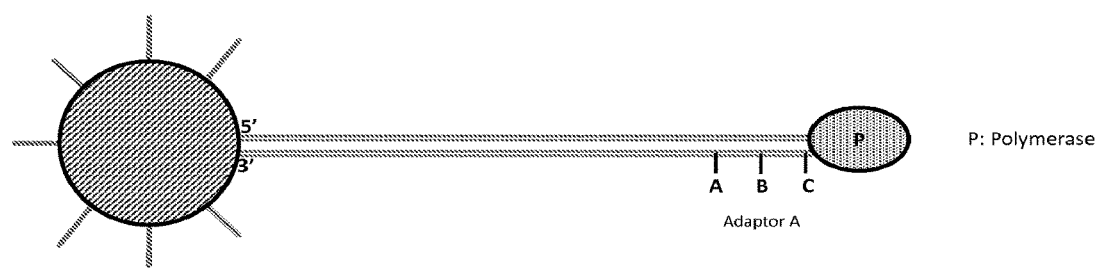
FIG. 13 is a schematic of an example step in an amplification method.

In one embodiment, the DNA polymerase (P) can extend the first primer to the 5' end of the template DNA in order to form double stranded DNA, as shown in FIG. 13. The nick restriction enzyme sites of Adaptor A in the template DNA strand may also form in the double stranded DNA once DNA polymerase has extended the Adaptor A portion of the template DNA strand.

Figure 14:
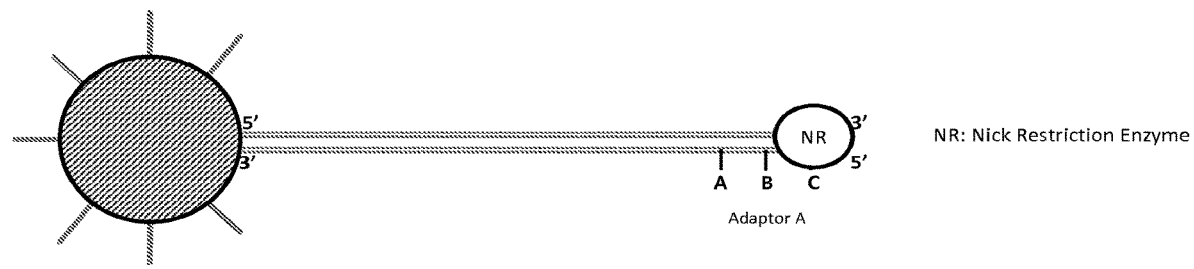
FIG. 14 is a schematic of an example step in an amplification method.
Figure 15:
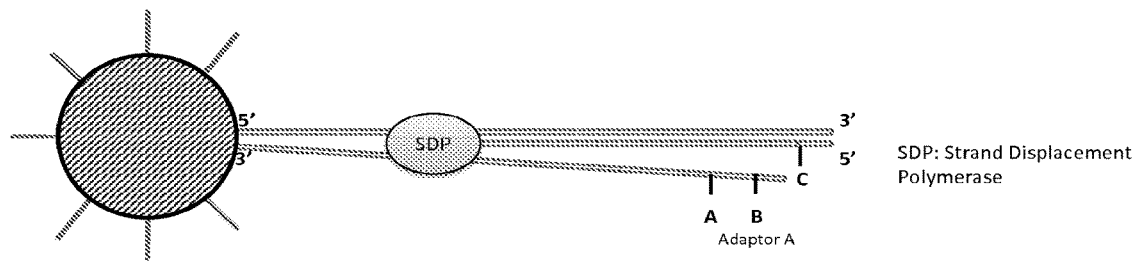
FIG. 15 is a schematic of an example step in an amplification method.

In some embodiments, a nick may be introduced into the Adaptor A region of the template DNA strand by utilizing one or more nick restriction (NR) enzymes, as shown in FIG. 14. In a further embodiment, strand displacement DNA polymerase may be added to bind to the nicked site on the template DNA and perform strand displacing polymerization, as shown in FIG. 15. This may result in the release of the newly-generated single stranded DNA.

Some examples of suitable strand displacement polymerases according to some embodiments include VENT DNA polymerase, Phi29, Klenow fragment polymerase, T4 DNA polymerase, Bst polymerase, etc. Any one of the polymerases discussed above or elsewhere herein may be used.

In some embodiments, it may be desirable to select a strand displacing DNA polymerase that lacks 5' to 3' exonuclease activity or 3' to 5' exonuclease activity, in order to help avoid degradation of the DNA strand being displaced or degradation of the newly synthesized DNA strand, respectively. In other embodiments, selecting a strand displacing DNA polymerase with exonuclease activity may be desirable. In a further embodiment, a thermostable strand displacing polymerase may be selected.

In another embodiment, a strand displacement factor may be used to enhance strand displacement activity of the polymerase. Some examples of strand displacement factors and the corresponding polymerase that they interact with include, but are not limited to: E. coli SSB (DNA polymerase II), gp32 protein of T4 bacteriophage (Polymerase gp43), and gp2.5 encoded by T7 bacteriophage (T7 DNA polymerase), recA, betaine, etc.

In a further embodiment, a strand displacing enzyme may be used to perform the strand displacing step and then a polymerase may be added to perform the extension step. Some examples of strand displacing enzymes include, but are not limited to, helicase, mismatch repair enzymes (that have strand displacement capabilities), or modified enzymes (that have strand displacement capabilities), etc.

In some embodiments, it may be advantageous to select a DNA polymerase that has high processivity in order to enhance the speed, length, and efficacy of the amplification reaction. In a further embodiment, the processivity of the DNA polymerase may be increased by the addition of processivity factors, such as for example, E. coli thioredoxin (for use with T7 polymerase). Other processivity factors include, for example, sliding clamp proteins such as Archaeal PCNA—Proliferating Cell Nuclear Antigen associated with archaebacterial DNA polymerase ε, bacteriophage T4 gp45 protein associated with T4 DNA polymerase, β subunit of E. coli DNA polymerase III. In other embodiments, protein mediated correction enzymes may be utilized to improve the fidelity of the DNA polymerase. Protein mediated correction enzymes, such as for example MutS, may be used, or any other suitable enzyme can be used alone or in combination.

Figure 16:
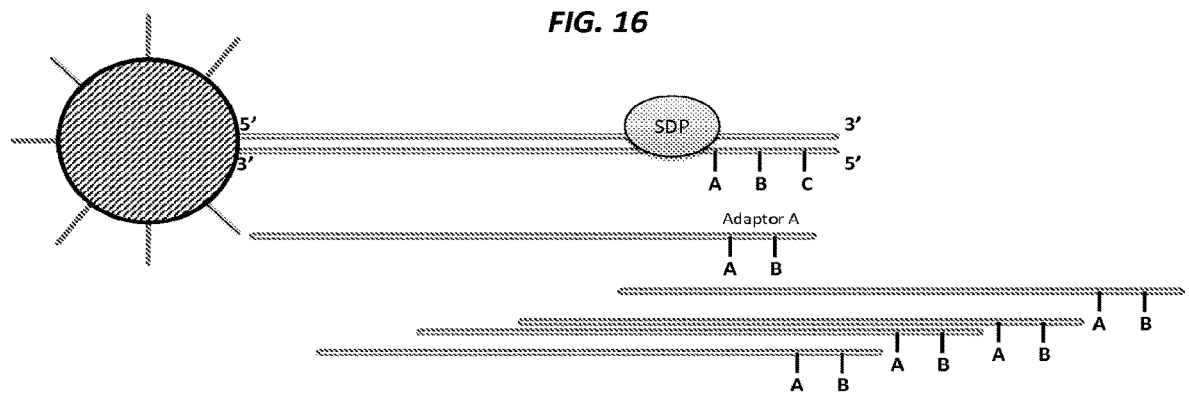
FIG. 16 is a schematic of an example step in an amplification method.
Figure 17:
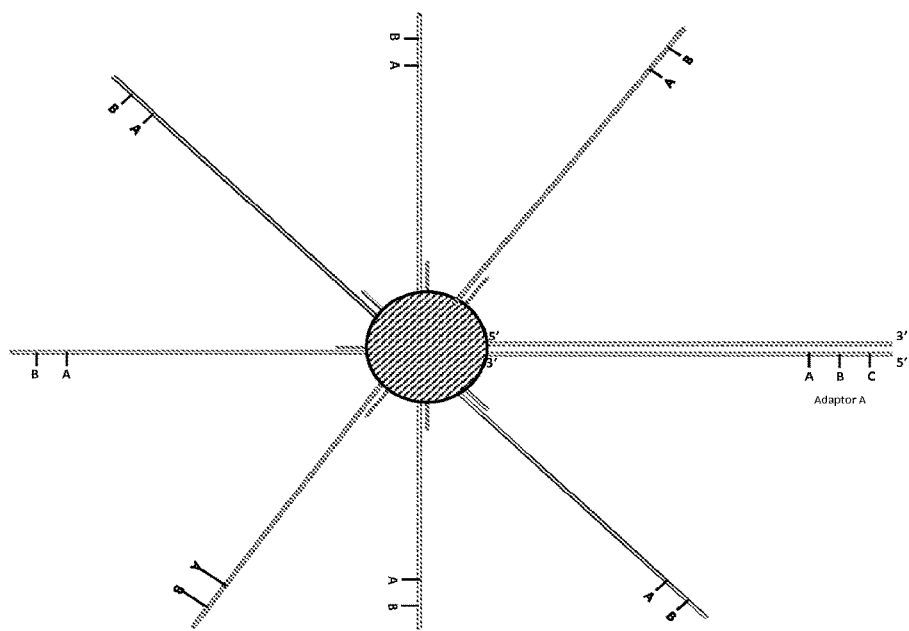
FIG. 17 is a schematic of an example step in an amplification method.
Figure 18:
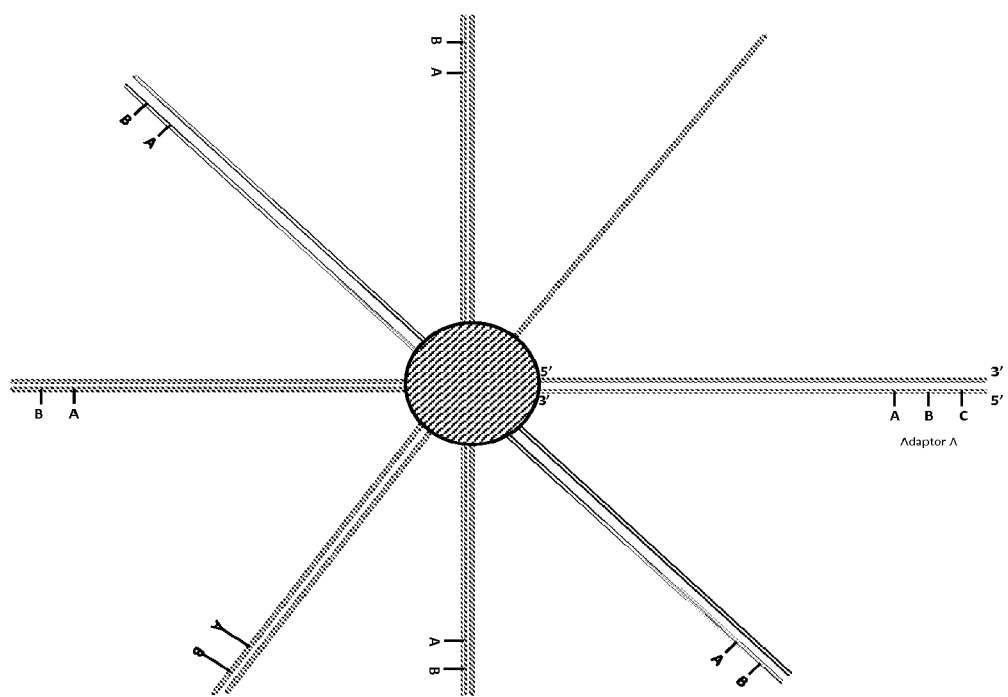
FIG. 18 is a schematic of an example step in an amplification method.

In some embodiments, the released single stranded DNA is then free to bind to another first primer at another location on the same or other bead, and the cycle may be started anew, as shown in FIG. 17. In further embodiments, a plurality of first primers, situated in various locations on the bead, may be extended by DNA polymerase to form double stranded DNA with the 5' end blunted, as shown in FIG. 18. Since the nicking restriction enzyme site can be restored when new double stranded DNA forms, the nicking, extension, and displacement may be repeated for multiple rounds in order to generate multiple copies of single stranded DNA wherein the sequence of the amplified single stranded DNA is the same as that of the original DNA template, as shown in FIG. 16.

Figure 19:
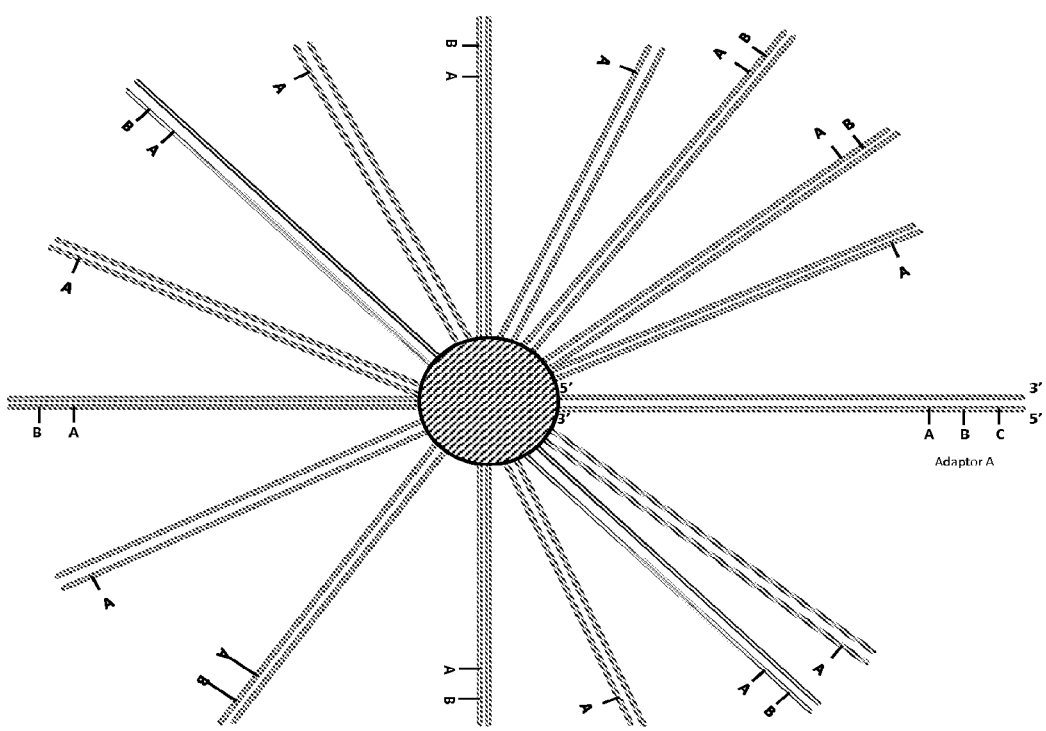
FIG. 19 is a schematic of an example step in an amplification method.

In some embodiments, the Adaptor A sequence may be designed such that it contains more than one restriction site. The Adaptor A sequence may have, for example, 2, 3, 4, 5, 10, etc. restriction sites. In the embodiment shown in FIG. 12, Adaptor A may contain 3 restriction sites (A, B, and C). If the Adaptor A sequence contains more than one restriction site, whatever nick restriction site that may remain on the newly formed double stranded DNA will be recognized by its corresponding nick restriction enzyme. This can create a new nick site on the newly formed double stranded DNA. This step results in rounds of nicking, extension, and displacement of the DNA, repeated until all or substantially all of the first primers on the substrate may be extended. FIG. 19 shows one embodiment of the result after a number of cycles of amplification with a nicking step. In the exemplary embodiment, the original template DNA had restriction sites A, B, and C and the amplified strands contain either A and B restriction sites, or just site A.

In some embodiments, isothermal amplification may be completed over a number of cycles using the method described above. Optionally, in some embodiments, there are additional steps that may be taken, described below, depending on individual needs and requirements.

Figure 20:
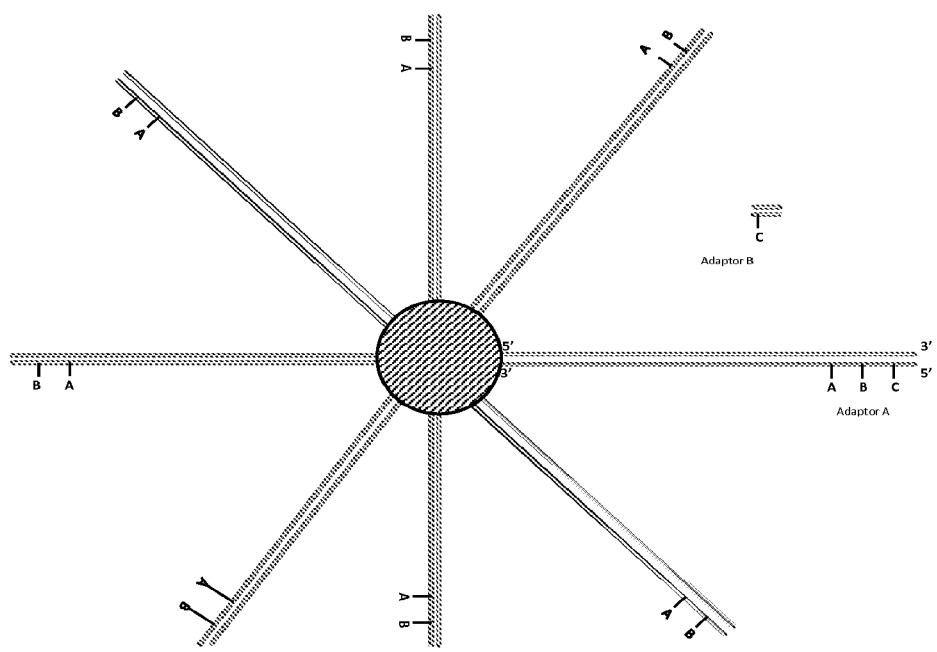
FIG. 20 is a schematic of an example step in an amplification method.
Figure 21:
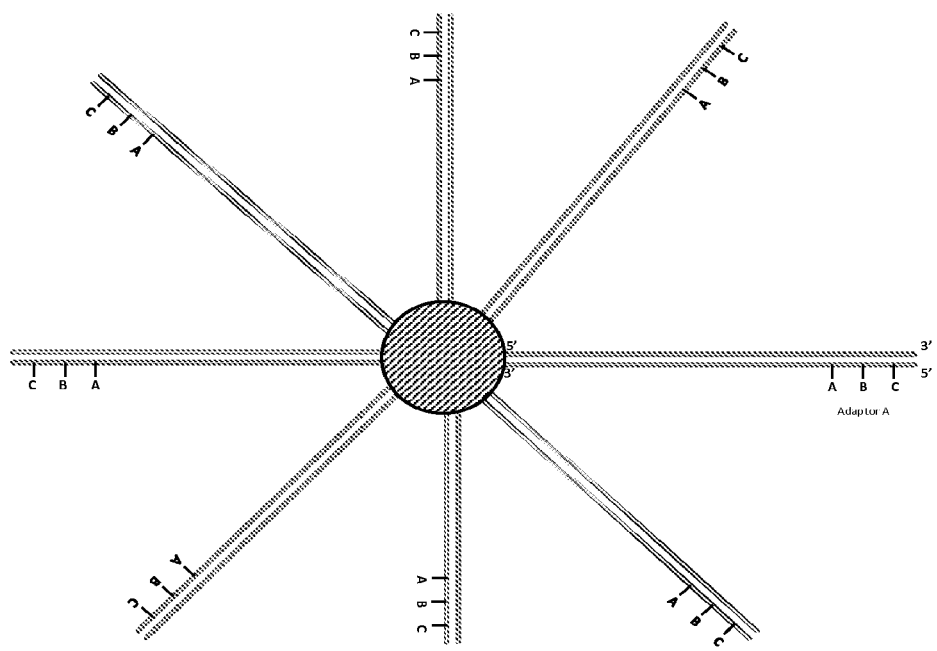
FIG. 21 is a schematic of an example step in an amplification method.

In a further embodiment, a short, double stranded DNA sequence (Adaptor B), may be used. This adaptor sequence may be, for example, 10, 20, 30, 40, 50, 100, etc. base pairs long. Adaptor B may contain one or more nick restriction enzyme sites, as shown in FIG. 20. Adaptor B can ligate to the 5' end of the double stranded DNA formed by the method described above. The steps of nicking, extension, and displacement of DNA may be repeated until all of the first primer on the substrate may be extended, as shown in FIG. 21.

In some embodiments, Adaptor B can be ligated to the 5' end of the double stranded DNA through suitable ligation methods. This may be accomplished by use of enzymes such as T4 DNA ligase, T3 DNA ligase, *E. coli* ligase, T7 DNA ligase, Taq DNA ligase, etc. Blunt end ligation may be enhanced by the addition of compounds, such as for example, PEG 6000, PEG 8000 etc.

In the amplification methods and exemplary embodiments described above, the amplification reaction may be isothermal. Unlike traditional amplification methods, such as PCR, no temperature cycling is required.

In another embodiment, the isothermal amplification methods described above may optionally be followed by an amplification method that comprises a nucleic acid denaturation step. Once double stranded DNA is formed using the above methods, the ends of the double stranded DNA that are not bound to the substrate may be denatured and opened up.

The ease with which double stranded DNA may be separated is represented by its melting temperature. The lower the melting temperature, the easier the double stranded DNA may be "unzipped". Double stranded DNA may be opened by denaturing due to heat or, in some embodiments, by "DNA breathing". In some cases, DNA base pairs can stay closed on the order of a few milliseconds. The localized fluctuations of DNA base pairs opening and closing may be referred to as "DNA breathing" and it is spontaneous, depending in part on thermal fluctuations.

Figure 22:
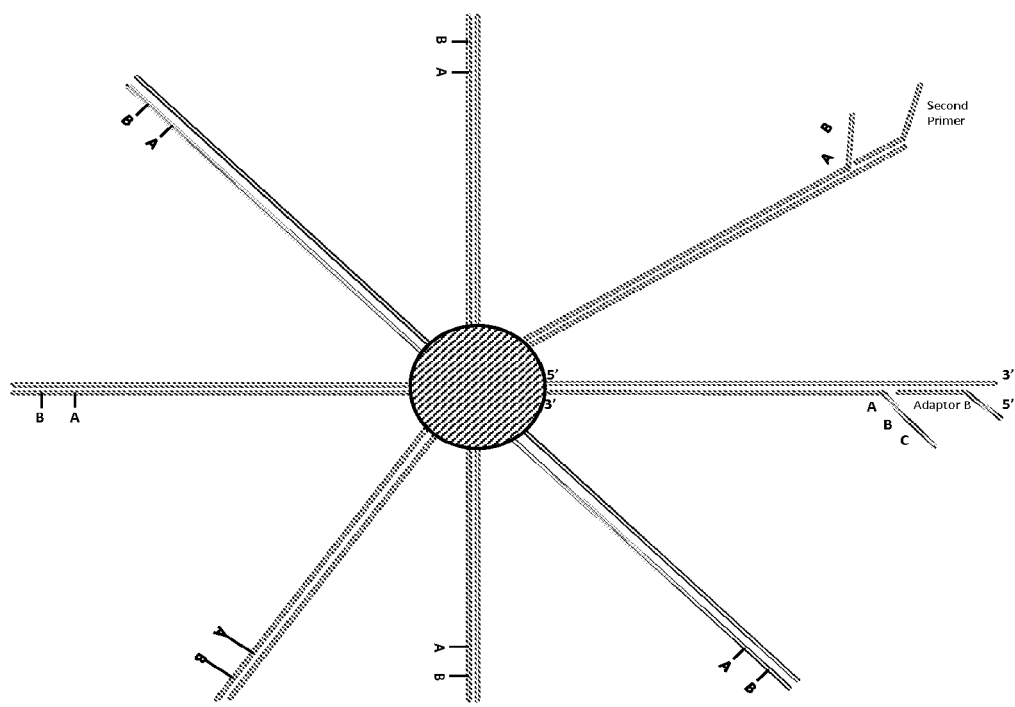
FIG. 22 is a schematic of an example step in an amplification method.
Figure 23A:
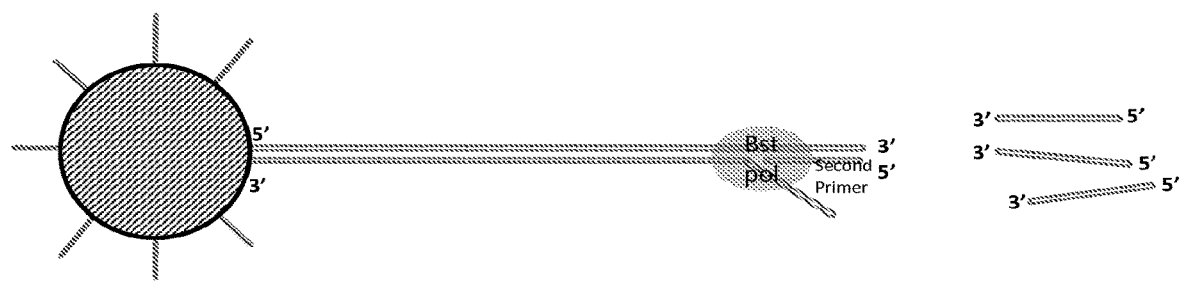
FIGS. 23A-F are schematics of example steps in an amplification method.
Figure 23B:
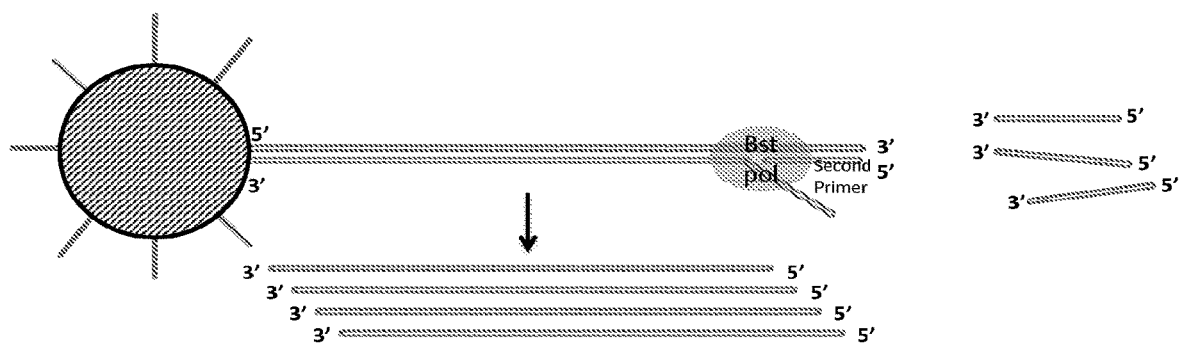
Figure 23C:
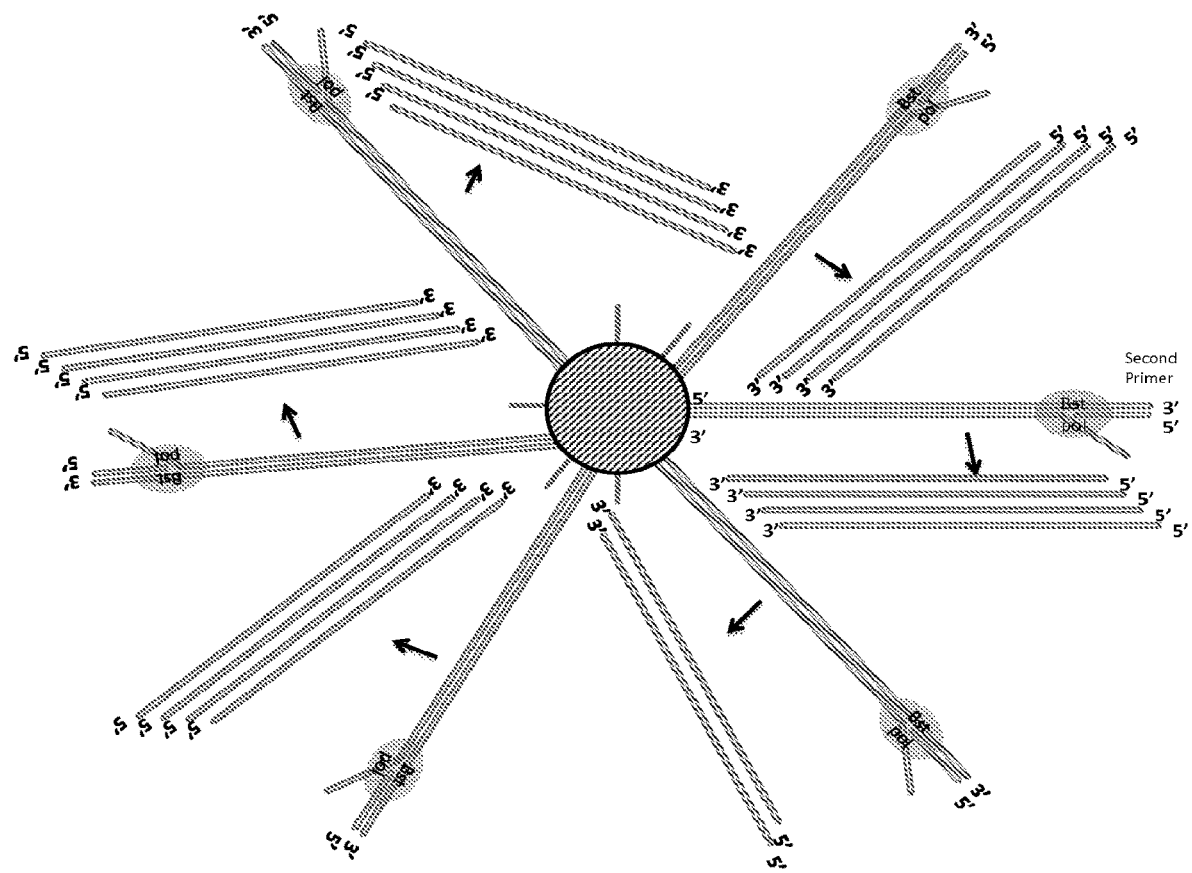
Figure 23D:
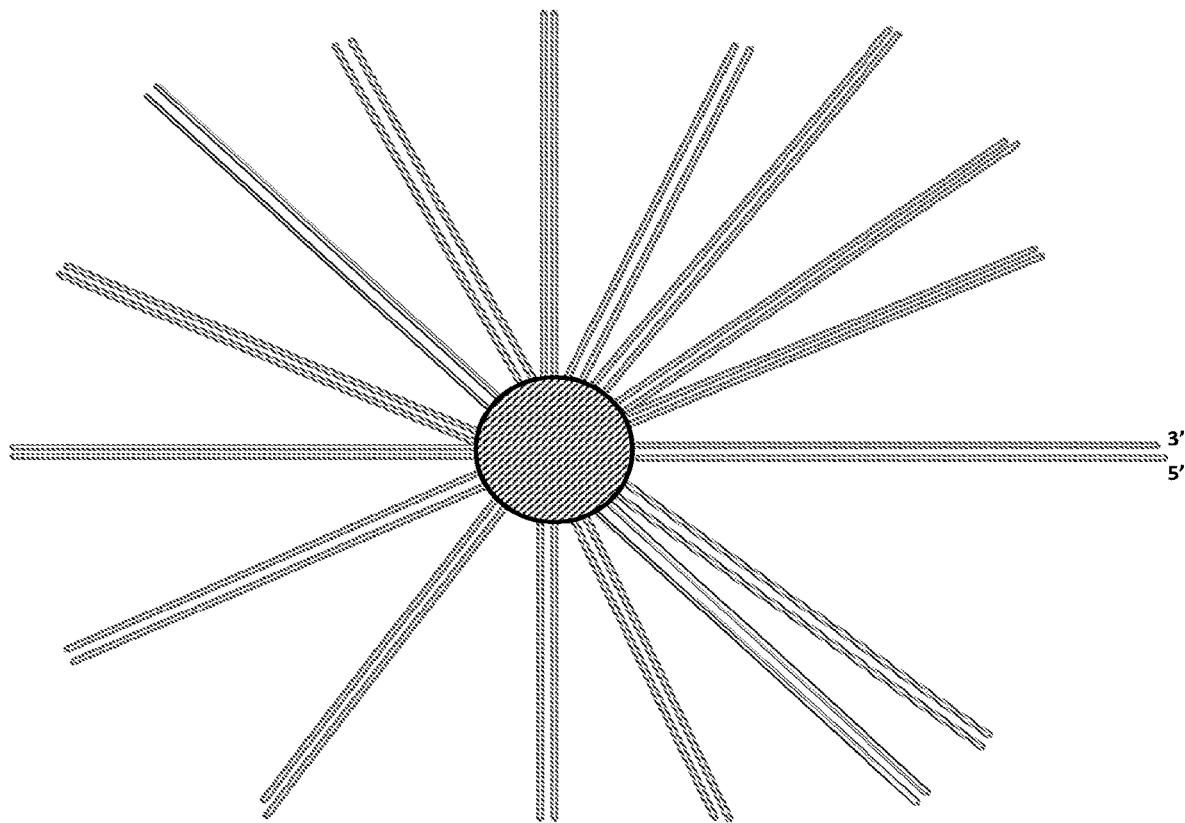
Figure 23E:
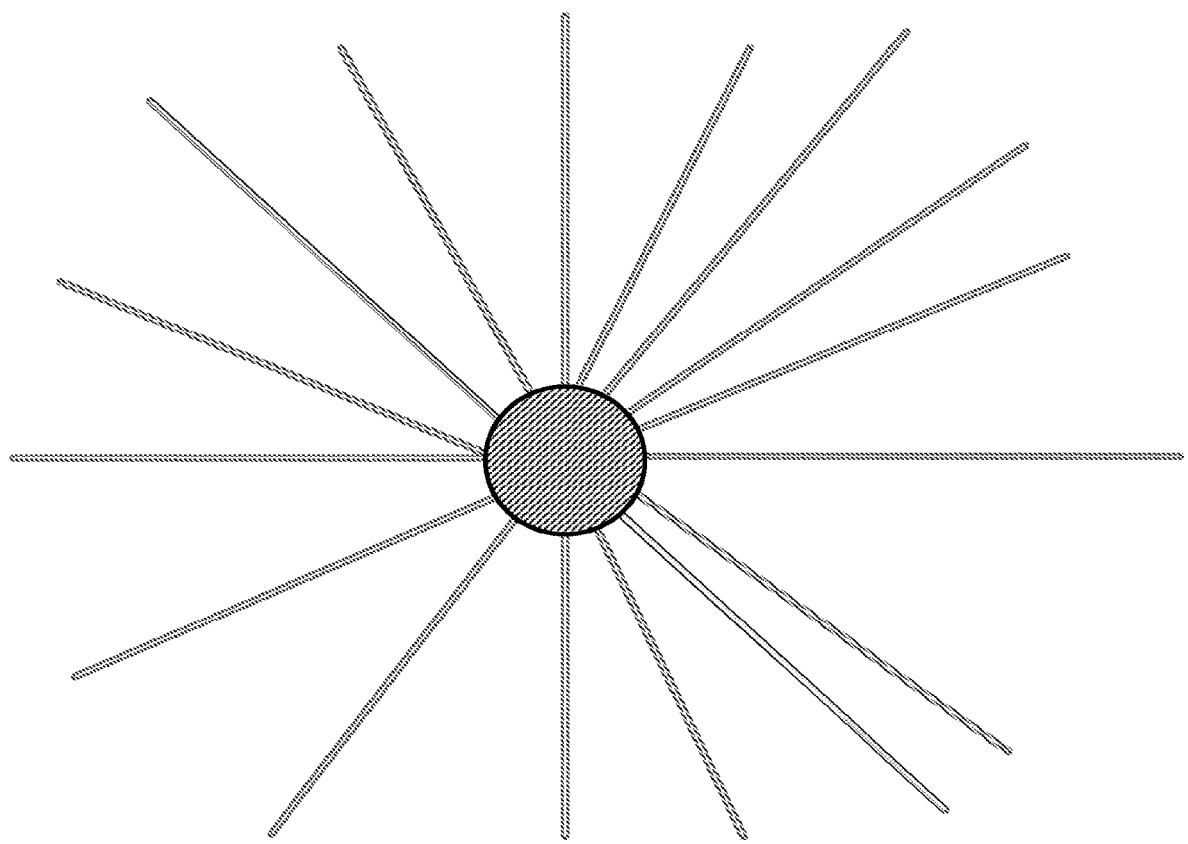
Figure 23F:
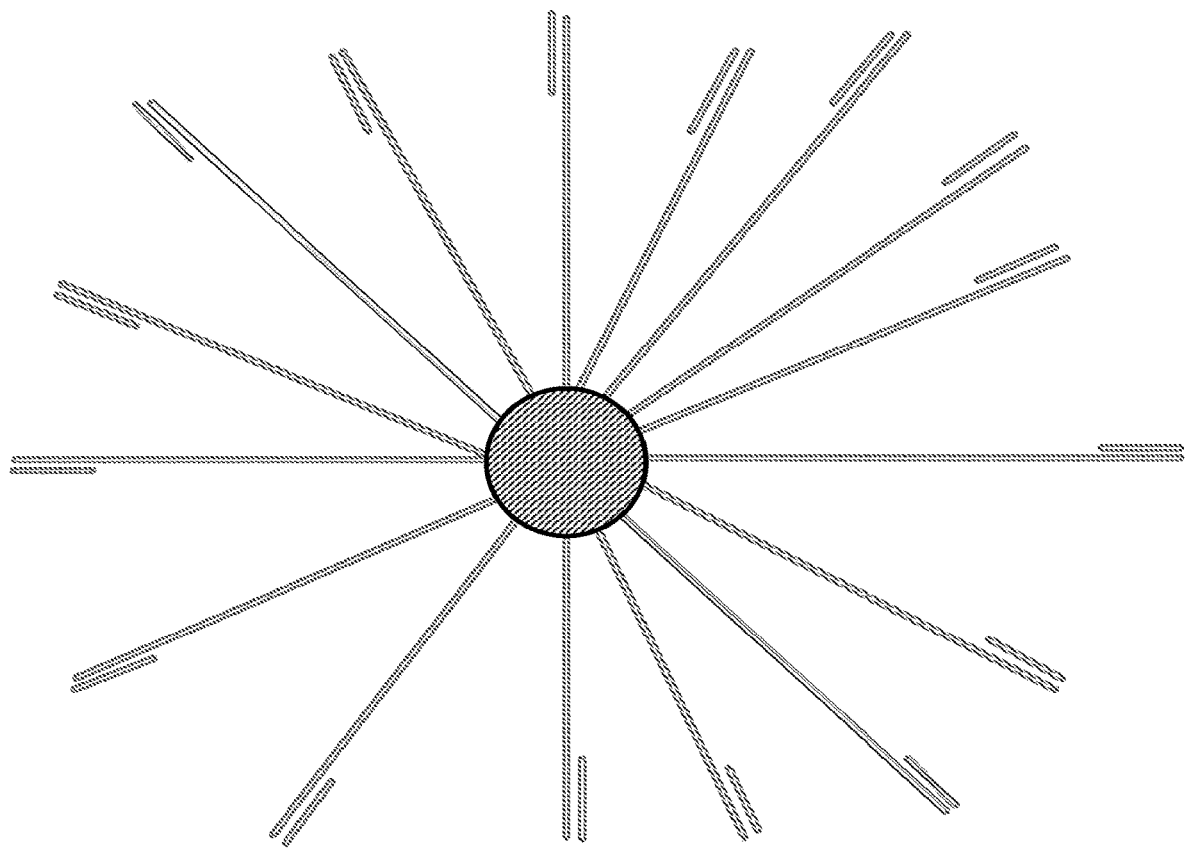

In some embodiments, the opening of the double stranded DNA may allow for a second primer containing a sequence complementary to the 3' end of the double stranded DNA away from the substrate and with or without nick restriction enzyme sites to hybridize to that end, as shown in FIG. 22. In other embodiments, an Adaptor C that is partially single stranded and partially double stranded may be used in the same fashion, as shown in FIG. 22. Alternative embodiments are listed below and may be used alone or in combination.

In one embodiment, a second primer containing a sequence complementary to the 3' end of the DNA may be hybridized to that end. If the second primer does not contain any nick restriction enzyme sites, a strand displacement DNA polymerase may be used to bind to the 3' end of the second primer and can perform strand displacing polymerization, as shown in FIGS. 23 A-F. This may result in the release of single stranded DNA. This method may be repeated until all or substantially all of the first primers on the bead may be extended.

In another embodiment, the second primer may contain one or more nick restriction enzyme sites. The second primer may hybridize to the complementary DNA strand and a nick restriction enzyme site may form in the double stranded DNA. Nick restriction enzymes can then be added in order to release the single stranded DNA. This method may be repeated until all or substantially all of the first primers on the bead may be extended.

In a further embodiment, if using Adaptor C, the nick between Adaptor C and the double stranded DNA may be repaired by ligase or DNA polymerase. All or substantially all of the first primers on the bead may be extended either by strand displacement DNA polymerase alone (Adaptor C without a nick restriction site) or along with a nick restriction enzyme (Adaptor C with a nick restriction enzyme site), The denaturing step may be achieved by either the application of heat or through heat plus chemical means. In certain embodiments, the nucleic acid may be denatured by a temperature cycle of, for example, 50-60° C.

In a further embodiment, chemical means of denaturing the nucleic acid may be utilized in addition to heat. For example, NaOH may be applied to the reaction area in order to denature the nucleic acid. Other chemical means of denaturing the nucleic acid include, but are not limited to: Formamide, Urea, Betain, DMSO, etc.

In some embodiments clonal amplification of the target DNA may be achieved by isothermal transcription-mediated amplification. Single-stranded target DNA can be flanked by two different adapter sequences (A and B). The 5'-end adapter B may contain a unique sequence on its 3'-side and sequence of the upper strand of the T7 promoter on its 5'-side. The 3'-end adapter A may be complementary to the primer A', which can be attached to a bead at its 5'-end. The target may attach to the bead through hybridization between adapter A and the A' primer. The 3'-end of the primer can be extended by Reverse Transcriptase (RT) up to the 5'-end of the B adapter on target DNA. That may create a double stranded promoter for T7 RNA Polymerase (T7 RNAP) at the distant end of the target DNA. T7 RNAP can initiate transcription of that promoter, synthesizing hundreds of RNA transcripts comprising target DNA sequences flanked by sequences of adapter A and unique part of adapter B. The RNA transcripts discussed above may hybridize to other A' primers on the same bead. In some embodiments, those primers can be extended by RT up to the 5'-end of RNA transcripts, thus creating DNA:RNA heteroduplexes.

In one embodiment, the RNA strand of the duplexes discussed above may be hydrolyzed by either RNase H activity of the RT or by the addition of RNase H enzyme. The second primer (T7 primer) comprising of the sequence identical to the B adapter hybridizes to the cDNA strand. The RT may continue to extend the cDNA strand up to the 5'-end of T7 primer. The T7 primer may be blocked at its 3'-end and may not be extended. At this point the double-stranded T7 promoter may be created at the end of the target that is distant from the bead. T7 RNAP may synthesize hundreds of RNA transcripts off the template described above. Those transcripts may hybridize to other A' primers on the same bead thus initiating another cycle of repetitive cDNA and RNA synthesis. The process can continue until all primers on the bead are extended and turn into single-stranded DNA molecules that may be attached to the bead and can comprise of the sequence complementary to the original DNA target flanked by adapters. The adapter sequence at the 3'-end of the above molecules may be complementary to the adapter B and can be used for hybridization of a sequencing primer.

In one embodiment, the amplification methods described above may be carried out in a reaction chamber, a well, a virtual well, an array, etc. The amplification methods may be used in conjunction with an integrated system. For example, the integrated system may be an integrated sequencing platform and may include a DNA extraction system, a library construction system, an amplification system an enrichment system, and a sequencing system. The integrated sequencing platform can include all of these systems within a single microfluidic/microelectronic device (or "chip").

Various types of amplification protocols are contemplated by this method such as, for example, isothermal amplification, rolling circle amplification, strand-displacement amplification (SDA), self-sustaining sequence replication (3SR), bridge amplification, nucleic acid sequence-based amplification (NASBA), polymerase chain reaction, transcription-mediated amplification (TMA), ligase chain reaction (LCR), etc. or a combination of amplification protocols.

The amplification methods described above may also be used for amplification applications wherein clonally amplification is not desired. For example, the methods may be used for creating amplicons from different sample populations. Methods for keeping samples separate may be used, such as for example, DNA barcoding or using carriers of different sizes/colors. In some embodiments, the amplification methods described above may be used for amplification of different sample populations before using a DNA hybridization array to determine the presence of a gene of interest.

Solid Phase Amplification

Figure 68A:
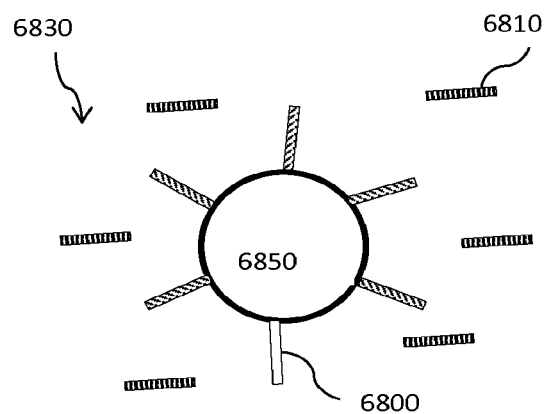
FIGS. 68A-C are schematics of example species that can be used in nucleic acid amplification.
Figure 68B:
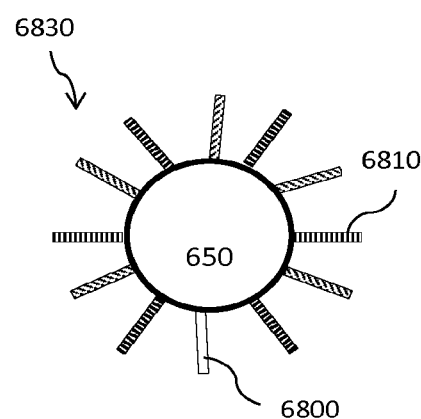
Figure 68C:
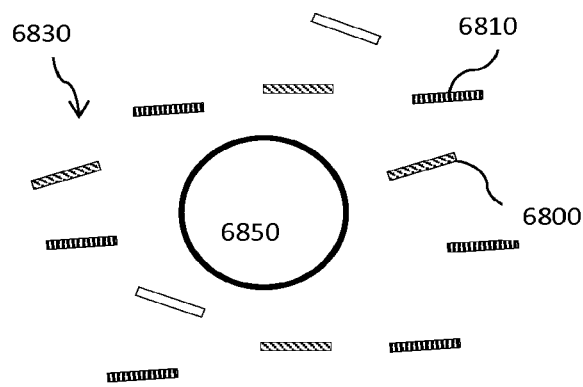

In some embodiments, as shown in examples of FIGS. 68A, 68B, and 68C, an amplification reaction may be a solid phase amplification reaction, using primers configured in a variety of fashions. In some embodiments, as shown in FIG. 68A, a first primer 6800 may be on a surface, such as the surface of a bead 6850, and a second primer 6810 may be in solution 6830. In other embodiments as shown in FIG. 68B, primers 6800 & 6810 may be on the bead 6850. In other embodiments, as shown in FIG. 68C, primers 6800 & 6810 may be present in solution 6830. In some embodiments, one primer of 6800 and 6810 or both primers may be also present on the bead 6850. In a further embodiment, the amplification may be performed whereby one primer of 6800 & 6810 is present in solution 6830, and one primer or both primers are also present on the bead 6850.

Joule Heating for Improved Isolation and/or Concentration of Species and Control Via Heat Cycling Joule Heating for Improved Concentration of Species As described elsewhere herein, species such as reagents suitable for nucleic acid amplification and sample nucleic acid can be concentrated at pixels of array via the generation of electric fields. Examples of such concentrating are also described in PCT Patent Application No. PCT/US2011/054769, PCT Patent Application No. PCT/US2012/039880, PCT Patent Application No. PCT/US2012/067645, and U.S. patent application Ser. No. 13/481,858, which applications are incorporated herein by reference in their entireties.

In some embodiments, electric fields can be used to attract template nucleic acids (e.g., template DNA), dNTPs, and primers to a "confinement cell" region or "chamber-free amplification" region. In some cases, a pixel of an array may comprise such a confinement cell region or chamber-free amplification region. In some cases, each pixel of an array may comprise its own confinement cell region or chamber-free amplification region. Following the attraction of reagents and template nucleic acid, amplification of the template can begin in regions of each cell where template nucleic acid is located. During amplification, the electric fields may aid in preventing cross contamination between different confinement cells undergoing amplification by retaining amplicons. In order to insure that polyclonal regions are not generated, the concentration of input nucleic acid (e.g., DNA) may need to be low enough such that most confinement cells have one or zero sample DNA molecules. Nucleic acid samples can be single stranded or double stranded depending on the amplification methodology. Moreover, as described elsewhere herein, sample nucleic acid may be associate with a carrier, such as, for example, a bead. In some embodiments, sample nucleic acid molecules may be added to carriers (e.g., beads) prior to or after loading of the carriers into an amplification array. In some cases, electric fields may also be useful in concentrating reagents and other species in sequencing reactions.

Some factors associated with amplification methods that include the confinement of reagents at pixels of an array via an electric field and potentially subject to optimization include the frequency, voltage, type of signal input, shape of signal input, absolute value of voltage, duty cycle, and dimensions of the electric field confinement cell used to confine sample nucleic acid (e.g., template DNA) and reagents such as a polymerase and generated amplicons. If confinement were the only consideration, it may be possible to confine almost any size of amplicon, including amplicons of fairly small size. An electric field that is strong enough to ensure proper confinement, however, may also prevent proper activity of other reagents, such as, for example, a polymerase, during an amplification reaction (e.g., PCR, isothermal amplification, primer extension, etc.). For example, a strong electric field may prevent a polymerase from binding with a template nucleic acid and/or may exert a force on a polymerase that dissociates it from a template nucleic acid and extended primer. In another example, a strong electric field may exert a force on an extended primer that dissociates it from a template nucleic. Proper arrangement and operating conditions (e.g., applied voltage, frequency, duty cycle, reaction conditions, etc.) of an electric field may help to ensure that the electric field does not pull the polymerase and/or extended primer from a complex of the template nucleic acid (e.g., template DNA), extended primer, and polymerase.

In some embodiments, it may be desirable to optimize a combination of frequency, voltage, and size of a confinement cell, depending on the size of an amplicon generated in the confinement cell. For example, the size of a confinement cell can be about 1, 2, 3, 4, 5, 6, 7, 8, 9, 10, 11, 12, 13, 14, 15, 16, 17, 18, 19, 20, 25, 30, 35, 40, 45, 50, or more µm in length or diameter and of various shapes that include, for example, squares, rectangles, circles, hexagons, etc. or any other shape. In some embodiments, the frequency can range from a DC signal (0 Hz) to an AC signal of a few Hz to several kHz or MHz. In some embodiments, the voltage can consist of, for example, 0.5 V or 1V AC with 500 Hz frequency with a 0.8V or 1.2 V DC offset.

Amplification within a confinement cell can be achieved using either electrophoresis or a dielectrophoretic field, or both. In order to induce dielectrophoresis, an array of electrodes can be used to create non-uniform electric fields. The electrode configuration may take various forms, including an outer electrode that defines the outside of the confinement cell and an inner electrode, or there may be two inner electrodes proximate to a carrier, for example, a bead (e.g., a magnetic bead) with a magnet located such that it retains the carrier proximate to the electrodes.

In some embodiments, inner electrodes may have alternating positive and negative polarities or charges so as to concentrate template nucleic acid and reagents in close proximity to a carrier (e.g., bead) located between the inner electrodes. The inner electrodes can alternate back and forth between positive and negative charges. In this manner, template nucleic acid and reagents used for amplification may be passed back and forth between the inner electrodes, concentrated in an area on or proximate to the carrier, and also prevented from attaching to, passing by, or getting in close proximity to an electrode of opposite charge (outside electrode). In some cases, an outer electrode is negatively charged. The electric field generated by a negatively charged outer electrode can be an additional barrier, preventing the crossing and diffusion of negatively charged nucleic acid (e.g., DNA) away from the confinement cell. In this manner, template nucleic acid (e.g., DNA) and reagents may be concentrated on or near the carrier, which can allow for an increase in efficiency of the amplification reaction. In some embodiments, the impact of local pH change around a carrier may be controlled with the distance of the inner electrodes from the carrier or with a coating layer such as a bleach-type material (e.g., HQ), a polymer, or another coating material.

Figure 61A:
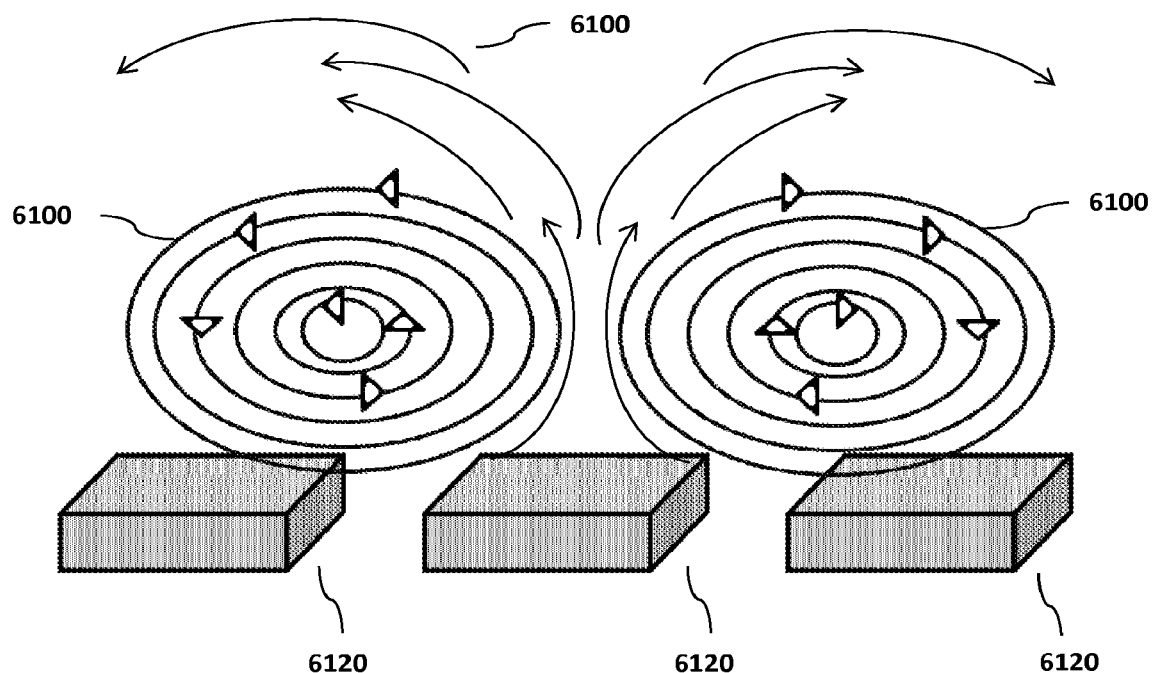
FIG. 61A is a schematic depicting an example of dielectrophoresis-induced flow generated by example electrodes.

In some cases, when using a dielectrophoretic field, flow may be generated by dielectrophoresis. FIG. 61A illustrates an example of dielectrophoresis-induced flow (or electroosmotic flow) 6100 above electrodes 6120 of a pixel. In some cases, the retaining of amplicons, reagents, and/or template nucleic acid, etc. in a confinement cell of the pixel may become problematic, as the flow 6100 can cause such species to drift to another area. If transport of the species via electroosmotic flow is sufficient, there may be contamination of other pixels, due to amplicons and/or other species such as template nucleic acid moving from a pixel to a neighboring pixel via transport. Furthermore, in the case of clonal amplification, the electroosmotic flow may negatively affect amplification efficiency if it interferes with amplicons binding to a carrier.

In some cases, Joule heating may be used to help address potential cross-contamination issues that may arise from electroosmotic transport of species. Joule heating generally refers to heat that can be generated due to electric current passing through a conductor, such as an electrode. Such heat can create a counter flow, in some cases, suitable to offset the flow that can be generated due to dielectrophoresis. Joule heating can be described by the following equation:

$$Q = I^2 R t$$

where Q is heat (e.g., heat in Joules), I is electrical current (e.g., current in amps), R is electrical resistance (e.g., electrical resistance in ohms), and t is time (e.g., time in seconds).

Figure 61B:
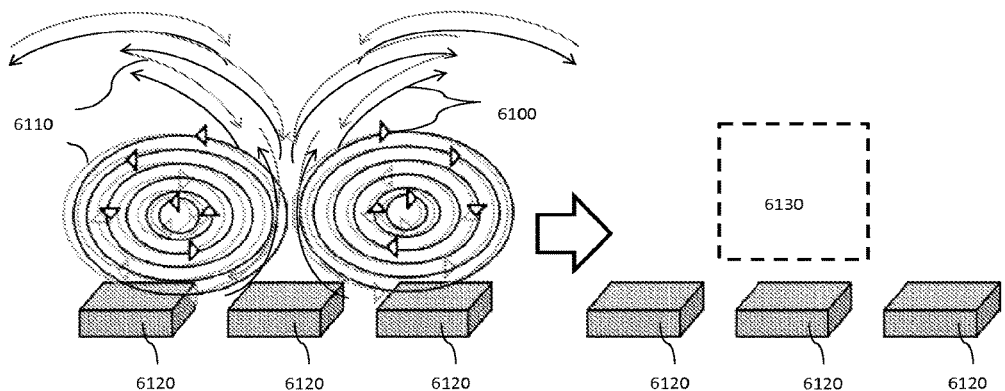
FIG. 61B is a schematic depicting an example of Joule heating induced flow.

In some embodiments, Joule heating may be used to generate movement in an opposite or other direction that can counter flow generated by dielectrophoresis. In some cases, such flow may cancel out flow from dielectrophoresis, an example of which is shown in FIG. 61B. Joule heating-induced flow 6110 moving in the opposite direction of the dielectrophoresis-induced flow 6100 may result in a flow that leads to the isolation and/or concentration of species, such as, for example nucleotides, polymerase, nucleic acids (e.g., DNA), other reagents, other charged species, etc. in and around area 6130, proximate to the electrodes 6120. In some cases, the flow may be circular, turbulent, laminar, or any other type of flow.

In some embodiments, there may be only one electrode per pixel. In other embodiments, as shown in the examples of FIGS. 61A-B, there may be one middle electrode and two electrodes proximate to the middle electrode in a pixel. Other configurations of 3 or more, 4 or more, 5 or more, etc. electrodes can be used depending on the level of confinement and the specific application. Joule heating may be used with such configurations or any other suitable configuration.

In some embodiments, electrophoresis may be combined with dielectrophoresis and Joule heating. A DC current may be generated by one or more outer electrodes in order to help contain the amplicons. There may be one or more inner electrodes that operate using DC current or AC current (electrophoresis or dielectrophoresis, respectively). In some embodiments, Joule heating-induced flow may be adjusted such that it does not cancel out the dielectrophoresis-induced flow. In some embodiments, dielectrophoresis-induced flow is permitted to create a flow, with or without using Joule heating.

In some cases, a flow around electrodes of a pixel may be desirable for applications, such as, for example, washing of reagents, electrodes, carriers, and/or an array. Such flow may be circular, turbulent, laminar, or any other type of flow. In some cases, flow around electrodes of a pixel may be used to mix or wash or may aid in washing the reagents off the array. In some embodiments, flow generated by Joule heating may be used to optimize reagent delivery. For example, flow generated by Joule heating may aid in distributing reagents and/or template nucleic acid across the array more efficiently than other forms of reagent delivery. Improvements in the efficiency of species delivery may lead to a decrease in delivery time and may shorten the time needed to conduct biological processes of interest, such as, for example, nucleic acid (e.g., DNA) amplification, or nucleic acid (e.g., DNA) sequencing.

Control Via Heat Cycling

When inner and/or outer electrodes use a DC current for electrophoretic concentration or confinement of amplicons, electrolysis may occur at higher voltages and may cause issues such as, for example, bubbles and/or a drop in pH in regions proximate to an electrode. In some embodiments the pH change can be reduced or eliminated by using a higher buffer concentration. In some embodiments, the generation of bubbles can be reduced or eliminated by coating the electrodes with a suitable material such as, for example, hydroquinone (HQ), or another type of coating layer. In some cases, the generation of bubbles can be reduced or eliminated by using electrodes with a larger surface area exposed to a liquid and/or by using porous electrodes. Examples of suitable porous electrodes include Black Platinum electrodes and Iridium electrodes.

In generating a DC field for electrophoretic concentration or confinement, electrolysis products can build up, with non-limiting examples of such electrolysis products that include hydronium and hydroxide ions. To minimize effects from these ions, the DC field can be pulsed so that the net DC effect is much lower. In some embodiments a pulsed duty cycle can be reduced after species (e.g., reagents, nucleic acid) have migrated closer to an electrode. In some embodiments, a DC field can be used to concentrate species and an AC field can be used to maintain concentration and/or confinement of electrolysis products. In other embodiments, both a DC field and an AC field can be used for concentration and confinement.

In generating a DC pulse, voltage can be raised to a higher voltage for a period of time, and then be reduced to zero volts (or a lower voltage) with no or minimum electrophoresis for a period of time. The lower or zero volt time period can allow for the diffusion of any bubbles that may have formed as a result of electrolysis.

Figure 62A:
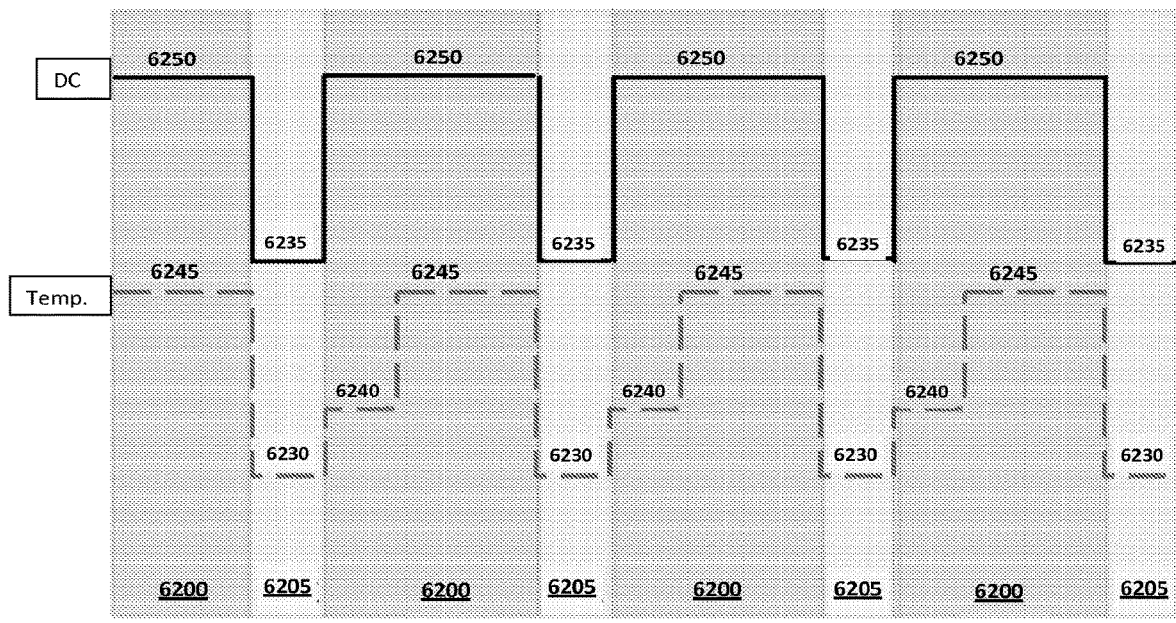
FIG. 62A is a schematic depicting an example of synchronizing a DC pulse with heat cycling.
Figure 62B:
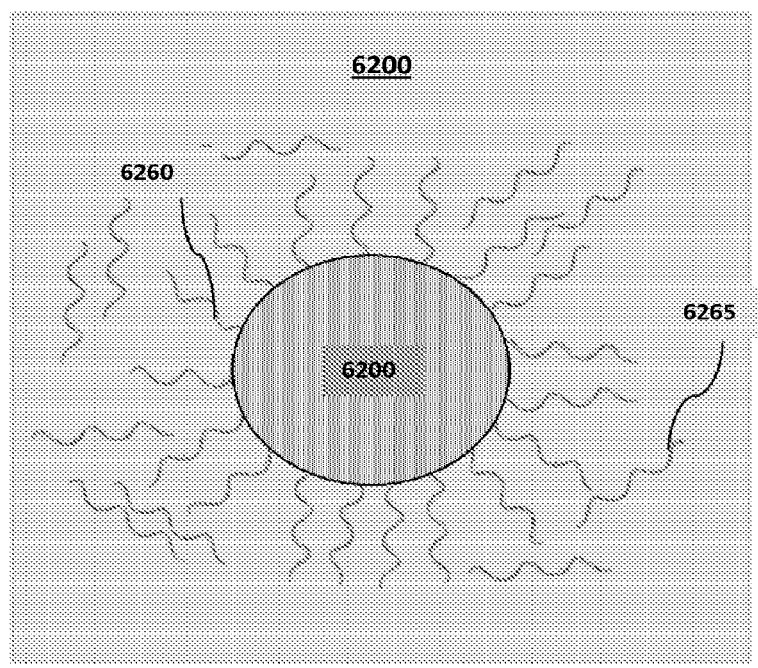
FIGS. 62B and 62C are schematics of nucleic acids coupled to beads.
Figure 62C:
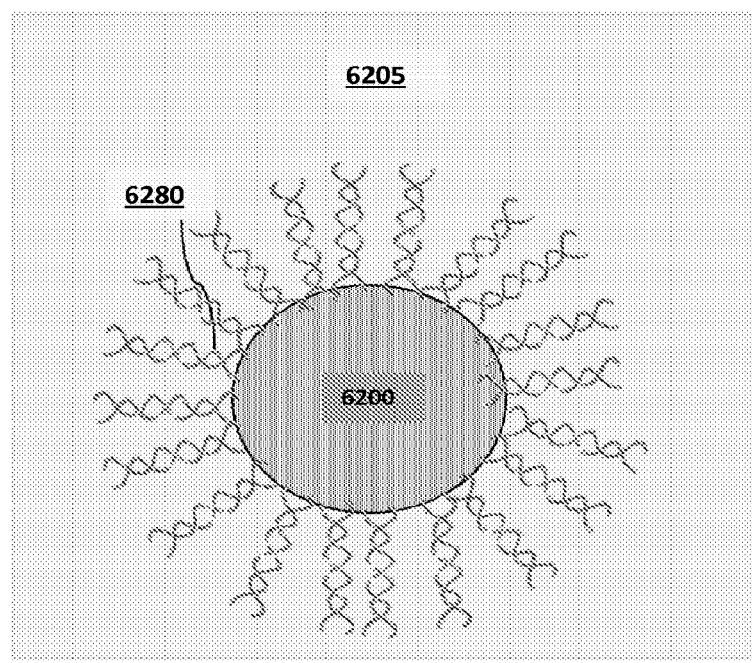

Although a pulsed DC field may be used to counter the negative effects of electrolysis, such as bubble generation or a pH change due to generation of byproducts, the pulsed signal may increase the likelihood that amplicons or other species are able to drift away from a confinement cell during the period in which the DC pulse is at a low voltage. In some embodiments, heat cycling during amplification can be used or synchronized with a DC pulse so that when the DC pulse is at a low voltage, a solution within the confinement cell is at a low temperature, and when the DC pulse is at a high voltage, a solution within the confinement cell is at a higher temperature, as example of which is shown in FIG. 62A. As shown in the example of FIG. 62A, when the DC pulse is at a higher voltage 6250, the temperature may also be set to a higher level 6245. During this time period 6200, as shown in FIG. 62B, nucleic acid (e.g., DNA) subject to amplification in a confinement cell may be a combination of double and single stranded nucleic acid. In some cases, a majority of the nucleic acid can be single stranded and some nucleic acid can be in solution. When the voltage is at a higher level 6250, there can be a reduced chance of nucleic acid in solution within a confinement cell migrating into another confinement cell.

During the second time period 6205, however, when the voltage is reduced 6235, the temperature may also be reduced 6230. In some cases, during such a time period, the number of double-stranded nucleic acids bound to a carrier (e.g., bead) within a confinement cell can be increased, such that most of the nucleic acid is bound to the carrier. Binding can help reduce migration of amplicons from the confinement cell.

In some embodiments, a DC field may be applied in a pulsed fashion in order to prevent heating of the electrodes. Excessive heat generated by the electrodes may have a negative impact on a biochemical reactions of interest, such as for example nucleotide incorporation, amplification, sequencing, etc. Pulsing of a DC field may provide time for an electrode to cool down between pulses.

In some embodiments, the voltage of a DC and/or AC electric field may be adjusted such that it promotes dielectrophoretically-induced flow, electroosmotic flow, or other similar effect. In some embodiments, voltage, frequency, electrode shape, electrode configuration, etc. may all be configured in order to promote a specific type of desired flow. In some cases, an electrode array may be patterned such that the arrangement of the electrodes in the array is conducive to creating a desired flow pattern. Such a configuration may be desirable for better washing of reagents, carriers, the array, etc. and/or optimized delivery of reagents. The mixing due to the flow may allow for better distribution, and thus faster delivery of reagents. The flow may also aid in the removal of reagents from the array.

In some embodiments, a combination of AC and DC applied fields may be used. In some embodiments, Joule heating or heat generation may be used in applications requiring heat, such as for example, thermocycling, to provide localized heating and/or temperature cycling.

Library Construction Systems and Nucleic Acid Fragmentation Methods

An integrated system may comprise a library construction system (e.g., nucleic acid library construction system), which may include a fragmentation and/or size selection element. An example of a library construction system is shown in FIG. 63. As shown in FIG. 63, a library construction system may include a nucleic acid (e.g., DNA) fragmentation and size selection element 6316. The fragmentation and size selection element 6316 can be configured to produce double-stranded nucleic acid fragments, which may or may not have blunted ends, via the elements and methods described below. The fragmentation and size selection element 6316 can include one or more microfluidic channels 6322 within which nucleic acid may be disposed along with a set of fragmentation beads 6324. Nucleic acid 6312 collected in a nucleic acid (e.g., DNA) extraction system (shown for example in FIG. 63) can be conveyed or "injected" into the nucleic acid (e.g., DNA) fragmentation and size selection element 6316 by any suitable means (e.g., pressurized injection, electrophoretic movement, gravity feed, heat-induced movement, ultrasonic movement and/or the like). Similarly, fragmentation beads 6324 can be conveyed into the nucleic acid (e.g., DNA) fragmentation element and size selection element 6316 by any suitable means.

The fragmentation element and/or size selection element 6316 may include a pump 6326 to produce movement of a fluid (e.g., a fluid comprising nucleic acid (e.g., DNA) and fragmentation beads 6324) within a microfluidic channel 6322. The pump 6326 can be, for example, a peristaltic pump. In some embodiments, the pump 6326 can include one or more microfluidic elements in fluid communication with the microfluidic channel 6322, and may have a flexible side-wall that, when deformed, produces a flow within the microfluidic channel 6322. In other embodiments, however, any other suitable mechanism can be used as an alternative or in addition to produce movement fluid within the microfluidic channel 6322, with non-limiting examples, that include selective heating and cooling of the fluid, pneumatic pressurization of the microfluidic channel, electrophoretic motion, or the like.

The fragmentation beads 6324 can be constructed from any material suitable for separating, cutting and/or otherwise dividing a nucleic acid (e.g., DNA) into nucleic acid fragments (e.g., DNA fragments). In some embodiments, the fragmentation beads 6324 can be constructed from glass, polydimethylsiloxane (PDMS), ceramic or the like. Moreover, the fragmentation beads 6324 can have any suitable size and/or geometry such that the fragmentation element produces fragments having the desired characteristics (e.g., length, strand characteristics, or the like). For example, in some embodiments, the fragmentation beads 6324 can be substantially spherical and can have a diameter of 50 μm or less. In other embodiments, the fragmentation beads 6124 can have a diameter of 500 nm or less, or any diameter between 50 μm and 500 nm.

Moreover, the size and/or geometry of the microfluidic channel 6322 (e.g., cross-sectional shape, aspect ratio or the like) can be selected such that the movement of the nucleic acid (e.g., DNA) within the microfluidic channel 6322 and contact of the nucleic acid with the fragmentation beads 6324 fragments (e.g., via shearing) the nucleic acid as desired. In some embodiments, the microfluidic channel 6322 may be in the range of 1 to 500 μm in hydraulic diameter (i.e., the cross-sectional area of the microfluidic channel 6322 can be substantially rectangular, thus the size can be represented as a hydraulic diameter). In other embodiments, the hydraulic diameter of the microfluidic channel 6322 can be in the range of 10 to 200 μm. In yet other embodiments, the hydraulic diameter of the microfluidic channel 6322 can be in the range of 500 nm or less. In other embodiments, the microfluidic channel 6322 can have any suitable shape, such as semi-circular, oval, tapered or the like. In some embodiments enzymatic polishing of sheared nucleic acid (e.g., DNA) ends can be done such that the ends are blunt ends.

In other embodiments, an enzymatic solution can be conveyed into the microfluidic channel 6322 to, at least partially, produce enzymatic fragmentation of nucleic acid (e.g., DNA).

Figure 64A:
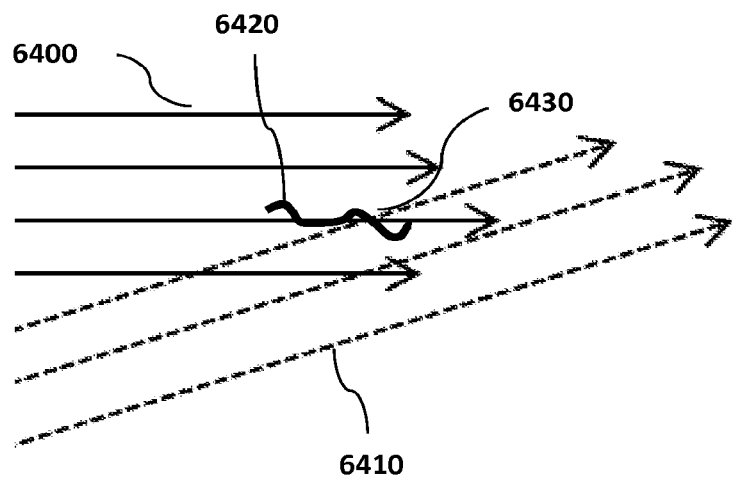
FIGS. 64A-B are schematics that depict example steps of an example method that can be used to fragment nucleic acids.
Figure 64B:
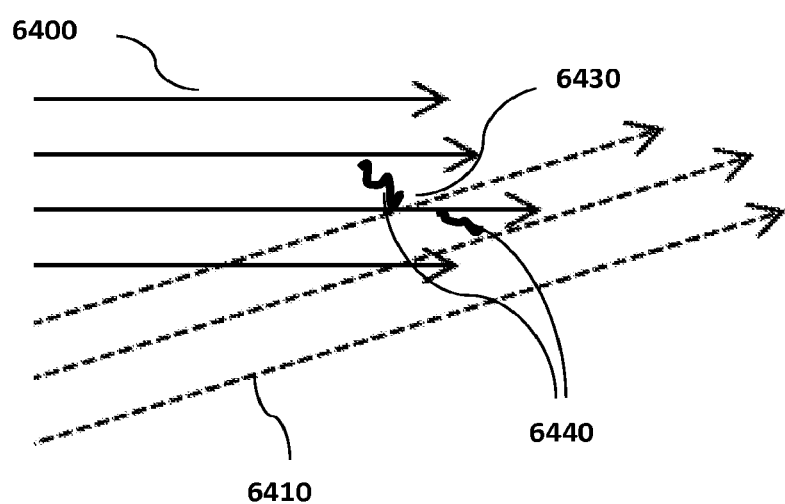

In some embodiments, as shown in an example of FIGS. 64A and 64B, liquids with different flow rates may be used to fragment nucleic acids (e.g., DNA). The flow rate of the first liquid 6400 may be faster or slower than the flow rate of the second liquid 6410. When the nucleic acids, such as for (e.g., DNA) 6420, comes into contact with the interface 6430 that exists between the two liquids due to the differences in flow rate, the resulting shear force on the nucleic acid 6420 may result in nucleic acid fragmentation 6440.

Moreover, the nucleic acid can be elongated or stretched via the aid of an electric field. The effect of shear force, electric force, or other forces may result in the fragmentation of the nucleic acid.

Figure 65A:
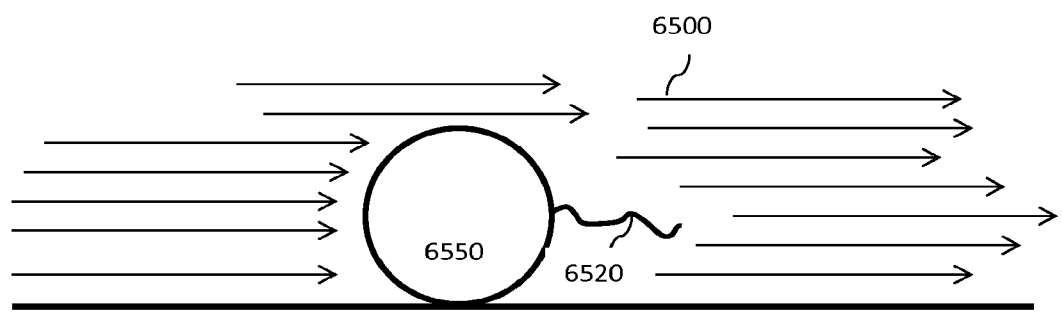
FIGS. 65A-B are schematics that depict example steps of an example method that can be used to fragment nucleic acids.
Figure 65B:
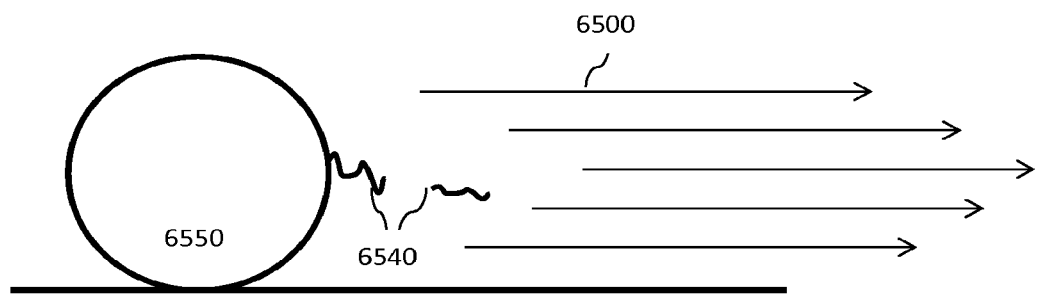

In some embodiments, illustrated in an example of FIGS. 65A and 65B, nucleic acid (e.g., DNA) 6520 may be fixed to a surface, such as for example a bead 6550. The bead-bound nucleic acid 6520 may be exposed to fluid flow 6500 from a surrounding bulk solution. Since some part of the nucleic acid 6520 is bound to a fixed point, exposure to flow 6500 may result in a shear force on the nucleic acid, which can lead to nucleic acid fragmentation 6540.

Figure 66A:
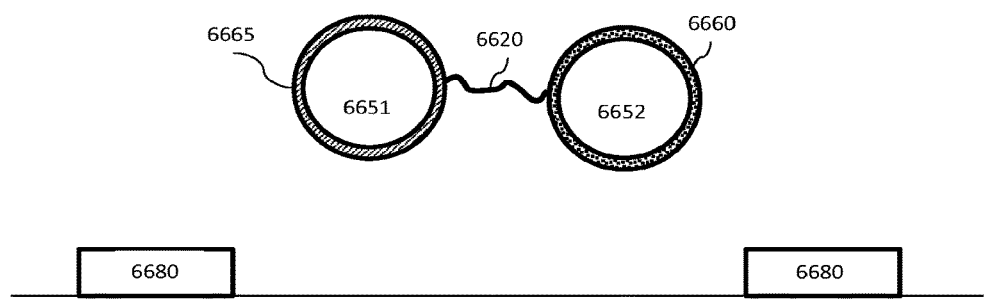
FIGS. 66A-B are schematics that depict example steps of an example method that can be used to fragment nucleic acids.
Figure 66B:
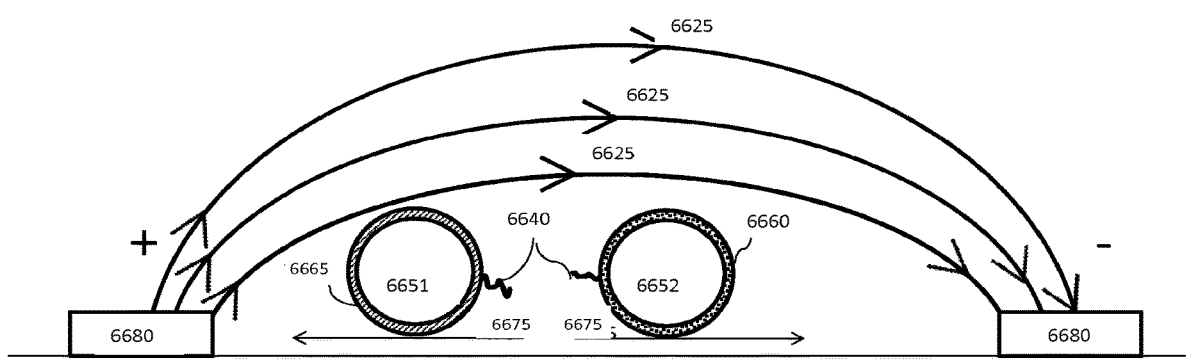

In some embodiments, as shown in an example of FIGS. 66A and 66B, each end of a nucleic acid (e.g., DNA) 6620 may be fixed at each end to a carrier, such as beads 6651 and 6652. One bead 6652 may be coated with a positively charged material 6660. Materials that may be used to create a positively charged coating on the bead 6650 include, for example, materials comprising amines. The other bead 6651 may be coated with a material that imparts a negative charge 6665 on the bead 6651. Examples of suitable materials include, for example, materials comprising carboxyl groups. Once each end of the nucleic 6620 is fixed to beads, the bead-nucleic acid structure may be exposed to an electric field 6625, the can be generated by one or more electrodes 6680. The electric field 6625 may induce movement in the beads in opposite directions 6675, due to their respective charge, and the resulting tensional stress on the nucleic acid 6620 may result in nucleic acid fragmentation 6640. In some embodiments, one bead can be held in a fixed location and a second bead may move due to electric fields (electrophoretic or dielectrophoretic force or fluidics). The separated beads can then be directed to sensors for analysis, such as nucleic acid sequencing, as described elsewhere herein.

Figure 67A:
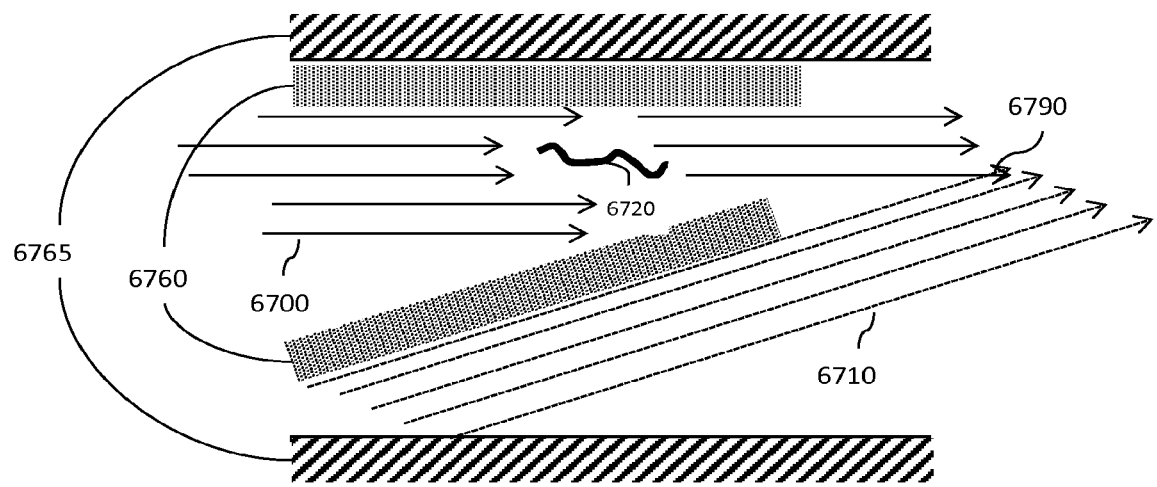
FIGS. 67A-B are schematics that depict example steps of an example method that can be used to fragment nucleic acids.
Figure 67B:
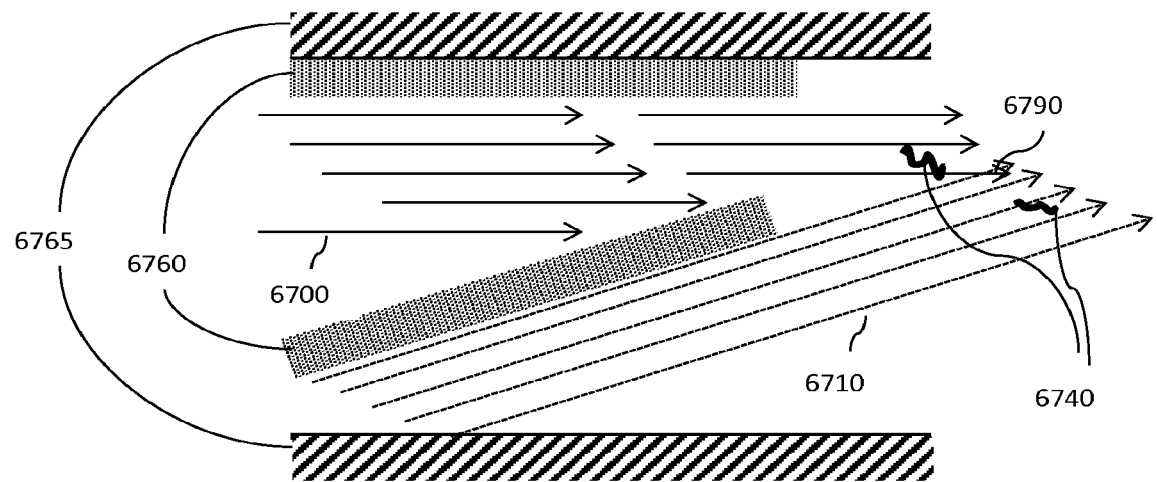

In some embodiments, as shown in an example of FIGS. 67A and 67B, nucleic acid (e.g., DNA) 6720 may be passed through a nanochannel 6760. A microchannel 6765 may be located within or proximate to the nanochannel 6760 such that the microchannel 6765 and nanochannel 6760 are in fluidic contact. The difference in flow rate of the nanochannel fluid 6710 versus microchannel fluid 6700 may result in a shearing force on the nucleic acid 6720 such that nucleic acid fragmentation 6740 result at the fluidic interface 6790. In some cases, the nucleic acid 6720 may be bound to a carrier, such as a bead, or it may be free in solution.

In some embodiments, sonication may be used to fragment nucleic acids. Any suitable sonication method may be used. For example, sonication can be created by MEMS structures or other structures (e.g., structures with concentric arcs with different radius). In some embodiments, sonication can create microbubbles in a fluid in which the nucleic acid (e.g., DNA) is suspended. Gaseous cavitation that results from the microbubbles can create microstreams that may fragment the surrounding nucleic acid. Fragmentation methods described herein may be performed in a microfluidic channel, in a separate microchamber, on a microchip, etc.

Microfluidic Field-Programmable Gate Array (FPGA) Grid and Modules

The integrated devices described herein provide a customizable platform for high throughput analysis of biological and chemical reactions of interest. In some cases, an integrated may include microfluidic technology for high throughput analyses. Accordingly, an integrated platform may comprise one or more integrated microfluidic devices. Methods for configuring such microfluidic devices to suit individual requirements are provided herein.

In some embodiments, the integrated microfluidic devices may be formed from a substrate wherein a plurality of microfluidic channels may be embedded into the substrate.

In some embodiments, the microfluidic channels may be configured to form a grid pattern throughout the substrate or in some portion thereof. For example, the microfluidic channels may be arranged as a plurality of intersecting microfluidic channels along the x, y, and z-axes of the substrate. This configuration may allow for a customizable platform wherein the microfluidic channels of the grid may be selectively opened, closed, and/or allowed to intersect with other channels. In another embodiment, the microfluidic channels may have valves for controlling flow.

The microfluidic channels may be in fluidic contact with one or more modules. The module may perform a desired function, for example, as a sample preparation module, a nucleic acid (e.g., DNA) amplification array module, a nucleic acid (e.g., DNA) sequencing array module, etc. or a combination of functions. The modules may be in fluidic contact with one or more microfluidic channels via a connection, such as for example a socket connection, wherein there may be an air-tight and fluid-tight seal at the connection juncture.

Various fluidic "paths" may be created wherein one or more modules may be interconnected via one or more channel paths. The number and/or type of input or output microfluidic channels in fluidic contact with the modules may be determined in the same manner.

In some embodiments, the integrated microfluidic devices may be formed from a substrate wherein a plurality of microfluidic channels may be embedded into the substrate. The substrate material may be PDMS, Plexiglass, polycarbonate, poly (methyl methacrylate) (PMMA), cyclic olefin copolymer (COC), polyamide, silicon, glass, quartz, etc. or another material. Depending on the particular application, the substrate material may be rigid or it may be flexible.

The microfluidic channels may have a cross section that is circular, elliptical, square, rectangular, etc. or another shape. The dimensions of the microfluidic channel may vary. In some embodiments, the microfluidic channel may have a diameter of about 100 nm, 500 nm, 1 μm, 10 μm, 50 μm, 100 μm, 500 μm, etc.

Figure 69:
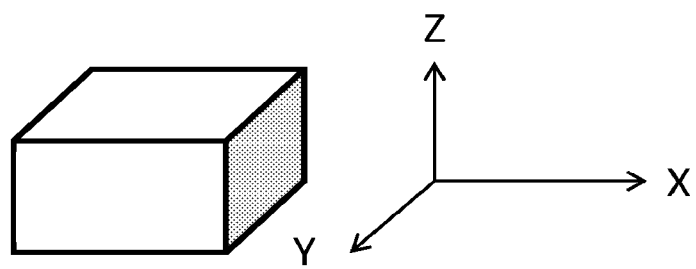
FIG. 69 is a schematic depicting a three-dimensional line drawing of X, Y, and Z directions.
Figure 70A:
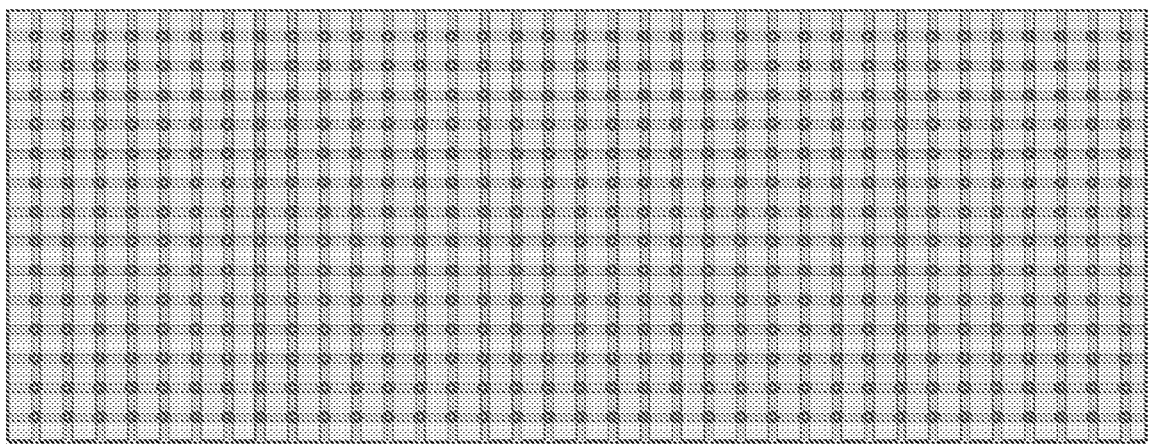
FIGS. 70A-E are schematics of views of example microfluidic devices.
Figure 70B:
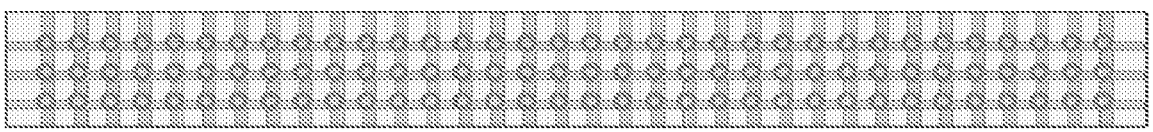
Figure 70C:
Figure 70D:
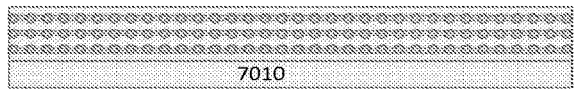
Figure 70E:
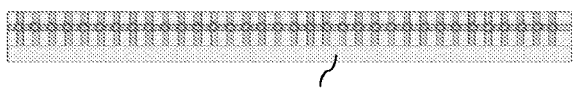

The microfluidic channels may be configured to form a grid pattern throughout the substrate or in some portion thereof. In some embodiments, for example, the microfluidic channels may be arranged as a plurality of intersecting microfluidic channels along the x, y, and z-axes of the substrate. This configuration may allow for a customizable platform wherein the microfluidic channels of the grid may be selectively opened, closed, and/or allowed to intersect with other channels. FIG. 69 shows a 3D line drawing of the x, y, and z axes for clarification. FIG. 70A shows one embodiment of the top view of the microfluidic device. FIGS. 70B and 70C show side views of the microfluidic device, in two different embodiments. FIG. 70B shows a device with three layers of channels on the x and y axes whereas FIG. 70C shows a device with just one layer of channels on the x and y axes. In some embodiments, the microfluidic device may have 1, 2, 3, 4, 5, 10, 50, etc. layers of channels on the x and y axes. FIGS. 70D and 70E show side views of a microfluidic device with three layers and one layer, respectively, but with an optional base layer 7010 for support.

Figure 71:
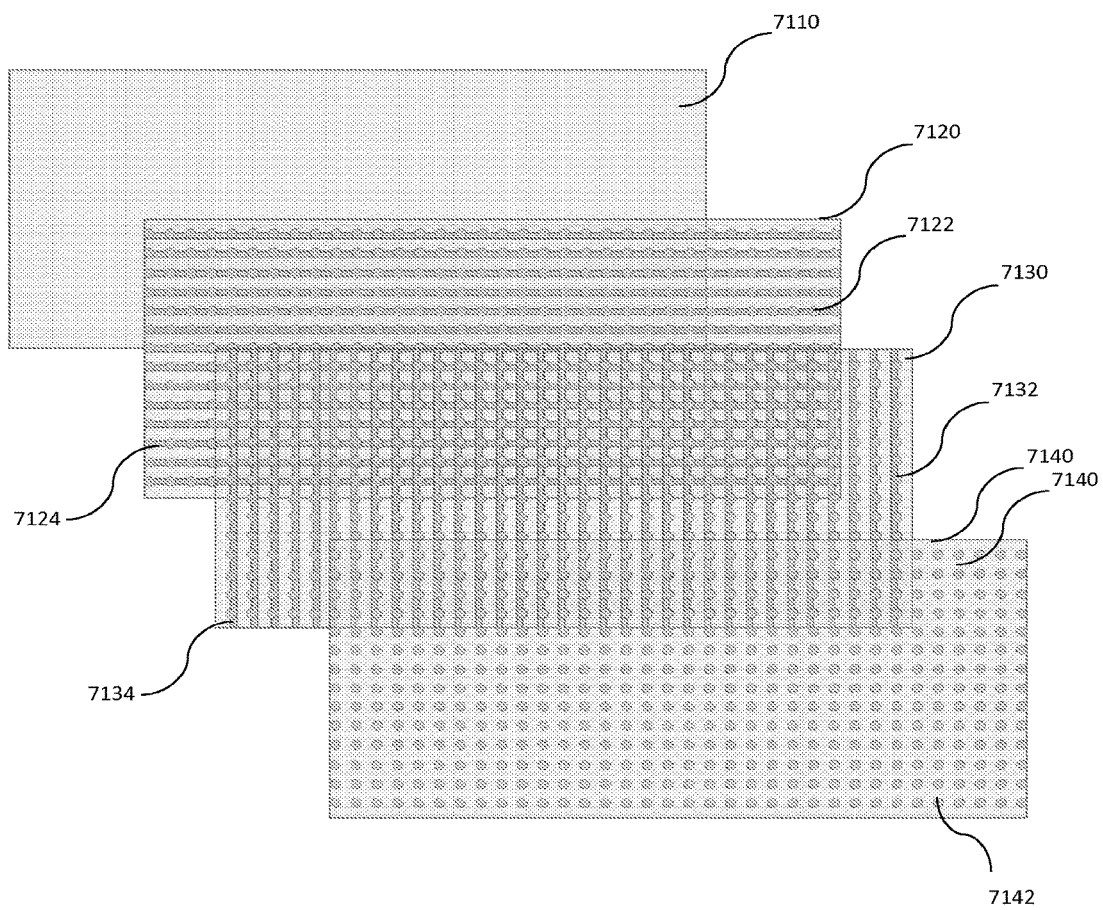
FIG. 71 is a schematic of layers of an example microfluidic device.

In some embodiments, the microfluidic device may be fabricated using a plurality of layers. FIG. 71 illustrates an exploded view top view of an exemplary device with four layers. There may be a base layer 7110, optionally with openings along the z-axis of the substrate (openings not shown). The second layer 7120 may have openings along the z-axis of the substrate for channels running along the z-axis 7122 in conjunction with microfluidic channel along the x-axis 7124. The third layer 7130 may have openings along the z-axis of the substrate for microfluidic channels running along the z-axis 7132 in addition to microfluidic channels along the y-axis of the substrate 7134. Finally, there may be a top layer 7140 with openings along the z-axis for the microfluidic channels running along the z-axis 7142. The openings and channels may be aligned such that they intersect in a grid format, as shown by the top view in FIG. 70A. Thus, the "default" position of this configuration is with all the channels intersecting and in the "open" position. In other embodiments, some portion of the substrate may have channels that intersect while other portions of the substrate may have channels that do not intersect.

Figure 72A:
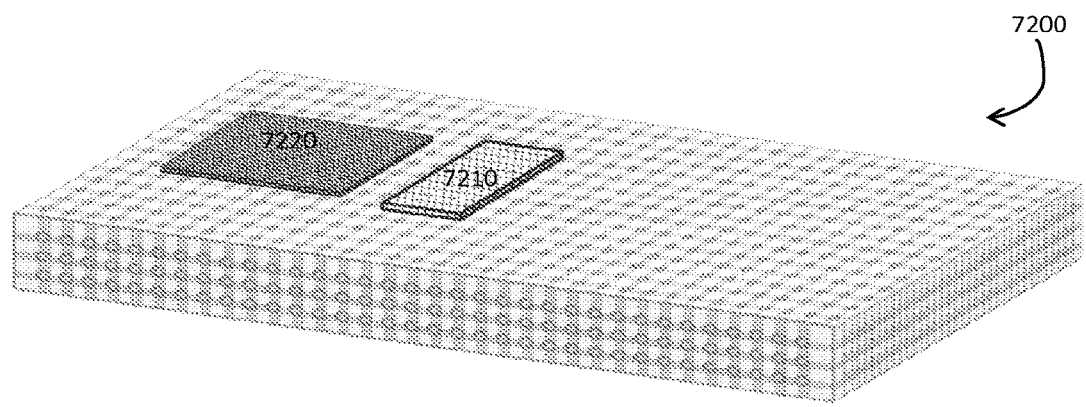
FIGS. 72A-C are schematics of views of an example microfluidic device comprising example modules.

These microfluidic channels may be in fluidic contact with one or more modules. The module may perform a desired function, for example, as a sample preparation module, a nucleic acid (e.g., DNA) amplification array module, a nucleic acid (e.g., DNA) sequencing array module, etc. or a combination of functions. FIG. 72A shows one embodiment of the microfluidic device 7200 with a sample preparation module 7210 and a nucleic acid (e.g., DNA) amplification module 7220.

Figure 72B:
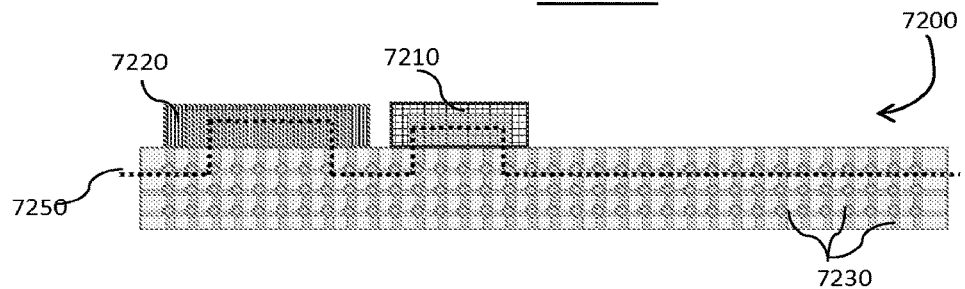
Figure 72C:
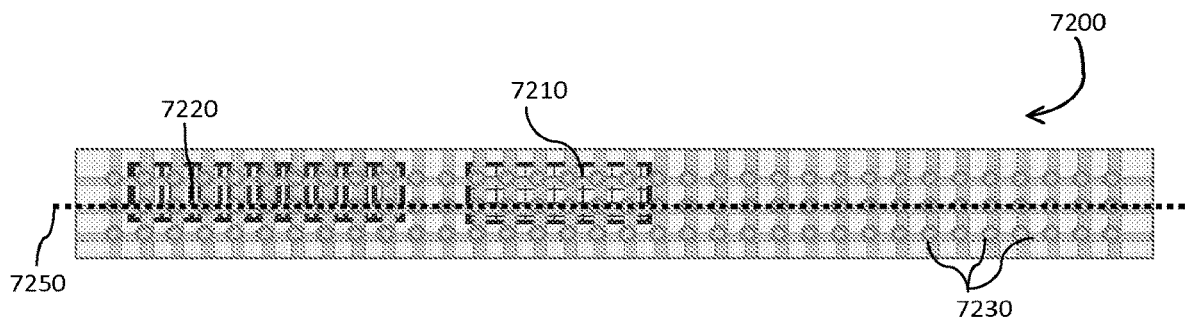

In a further embodiment, modules may be placed above, within, or below the channels of the microfluidic device. FIG. 72B shows a side view of the microfluidic device 7200 of FIG. 72A wherein the amplification module 7220 and the sample preparation module 7210 are located on top of the microfluidic device 7200, above the microfluidic channels 7230. One potential connection path is shown by a dashed line 7250, where the microfluidic channels along the path are open and in fluidic contact with the modules. FIG. 72C shows another embodiment of microfluidic device 7200, wherein the amplification module 7220 and the sample preparation module 7210 are embedded within microfluidic device 7200. One possible connection path 7250 is shown.

Figure 73A:
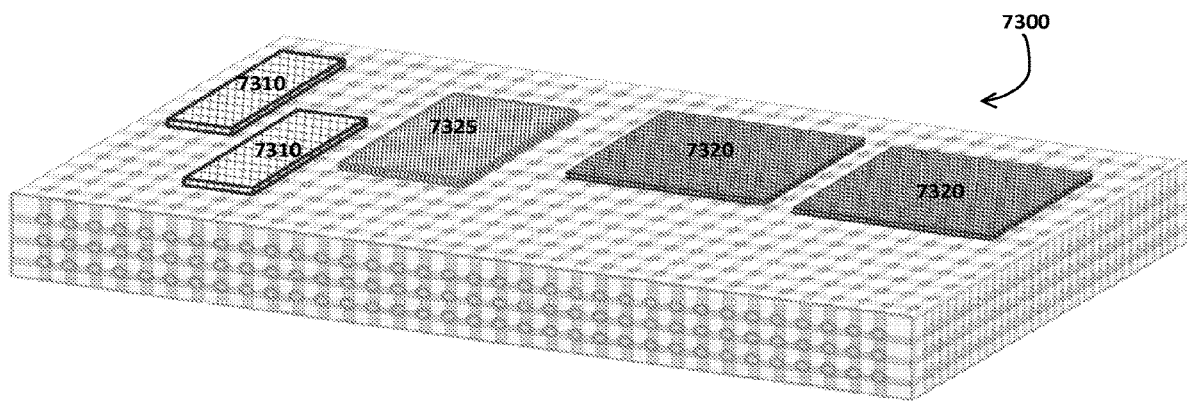
FIGS. 73A-C are schematics of views of an example microfluidic device comprising example modules.
Figure 73B:
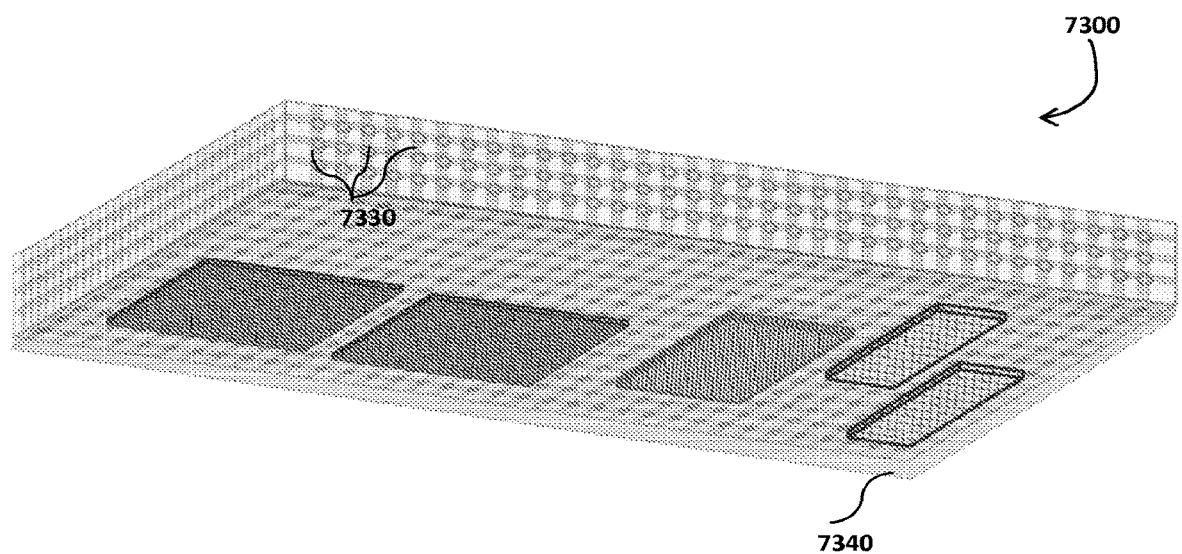
Figure 73C:
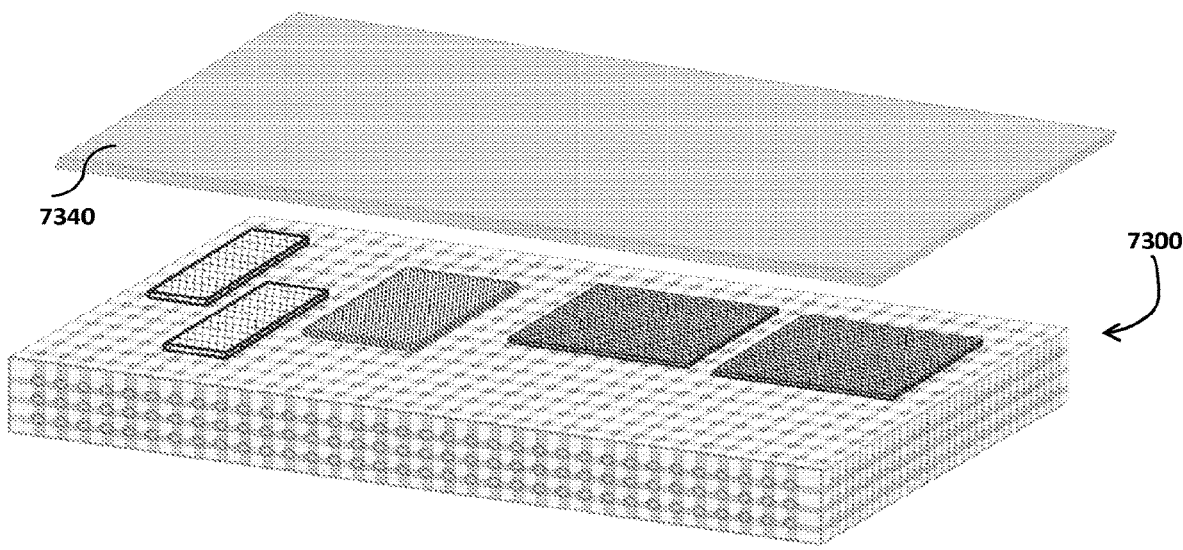

There may be 1, 2, 3, 4, 5, 6, 7, 8, 9, 10, 11, 12, 13, 14, 15, 16, 17, 18, 19, 20, etc. modules wherein all or some number of the modules are connected. FIG. 73A shows a microfluidic device 7300 with five modules. There may be, for example, two sample preparation modules 7310, two nucleic acid (e.g., DNA) amplification modules 7320 and a nucleic acid (e.g., DNA) sequencing module 7325. FIG. 73B shows the microfluidic device 7300 in a configuration where the modules are located below the microfluidic channels 7330 and on the bottom of microfluidic device 7300. A cover component 7340 for the microfluidic device 7300 in this type of configuration may be desirable since the modules are "upside down". FIG. 73C shows an exploded view of the microfluidic device 7300 and the cover component 7340 for clarification.

Figure 74A:
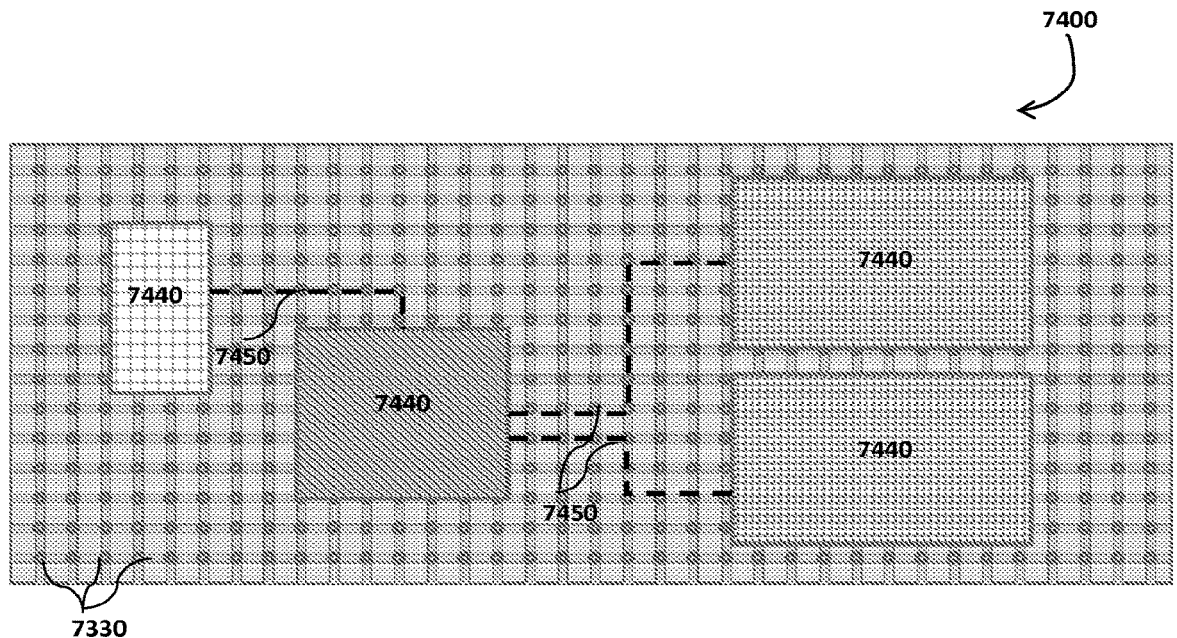
FIGS. 74A-B are schematics of views of an example microfluidic device comprising example modules.
Figure 74B:
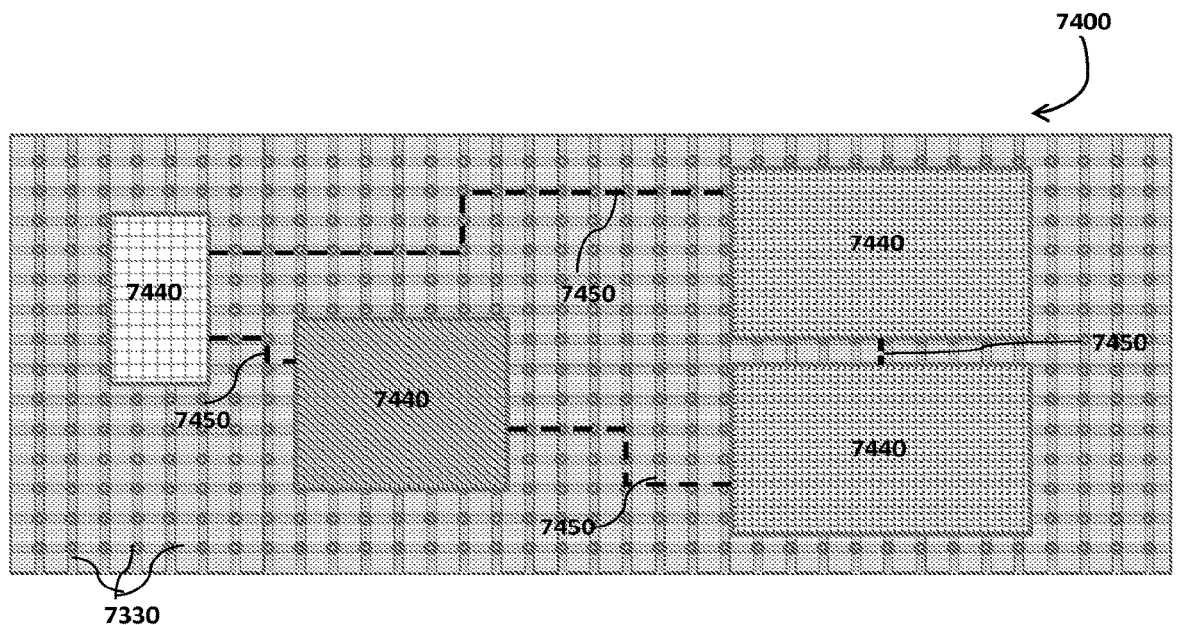

The connection path between the modules may vary and depend upon individual needs. FIGS. 74A and 74B show two exemplary microfluidic devices 7400 with different connection paths 7450 through the microfluidic channels 7330 that connect the modules 7440. The modules 7440 may be of the same or different types. Since the channels are in an "open" position, once a desired connecting path between the modules is determined, the remaining channels not on the path may be closed through a variety of methods. The connecting path may be a straight line between one or more points, or it may travel along the x, y, and z axes in any configuration. This type of more convoluted path may be likened to the concept of Manhattan routing for field-programmable gate array (FPGA) circuits.

Methods for closing the microfluidic channels that are not along the connection path may depend on the substrate material being used. In some embodiments, the microfluidic channels may be partially or completely closed, either at some point along their length or at an intersection of two or more channels. Methods for fusing materials may be used to close the channels, such as for example, lasers, targeted ultrasound, UV light, etc. In other embodiments, the channels may be closed using valves or gates. In another embodiment, the channels may be closed by using one or more polymers to dissolve the structure in the desired area of the channel, fusing the area closed.

Figure 75:
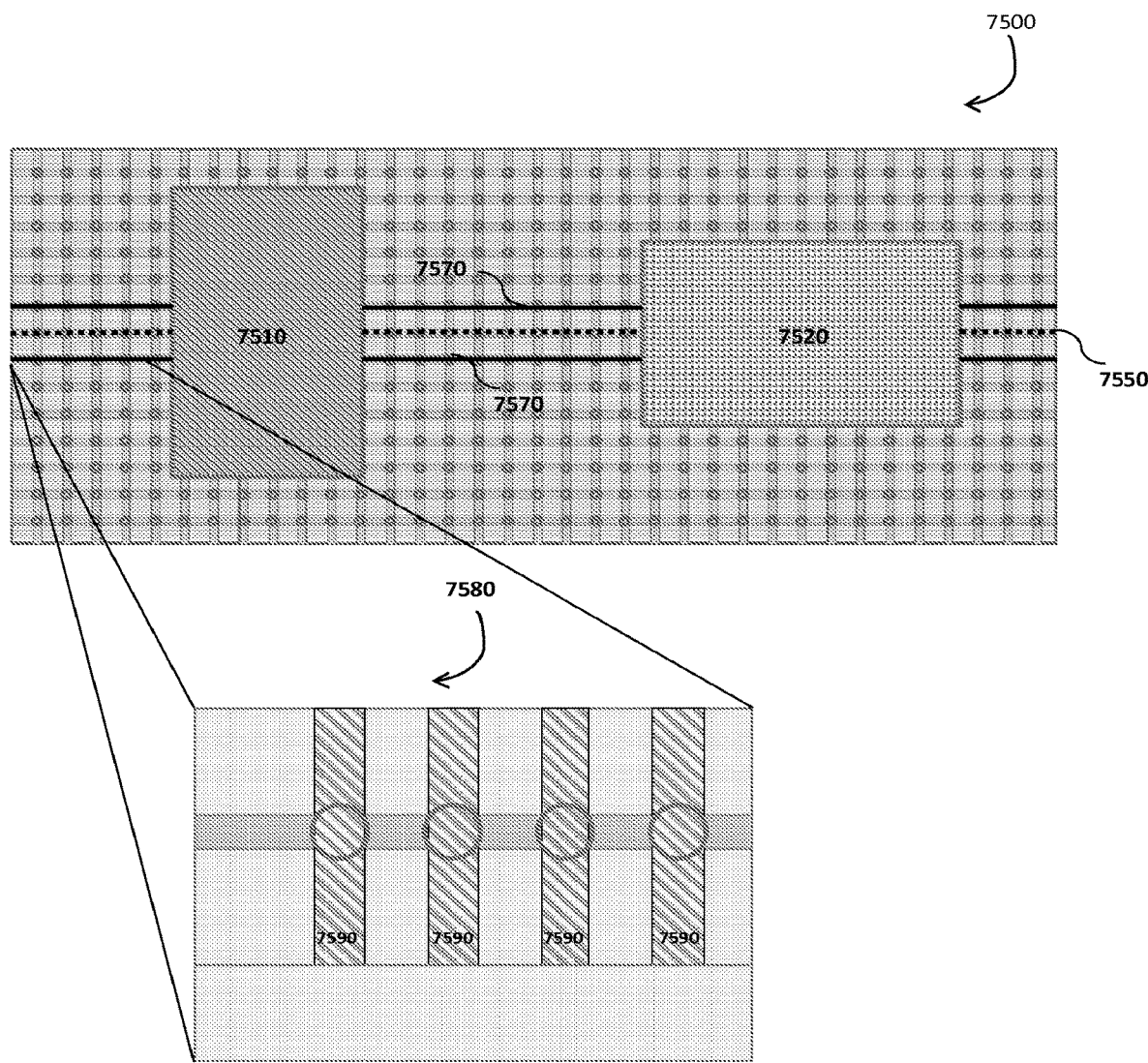
FIG. 75 is a schematic of an example microfluidic device comprising example pins to direct flow in the device.

In some embodiments, the channels may be closed using pins. The pins may be constructed of metal, plastic, glass, etc. or any other suitable material. FIG. 75 shows a microfluidic device 7500 with a sample preparation module 7510 and a nucleic acid (e.g., DNA) sequencing module 7520. The connection path 7550 runs in a straight line along the microfluidic channels 7530. The solid line 7570 is used to illustrate the area of the channels that should be closed in order to ensure that the fluid remains only in the modules and the connection path 7550. The connection path 7550 is shown to extend to the ends of microfluidic device 7500 (e.g., may be connected to an outside source for reagents), but in other embodiments the connection path 7550 may only be between the modules (e.g., with reagents being applied directly to the module, without using microfluidic channels 7530). A cross sectional, side-view 7580 is also shown of a closed area 7570. Pins 7590 are inserted into the microfluidic channels 7530 and, in this embodiment, run along the z-axis. The pins 7590 serve to close the desired area 7570 in order to help ensure there is no leakage into other parts of the microfluidic device 7500 from the connection path 7550.

Figure 76:
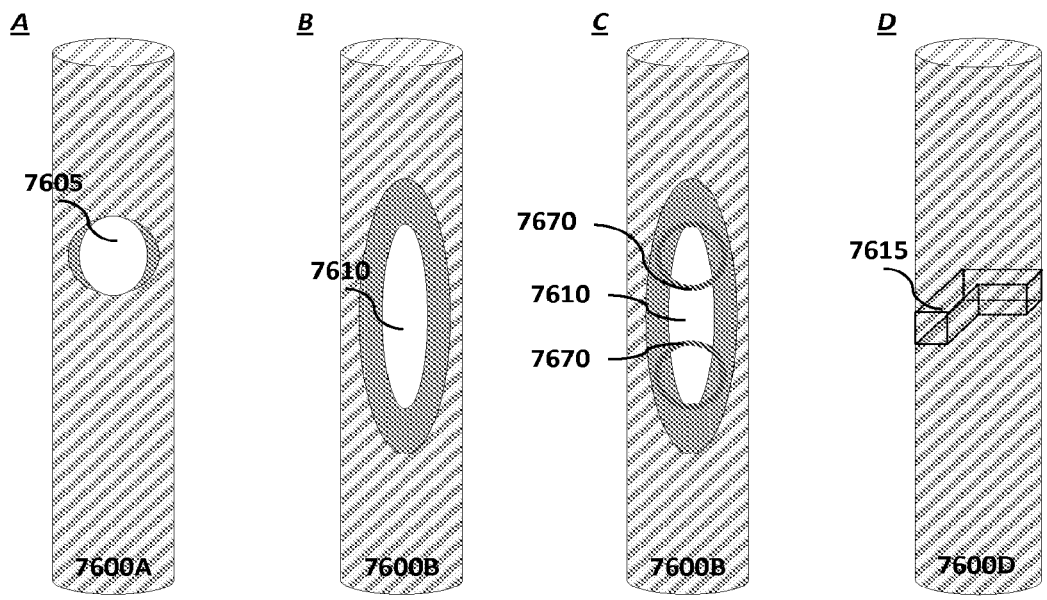
FIG. 76, panels "A"-"D", are schematics of example pins for use in a microfluidic device.

FIG. 76, panels "A"-"D", show a variety of example pins that may be used to close the channels. These pins may be inserted along the x, y, and/or z-axes. Their dimensions depend on the dimensions of the microfluidic channels and the pins generally may be flush with the walls of the microfluidic channel in order to prevent leakage. FIG. 76, panel "A", shows a pin 7600A that closes some channels, but leaves an opening 7605 for one channel on one layer. FIG. 76, panel "B", shows a pin 7600B with an opening 7610 that connects two channels and two different layers. FIG. 76, panel "C", shows a cross section of the channels 7670 that pin 7600B connects, for clarification. FIG. 76, panel "D", illustrates a pin 7600D that has an elbow-shaped opening 7615 that can be used to connect a channel running along the x-axis with a channel running along the y-axis. Pin 7600D may be used to close other channels at levels above and below the opening 7615.

Figure 77:
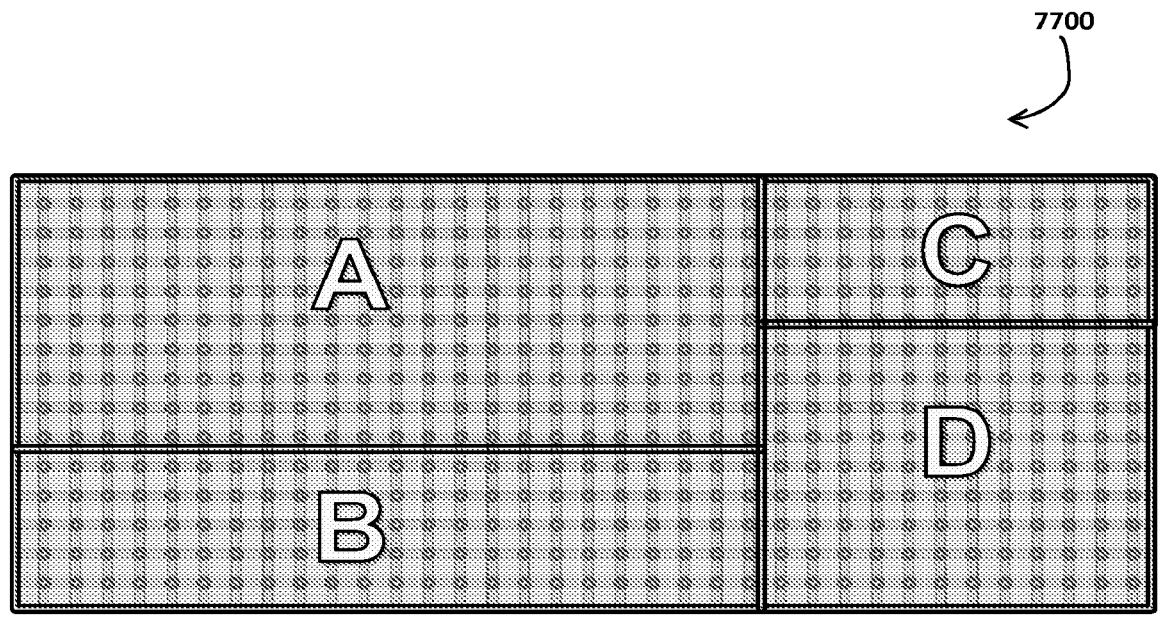
FIG. 77 is a schematic of an example microfluidic device.

In some embodiments, the substrate may be constructed from a variety of materials. In some embodiments, the channels may be closed using a variety of methods, depending on the physical characteristics of the material where the channels are being closed. In one embodiment, if the substrate is constructed from a variety of materials, a polymer that interacts with less than all of the materials to close the channels in those materials may be used. For example, as shown in FIG. 77 if the substrate of the microfluidic device 7700 is constructed from materials "A", "B", "C", and "D", a polymer that only has an effect on substrates "A" and "B" may be used in order to close the channels in those regions, leaving the microfluidic channels in regions constructed of materials "C" and "D" open. The boundary lines in FIG. 77 are for illustration purposes, as the substrate materials A, B, C, and D may be fused together to form a single structure.

In another embodiment, all or some portion of the microfluidic channels on the x-axis, y-axis, and/or z-axis are configured such that they do not intersect. Accordingly, the microfluidic channels that do not intersect are "closed" in that area in that they are not connected such that fluid may pass from one channel to the other.

In some embodiments, the microfluidic device may be fabricated using a plurality of layers. There may be a base layer, optionally with openings along the z-axis of the substrate. The next layer may have openings along the z-axis of the substrate in conjunction with microfluidic channels along the x-axis. The following layer may have openings along the z-axis of the substrate in addition to microfluidic channels along the y-axis of the substrate. Finally, there may be a top layer with openings along the z-axis. The openings and channels may be aligned such that they are in a grid format, but do not intersect. Thus, the "default" position of this configuration is with all the channels in a "closed" position. In other embodiments, some portion of the substrate may have channels that intersect while other portions of the substrate may have channels that do not intersect.

These microfluidic channels may be in fluidic contact with one or more modules. The module may perform a desired function, for example, as a sample preparation module, a nucleic acid (e.g., DNA) amplification array module, a nucleic acid (e.g., DNA) sequencing array module, etc. or a combination of functions.

In a further embodiment, modules may be placed above, within, or below the microfluidic device. There may be 1, 2, 3, 4, 5, 6, 7, 8, 9, 10, 11, 12, 13, 14, 15, 16, 17, 18, 19, 20, etc. modules wherein all or some number of the modules are connected. The connection path between the modules may vary and depend upon individual needs. Since the channels are in an "closed" position, once a desired connecting path between the modules is determined, the channels along the path may be connected using a variety of methods. The connecting path may be a straight line between one or more points, or it may travel along the x, y, and z axes in any configuration. This type of more convoluted path may be likened to the concept of Manhattan routing for FPGA circuits.

The methods for connecting the microfluidic channels that are along the connection path may depend on the substrate material being used. Methods for connecting channels in a substrate that do not intersect may be used, such as for example, lasers, polymers, pins etc. FIGS. 76B and 76C show how pin 7600B can be used to connect two channels on different layers. In other embodiments, the channels may be open using valves or gates.

The modules may be in fluidic contact with one or more microfluidic channels via a connection, such as for example a socket connection, wherein there may be an air-tight and fluid-tight seal at the connection juncture.

Various fluidic "paths" may be created wherein one or more modules may be interconnected via one or more channel paths. The number and/or type of input or output microfluidic channels in fluidic contact with the modules may be determined in the same manner.

Integrated Biological Analysis Systems

The devices and methods provided herein are related to reconfigurable, multiplexed autonomous diagnostic platforms that can enable disease prevention and facilitate the accurate administration of therapeutics. The integrated point-of-care systems (an example system shown in FIG. 78) incorporate automated sample (e.g., biospecimen) collection and preservation in addition to simultaneous on-chip analysis of one or more various analytes, such as, for example, nucleic acids, proteins, antibodies, antigens, cells, and/or other biomolecules of the sample. A sample may be, for example, blood (e.g., whole blood), a culture swab, urine, stool, tissue, or other biological sample and analysis may be, for example, for the purpose of screening for drug-resistant biomarkers. The sample can be obtained from a subject, such as a subject receiving therapy, having a disease or other health condition, or suspected of having a disease or other heath condition. In some embodiments, such technology can be used to construct an integrated, self-powered, microfluidic biological sample analysis system suitable for low-cost, sample-to-answer point of care (POC) or point of service (POS) diagnostics. An example of a integrated, self-powered, microfluidic biological sample analysis system can be found in I. K. Dimov et al., *Lab Chip* 11, 845, which is incorporated herein by reference in its entirety.

In some embodiments, a biospecimen tested within a diagnostic system may be blood. In some embodiments, well analyses of blood components containing pathogenic biological molecules can improve functions of diagnostics (e.g., emerging infectious diseases), and, thus, a diagnostic system may be configured to simultaneously examine pathogenic DNA, RNA, and/or protein in blood. In other embodiments, well analyses of blood components containing biological molecules can provide useful information with respect to pre-natal, oncological or other applications, and, thus, a diagnostic system may be aimed to simultaneously examine DNA/RNA/protein in blood. Example capabilities and components of a diagnostic system may include a sample collection module, sample separation module (e.g., plasma separation), a lysis module, a sample preservation module, detection/analysis module (e.g., modules for detecting/analyzing proteins or nucleic acids), and/or an integrated readout module.

A point of care system of the present disclosure can include a chip that comprises a plurality of sensors, as described elsewhere herein (e.g., impedance measurement sensors). The chip can be part of a housing or cartridge that may be integrated with other modules for sample retrieval and processing, as well as a computer processor or other logic for facilitating sample processing and analysis.

As an alternative, the chip can be part of a housing or cartridge that is separate from other components of the system. For example, the chip can be part of a cartridge that can be inserted into or removed from a housing containing the computer processor (or other logic), such as through a port. The housing in such a case can include other components for sample processing, such as a sample retrieval port and a fluid flow system (e.g., pump) or apparatus, which can be brought in fluid communication with the chip when the cartridge has been inserted into the housing. In some embodiments, a fluid flow apparatus or system may be or may comprise a microfluidic device.

Figure 78:
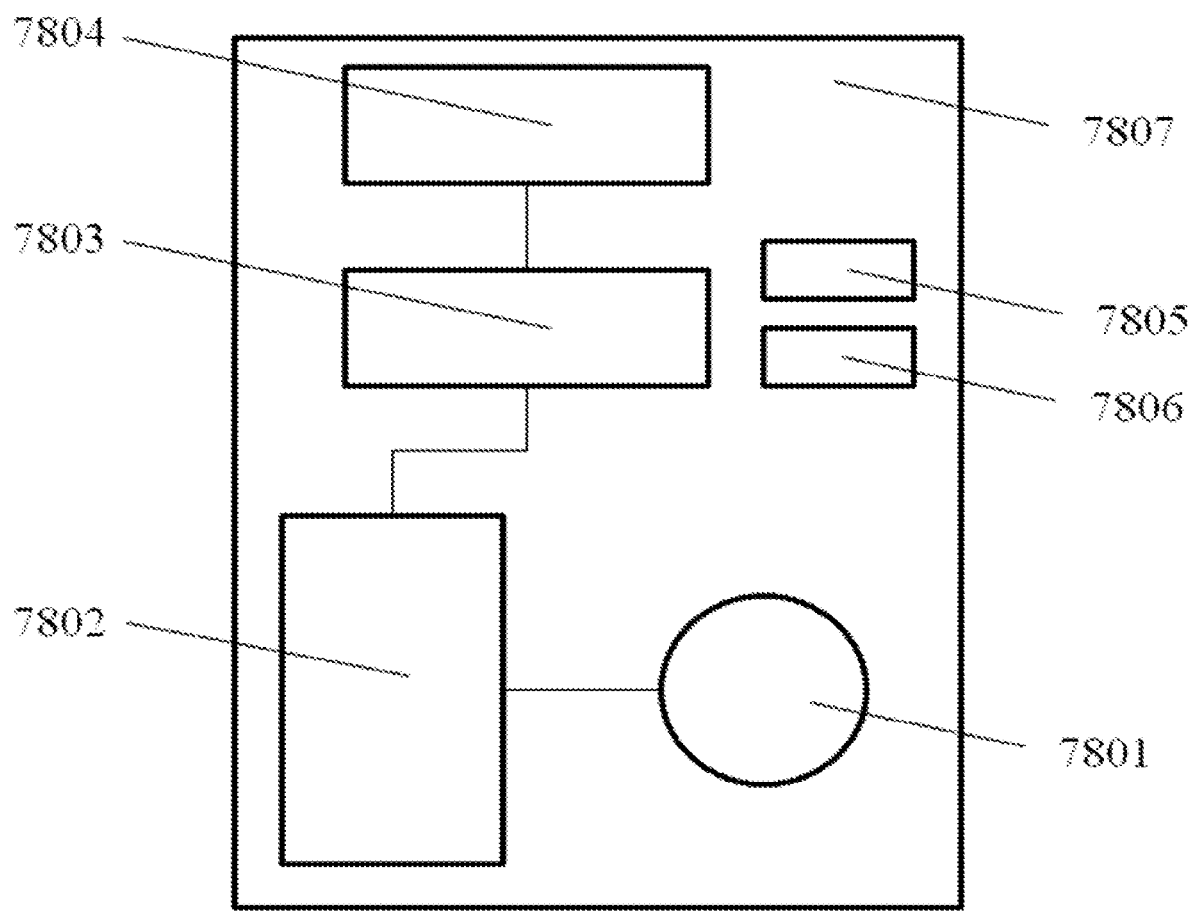
FIG. 78 is a schematic depicting an example integrated sample analysis system.

FIG. 78 shows an example integrated sample analysis system. The system comprises a sample collection module 7801, sample processing module 7802, a sensing module 7803 comprising an array of sensors, fluid flow module 7804 comprising a fluid flow system, and other modules 7805 and 7806 all integrated in a housing 7807. The housing 7807 can be a cartridge. The modules can be in fluid communication with one another through channels in the housing 7807, or in one or more layers adjacent to the housing 7807. The system of FIG. 78 can be a point of care system.

Preservation of Biological Samples

A diagnostic system may be a microfluidic, powerless, and/or reagentless. In some embodiments, a diagnostic system may include a sample preservation module that may not require medical training, and may stably store DNA, RNA, proteins, etc. for extended periods, such as up to about five days, fifteen days, one month, two months, three months, four months, five months, or more at room temperature. In some embodiments, a sample preservation module can comprise sugar and silica gel (e.g., Trehalose, sucrose, sol-gel, etc.) matrixes for the preservation of biological targets of interest. Moreover, a sample preservation module may make use of bio-inspired micropore evaporation microfluidics that can enhance drying processes useful for sample preservation.

In some embodiments, a sample preservation module may separately store blood components, such as, for example, serum and whole blood. Each species can be purified via monolithic filters so that DNA/RNA/Proteins can be stored in separate storage chambers. For serum, blood cells may be filtered (e.g., filtered via a sample preparation module that includes filtration capabilities), and pathogens in serum may be lysed. In some embodiments, serum may be preserved for the lower interference of false signals for downstream analysis. The process may be the same for whole blood, with the exclusion of filtration. Preservation of whole blood can be of interest because some pathogens such as, for example, *Plasmodium* parasites (malaria) and HIV virus, can replicate in blood cells and can have high counts.

In some embodiments, monolithic filters may be used to selectively allow only lysate DNA, RNA, or proteins to flow into each storage chamber. These filters may function by negative filtration based on size, charge, and selective degradation enzymes (e.g., RNAase, DNAase, Proteases, etc.). In some embodiments, filtration can provide a convenient pretreated specimen for downstream analysis.

In some embodiments, biospecimens may be preserved using Trehalose sugar based glassification. The protective effect of Trehalose can stabilize membranes and lipid assemblies at low levels of hydration that would normally promote their denaturation. The properties of Trehalose can make it a suitable candidate for sample preservation, including delicate biological structures in dehydrated forms at ambient temperature. In some embodiments, other components, such as sucrose and dextran, have been shown to be complementary to Trehalose preservation of biomolecules.

In some embodiments, silica gels, which are nanoporous sol-gels, may enhance protein preservation along with Trehalose by removing excess water content. Silica gel is inorganic and inert, thus it does not chemically affect the quality of the stored samples. Trehalose treated samples may be dehydrated to preserve the biomolecules. Silica gel may be used as a desiccant due to its large surface area and strong affinity with water.

In some embodiments, sugar-based 3D micropillar structures may be created in the storage area using material jet printers (e.g., FUJIFILM Dimatrix Materials jet). These sugar microstructures can have nanopores so as to significantly increase reaction surface area for Trehalose-biospecimen stabilization.

In some embodiments, a microporous top membrane structure for the rapid dehydration of biosamples stored in Trehalose may be utilized. A short duration (e.g., a few minutes) of infrared irradiation may aid in the evaporation of excess water content. Moreover, air drying may be used to aid in dehydrating samples after Trehalose treatment. In some embodiments, the leaf-like micropore structures of a top membrane may help facilitate on-chip drying. Silica gel may be incorporated near micropore to assist in desiccation.

In some embodiments, the packing of the entire device may be in a vacuum capsule that has a silica gel component and may have the ability to be resealed in an airtight fashion. The vacuum capsule may be used in keeping the a system viable. It may also help to protect on-chip lyophilized reagents from oxidizing. An air-tight seal and silica gel can be used to isolate chips and keep humidity low to stabilize storage conditions.

In some embodiments, the biomolecule of interest (e.g., DNA, RNA, protein, etc.) may be stored in Trehalose based sugars. The preserved samples may be compatible with standard downstream analysis techniques, including western blotting, ELISA, PCR, MALDI, conventional mass spectroscopy, etc., or other suitable technique.

Fabrication may be via standard industrial techniques for mass production, such as for example, injection molding and fabrication. In some embodiments, patterned sugars may be fabricated by 3D printing.

Sample Collection

Systems of the present disclosure may comprise systems or devices capable of obtaining a sample from a subject, such as for example, a blood sample. In some embodiments, an array of microneedles may be integrated into the device for a painless medium for conducting blood from the subject to the microfluidic channels of a device. Microfabrication methods may allow for the creation of arrays of microneedles to painlessly withdraw small blood samples. See, e.g., H. J. G. E. Gardeniers et al., *J Microelectromech S* 12, 855, and R. K. Sivamani, D. Liepmann, H. I. Maibach, *Expert Opin Drug Deliv* 4, 19, each of which is entirely incorporated herein by reference. In some embodiments, the microneedles penetrate up to about 100, 200, 300, 400, 500, 600, 700, 1000, or more microns into the dermis of the skin, where the microneedles can reach capillaries, but not nerves. In other embodiments, the depth of penetration may be smaller or greater that about 400 microns. Moreover, at lengths such as about 400 microns, a small diameter array may also permit stretching and compression of surrounding tissues, allowing for painless withdrawal of blood from a subject. See, e.g., S. Kaushik et al., *Anesth Analg* 92, 502, which is entirely incorporated herein by reference.

In some embodiments, a microneedle array may also incorporate a dried anticoagulant coating. The microneedle array may be pre-treated with an anticoagulant to help sustain blood flow to the microfluidic device.

In some embodiments, a sedimentation based sample fractionation system may be used in order to harness gravity based differential sedimentation to separate plasma from whole blood. In some embodiments, autonomous pumping through the fractionation system can be based on slow release of vacuum pressure through nanoporous polymers (e.g., PDMS). An example of other sedimentation systems that may be employed for use with methods, devices and systems of the present disclosure are described in I. K. Dimov et al., *Lab Chip* 11, 845, which is entirely incorporated herein by reference.

In some embodiments, sedimentation based separation of red blood cells and white blood cells may be used to remove mammalian DNA and amplification inhibitors (e.g., hemoglobin). The plasma separated from the trenches may then flow downstream, into, for example, a electrochemical lysis module for the lysing of bacterial, *plasmodium*, and/or viral pathogens.

In some embodiments, the separation of red blood cells and white blood cells from the smaller and lighter bacterial,

*plasmodium*, and/or viral cells via differential sedimentation can leverage the large difference in sedimentation rates between the bloods cells and the bacteria/*plasmodium*/viruses. This may allow for high efficiency separation in a microfluidic environment. A trench based filter structure may be used, wherein the trenches can be placed at regular intervals along the channel to capture the contaminating host cells. In one example, the channel height may be about 80 μm with deep trenches of about 1 mm in height, and a cross sectional area of 24 mm$^2$. In some other embodiments, the channel height may be smaller than 80 μm for integration and smaller sample volume. In other embodiments, where the larger sample sizes are desired the channel height may be in 100s of μm or larger. In some cases, the volume can be optimized based on the application and the biological sample size (e.g., blood). In some embodiments, tube-less and power-less fluid propulsion systems may be used in a system. The system may include a block of porous material (such as PDMS) that has been degassed (vacuumed) during packaging. Blood can be sucked into the microfluidic device due expansion of the pores within the PDMS block that cause the re-absorption of air present in the unprimed microfluidic system that drives blood flow into the chip. The chip may be prepackaged in vacuum bags. Other porous polymers that are compatible with the device design and easily manufacturable with hot embossing and/or injection molding may be used.

Electrochemical Lysis

In some embodiments, after plasma separation from blood, the plasma may be transported to a lysis module, such as, for example, an electrolysis module, in some cases, a tunable hybrid electrolysis module. A tunable hybrid electrolysis module may possess both electroporation and electrochemical lysis capabilities, which can be used for lysing both pathogenic and human cells selectively. Selective lysis can allow flexibility of processed sample output for use in downstream assays, as lysate of select pathogens can be obtained. Moreover, electrolysis based lysis is reagentless, and, thus, does not generally interfere with downstream assay(s). Moreover, low power operation may also be possible since electrical fields can be concentrated in microscale geometries. Furthermore, device complexity may be reduced, as the number of fluidic inputs can be reduced since lysis is completed with electrodes, rather than reagents.

In some embodiments, an electric current may be used to generate lytic hydroxide ions on-chip that can function as lysis agents in cell membrane lysis. Hydroxide ions can function as cell lysis agents by cleaving fatty acid groups within cell membrane phospholipids. Hydroxide ions can be generated at low voltages (~2.5 V) and little amounts of power (currents ~10 μA). Higher voltages can be assumed to generate higher hydroxide concentrations and thus accelerate lysis; however, increasing the voltage to high levels (e.g., above 3V) where electrode degradation can occur, may not significantly decrease cell lysis time. In some embodiments, the lysis time is typically about 0.5 minutes, 1 minute, 1.5 minutes, 2 minutes, 2.5 minutes, 3 minutes, 3.5 minutes, 4.0 minutes, 4.5 minutes, 5 minutes, 6 minutes, 7 minutes, 8 minutes, 9 minutes, 10 minutes, or more.

For the pathogens of interest, which include bacteria, *plasmodium*, and viruses, membrane properties may be similar to mammalian cells and, thus, cells can be lysed on-chip. Additionally, electrolysis may not contaminate sample because excess OH$^-$ ions can be quenched downstream via recombination with H$^+$ ions generated at, for example, an anode. The pH for lysis of cells can be above 11.2 and some biological species (e.g., DNA) are not damaged at this pH. For example, plasmid extraction is frequently performed at pH levels of 12.0 and above.

In some embodiments, the tunable electrochemical lysis module may be able to selectively lyse and release the genomic content of the *plasmodium*/viral cells based on a hybrid system of electrochemical lysis and electroporation lysis. Platelet cells present can also be lysed, but the absence of genomic DNA may minimize contamination concerns.

*Plasmodium* parasites have lipid membranes, which may be lysed with electrochemical techniques described herein by generating H+ and OH− ions (similar to mammalian cell lysing). Viruses, however, have protein capsids and matrixes which may not be easily lysed by just changes in pH. In some embodiments, short pulses of high voltage spikes can be used to porate viral membranes (electroporation), in conjunction with high pH generated by electrochemical lysis (a low constant voltage) lyse the viral membranes. By operating at different regimes (e.g., introducing different amplitudes of pulses and constant voltages), the tunable electrolysis module may be able to lyse pathogens selectively. In some embodiments, bacterial cells may be selectively lysed. In other embodiments, other possible biomolecules can be selectively separated with similar techniques.

In some embodiments, cell lysis may be performed on-chip using other means such as using detergents, high electric fields, mechanical, electroporation techniques, and/or thermal stresses.

Pre-Concentration of DNA

Systems of the present disclosure may comprise systems or devices capable of enriching species such as nucleic acids, proteins, or other species. Systems of the present disclosure can be used to enrich at least a 10, 20, 30, 40, 50, 60, 70, 80, 90, 100, 200, 300, 400, 500, or 1000-base nucleic acid sequence (e.g., DNA or RNA) by up to 2, 3, 4, 5, 6, 7, 8, 9, 10, 20, 30, 40, 50, 100, 200, 300, 400, 500, 1000, 2000, or 5000-fold into a concentrated band using bipolar electrodes (BPEs). In some embodiments, the enrichment can be monitored using electronic or fluorescent-based approach (e.g., fluorescence microscopy). Once enrichment is initiated, the location of the concentrated band can be manipulated by changing the velocity of the PDF. The flow rates that occur with the chip can be within the PDF rates that enable pre-concentration with BPEs.

Upon liberation of pathogenic biomarkers using electrochemical lysis, enrichment of liberated nucleic acids (e.g., DNA) using bipolar electrodes (BPEs) integrated within a device may be performed. When sufficient potential is applied across a buffer filled microchannel containing a BPE, faradaic reactions can be induced at its poles. Hydroxide produced by water reduction at the BPE cathode can neutralize buffer cations resulting in the formation of a depletion zone and consequently, an electric field gradient. Enrichment of analyte anions (e.g., nucleic acids) may occur at the position on the electric field gradient where the velocity due to bulk convection, (nearly uniform along the length of the channel), is exactly balanced by an equal and opposite electrophoretic velocity (which is a function of location along the electric field gradient), where convective flow may be due to electroosmosis and pressure-driven flow (PDF) combined.

The location on the electric field gradient at which enrichment occurs can be dependent on the electrophoretic mobility ($\mu_{ep}$) of the enriching species. Therefore, species with different $\mu_{ep}$ values may enrich into separate concentrated bands within the same channel. Different DNA oligomers may be separated using this same approach and valving with cross channels may enable selective capture.

Nucleic Acid and Protein Signal Amplification

Systems of the present disclosure may comprise systems or devices capable of nucleic acid amplification. Traditionally, nucleic acid amplification-based diagnostics have been performed using PCR. With the emerging need for integrated and portable molecular diagnostic solutions, PCR reactions have been adapted for microfluidic chips. However, PCR necessitates thermocycling, which adds significant power consumption, complexity, and cost to the process. To this end, isothermal nucleic acid amplification schemes may be used, in particular Loop Mediated Isothermal Amplification (LAMP).

LAMP is an amplification process in which DNA of interest is amplified using a set of primers at a constant temperature of 65° C.~70° C. See, e.g., T. Notomi et al., *Nucleic Acids Res* 28, E63, which is entirely incorporated herein by reference. LAMP-based assays may be integrated on-chip using the self-powered degassing method for automated molecular detection. The assay may allow for visualization by naked-eye and proper illumination facilitates fluorescent excitation for quantitative analysis. In some embodiments, the reagents and Bst DNA Polymerase may be lyophilized on-chip for long-term storage. Upon sample loading, the serum reconstitutes the lyophilized reagents and the amplification process begins. In one embodiment, primers for a region of the 16S rDNA gene that is universally conserved among both gram negative and positive bacteria may be used. However, the 16S rDNA gene itself is hypervariable, thus allowing the generation of amplicons that are species specific and can be detected downstream using, for example, aptamer and aptazyme probes (discussed below). In some embodiments, a system may be used for the detection of drug-resistant bacteria. In other embodiments, a system can detect the conserved and drug-resistant genomic regions for a number of infectious disease pathogens. In some embodiments, primer sets can be designed for drug-resistant genes such as those that encode β-lactamase, mecA (methicillin-resistant *Staphylococcus aureus*), and rpoB (Rifampicin-resistant Tuberculosis).

Figure 79:
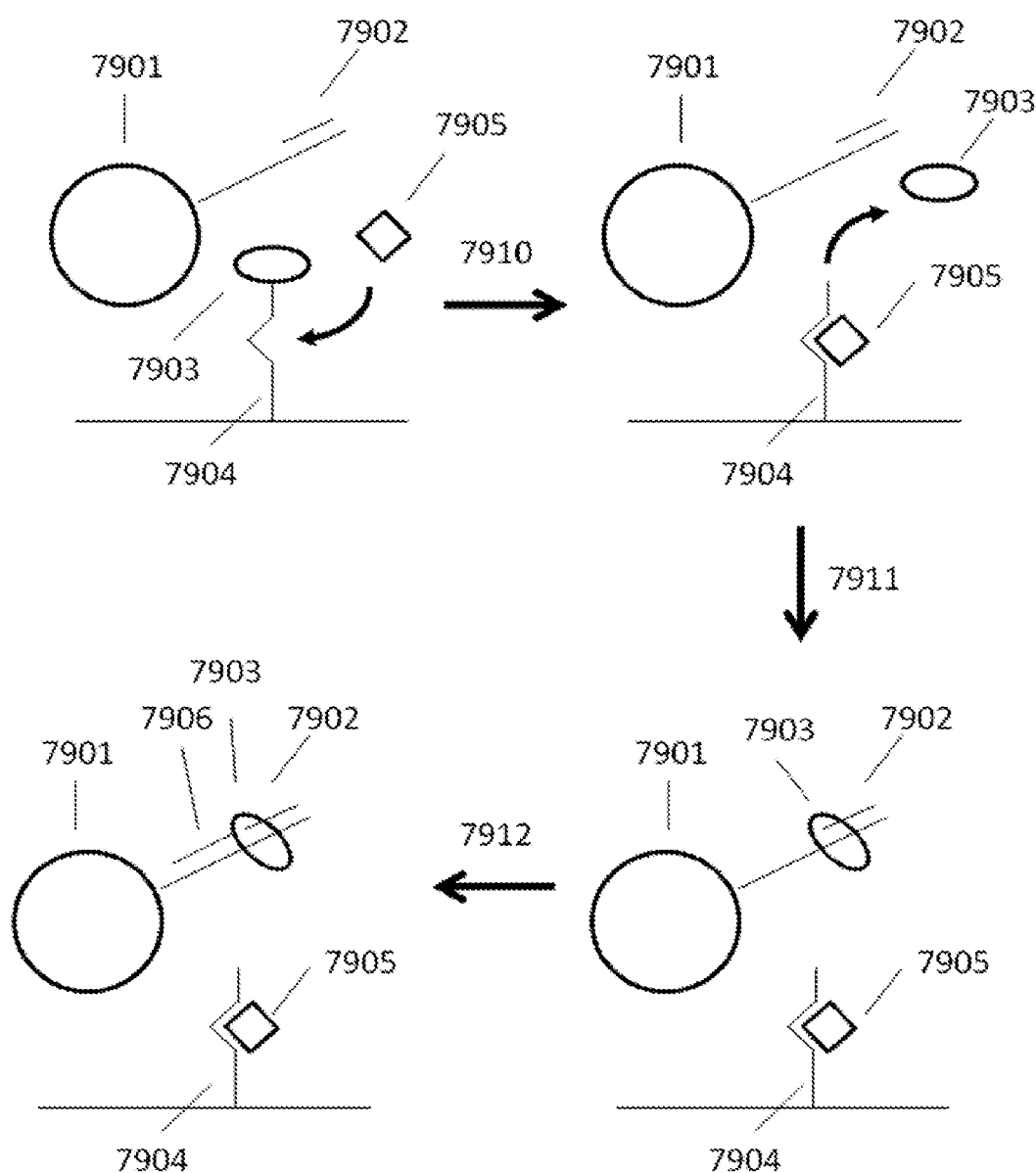
FIG. 79 is a schematic depicting an example of aptamer-based detection.
Figure 80A:
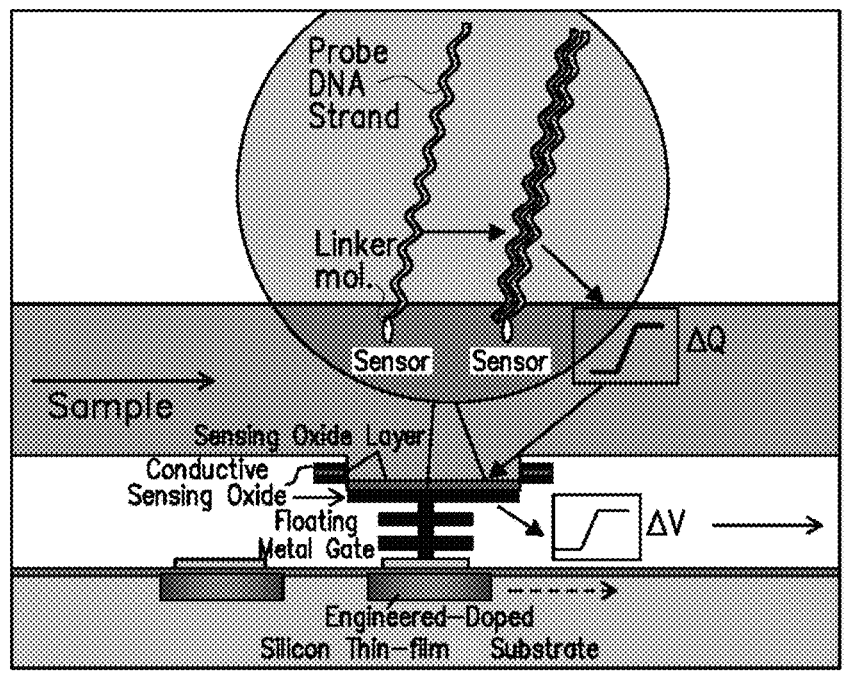
FIGS. 80A-80C are schematics depicting example sensors.
Figure 80B:
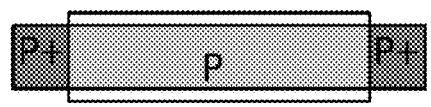
Figure 80C:
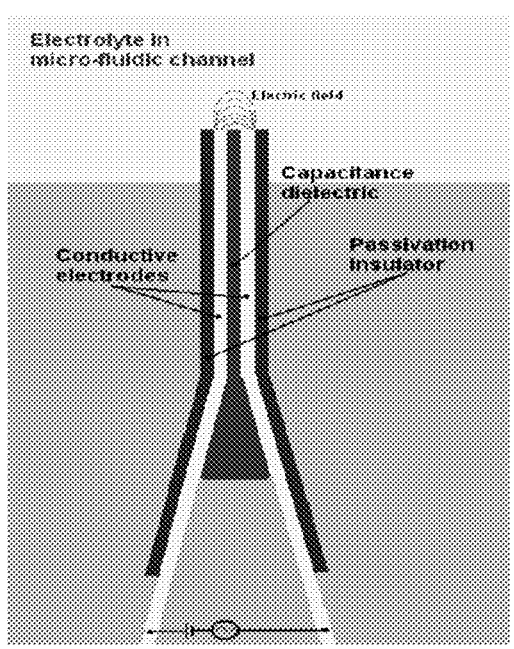
Figure 80D:
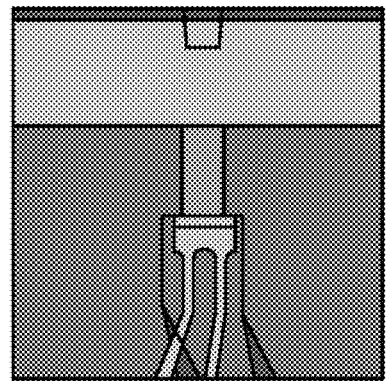
FIG. 80D is a photograph depicting an example sensor.

Systems of the present disclosure may comprise systems or devices capable of detecting proteins. In some embodiments, the system may be a detection platform, integrating biomolecular sensor and actuator components into a high-throughput microfluidic system. Sensitive protein detection may be achieved, for example, by way of a specific protein-aptamer conjugate. Target-specific aptamers can be easily generated regardless of immunogenicity or target toxicity. Once a specific aptamer has been selected and sequenced, unlimited amounts of the same aptamer can be synthesized with little effort and investment. See, e.g., A. D. Ellington, J. W. Szostak, *Nature* 346, 818, which is entirely incorporated herein by reference. Aptamers can be linked with catalytic oligonucleotide regions to create aptazymes. See, e.g., S. Cho, J. E. Kim, B. R. Lee, J. H. Kim, B. G. Kim, *Nucleic Acids Res* 33, E177, which is entirely incorporated herein by reference. Upon specific binding with a target molecule, such as, for example, a cytokine or antibody, the aptamer region may undergo a conformation change that may activate the linked catalytic region, leading to a signaling event, as shown in FIG. 79. For example, by conjugating Bst DNA Polymerase to the portion of the aptazyme that undergoes nucleolytic cleavage, this signaling event may be detected downstream. In some cases, the signaling event may be amplification of a nucleic acid. In some embodiments, signal amplification is achieved via a LAMP amplification reaction as described elsewhere herein. For example, the combination of aptazymes and LAMP may be referred to as AptaLAMP. A visual signal can enable naked-eye readout or a quantified signal may be measured via an optical reader or CMOS-based electronic detection.

An example of an aptazyme approach is shown in FIG. 79. As shown in FIG. 79, a bead 7901 may be linked to a nucleic acid 7902 hybridized with a primer. The bead 7901 may be proximate an aptamer 7904 linked to a polymerase 7903 (e.g., Bst DNA polymerase). A substrate 7095 (e.g., a target analyte such as a protein, nucleic acid, small molecule, etc.) can bind 7910, with apatmer 7904. Upon binding of substrate 7904, the aptamer functions as an aptazyme an releases 7911 its bound polymerase 7903. The released polymerase can bind 7912 to nucleic acid 7902 and extension of the primer of nucleic acid 7902 can commence. Nucleotide incorporation 7906 can be detected using methods described herein (e.g., detecting a local impedance change), effectively functioning as a signaling event for binding of substrate 7905 to aptamer 7904.

RNA Biomarker Transduction Using RNA Restriction Enzymes

Systems of the present disclosure may comprise systems or devices capable of detecting RNA. The system may allow for RNA detection within blood pathogen samples that employs a recently identified class of endoribonucleases involved in the prokaryotic immune system (see e.g., S. J. Brouns et al., Science 321, 960, which is incorporated herein by reference in its entirety). In host bacteria, RNA transcripts can be derived from Clustered Regularly Interspaced Short Palindromic Repeats (CRISPRs) that can be processed by these enzymes into shorter CRISPR-derived RNAs (crRNAs). Such crRNAs may be subsequently used to target and destroy viral nucleic acids in a process. See, e.g., J. van der Oost, M. M. Jore, E. R. Westra, M. Lundgren, S. J. Brouns, *Trends Biochem Sci* 34, 401, and M. P. Terns, R. M. Terns, *Curr Opin Microbiol*, each of which is entirely incorporated herein by reference. Although enzymes within this superfamily share common structural and catalytic properties, their ability to recognize diverse RNA sequences has evolved in response to rapid bacteriophage evolution. See, e.g., K. S. Makarova, N. V. Grishin, S. A. Shabalina, Y. I. Wolf, E. V. Koonin, *Biol Direct* 1, 7 and V. Kunin, R. Sorek, P. Hugenholtz, *Genome Biol* 8, which is entirely incorporated herein by reference. As a result, enzymes exist that recognize a large number of distinct RNA sequences—analogous to the diversity of substrate specificity observed among DNA restriction enzymes. These enzymes may be used, which will be referred to as RNA restriction enzymes (RREs), to develop a simple, low-cost method of detecting pathogen RNAs.

For example, in order to obtain a large orthogonal set of proteins for specific and selective RNA sequence detection, CRISPR transcripts have been processed in *Escherichia coli, Pyrococcus furiosus*, and *Pseudomonas aeruginosa*. In each case, a single enzyme responsible for this activity has been identified: CasE in *E. coli* (see, e.g., S. J. Brouns et al., *Science* 321, 960), Cas6 in *P. furiosus* (see, e.g., J. Carte, R. Y. Wang, H. Li, R. M. Terns, M. P. Terns, *Gene Dev* 22, 3489), and Csy4 in *P. aeruginosa* (see, e.g., R. E. Haurwitz, M. Jinek, B. Wiedenheft, K. H. Zhou, J. A. Doudna, *Science* 329, 1355). These enzymes are specific for their own associated crRNA sequence and do not cleave heterologous CRISPR RNAs (see, e.g., R. E. Haurwitz, M. Jinek, B. Wiedenheft, K. H. Zhou, J. A. Doudna, *Science* 329, 1355). However, crystal structures of Cas67 (see, e.g., R. Wang, G. Preamplume, M. P. Terns, R. M. Terns, H. Li, *Structure* 19, 257), CasE (see, e.g., Y. Kurosaki et al., *J Virol Methods* 141, 78), and Csy4 (see, e.g., R. E. Haurwitz, M. Jinek, B.

Wiedenheft, K. H. Zhou, J. A. Doudna, *Science* 329, 1355) revealed that they comprise similar protein folds, indicating an evolutionarily conserved architecture. Furthermore, co-crystal structures of these RREs bound to their crRNA targets highlighted mechanisms of substrate recognition that impart the high degree of sequence specificity critical to their application. Because CRISPR systems in different organisms contain distinct RNA sequences that constitute the sites of RRE processing, the diversity of RNA recognition may be large. RNA recognition sites may be minimal (e.g., 5-10 base pairs) and can be reconstituted by two oligonucleotides hybridized in trans. These attributes may lend themselves well to the analysis of diverse RNA molecules.

In some embodiments, pathogen RNAs may be recognized and detected within a system module. In the presence of exogenously supplied, nuclease-resistant oligonucleotides, pathogen RNAs in human blood samples—if present—can efficiently base-pair with their complementary sequence found in guide oligonucleotides associated with the module. This hybridization can generate double-stranded RNAs that are fully competent substrates for endoribonucleolytic cleavage by RREs. Taking advantage of the limited interactions that RREs exhibit with nucleic acid downstream of the cleavage site, Bst DNA Polymerase reporter can be chemically conjugated to the 3' end of guide oligonucleotides. See, e.g., R. E. Haurwitz, M. Jinek, B. Wiedenheft, K. H. Zhou, J. A. Doudna, *Science* 329, 1355, which is entirely incorporated herein by reference. These reporters may be released after RRE-mediated cleavage, resulting in a spectrophotometric signal that is easily detected.

RREs can be chemically tethered to the surface of the microfluidics chip using standard protein conjugation techniques. A positive signal within this approach may only be generated if the target RNA sequence exists in the pathogen sample; if no such sequence is present, the double-stranded substrate is not formed and the RRE remains inert. By multiplexing through use of multiple RREs and guide oligonucleotides, each finely tuned to probe for a specific pathogen RNA sequence, this approach can enable sensitive yet accurate RNA biomarker detection.

Surface Functionalization with Nucleic Acids

In some embodiments, in order to integrate LAMP, Apta-LAMP, and RRE detection on-chip, various types of biomolecules may be patterned on-chip. Methods described herein may be used to covalently immobilize nucleic acids (e.g., DNA) directly onto a microchannel surface, a configuration which may be useful, for example, for an enzyme-linked DNA hybridization assay. In some embodiments, DNA can be directly attached to PDMS microfluidic channels, and the use of these PDMS-immobilized capture probes can be used for further immobilization of proteins. Such an approach may be used with other approaches for controlling surface properties of PDMS and the use of surface modifications for immobilization of DNA, RNA, and proteins, such as those described in D. Liu, R. K. Perdue, L. Sun, R. M. Crooks, *Langmuir* 20, 5905, which is entirely incorporated herein by reference.

In some embodiments, the immobilization of nucleic acid (e.g., DNA) onto a PDMS surface may involve a plurality of steps which can include: plasma-induced oxidation of the PDMS surface, functionalization of the oxidized surface with a silane coupling agent bearing a distal thiol group (mercaptopropylsilane, MPS), and subsequent reaction of the thiol groups with acrylamide-modified DNA. The silanization step can be carried out using a vapor-phase reaction method. The plasma-treated PDMS may be exposed to acid (e.g., HCl) vapor before the MPS vapor, as the acid can act as a catalyst that increases the rate of MPS immobilization on the PDMS surface. Subsequent exposure of the PDMS-linked DNA to its biotinylated complement can provide a platform for immobilization of a protein (e.g., alkaline phosphatase (AP)). PDMS immobilization of species can be compatible a variety of species, including those described herein. In some cases, PDMS immobilization can provides a means for immobilizing any suitable oligonucleotide or streptavidin-modified protein onto a PDMS surface.

Nucleic Acid Patterning and Replication for Mass Fabrication

In some embodiments, a method for parallel replication of DNA and RNA microarrays of arbitrary size may be used. Other approaches for parallel replication of DNA and RNA are described in, for example, J. Kim, R. M. Crooks, *Anal. Chem.* 79, 7267, 8994, which is entirely incorporated herein by reference.

For DNA arrays, approach can consist of a number of steps, with examples of such steps described below. For example, a master DNA array may be prepared by covalent immobilization of amine-functionalized DNA templates on an epoxy-modified glass substrate. Second, biotinylated primer oligonucleotides, consisting of a single sequence, can be hybridized to the distal end of the template DNA, and the primers may be extended using a T4 DNA polymerase enzyme. Third, a streptavidin-coated poly(dimethylsiloxane) (PDMS) monolith can be brought into contact with the master array. This may result in binding of the extended, biotinylated primers to the PDMS surface. Fourth, the PDMS substrate can be mechanically separated from the glass master array. This may result in transfer of the extended primers to the PDMS surface, and it may leave the original master array ready to prepare a second replicate array.

An approach similar to that described above can be used to pattern proteins appended with short DNA labels. In this case, a DNA zip code array may be prepared, and it directs the protein to the specified location. See, e.g., H. Lin, J. Kim, L. Sun, R. M. Crooks, *J Am Chem Soc* 128, 3268, which is entirely incorporated herein by reference.

Signal Transduction

Systems of the present disclosure may comprise systems or devices capable of detecting proteins, nucleic acids (e.g., DNA or RNA), or other species either directly or indirectly. Real-time monitoring of polymerase reactions are typically performed with fluorescent molecules, which transduce the product of the reaction into an optical signal. In some embodiments, signal detection methods may be used to monitor polymerase reactions in real-time, with non-limiting examples that include optical-based and CMOS-based modalities.

In one embodiment, an optical-based method, such as for example, an optical readout technique may use reporter molecules to generate a fluorescent signal. For quantitative readout of the assay, the chip can then be inserted into an instrument, which can maintain assay temperature, illuminate the chip, and detect fluorescence emission from the reaction chambers using an array of phototransistors. The instrument may be designed to perform its functions without the use of costly optical components and without the need for alignment or focusing.

In one embodiment, the instrument may be automated, for example, a microcontroller board. In some embodiments, the instrument may feature a USB interface, a Secure Digital (SD) Flash memory card reader for storing assay parameters and results, and color touch screen user interface. In a further embodiment, to run an assay, the microfluidic chip can inserted directly on top of a 4 indium tin oxide (ITO) coated glass slide, which heats the chip to an appropriate temperature (e.g., 60° C.). In an exemplary embodiment, blue InGaN LEDs (peak=472 nm) can illuminate the chip from its sides through a glass waveguides cladded with black paint to minimize stray light. The waveguides promote may total internal reflection (TIR) of excitation light within the chip.

In some embodiments, the reporter molecules used in a LAMP reaction may emit green fluorescence (peak excitation=480 nm, peak emission=515 nm). This fluorescence can be detected with a phototransistor located directly underneath each reaction chamber. There may be a small air gap between the phototransistor housings and the ITO heater, which helps ensure TIR and prevent feedthrough of the excitation light into the phototransistors. A microcontroller can use such multiplexers to raster through the phototransistor array, selecting one at a time for interrogation and the entire array can be sampled at specified intervals (e.g., typically every 10 seconds).

In one embodiment, an instrument can be powered by a lithium polymer battery (e.g., a 3.7 V, 2000 mAh battery). In an exemplary embodiment, the system can run a typical assay in approximately 0.5, 1, 1.5, 2.0, 2.5, 3.0, 3.5, 4 or more hours and 0.5, 1.0, 1.5, 2.0, 2.5, 3.0, 3.5, 4.0, or more amp-hours are consumed. An enclosure featuring better thermal insulation that will greatly reduce this power consumption is envisioned and this can extend the life of the battery. In some embodiments, the instrument is a fully-integrated, portable instrument which addresses the needs of a small clinical setting.

In some embodiments, impedance biosensors (e.g., complementary metal-oxide-semiconductor impedance sensors) may be used to probe for biomolecular binding in real-time. Impedance sensors can be used for impedance, charge and/or conductivity measurements, such as measurements across a particle (e.g., bead), through the particle, across a surface of the particle, or locally in or within a fluid environment of the particle. This technique utilizes the cheap, mass produced semiconductor fabrication processes that have been optimized over the past decades for the integration of label-free biosensing with point-of-care molecular diagnostic systems.

In some embodiments, a CMOS nanosensor array may be used for the detection of both protein and nucleic acids. The geometry of impedance sensors (e.g., two impedance sensors) and their co-localization can allow for dual and independent readouts of the same biomolecular binding event. Co-localized sensors may each measure impedance changes as an electrical 'signature' of nucleic acid hybridization or protein interaction, but via different mechanisms, as shown in FIGS. 80A-80D. One sensor, for example a NanoNeedle, can be an ultra-sensitive, localized impedance biosensor, which can detect local changes in impedance via electrical current changes. In some embodiments of the NanoNeedle, an active (20 nm) double electrode tip may be in immediate contact with the reaction solution, resulting in the ability to measure minute changes in resistance down to the aM concentration change level.

In a further embodiment, the second sensor, for example, may be configured as a NanoBridge and may function as a double gated ion-sensitive semiconductor sensor based on a depletion mode 'nanoresistor' and can use electrical current as readout. In some embodiments, the NanoBridge may be fabricated of semiconductor material with an optimized engineered doping profile that significantly can significantly increase the sensitivity of the system. In contrast to a FET, this device can be always in the "ON" state, and no threshold voltage may be needed to turn it to active sensing mode. In addition, signal calibration may not be needed due to the linear I-Vg response at low Vg. The NanoBridge design may be optimized for maximal $\Delta I/I$. The response can be linear and the linearity of the response can show that the design can allow for a measurement of charge induced changes over a wide concentration range with low threshold and good signal to noise ratios.

In one embodiment, for the detection of nucleic acid and protein, a silicon oxide surface of a sensor may be directly functionalized with capture nucleic acid (e.g., DNA) or aptamers using 3-aminopropyltriethoxysilane (APTES). APTES can form a monolayer by specifically and covalently interacting (via formation of a Schiff base) with silicon oxide. The amino group may then be used to immobilize a single stranded oligonucleotide for DNA hybridization or an aptamer for direct protein detection. In some embodiments, the method of deposition may either follow a photolithographic process to generate individually addressable pixels or may be through the application of a mask and direct 'implantation' of the capture molecules. In another embodiment, functionalized sensors can be embedded in microwells that are individual reaction 'chambers' to which sample can be delivered through microfluidic channels.

Nucleic Acid Detection Via Hybridization

Figure 81A:
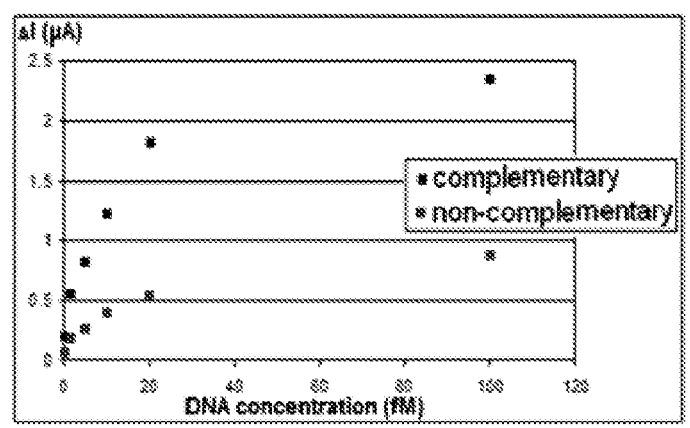
FIGS. 81A-B are graphic depictions of the sensitivity of example sensors.
Figure 81B:
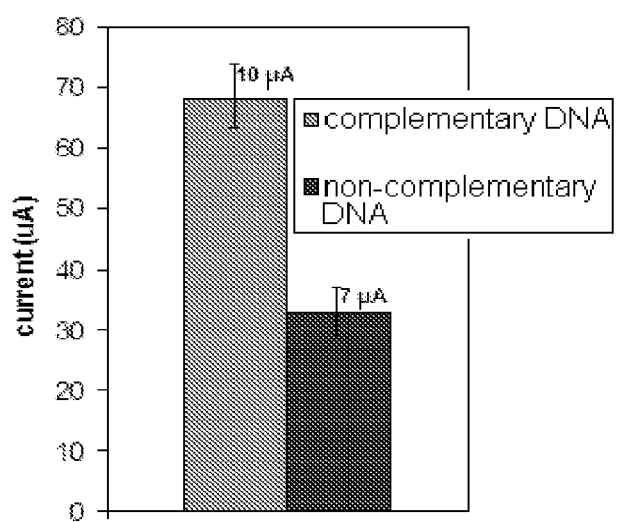

In one embodiment, nucleic acid (e.g., DNA) hybridization detection for a NanoBridge sensor can have sensitivity down to 3600-4000 molecules, as shown in FIGS. 81A and 81B. In some embodiments, a NanoBridge sensor may have sensitivity less than 3600 molecules, for example, down to 2000 molecules or less, or 1000 molecules or less, etc. In some embodiments, LAMP based amplification of the conserved 16S rDNA from bacteria may be followed by individual strain identification via hybridization to subtype specific regions of the LAMP generated amplicons. The amplicons can be detected via the specific capture/hybridization probes on functionalized sensors. Each specific binding event of a complementary DNA strand may increase negative surface charge and result in a measurable increase in conductance.

Methods for Protein Detection

Figure 82:
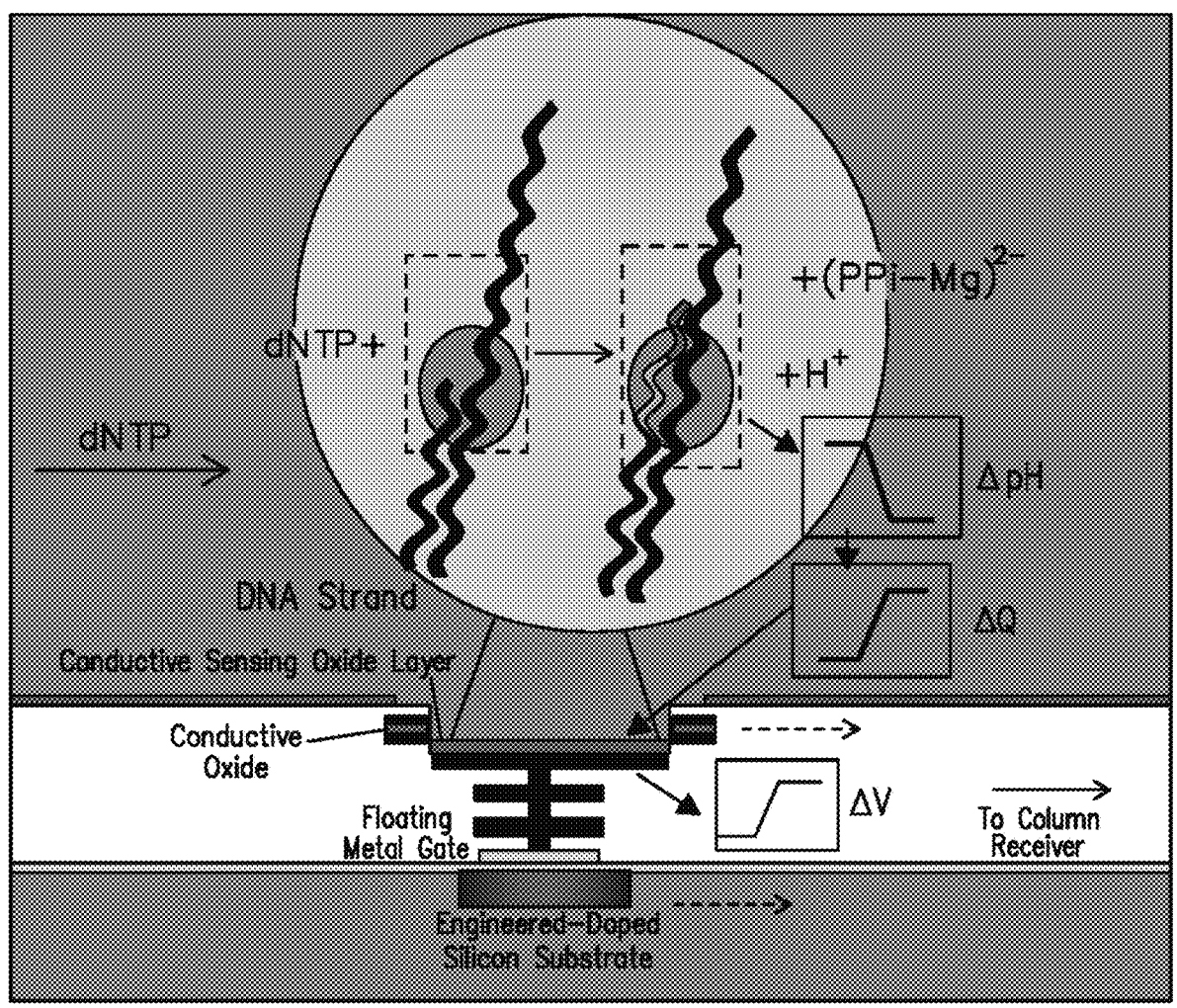
FIG. 82 is a schematic depicting an example sensor.

In some embodiments, the use of the CMOS nanosensors (e.g., an example shown in FIG. 82) can allow for the direct detection of proteins of interest using aptamer functionalized sensors. The NanoNeedle can detect antibody-protein binding events down to the aM concentration. In some embodiments, the detection of proteins may be achieved by two exemplary methods 1) direct aptamer functionalization of the sensor surface and detection of the interaction with its specific target protein and 2) use of the aptaLAMP amplification methods by detection of downstream secondary amplicons generated upon protein detection.

In one embodiment, the device may be a disposable chip that contains the sensors, microfluidic and electric wiring components to allow the detection of protein biomarkers (host and parasite) and corresponding DNA species of interest for one to multiple samples. In some embodiments, a device may be modular and can be configured quickly to incorporate capture molecules for new biomolecules of interest.

In an exemplary embodiment, a sensitive, accurate dual CMOS electronic nanosensor array embedded within a micro-channel structure may be used to detect an impedance change resulting from protein or nucleic acid binding in real time. These electrical nano-biosensors may generate data in real time, rely on fabrication processes long optimized in the semiconductor industry, do not require expensive labeling reagents, and do not require expensive optical readout systems.

USB Compatible Interface

Systems of the present disclosure may comprise systems or devices capable of detecting proteins. In one embodiment, lysing and electrokinetic pre-concentration may be designed to be within the operational range of USB 2.0 specifications (e.g., under 5 V and 500 mV loading). This can enable plug and play USB capabilities with a downstream reader. In some embodiments, utilizing common peripherals such as mobile phones/laptops/desktops and PDAs to become potential readers and power supply sources of a device is envisioned. Moreover, standard commercial batteries may also be able to power a device.

Fabrication

In some embodiments, devices can be composed of three layers polymeric material such as polystyrene. The bottom layer, for example, may be ITO or graphite electrodes coated onto plastic. The middle layer, for example, may contain any desired fluidic channels. The middle layer may also have microchannels and trenches on both sides. Such a configuration can be achieved by sandwiching two molds on each side during injection molding. The top layer may simply be a flat plastic sheet to seal the microchannels. In one embodiment, a device can be manufactured with plastics and/or with the aid of common mass production techniques such as injection molding and semiconductor processes (electrodes patterning).

Integration Approach with Other Devices

In some embodiments, a device or system may utilize an embedded microprocessor (e.g., PC/104+ Linux operating system) for ease of re-configurability and programming. Moreover, a device may be suitable for interfacing via USB or any of several wireless protocols for communication and display of results on an external laptop or other device.

Wireless System Integration for Networked Readout

The system may enable multiplexed, simultaneous readout from specimen collected with multiple devices. Wireless communication can enable electronic transmission for diagnostic interpretation, such as, for example, by a remote physician.

Control Systems

Figure 83:
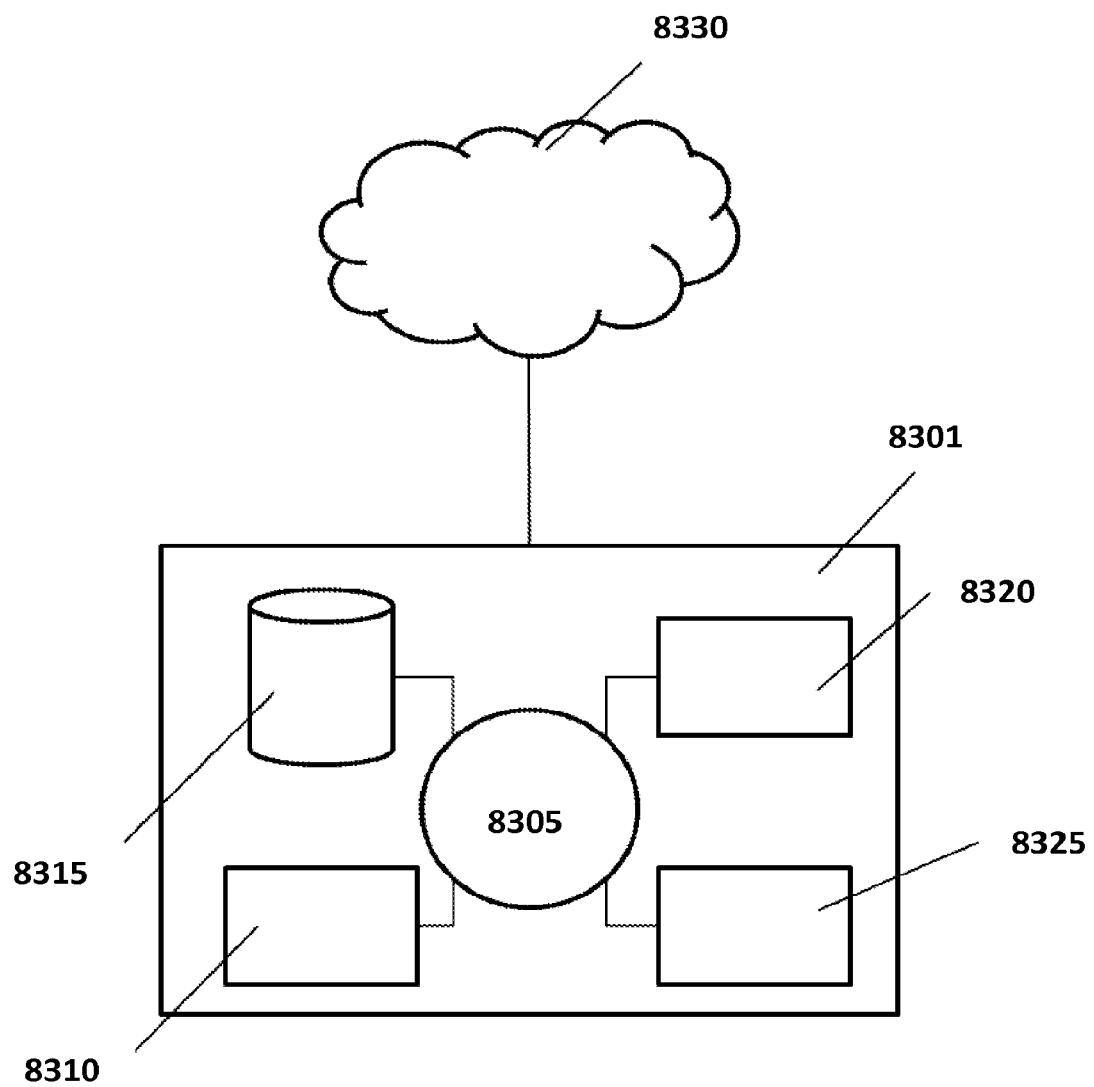
FIG. 83 is a schematic of an example control system.

The present disclosure provides computer control systems that are programmed to implement methods of the disclosure. FIG. 83 shows a computer system 8301 that is programmed or otherwise configured to receive, store, and analyze data output from the integrated microfluidic device. The computer system 8301 can regulate various aspects of data analysis and storage of the present disclosure, such as, for example, using a base-calling algorithm for sequencing analysis or interfacing with a cloud-based platform for storage of data associated with experimental runs.

The computer system 8301 includes a central processing unit (CPU, also "processor" and "computer processor" herein) 8305, which can be a single core or multi core processor, or a plurality of processors for parallel processing. The computer system 8301 also includes memory or memory location 8310 (e.g., random-access memory, read-only memory, flash memory), electronic storage unit 8315 (e.g., hard disk), communication interface 8320 (e.g., network adapter) for communicating with one or more other systems, and peripheral devices 8325, such as cache, other memory, data storage and/or electronic display adapters. The memory 8310, storage unit 8315, interface 8320 and peripheral devices 8325 are in communication with the CPU 8305 through a communication bus (solid lines), such as a motherboard. The storage unit 8315 can be a data storage unit (or data repository) for storing data. The computer system 8301 can be operatively coupled to a computer network ("network") 8330 with the aid of the communication interface 8320. The network 8330 can be the Internet, an internet and/or extranet, or an intranet and/or extranet that is in communication with the Internet. The network 8330 in some cases is a telecommunication and/or data network. The network 8330 can include one or more computer servers, which can enable distributed computing, such as cloud computing. The network 8330, in some cases with the aid of the computer system 8301, can implement a peer-to-peer network, which may enable devices coupled to the computer system 8301 to behave as a client or a server.

The CPU 8305 can execute a sequence of machine-readable instructions, which can be embodied in a program or software. The instructions may be stored in a memory location, such as the memory 8310. Examples of operations performed by the CPU 8305 can include fetch, decode, execute, and writeback.

The storage unit 8315 can store files, such as drivers, libraries and saved programs. The storage unit 8315 can store programs generated by users and recorded sessions, as well as output(s) associated with the programs. The storage unit 8315 can store user data, e.g., user preferences and user programs. The computer system 8301 in some cases can include one or more additional data storage units that are external to the computer system 8301, such as located on a remote server that is in communication with the computer system 8301 through an intranet or the Internet.

The computer system 8301 can communicate with one or more remote computer systems through the network 8330. For instance, the computer system 8301 can communicate with a remote computer system of a user (e.g., subject, researcher, or healthcare provider). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 8301 via the network 8330.

Methods as described herein can be implemented by way of machine (e.g., computer processor) executable code stored on an electronic storage location of the computer system 8301, such as, for example, on the memory 8310 or electronic storage unit 8315. The machine executable or machine readable code can be provided in the form of software. During use, the code can be executed by the processor 8305. In some cases, the code can be retrieved from the storage unit 8315 and stored on the memory 8310 for ready access by the processor 8305. In some situations, the electronic storage unit 8315 can be precluded, and machine-executable instructions are stored on memory 8310.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 8301, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 8301 can include or be in communication with an electronic display that comprises a user interface (UI) for providing, for example, raw data as well as graphs and charts associated with an experimental run. Examples of UI's include, without limitation, a graphical user interface (GUI) and web-based user interface.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for detecting at least a portion of a biological molecule, comprising:
    (a) providing an array of sensors, wherein a sensor of said array of sensors comprises a transmitter electrode and a receiver electrode, which transmitter electrode or receiver electrode is coupled to at least another sensor of said array of sensors;
    (b) directing a solution containing or suspected of containing said biological molecule to said array of sensors under conditions sufficient to bring said biological molecule to said sensor;
    (c) using said transmitter electrode and said receiver electrode to measure a change in impedance in an electrical flow path comprising said at least said portion of said biological molecule; and
    (d) using said change in impedance to detect said at least said portion of said biological molecule.

2. The method of claim 1, wherein said electrical flow path comprises a double layer comprising said at least said portion of said biological molecule.

3. The method of claim 2, wherein in (c), said at least said portion of said biological molecule is in said double layer.

4. The method of claim 1, wherein subsequent to (b), said biological molecule interacts with another biological molecule adjacent to said sensor.

5. The method of claim 4, wherein said another biological molecule is an aptamer, and wherein said biological molecule interacting with said aptamer generates said change in impedance.

6. The method of claim 4, wherein said another biological molecule is coupled to a support, and wherein said support is in said electrical flow path.

7. The method of claim 1, wherein said sensor and said at least another sensor are individually addressable.

8. The method of claim 1, further comprising directing a plurality of particles to said array of sensors, wherein a particle of said plurality of particles is coupled to said biological molecule or another biological molecule configured to interact with said biological molecule, and wherein in (c), said particle is associated with said electrical flow path.

9. The method of claim 8, wherein said particle is electrically coupled to a double layer comprising said at least said portion of said biological molecule or said another biological molecule.

10. The method of claim 8, wherein said transmitter electrode and said receiver electrode are electrically isolated in the absence of said particle positioned adjacent thereto.

11. The method of claim 8, wherein said change in impedance is across (i) said particle or (ii) a fluid environment comprising said particle.

12. The method of claim 8, further comprising using a magnetic field to position said particle within said electrical flow path.

13. The method of claim 8, further comprising using an electric field to position said particle within said electrical flow path.

14. The method of claim 8, further comprising binding said biological molecule to an aptamer coupled to a catalytic unit, wherein binding of said biological molecule to said aptamer releases said catalytic unit into said solution, and wherein, upon release of said catalytic unit, said catalytic unit interacts with a nucleic acid molecule coupled to said particle.

15. The method of claim 14, wherein said nucleic acid molecule is hybridized to a primer, and wherein said catalytic unit is a polymerase that extends said primer.

16. The method of claim 1, wherein said biological molecule is a protein.

17. The method of claim 1, wherein said biological molecule is a nucleic acid.

18. A method for detecting at least a portion of a biological molecule, comprising:
(a) providing an array of sensors, wherein a sensor of said array of sensors comprises a transmitter electrode and a receiver electrode, which transmitter electrode or receiver electrode is coupled to at least another sensor of said array of sensors;
(b) directing a solution containing or suspected of containing said biological molecule to said array of sensors under conditions sufficient to bring said biological molecule to said sensor;
(c) using said transmitter electrode and said receiver electrode to measure one or more signals that are indicative of a change in impedance in an electrical flow path comprising said at least said portion of said biological molecule, wherein said electrical flow path is between said transmitter electrode and said receiver electrode; and
(d) using said one or more signals to detect said at least said portion of said biological molecule.

19. The method of claim 1, wherein said electrical flow path comprises said biological molecule.

20. The method of claim 1, wherein said transmitter electrode or receiver electrode is shared with said at least another sensor.

21. The method of claim 18, wherein said transmitter electrode or receiver electrode is shared with said at least another sensor.

22. The method of claim 18, wherein said electrical flow path comprises a double layer comprising said at least said portion of said biological molecule.

23. The method of claim 22, wherein in (c), said at least said portion of said biological molecule is in said double layer.

24. The method of claim 18, wherein said sensor and said at least another sensor are individually addressable.

25. The method of claim 18, further comprising directing a plurality of particles to said array of sensors, wherein a particle of said plurality of particles is coupled to said biological molecule or another biological molecule configured to interact with said biological molecule, and wherein in (c), said particle is associated with said electrical flow path.

* * * * *